US008524241B2

(12) United States Patent
Seed et al.

(10) Patent No.: US 8,524,241 B2
(45) Date of Patent: *Sep. 3, 2013

(54) **FUSION PROTEINS COMPRISING A FRAGMENT OF *VIBRIO CHOLERAE* EXOTOXIN A**

(75) Inventors: Brian Seed, Boston, MA (US); Jia Liu Wolfe, Winchester, MA (US); Chia-Lun Tsai, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/669,712

(22) PCT Filed: Jul. 18, 2008

(86) PCT No.: PCT/US2008/008786
§ 371 (c)(1),
(2), (4) Date: Jun. 9, 2010

(87) PCT Pub. No.: WO2009/014650
PCT Pub. Date: Jan. 29, 2009

(65) Prior Publication Data
US 2010/0256070 A1  Oct. 7, 2010

Related U.S. Application Data

(60) Provisional application No. 60/961,308, filed on Jul. 20, 2007.

(51) Int. Cl.
*C07K 19/00* (2006.01)
*C07K 14/28* (2006.01)
*C12P 21/00* (2006.01)
*C12N 15/31* (2006.01)
*C07H 21/04* (2006.01)

(52) U.S. Cl.
USPC .................. 424/183.1; 435/69.7; 435/320.1; 514/21.2; 530/350; 530/387.3; 536/23.4; 536/23.7

(58) Field of Classification Search
None
See application file for complete search history.

(56) References Cited

U.S. PATENT DOCUMENTS

| | | |
|---|---|---|
| 4,892,827 A | 1/1990 | Pastan et al. |
| 5,602,095 A | 2/1997 | Pastan et al. |
| 5,705,156 A | 1/1998 | Pastan et al. |
| 5,863,745 A | 1/1999 | Fitzgerald et al. |
| 6,086,900 A | 7/2000 | Draper |
| 6,099,842 A | 8/2000 | Pastan et al. |
| 6,426,075 B1 | 7/2002 | Fitzgerald et al. |
| 6,566,500 B1 | 5/2003 | Vitetta et al. |
| 2005/0136076 A1 | 6/2005 | Pizza et al. |
| 2006/0159708 A1 | 7/2006 | Harrison et al. |
| 2006/0264364 A1 | 11/2006 | Wagner et al. |

FOREIGN PATENT DOCUMENTS

| | | |
|---|---|---|
| WO | WO 2008/011157 | 1/2008 |
| WO | WO 2009/149281 | 12/2009 |

OTHER PUBLICATIONS

Li et al (1995. Proc Natl Acad Sci USA. 92: 9308-9312).*
Wells (1990) Biochemistry 29(37): 8509-8517.*

(Continued)

*Primary Examiner* — Zachary Howard
(74) *Attorney, Agent, or Firm* — Clark & Elbing LLP

(57) ABSTRACT

The invention features recombinant exotoxins from *Vibrio cholerae* are for the therapeutic treatment of a variety of human diseases, particularly diseases characterized by an abundance or excess of undesired cells.

8 Claims, 13 Drawing Sheets

(56) References Cited

OTHER PUBLICATIONS

Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Purdy. "Discovery and Description of a Novel Toxin Within the Pan-Genome of the Waterborne Pathogen *Vibrio cholerae*". Doctoral Dissertation dated Feb. 2008 in the UMI ProQuest Dissertations & Theses collection. 183 pages total as printed.*
Abi-Habib et al., "A urokinase-activated recombinant diphtheria toxin targeting the granulocyte-macrophage colony-stimulating factor receptor is selectively cytotoxic to human acute myeloid leukemia blasts" Blood. Oct. 1, 2004;104(7):2143-2148.
Ahn and Brown, "Targeting tumors with hypoxia-activated cytotoxins" Front Biosci. May 1, 2007;12:3483-3501.
Alderson et al., "Characterization of a CC49-based single-chain fragment-beta-lactamase fusion protein for antibody-directed enzyme prodrug therapy (ADEPT)" Bioconjug Chem. Mar.-Apr. 2006;17(2):410-418.
Allen, "Ligand-targeted therapeutics in anticancer therapy" Nat Rev Cancer. Oct. 2002;2(10):750-763.
Bagshawe, "Antibody-directed enzyme prodrug therapy (ADEPT) for cancer" Expert Rev Anticancer Ther. Oct. 2006;6(10):1421-1431.
Bendel et al., "A recombinant fusion toxin targeted to the granulocyte-macrophage colony-stimulating factor receptor" Leuk Lymphoma. Apr. 1997;25(3-4):257-270.
Chadwick et al., "Differential sensitivity of human myeloma cell lines and normal bone marrow colony forming cells to a recombinant diphtheria toxin-interleukin 6 fusion protein" Br J Haematol. Sep. 1993;85(1):25-36.
Chwieralski et al., "Cathepsin-regulated apoptosis" Apoptosis. Feb. 2006;11(2):143-149.
Ebihara et al., "Preparation of a claudin-targeting molecule using a C-terminal fragment of *Clostridium perfringens* enterotoxin" J Pharmacol Exp Ther. Jan. 2006;316(1):255-260.
Fenton and Perry, "Gemtuzumab ozogamicin: a review of its use in acute myeloid leukaemia" Drugs. 2005;65(16):2405-2427.
Foss, "DAB(389)IL-2 (ONTAK): a novel fusion toxin therapy for lymphoma" Clin Lymphoma. Sep. 2000;1(2):110-116; discussion 117.
Frankel et al., "Diphtheria toxin fused to human interleukin-3 is toxic to blasts from patients with myeloid leukemias" Leukemia. Apr. 2000;14(4):576-585.
Fynbo et al., Characterization of a recombinant granzyme B derivative as a "restriction" protease, Protein Expr Purif. Feb. 2005;39(2):209-218.
Harding et al., "A beta-lactamase with reduced immunogenicity for the targeted delivery of chemotherapeutics using antibody-directed enzyme prodrug therapy" Mol Cancer Ther. Nov. 2005;4(11):1791-1800.
Harris el al., "Definition and redesign of the extended substrate specificity of granzyme B" J Biol Chem. Oct. 16, 1998;273(42):27364-27373.
He et al., "Arg9-peptide facilitates the internalization of an anti-CEA immunotoxin and potentiates its specific cytotoxicity to target cells" Int J Biochem Cell Biol. Jan. 2005;37(1):192-205.
Hilgenbrink and Low, "Folate receptor-mediated drug targeting: from therapeutics to diagnostics" J Pharm Sci. Oct. 2005;94(10):2135-2146.
Ho et al., "A self-immolative reporter for beta-galactosidase sensing" Chembiochem. Mar. 26, 2007;8(5):560-566.
Ho et al., "Mesothelin expression in human lung cancer" Clin Cancer Res. Mar. 1, 2007;13(5):1571-1575.
Holbourn et al., "A family of killer toxins. Exploring the mechanism of ADP-ribosylating toxins" FEBS J. Oct. 2006;273(20):4579-4593.
Ichinose et al., "Extracellular Bad fused to toxin transport domains induces apoptosis" Cancer Res. Mar. 1, 2002;62(5):1433-1438.
International Preliminary Report on Patentability for PCT/US2008/008786, issued Feb. 4, 2010.
Jorgensen et al., "Cholix toxin, a novel ADP-ribosylating factor from *Vibrio cholera*" J Biol Chem. Apr. 18, 2008;283(16):10671-10678.
Kanazawa et al., "Distinct roles for the N- and C-terminal regions in the cytotoxicity of pierisin-1, a putative ADP-ribosylating toxin from cabbage butterfly, against mammalian cells" Proc Natl Acad Sci U S A. Feb. 27, 2001;98(5):2226-2231.
Kipriyanov, "Generation and characterization of bispecific tandem diabodies for tumor therapy" Methods Mol Biol. 2003;207:323-333.
Kohchi et al., "Design and synthesis of novel prodrugs of 2'-deoxy-2'-methylidenecytidine activated by membrane dipeptidase overexpressed in tumor tissues" Bioorg Med Chem Lett. Apr. 15, 2007;17(8):2241-2245.
Krueger and Barbieri, "The family of bacterial ADP-ribosylating exotoxins" Clin Microbiol Rev. Jan. 1995;8(1):34-47.
Li and Ramakrishnan, "Recombinant hybrid toxin with dual enzymatic activities" Potential use in preparing highly effective immunotoxins, J Biol Chem. Jan. 28, 1994;269(4):2652-2658.
Liu et al., "Expression of an anti-CD3 single-chain immunotoxin with a truncated diphtheria toxin in a mutant CHO cell line" Protein Expr Purif. Jul. 2000;19(2):304-311.
Mahrus et al., "Granzyme M is a regulatory protease that inactivates proteinase inhibitor 9, an endogenous inhibitor of granzyme B" J Biol Chem. Dec. 24, 2004;279(52):54275-54282.
Méré et al., "Acid-triggered membrane insertion of *Pseudomonas* exotoxin A involves an original mechanism based on pH-regulated tryptophan exposure" J Biol Chem. Jun. 3, 2005;280(22):21194-21201.
Nakano et al., "Purification and molecular cloning of a DNA ADP-ribosylating protein, CARP-1, from the edible clam *Meretrix lamarckii*" Proc Natl Acad Sci U S A. Sep. 12, 2006;103(37):13652-13657.
Negri et al., "Modulators of pain: bv8 and prokineticins" Curr Neuropharmacol. Jul. 2006;4(3):207-215.
Niculescu-Duvaz et al., "Self-immolative nitrogen mustard prodrugs for suicide gene therapy" J Med Chem. Dec. 17, 1998;41(26):5297-5309.
Nunn et al., "Crystal structure of tobacco etch virus protease shows the protein C terminus bound within the active site" J Mol Biol. Jul. 1, 2005;350(1):145-155.
Pallen et al., "An abundance of bacterial ADP-ribosyltransferases—implications for the origin of exotoxins and their human homologues" Trends Microbiol. Jul. 2001;9(7):302-307; discussion 308.
Papot et al., "A new spacer group derived from arylmalonaldehydes for glucuronylated prodrugs" Bioorg Med Chem Lett. Sep. 22, 1998;8(18):2545-2548.
Pastan et al., "Immunotoxin treatment of cancer" Annu Rev Med. 2007;58:221-237.
Pitcher et al., "Generation of a potent chimeric toxin by replacement of domain III of *Pseudomonas* exotoxin with ricin A chain KDEL" Bioconjug Chem. Sep.-Oct. 1995;6(5):624-629.
Prior et al., "Translocation mediated by domain II of *Pseudomonas* exotoxin A: transport of barnase into the cytosol" Biochemistry. Apr. 14, 1992;31(14):3555-3559.
Purdy et al., "A glimpse into the expanded genome content of *Vibrio cholerae* through identification of genes present in environmental strains" J Bacteriol. May 2005;187(9):2992-3001.
Rooseboom et al., "Enzyme-catalyzed activation of anticancer prodrugs" Pharmacol Rev. Mar. 2004;56(1):53-102.
Shulga-Morskoy and Rich, "Bioactive IL7-diphtheria fusion toxin secreted by mammalian cells" Protein Eng Des Sel. Jan. 2005;18(1):25-31.
Spaeny-Dekking et al., "Extracellular granzyme A, complexed to proteoglycans, is protected against inactivation by protease inhibitors" Blood. Feb. 15, 2000;95(4):1465-1472.
Takahashi et al., "Role of C-terminal regions of the C-terminal fragment of *Clostridium perfringens* enterotoxin in its interaction with claudin-4" J Control Release. Nov. 2, 2005;108(1):56-62.

Takamura-Enya et al., "Mono(ADP-ribosyl)ation of the N2 amino groups of guanine residues in DNA by pierisin-2, from the cabbage butterfly" *Pieris brassicae*, Biochem Biophys Res Commun. Oct. 15, 2004;323(2):579-582.

Tan et al., "Multidrug resistance transporters and modulation" Curr Opin Oncol. Sep. 2000;12(5):450-458.

Timmer and Salvesen, "Caspase substrates" Cell Death Differ. Jan. 2007;14(1):66-72.

Toki et al., "Protease-mediated fragmentation of p-amidobenzyl ethers: a new strategy for the activation of anticancer prodrugs" J Org Chem. Mar. 22, 2002;67(6):1866-1872.

Tözsér et al., "Comparison of the substrate specificity of two potyvirus proteases" FEBS J. Jan. 2005;272(2):514-523.

Yates et al, "Stealth and mimicry by deadly bacterial toxins" Trends Biochem Sci. Feb. 2006;31(2):123-133.

UniProt XP002613809, EBI Accession No. UniProt:Q5EK40, Mar. 15, 2005.

UniProt XP002613810, EBI Accession No. UniProt:A6AIC9, Jul. 24, 2007.

UniProt XP002613811, EBI Accession No. UniProt:A6A455, Jul. 24, 2007.

UniProt XP002613812, EBI Accession No. UniProt:A2PB96, Mar. 6, 2007.

Extended European Search Report for EP08794573, dated Jan. 4, 2011.

* cited by examiner

| PEA domains | % identities/positives |
|---|---|
| Domain I (1-252) | 31/48 |
| Domain II (253-364) | 31/46 |
| Domain Ib (365-404) | 28/50 |
| Domain III (405-613) | 39/54 |
| Overall | 33/49 |

B

```
VCE  A R S R K P R    D L T
PEA  T R H Q P R      G W E
DT   A G N   V R R    S V G
```

C

```
PEA    2  EEAFDLWNECAKACVLDLKDGVR-SSRMSVDPAIADTNGQGVLHYSMVLEGNDALKLAI      60
          E+ ++++EC   C L   + G   S++S+   +    +GVL+YSM +    + ++K
VCE   34  EDELNIFDECRSPCSLTPEPGKPIQSKLLSIPSDVV--LDEGVLYYSMTINDEQNDIKDE-     90

PEA   61  DNALSITSDG-------------------LTIRLEGGVEPNKPVRYSYTRQARGSWS        98
          D  SI + G                    L I E G +     YSY R+  G ++
VCE   99  DKGESIITIGEFATVRATRHYVNQDAPPGVIHLDITTENGTKT-----YSYNRK-EGEFA    144

PEA   99  LNWLVPIGHEKPSNIKVFIHELNAGNQLSHMSPIYTIEMGDELLA--KLARDATFFVRAH    156
          +NWLVPIG + P+++K+ + EL+     +  + +Y+I++  ++  L   K    ++F V
VCE  145  INWLVPIGEDSPASIKISVDELDQQRNIIEVPKLLYSIDLLDNQTLEQWKTQGNVSFSVTRP   204

PEA  157  ESNEMQPTLAISHAGVSVVMAQTQPRREKRWSEWASGKVLCLLDPLLDGVYNYLAQQRCNL    216
          E N   +AIS   VS   AQ +  R KRW+ W +G   LC L P+D +YNY+ QQ  C L
VCE  205  EHN-----IAISWPSVSYKAAQKEGSRHKRWAHWHTGLALCWLVPMDAIYNYITQQNCTL    259

PEA  217  DDTWEGKIYRVLAGNP----AKHDLDIKPTVISHRLHFPEGGSLAALTAHQACHLPLETF    272
          D W G Y  +AG P     K ++ KP  +  R+HF  +G +++AL AH+ C  +PLET
VCE  260  GDNWFGGSYETVAGTPKVITVKQGIEQKP--VEQRIHFSKGNAMSALAAHRVCGVPLETL    317

PEA  273  TRHRQPRGWEQLEQCGYPVQRLVLYLAARLSWNQVDQVIRNALASPGSG------GDLGE    327
          R R+PR       C Y  Q  +V+L++A R+ ++  +D V    L         DL
VCE  318  ARSRKPRDLITDDLSCAYQAQNIVSLFVATRILFSHLDSVFTLNLDEQEPEVAERLSDLRR   377

PEA  328  AIREQPEQARLALTLAAAESERFVRQGTG---NDEAGAANADVVSLTCPVAAGECAGPA    383
          P        LT+A     +V  G     AGA  AD++SL  CP  A    C   +
VCE  378  INENNPGMVTQVLTVARQIYNDYVTHHPGLITPEQTSAGAQADILSLFCPDADKSCVA-S    436

PEA  384  DSGDALLERNYPTGAEFLGDGGDVSFSTRGTQNMTVERLLQAHRQLEERGYVVGYHGTF    443
          ++  A +   +G  +L +  V  ++G NWT + L  H+ L  GYVFVGYHGT
VCE  437  NNDQANINIESRSGRSYLPENRAV-ITPQGVTNMTYQELEATHQALTREGYVFVGYHGTN    495

PEA  444  LEAAQSIV---FGGVRARSQDLDAIWRGFYIAGDPALAVGYAQDQE-------PDARGRI    493
          +AAQ+IV      R  + ++  W G Y+A   +A+GYA+ +E        P   R
VCE  496  HVAAQTIVNRIAPVPRGNNTENEEKWGGLYVATHAEVAHGYARIKEGTGEYGLPTRAERD    555

PEA  494  RNGALLRVYVPRSSLPGFYRTSLTLAAPEAAGEVERLIGHPLPLRLDAITGPEEGGRLE    553
          G  +LRVY+PR+SL  FYRT+  L  A   + ++IGH  LPLR +A TGPE  GG   E
VCE  556  ARGVMLRVYIPRASLERFYRTNTPL--ENAEEHITQVIGHSLPLRNEAFTGPESAGGEDE    613

PEA  554  TILGWPLAERTVVIPSAIPTDPRNVGGDLDPSSIPDKEQAISALPDYASQPGKPPREDLK    613
          T++GW +A  V  IPS IP  +D  ++  KEQ+IS  P Y    K  ++LK
VCE  614  TVIGWDMAIHAVAIPSTIPGNAYEELA-IDEEAVA-KEQSISTKPPY----KERKDELK    666
```

Fig. 1

FUSION PROTEINS COMPRISING A FRAGMENT OF *VIBRIO CHOLERAE* EXOTOXIN A

CROSS-REFERENCE TO RELATED APPLICATIONS

This application is the National Stage of International Application No. PCT/US2008/008786, filed Jul. 18, 2008, which claims benefit of U.S. Provisional Application No. 60/961,308, filed Jul. 20, 2007, each of which is incorporated by reference herein.

THE FIELD OF THE INVENTION

The present invention relates to therapies based on *Vibrio cholerae* exotoxin (VCE), and methods and compositions to utilize the exotoxin and its derivatives as selective cytotoxic or cytostatic agents for selected target cells.

BACKGROUND OF THE INVENTION

Selective killing of particular types of cells is desirable in a variety of clinical settings, including the treatment of cancer, which is usually manifested through growth and accumulation of malignant cells. An established treatment for cancer is chemotherapy, which kills tumor cells by inhibiting DNA synthesis or damaging DNA (Chabner and Roberts, Nat. Rev. Cancer 5:65 (2005)). However, such treatments often cause severe systemic toxicity due to nondiscriminatory killing of normal cells. Because many cancer chemotherapeutics exert their efficacy through selective destruction of proliferating cells, increased toxicities to normal tissues with high proliferation rates, such as bone marrow, gastrointestinal tract, and hair follicles, have usually prevented their use in optimal doses. Such treatments often fail, resulting in drug resistance, disease relapse, and/or metastasis. To reduce systemic toxicity, different strategies have been explored to selectively target a particular cell population. Antibodies and other ligands that recognize tumor-associated antigens have been coupled with small molecule drugs or protein toxins, generating conjugates and fusion proteins that are often referred to as immunoconjugates and immunotoxins, respectively (Allen, Nat. Rev. Cancer 2:750 (2002)).

In addition to dose-limiting toxicities, another limitation for chemotherapy is its ineffectiveness for treatment of cancers that do not involve accelerated proliferation, but rather prolonged survival of malignant cells due to defective apoptosis (Kitada et al., Oncogene 21:3459 (2002)). For example, B cell chronic lymphocytic leukemia (B-CLL) is a disease characterized by slowly accumulating apoptosis-resistant neoplastic B cells, for which currently there is no cure (Munk and Reed, Leuk. Lymphoma 45:2365 (2004)).

Cancer stem cells (CSCs) are a small fraction of tumor cells that have a capacity for self-renewal and unlimited growth, and therefore are distinct from their progeny in their capacity to initiate cancers (Schulenburg et al., Cancer 107:2512 (2006)). Current cancer therapies do not target these cancer stem cells specifically, and it is hypothesized that the persistence of CSCs results in an ineradicable subset of cells that can give rise to progeny cells exhibiting drug resistance and/or contributing to the formation of metastases. In those tumors which harbor CSCs it is highly desirable to be able to eliminate these cells. CSCs have been thought to possess many properties similar to that of normal stems cells, e.g., long life span, relative mitotic quiescence, and active DNA repair capacity, as well as resistance to apoptosis and to drug/toxins through high level expression of ATP-binding cassette drug transporters such as P-glycoprotein. Consequently, CSCs are thought to be difficult to target and destroy by conventional cancer therapies (Dean et al., Nat. Rev. Cancer 5:275 (2005)). Conversely, it is critically important to distinguish CSCs from normal stem cells because of the essential roles that normal stem cells play in the renewal of normal tissues.

To increase the selectivity of highly toxic anti-tumor agents, various attempts have been made to take advantage of specific features of the tumor microenvironment, such as the low pH, low oxygen tension, or increased density of tumor specific enzymes, that are not found in the vicinity of normal cells in well-perfused tissues. Environmentally sensitive anti-tumor agents have been developed that are hypothesized to exhibit increased toxicity in the solid tumor. For example "bioreductive prodrugs" are agents that can be activated to cytotoxic agents in the hypoxic environment of a solid tumor (Ahn and Brown, Front Biosci. 2007 May 1; 12:3483-501.) Similarly Kohchi et al. describe the synthesis of chemotherapeutic prodrugs that can be activated by membrane dipeptidases found in tumors (Bioorg Med Chem. Lett. 2007 Apr. 15; 17(8):2241-5.) The use of selective antibody conjugated enzymes to alter the tumor microenvironment has also been explored by many groups. In the strategy known as antibody-directed enzyme prodrug therapy (ADEPT), enzymes conjugated to tumor-specific antibodies are intended to be delivered to the patient, followed by a chemotherapeutic agent that is inactive until subject to the action of the conjugated enzyme (see for example Bagshawe, Expert Rev Anticancer Ther. 2006 October; 6(10):1421-31 or Rooseboome et al. Pharmacol Rev. 2004 March; 56(1):53-102) To date the clinical advantages of these strategies remain undocumented and there remains a high interest in developing more selective and more potent agents that can show therapeutic utility.

SUMMARY OF THE INVENTION

The present invention features compositions and therapies based on a recombinant *Vibrio cholerae* Exotoxin (VCE). The invention includes mutant VCE fusion proteins that comprise the native ADP-ribosyltransferase activity, a modified cell binding domain that binds to one or more specific cell surface proteins, as well as a modified translocation domain cleavable by selected proteolytic activities.

In one aspect, the invention features a recombinant VCE including an amino acid sequence with greater than 70, 80%, 90%, 95%, 96%, 97%, 98%, 99%, sequence identity or has 100% sequence identity to SEQ ID NO:1.

In another aspect, the invention features a protein (e.g., a fusion protein) including a fragment of VCE, wherein the fragment includes an amino acid sequence with greater than 70, 80%, 90%, 95%, 96%, 97%, 98%, 99%, sequence identity or has 100% sequence identity to SEQ ID NO:2. This protein can contain ADP-ribosylating activity and/or cell-membrane translocation activity (e.g., by having a VCE cell-membrane translocation domain). In another aspect, this protein does not include the VCE cell binding domain.

In any of the forgoing aspects the VCE fragment or protein can be fused to a the non-native cell targeting moiety (e.g., an antibody, or functional fragment thereof, an artificially diversified polypeptide binder, or a ligand for a receptor). The non-native cell targeting moiety can target, for example, a cell surface target that is expressed on cancer cells, or can target a cell selected from the group consisting of a hematopoietic cell, lymphocyte, and a nociceptive neuron.

In any of the forgoing aspects, the native furin cleavage site of the VCE fragment or protein is replaced with a modifiable activation domain, wherein the modifiable activation domain includes a substrate for an exogenous enzyme (e.g., a substrate for granzyme B activity). The exogenous enzyme can be a protease, including an exogenous human protease or non-human (or non-mammalian) protease (e.g., a viral protease). The modifiable activation domain may include a post-translational modification of a protease cleavage site or a substrate for an enzyme capable of removing a post-translational modification.

In another aspect, the invention features a vector including a nucleic acid encoding any of the forgoing proteins or protein fusions. In another aspect, the invention features a host cell containing any of forgoing vectors.

In yet another aspect, the invention features an antibody (e.g., a monoclonal antibody) that specifically binds any of the forgoing proteins or protein fusions.

In another aspect, the invention features a method of destroying a target cell (e.g., a cancer cell, a hematopoietic cell, a lymphocyte, and a nociceptive neuron) by contacting the target cell with a protein including a fragment of VCE, where the fragment includes an amino acid sequence with greater than 70, 80%, 90%, 95%, 96%, 97%, 98%, 99%, or has 100% sequence identity to SEQ ID NO:2 (or a protein encoded by SEQ ID NO:3). This protein can contain ADP-ribosylating activity and/or cell-membrane translocation activity (e.g., by having a VCE cell-membrane translocation domain). In another aspect, this protein does not include the VCE cell binding domain.

In any of the forgoing methods, the VCE fragment or protein can be fused to a the non-native cell targeting moiety (e.g., an antibody, or functional fragment thereof, an artificially diversified polypeptide binder, or a ligand for a receptor). The non-native cell targeting moiety can target, for example, a cell surface target that is expressed on cancer cells, or can target a cell selected from the group consisting of a hematopoietic cell, lymphocyte, and a nociceptive neuron.

Also, in any of the forgoing methods, the native furin cleavage site of the VCE fragment or protein is replaced with a modifiable activation domain, wherein the modifiable activation domain includes a substrate for an exogenous enzyme (e.g., a substrate for granzyme B activity). The exogenous enzyme can be a protease, including an exogenous human protease or non-human (or non-mammalian) protease (e.g., a viral protease). The modifiable activation domain may include a post-translational modification of a protease cleavage site or a substrate for an enzyme capable of removing a post-translational modification.

As used herein the specification, "a" or "an" may mean one or more; "another" may mean at least a second or more.

The term "polypeptide" or "peptide" as used herein refers to two or more amino acids linked by an amide bond between the carboxyl terminus of one amino acid and the amino terminus of another.

The term "amino acid" as used herein refers to a naturally occurring or unnatural alpha or beta amino acid, wherein such natural or unnatural amino acids may be optionally substituted by one to four substituents, such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The term "modified" as used herein refers to a composition that has been operably changed from one or more predominant forms found naturally to an altered form by any of a variety of methods, including genetic alteration or chemical substitution or degradation and comprising addition, subtraction, or alteration of biological components or substituents such as amino acid or nucleic acid residues, as well as the addition, subtraction or modification of protein post-translational modifications such as, without limitation, glycan, lipid, phosphate, sulfate, methyl, acetyl, ADP-ribosyl, ubiquitinyl, sumoyl, neddoyl, hydroxyl, carboxyl, amino, or formyl. "Modified" also comprises alteration by chemical or enzymatic substitution or degradation to add, subtract, or alter chemical moieties to provide a form not found in the composition as it exists in its natural abundance comprising a proportion of greater than 10%, or greater than 1%, or greater than 0.1%. The term "modified" is not intended to refer to a composition that has been altered incidentally as a consequence of manufacturing, purification, storage, or expression in a novel host and for which such alteration does not operably change the character of the composition.

The term "*Vibrio Cholerae* exotoxin A" or "VCE" as used herein refers to a protein selected from the family of protoxins, the prototype of which is a diphthamide-specific toxin encoded by the toxA gene of *Vibrio cholerae*. The prototypical VCE possesses a conserved DT-like ADP-ribosylation domain, and adopts an overall domain structure very similar to that of *Pseudomonas* exotoxin A (PEA), with moderate amino acid sequence identity (~32%). Full length "*Vibrio Cholerae* exotoxin A" or "VCE" has 70%, 80%, 85%, 90%, 95%, 98%, 99%, or 100% sequence identity with SEQ ID NO:1. At minimum, "*Vibrio Cholerae* exotoxin A" or "VCE" has the ADP-ribosylating activity of full length VCE (SEQ ID NO:2, and the protein encoded by SEQ ID NO:3). Sequence alignment suggests, and crystal structure confirms, that like PEA, the VCE possesses an N-terminal cell-targeting moiety (residues Met1-Lys297 and residues Ala419-Asn457) followed by a translocation domain (Gly298 to Ala418) and a C-terminal ADP-ribosyltransferase (Arg458 to Lys666) comprising an ER retention signal $^{662}KDEL^{665}$ (SEQ ID NO:4). A putative furin cleavage site ($^{321}RKPK\downarrow DL^{326}$) (SEQ ID NO:5) is located near the N-terminus of the putative translocation domain.

The term "modified VCE", "modified VCE", or "engineered VCE" are used interchangeably herein to describe a recombinant or synthetic VCE protein that is modified to confer amino acid sequence changes as compared with that of VCE, including adding, deleting, and replacing amino acid sequences within the original sequence. In particular, the terms may refer to VCE proteins with sequence changes at the furin cleavage site to provide a mutated sequence that is a recognition site for proteases other than furin, and/or VCE fusion proteins with their native cell-targeting moiety partially or completely removed, mutationally altered, or changed to comprise other cell-targeting moieties. The term may also refer to VCE with amino acid covalent modifications such as glycosylation and PEGylation.

The term "VCE fusion" as used herein refers to a fusion protein containing a VCE or modified VCE, fused directly or indirectly to a heterologous sequence, for example, and a polypeptide that can bind to a targeted cell surface. The VCE or modified VCE is preferably located at the C-terminus of the fusion protein and the cell-targeting polypeptide attached to the N-terminus of the VCE or modified VCE. When discussed in the context of fusion toxins, "modified VCE" may simply be referred to as "VCE." The term "cell targeting moiety" as used herein refers to one or more protein domains that can bind to one or more cell surface targets, and thus can direct VCE or modified VCE to those cells. Such cell targeting moieties include, among others, antibodies or antibody-like molecules such as monoclonal antibodies, polyclonal antibodies, antibody fragments, single antibody domains and related molecules, such as scFv, diabodies, engineered lipocalins, camelbodies, nanobodies and related structures. Also included are soluble mediators, cytokines, growth factors, soluble receptor fragments, matrix fragments, synthetic molecules, or other structures that are known to have cognate binding structures on the targeted cell. In addition, protein domains that have been selected by diversification of an invariant or polymorphic scaffold, for example, in the formation of binding principles from fibronectin, anticalins, titin and other structures, are also included. Cell targeting moieties can also include combinations of moieties (e.g., an scFv with a cytokine and an scFv with a second scFv).

The terms "fusion protein", "protoxin fusion," "toxin fusion", "protoxin activator fusion" and "protease fusion" as used herein refer to a protein that has a peptide component operably linked to at least one additional component and that differs from a natural protein in the composition and/or organization of its domains. The additional component can be peptide or non-peptide in nature. Additional peptide components can be derived by natural production or by chemical synthesis, and in the case of a peptide component that acts as an inhibitor moiety, a cell-targeting moiety, or a cleavage site, the additional peptide components need not be based on any natural template but may be selected for the desired purpose from an artificial scaffold or random sequence or by diversification of an existing template such that substantially all of the primary sequence similarity is lost but the functional attributes are preserved. Non-peptide additional components can include one or more functional chemical species. The chemical species may comprise a linker or a cleavage site, each optionally substituted with one or more linkers that may provide flexible attachment of the chemical species to a polypeptide or to another chemical species.

The term "selectively modifiable activation moiety" refers to an unnatural or not naturally found moiety of a protoxin or protoxin activator that, upon modification, converts a protoxin to a toxin or natively activatable protoxin or activates a protoxin proactivator or modifies the protoxin proactivator so that it becomes natively activatable. When the selectively modifiable activation moiety is a component of the protoxin fusion protein, modification of the modifiable activation moiety by the protoxin activator can result directly in the protoxin becoming toxic to the target cell, or can result in the protoxin assuming a form that is natively activatable to become toxic to the target cell. When the selectively modifiable activation moiety is a component of the protoxin proactivator protein, modification of the modifiable activation moiety by the proactivator activator can result directly in the proactivator becoming activated to a form that can modify the protoxin, or can result in the proactivator assuming a form that is natively activatable to become a form that can modify the protoxin. Natively activatable protoxins or proactivators comprise, for example, modification of the modifiable activation moiety such that it is sensitive to endogenous components of the target cell, or the environment surrounding the target cells (e.g., a target cell specific protease or a ubiquitous protease).

The terms "operably linked" or "operable linkage" encompass the joining of two or more peptide components covalently or noncovalently or both covalently and noncovalently as well as the joining of one or more peptide components with one or more chemical species covalently or noncovalently or both covalently and noncovalently, as well as the joining of two or more chemical species covalently.

Among suitable forms of covalent linkage for peptide components are direct translational fusion, in which a single polypeptide is formed upon translation of mRNA, or post-translational fusion, achieved by operable linkage through chemical or enzymatic means or by operable linkage through natural intermolecular reactions such as the formation of disulfide bonds. Operable linkage may be performed through chemical or enzymatic activation of various portions of a donor molecule to result in the attachment of the activated donor molecule to a recipient molecule. Following operable linkage two moieties may have additional linker species between them, or no additional species, or may have undergone covalent joining that results in the loss of atoms from one or more moieties, for example as may occur following enzymatically induced operable linkage.

The term "artificially diversified polypeptide binder" as used herein refers to a peptide or polypeptide comprising at least one domain that has been made to comprise multiple embodiments as a result of natural or in vitro mutation, including addition, deletion and substitution, so as to provide an ensemble of peptides or polypeptides from which a high affinity variant capable of binding to the desired cell surface target can be selected. Such artificially diversified polypeptide binders can comprise peptides, for example as selected by phage display, ribosome display, RNA display, yeast display, cell surface display or related methods, or polypeptides, similarly selected, and typically diversified in flexible loops of robust scaffolds so as to provide antibody variable region mimetics or related binding molecules.

The term "cell surface target" as used herein refers to any structure operably exposed on the surface of a cell, including transient exposure as for example may be the consequence of fusion of intracellular vesicles with the plasma membrane, and that can be specifically recognized by a cell targeting moiety. A cell surface target may include one or more optionally substituted polypeptide, carbohydrate, nucleic acid, sterol or lipid moieties, or combinations thereof, as well as modifications of polypeptides, carbohydrate, nucleic acid, sterol or lipid moieties separately or in combination. A cell surface target may comprise a combination of optionally substituted polypeptide and optionally substituted carbohydrate, an optionally substituted carbohydrate and optionally substituted lipid or other structures operably recognized by a cell-targeting moiety. A cell surface target may comprise one or more such optionally substituted polypeptides, carbohydrates, nucleic acid, sterol or lipids in complexes, for example heteromultimeric proteins, glycan-substituted heteromultimeric proteins, or other complexes, such as the complex of a peptide with a major histocompatibility complex antigen. A cell surface target may exist in a form operably linked to the target cell through another binding intermediary. A cell surface target may be created by some intervention to modify particular cells with an optionally substituted small molecule, polypeptide, carbohydrate, nucleic acid, sterol or lipid. For example a cell surface target may be created by the administration of a species that binds to a cell of interest and thereby affords a binding surface for the modified VCE of the present invention.

The term "combinatorial targeting" and "binary targeting" refer to the methods for treating various diseases through selective killing of targeted cells using a combinatorial targeting approach as described in PCT Application Publication No. 2008/011157, which is herein incorporated by reference in its entirety. Briefly, the strategy features protoxin fusion proteins containing a cell targeting domain, a modifiable activation moiety which is activated by an activation moiety not naturally operably found in, on, or in the vicinity of a target cell. These methods also include the combinatorial use of two or more therapeutic agents, at minimum comprising a protoxin and a protoxin activator, to target and destroy a specific cell population. Each agent contains at least one cell targeting moiety binding to an independent cell surface target of the targeted cells. The protoxin contains a modifiable activation moiety that may be acted upon by the protoxin activator. The protoxin activator comprises an enzymatic activity that upon acting on the modifiable activation moiety converts, or allows to be converted, the protoxin to an active toxin or a natively activatable toxin. The targeted cells are then inhibited or destroyed by the activated toxin. In cases where only two agents are involved, the strategy is referred to as "binary targeting". One example of a protoxin and protoxin activator pair is a modified VCE fusion protein and a protease fusion protein.

The term "activatable AB toxin" as used herein refers to any protein that comprises a cell-targeting and translocation domain (B domain) as well as a biologically active domain (A domain) and that requires the action of an endogenous target cell protease on an activation sequence to substantially promote their toxic effect. AB toxins have the capability to intoxicate target cells without requirement for accessory proteins or protein-delivery structures such as the type III secretion system of gram negative bacteria. AB toxins typically contain a site that is sensitive to the action of ubiquitous furin/kexin-like proteases, and must undergo cleavage to become activated. According to the present invention, the term "activatable AB toxin" is meant to include modified AB toxins in which the endogenous cell-targeting domain is replaced by one or more heterologous cell-targeting moiety, or in which one or more heterologous cell-targeting moiety is added to an intact endogenous cell-targeting domain, and the activation sequence is replaced with a modifiable activation moiety that may be modified by an exogenous activator.

The term "ADP-ribosylating toxin" refers to enzymes that transfer the ADP ribose moiety of $\beta$-NAD$^+$ to a eukaryotic target protein. This process impairs essential functions of target cells, leading to cytostasis or cytotoxicity. Examples of bacterial ADP-ribosylating toxins include Diphtheria toxin, *Pseudomonas aeruginosa* exotoxin A, *P. aeruginosa* cytotoxic exotoxin S, pertussis toxin, cholera toxin, heat-labile enterotoxins LT-I and LT-II from *E. coli* (Krueger and Barbieri, Clin. Microbiol. Rev. 8:34-47 (1995)), and Cholix toxin (Jorgensen et al. J. Biol. Chem. 283 (16):10671-10678 (2008)). Examples of nonbacterial ADP-ribosylating toxins include the DNA ADP-ribosylating enzymes pierisin-1, pierisin-2, CARP-1 and the related toxins of the clams *Ruditapes philippinarum* and *Corbicula japonica* (Nakano et al. Proc Natl Acad Sci USA. 103(37):13652-7 (2006)). In addition, the application of in silico analyses have allowed the prediction of putative ADP-ribosylating toxins (Pallen et al. Trends Microbiol. 9:302-307 (2001).

The term "activatable ADP-ribosylating toxin" or "activatable ADPRT" as used herein refers to toxins that are functionally conserved enzymes produced by a variety of species that share the ability to transfer the ADP ribose moiety of $\beta$-NAD$^+$ to a eukaryotic target protein and that require the action of an endogenous target cell protease on an activation sequence to substantially promote their toxic effect. This process impairs essential functions of target cells, leading to cytostasis or cytotoxicity. Examples of activatable bacterial ADPRTs are VLE, Diphtheria toxin (DT), *Pseudomonas aeruginosa* exotoxin A (PEA), pertussis toxin, cholera toxin, and heat-labile enterotoxins LT-I and LT-II from *E. coli* (Krueger and Barbieri, Clin. Microbiol. Rev. 8:34-47 (1995); Holbourn et al. The FEBS J. 273:4579-4593 (2006)). Examples of activatable nonbacterial ADP-ribosylating toxins include the DNA ADP-ribosylating enzymes from Cabbage butterfly, *Pieris Rapae* (Kanazawa et al Proc. Natl. Acad. Sci. 98:2226-2231 (2001)) and, by sequence homology, *Pieris brassicae* (Takamura-Enya et al., Biochem. Biophys. Res. Commun. 32:579-582 (2004)).

The terms "VCE protoxin" and "VCE related protoxin" refer to recombinant toxins comprising at least one functional domain from VCE, either the ADP-ribosylating domain or the translocation domain. In one embodiment, such a VCE protoxin comprises the ADP-ribosyltransferase domain of VCE (Arg458 to Lys666), a C-terminal ER retention signal, a cell binding moiety, and the translocation domain of another ADP-ribosylating toxin or activatable ADP-ribosylating toxin such as that of PEA, in which the proteolytic activation site may be altered to be a substrate of a selected protease. In another embodiment, a VCE protoxin comprises the translocation domain of VCE (Gly298 to Ala418), a C-terminal ER retention signal, a cell binding moiety, and a cytotoxic moiety such as the catalytic domain of an activatable ADPRT and the biologically active A domain of an activatable AB toxin.

The term "translocation domain" of a toxin as used herein refers to an optional domain of a toxin (for example, a naturally occurring or modified toxin) that has cell-membrane translocation activity. "Cell membrane translocation activity" is activity that is necessary for translocation into the cytoplasm or a cytoplasm-contiguous compartment an active domain of a toxin. Prior to translocation the active domain may be located on the cell surface, or may have been conveyed from the cell surface into an intracellular space excluded from the cytoplasm, for example a vesicular compartment such as the endosome, lysosome, Golgi, or endoplasmic reticulum. Examples of such domains are the translocation domain of DT (residues 187-389) and the translocation domain of *Pseudomonas* exotoxin A (residues 253-364). Not all toxins contain translocation domains (e.g., pore forming toxins).

The term "substrate" as used herein refers to the specific molecule, or the portion of a molecule, that is recognized and chemically modified by a particular enzyme.

The term "protease" as used herein refers to compositions that possess proteolytic activity, and preferably those that can recognize and cleave certain peptide sequences specifically. In one particular embodiment, the specific recognition site is equal to or longer than that of the native furin cleavage sequence of four amino acids, thus providing activation stringency comparable to, or greater than, that of native toxins. A protease may be a native, engineered, or synthetic molecule having the desired proteolytic activity. Proteolytic specificity can be enhanced by genetic mutation, in vitro modification, or addition or subtraction of binding moieties that control activity.

The term "heterologous" as used herein refers to a composition or state that is not native or naturally found, for example, that may be achieved by replacing an existing natural composition or state with one that is derived from another source. Thus replacement of a naturally existing, for example, furin-sensitive, cleavage site with the cleavage site for another enzyme, constitutes the replacement of the native site with a heterologous site. Similarly the expression of a protein in an organism other than the organism in which that protein is naturally expressed constitutes a heterologous expression system and a heterologous protein.

The term "exogenous" as used herein refers to any protein that is not operably present in, on, or in the vicinity of, a targeted host cell. By operably present it is meant that the protein, if present, is not present in a form that allows it to act in the way that the therapeutically supplied protein is capable of acting. Examples of a protoxin-activating moiety that may be present but not operably present include, for example, intracellular proteases, phosphatases or ubiquitin C-terminal hydrolases, which are not operably present because they are in a different compartment than the therapeutically supplied protease, phosphatase or ubiquitin C-terminal hydrolase (which when therapeutically supplied is either present on the surface of the cell or in a vesicular compartment topologically equivalent to the exterior of the cell) and cannot act on the protoxin in a way that would cause its activation. A protein may also be present but not operably present if it is found in such low quantities as not to significantly affect the rate of activation of the protoxin or protoxin proactivator, for example to provide a form not operably found in, on, or in the vicinity of, a targeted cell in a proportion of greater than 10%, or greater than 1%, or greater than 0.1% of the proportion that can be achieved by exogenous supply of a minimum therapeutically effective dose. As a further non-limiting example, replacement of a furin-sensitive site in a therapeutic protein with a site for a protease naturally found operably present on, in, or in the vicinity of a targeted host cell constitutes a heterologous replacement that can be acted on by an endogenous protease. Replacement of a furin-sensitive site in a therapeutic protein with a site for a protease not naturally found operably present in the vicinity of a targeted host cell constitutes a heterologous replacement that can be acted on by an exogenous protease.

The term "PEGylation" refers to covalent or noncovalent modifications of proteins with polyethylene glycol polymers of various sizes and geometries, such as linear, branched and dendrimer and may refer to block copolymers incorporating polyethylene glycol polymers or modified polymers with additional functionality, such as may be useful for the therapeutic action of a modified toxin. For example a polyethylene glycol moiety may join a modifiable activation sequence to an optional inhibitor sequence or may join one or more cell-targeting moieties to a modified toxin. Many strategies for PEGylating proteins in a manner that is consistent with retention of activity of the conjugated protein have been described in the art. These include conjugation to a free thiol such as a cysteine by alkylation or Michael addition, attachment to the N-terminus by acylation or reductive alkylation, attachment to the side chain amino groups of lysine residues, attachment to glutamine residues using transglutaminase, attachment to the N-terminus by native ligation or Staudinger ligation, or attachment to endogenous glycans, such as N-linked glycans or O-linked glycans. Numerous glycan addition strategies are known, including hydrazone formation with aldehydes generated by periodate oxidation, Staudinger ligation with glycan azides incorporated by metabolic labeling, and glycan substitution technology. Examples of noncovalent modification include the reaction of a high affinity ligand-substituted PEG with a protein domain binding such ligand, as for example the reaction of a biotin-substituted PEG moiety with a streptavidin or avidin fusion protein.

The term "PEG" refers to an optionally substituted polyethylene glycol moiety that may exist in various sizes and geometries, such as linear, branched or dendrimer and may refer to block copolymers or modified polymers with additional functionality, such as may be useful for the therapeutic action of a modified toxin. The number of optionally substituted or unsubstituted ethylene glycol moieties in a PEG moiety is at least two.

The term "PEGylated" refers to a composition that has undergone reversible or irreversible attachment of a PEG moiety.

The term "thiol-specific PEGylation" refers to attachment of an optionally substituted thiol-reactive PEG moiety to one or more thiol groups of a protein or protein substituent. The target of thiol-directed PEGylation can be a cysteine residue, or a thiol group introduced by chemical reaction, such as by the reaction of iminothiolane with lysine epsilon amino groups or N-terminal alpha amino or imino groups. A number of highly specific chemistries have been developed for thiol-directed PEGylation, i.e., PEG-ortho-pyridyl-disulfide, PEG-maleimide, PEG-vinylsulfone, and PEG-iodoacetamide. In addition to the type of thiol specific conjugation chemistry, commercially available thiol-reactive PEGs also vary in terms of size, linear or branched, and different end groups including hydroxyl, carboxylic acid, methoxy, or other alkoxy groups.

The term "carboxyl-reactive PEGylation" refers to the reaction of a protein or protein substituent with an optionally substituted PEG moiety capable of reacting with a carboxyl group, such as a glutamate or aspartate side chain or the C-terminus of a protein. The carboxyl groups of a protein can be subjected to carboxyl-reactive PEGylation using PEG-hydrazide when the carboxyl groups are activated by coupling agents such as N-(3-dimethylaminopropyl)-N'-ethyl-carbodiimide hydrochloride (EDC) at acidic pH.

The term "amine-reactive PEGylation" refers to the reaction of a protein or protein substituent with an optionally substituted PEG moiety capable of reacting with an amine, such as a primary amine or a secondary amine. A common route for amine-reactive PEGylation of proteins is to use a PEG containing a functional group that reacts with lysines and/or an N-terminal amino or imino group (Roberts et al. Adv. Drug Deliv. Rev. 54(4):459-476 (2002)). Examples of amine-reactive PEGs include PEG dichlorotriazine, PEG tresylate, PEG succinimidyl carbonate, PEG benzotriazole carbonate, PEG p-nitrophenyl carbonate, PEG carbonylimidazole, PEG succinimidyl succinate, PEG propionaldehyde, PEG acetaldehyde, and PEG N-hydroxysuccinimide.

The term "N-terminal PEGylation" refers to attachment of an optionally substituted PEG moiety to the amino terminus of a protein. Preferred protein fusions or protein hybrids for N-terminal PEGylation have at least one N-terminal amino group. N-terminal PEGylation can be carried out by reaction of an amine-reactive PEG with a protein, or by reaction of a thioester-terminated PEG with an N-terminal cysteine in the reaction known as native chemical ligation, or by reaction of a hydrazide, hydrazine or hydroxylamine terminated PEG with an N terminal aldehyde formed by periodate oxidation of an N-terminal serine or threonine residue. Preferably, a PEG-protein conjugate contains 1-5 PEG substituents, and may be optimized experimentally. Multiple attachments may occur if the protein is exposed to PEGylation reagents in excess. Reaction conditions, including protein:PEG ratio, pH, and incubation time and temperature may be adjusted to limit the number and/or sites of the attachments. Modification at active site(s) within a fusion protein may be prevented by conducting PEGylation in the presence of a substrate, reversible inhibitor, or a binding protein. A fusion protein with the desired number of PEG substitutions may also be obtained by isolation from a more complex PEGylated fusion protein mixture using column chromatography fractionation.

The term "unnatural amino acid-reactive PEGylation" refers to the reaction of a protein or protein substituent with an optionally substituted PEG moiety capable of reacting with unnatural amino acids bearing reactive functional groups that may be introduced into a protein at certain sites utilizing modified tRNAs. In particular, para-azidophenylalanine and azidohomoalanine may be specifically incorporated into proteins by expression in yeast (Deiters et al. Bioorg. Med. Chem. Lett. 14(23):5743-5 (2004)) and in E. coli (Kiicki et al. Proc. Natl. Acad. Sci. USA. 99(1):19-24 (2002)), respectively. These azide modified residues can selectively react with an alkyne derivatized PEG reagent to allow site specific PEGylation.

The term "glycan-reactive PEGylation" refers to the reaction of a protein or protein substituent with an optionally substituted PEG moiety capable of reacting with a glycosylated protein and the proteins containing N-terminus serine or threonine may be PEGylated followed by selective oxidation. Carbohydrate side chains may be oxidized enzymatically, or chemically using sodium periodate to generate reactive aldehyde groups. N-terminus serine or threonine may similarly undergo periodate oxidation to afford a glyoxylyl derivative. Both aldehyde and glyoxylyl groups can selectively react with PEG-hydrazine or PEG-amine.

The term "enzyme-catalyzed PEGylation" refers to the reaction of a protein or protein substituent with an optionally substituted PEG moiety through one or more enzyme catalyzed reactions. One such approach is to use transglutaminases, a family of proteins that catalyze the formation of a covalent bond between a free amine group and the gamma-carboxamide group of protein- or peptide-bound glutamine. Examples of this family of proteins include transglutaminases of many different origins, including thrombin, factor XIII, and tissue transglutaminase from human and animals. A preferred embodiment comprises the use of a microbial transglutaminase, to catalyze a conjugation reaction between a protein substrate containing a glutamine residue embedded within a peptide sequence of LLQG and a PEGylating reagent containing a primary amino group (Sato Adv. Drug Deliv. Rev. 54(4):487-504 (2002)). Another example is to use a sortase to induce the same conjugation. Accordingly a substituted PEG moiety is provided that is endowed with LPXTG or NPQTN, respectively for sortase A and sortase B, and a second moiety such as a polypeptide containing the dipeptide GG or GK at the N-terminus, or a primary amine group, or the dipeptide GG or GK attached to a linker, and said sortase A or sortase B is then provided to accomplish the joining of the PEG moiety to the second moiety. Alternatively, said LPXTG or NPQTN can be provided at the C-terminus of a polypeptide to be modified and the PEG moiety can be supplied that is substituted with a GG or GK or a primary amine, and the sortase reaction performed.

The term "glycoPEGylation" refers to the reaction of a protein with an optionally substituted PEG moiety through enzymatic GalNAc glycosylation at specific serine and threonine residues in proteins expressed in a prokaryotic host, followed by enzymatic transfer of sialic acid conjugated PEG to the introduced GalNAc (Defrees et al. Glycobiology. 16(9):833-843 (2006)). The term "intein-mediated PEGylation" refers to the reaction of a protein with an optionally substituted PEG moiety through an intein domain that may be attached to the C-terminus of the protein to be PEGylated, and is subsequently treated with a cysteine terminated PEG to afford PEGylated protein. Such intein-mediated protein conjugation reactions are promoted by the addition of thiophenol or triarboxylethylphosphine (Wood, et al., Bioconjug. Chem. 15(2):366-372 (2004)).

The term "reversible PEGylation" refers to the reaction of a protein or protein substituent with an optionally substituted PEG moiety through a linker that can be cleaved or eliminated, liberating the PEG moiety. Preferable forms of reversible PEGylation involve the use of linkers that are susceptible to various activities present at the cell surface or in intracellular compartments, and allow the useful prolongation of plasma half-life and/or reduction of immunogenicity while still permitting the internalized or cell-surface-bound protoxin or protoxin proactivator or proactivator activator to carry out their desired action without inhibition or impediment by the PEG substitution. Examples of reversible PEGylation linkers include linkers susceptible to the action of cathepsins, furin/kexin proteases, and lysosomal hydrolases such as neuraminidases, nucleases and glycol hydrolases.

The term "administering" and "co-administering" as used herein refer to the administration of one or more proteins to an organism in need of treatment. The one or more proteins can be, for example, fusion proteins, and can be administered simultaneously and/or sequentially to an organism in need of treatment. The sequential order, time interval, and relative quantity of the application may be varied to achieve an optimized selective cytotoxic or cytostatic effect. It may be preferable to use one agent in large excess, or to use two agents in similar quantities. One agent may be applied significantly before the addition of the second agent, or they may be applied in closer intervals or at the same time. In addition administering and co-administering may include injection or delivery from more than one site, for example by injection into two different anatomical locations or by delivery by more than one modality, such as by aerosol and intravenous injection, or by intravenous and intramuscular injection.

The term "selective killing" is used herein to refer to the killing, destroying, or inhibiting of more cells of one particular population than another, e.g., by a margin of 99:1 or above, 95:5 or above, 90:10 or above, 85:15 or above, 80:20 or above, 75:25 or above, 70:30 or above, 65:35 or above, or 60:40 or above.

The term "destroying or inhibiting a target cell" is used herein to refer to reducing the rate of cellular division (cytostasis) or causing cell death (cytotoxicity) of a particular cell type (e.g., a cell expressing the desired cell surface targets). Cytostasis or cytotoxicity may be achieved, for example, by the induction of differentiation of the cell, apoptosis of the cell, death by necrosis of the cell, or impairment of the processes of cellular division.

The term "glycosylation" refers to covalent modifications of proteins with carbohydrates. Glycosylation can be achieved through N-glycosylation or O-glycosylation. An introduction of consensus N-linked glycosylation sites may be preferred when the proteins are to be produced in a mammalian cell line or cell lines that create a glycosylation pattern that are innocuous to humans.

Human "granzyme B" (GrB) is a member of the granzyme family of serine proteases known to be involved in apoptosis. Specifically, GrB has been shown to cleave only a limited number of natural substrates, e.g., pro-caspase-3 and Bid. It has been shown that GrB is an enzyme with high substrate sequence specificity because of the requirement for interactions with an extended peptide sequence in the substrate for efficient catalysis, i.e., a consensus recognition sequence of IEPD. GrB is a single chain and single domain serine protease and is synthesized in a pro-form, which is activated by removal of the two amino acid pro-peptide by dipeptidyl peptidase I (DPPI). In the present invention, the term GrB for example refers to the mature form, i.e., the form without the propeptide.

Human "Granzyme M" (GrM) is another member of the granzyme family of serine proteases that is specifically found in granules of natural killer cells and is implicated in the induction of target cell death. It has been shown that GrM is an enzyme with high substrate sequence specificity because of the requirement for interactions with at least four amino acids in the peptide substrate for efficient catalysis, i.e., a preferred recognition sequence of KVPL.

The term "potyviral protease" refers to any of a variety of proteases encoded by members of the plant virus family Potyviridae and exhibiting high cleavage specificity. "Potyviral protease" encompasses the natural proteases as well as engineered variants generated by genetic mutation or chemical modification. The term "tobacco etch virus protease" or "TEV protease" refers to natural or engineered variants of a 27 kDa cysteine protease exhibiting stringent sequence specificity. It is widely used in biotechnology for removal of affinity tags of recombinant proteins. TEV protease recognizes a seven amino acid recognition sequence EXXYXQ↓S/G, where X is any residue.

The term "picornaviral protease" refers to any of a variety of proteases encoded by members of the animal virus family Picornaviridae and exhibiting high cleavage specificity. "picornaviral protease" encompasses the natural proteases as well as engineered variants generated by genetic mutation or chemical or enzymatic modification. The term "human Rhinovirus 3C consensus protease" refers to a synthetic picornaviral protease that is created by choice of a consensus sequence derived from multiple examples of specific rhinoviral proteases.

The term "retroviral protease" refers to any of a variety of proteases encoded by members of the virus family Retroviridae. "HIV protease" encompasses the natural proteases as well as engineered variants generated by genetic mutation or chemical or enzymatic modification.

The term "coronaviral protease" refers to any of a variety of proteases encoded by members of the animal virus family Coronaviridae and exhibiting high cleavage specificity. "coronaviral protease" encompasses the natural proteases as well as engineered variants generated by genetic mutation or chemical or enzymatic modification. The term "SARS protease" refers to a coronaviral protease encoded by any of the members of the family Coronaviridae inducing the human syndrome SARS.

By "substantially identical" is meant a nucleic acid or amino acid sequence that, when optimally aligned, for example using the methods described below, share at least 60%, 65%, 70%, 75%, 80%, 85%, 90%, 95%, 96%, 97%, 98%, 99%, or 100% sequence identity with a second nucleic acid or amino acid sequence, e.g., a SAA sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the full length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By the term "cancer cell" is meant a component of a cell population characterized by inappropriate accumulation in a tissue. This inappropriate accumulation may be the result of a genetic or epigenetic variation that occurs in one or more cells of the cell population. This genetic or epigenetic variation causes the cells of the cell population to grow faster, die slower, or differentiate slower than the surrounding, normal tissue. The term "cancer cell" as used herein also encompasses cells that support the growth or survival of a malignant cell. Such supporting cells may include fibroblasts, vascular or lymphatic endothelial cells, inflammatory cells or co-expanded normeoplastic cells that favor the growth or survival of the malignant cell. The term "cancer cell" is meant to include cancers of hematopoietic, epithelial, endothelial, or solid tissue origin. The term "cancer cell" is also meant to include cancer stem cells. The cancer cells targeted by the fusion proteins of the invention include those set forth in Table 1.

DESCRIPTION OF THE FIGURES

FIG. 1A is sequence alignment of PEA (SEQ ID NO:8) and VCE (SEQ ID NO:9) by BLAST. The PEA sequence is numbered from the mature N-terminus and the VCE is numbered from the N-terminus of the putative pre-protein.

FIG. 1B is an analysis of overall sequence identity and similarity between PEA and VCE as well as the sequence identity and similarity of individual domains of PEA and VCE.

FIG. 1C is the sequence of the putative furin cleavage site in VCE in comparison with the furin cleavage sites of PEA and DT. Residues that are known or hypothesized to be important for efficient in vitro furin cleavage are highlighted in gray.

FIGS. 2B-2D are immunoblots showing the result of affinity capture of biotin-ADP-ribosylated proteins followed by immunoblotting with anti-eEF2 antibody (FIG. 2B) or with anti-GrB2 antibody (FIG. 2C). The first two lanes of FIG. 2B show the presence of eEF2 in the lysate and the second two lanes demonstrate that eEF2 is selectively recovered by avidin beads following reaction of the lysate with VCE in the presence of biotin-NAD. FIGS. 2C and 2D demonstrate that an antibody against an unrelated protein (Grb2) detects Grb2 in lysates (first two lanes) but no Grb2 is detected among the products released from avidin beads (last two lanes). This helps rule out the possibility that lysate proteins in general bind to avidin beads.

FIG. 3A is an immunoblot showing that 293T, CHO-K1 and Re1.22C express similar amount of eEF2 as detected by an eEF2-specific antibody.

Figure 3:
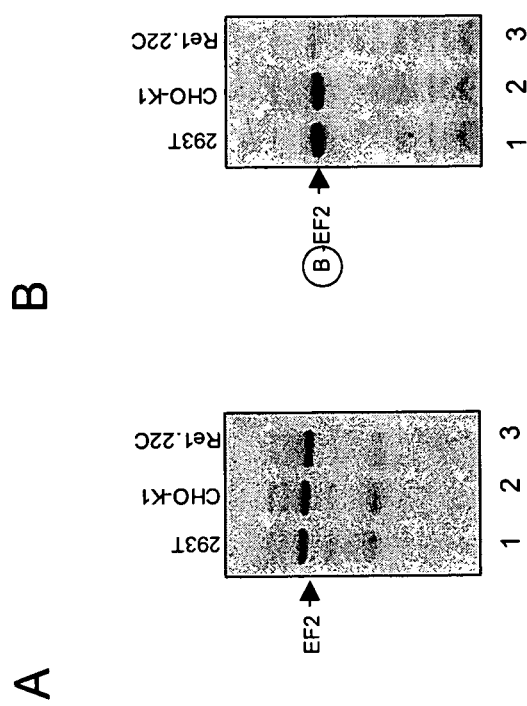

FIG. 3B is an immunoblot showing that eEF2 from Re1.22C is resistant to the ADP-ribosylation activity of VCE, whereas eEF2 from 293T and CHO-K1 can be modified by VCE-ADPRT.

Figure 4:
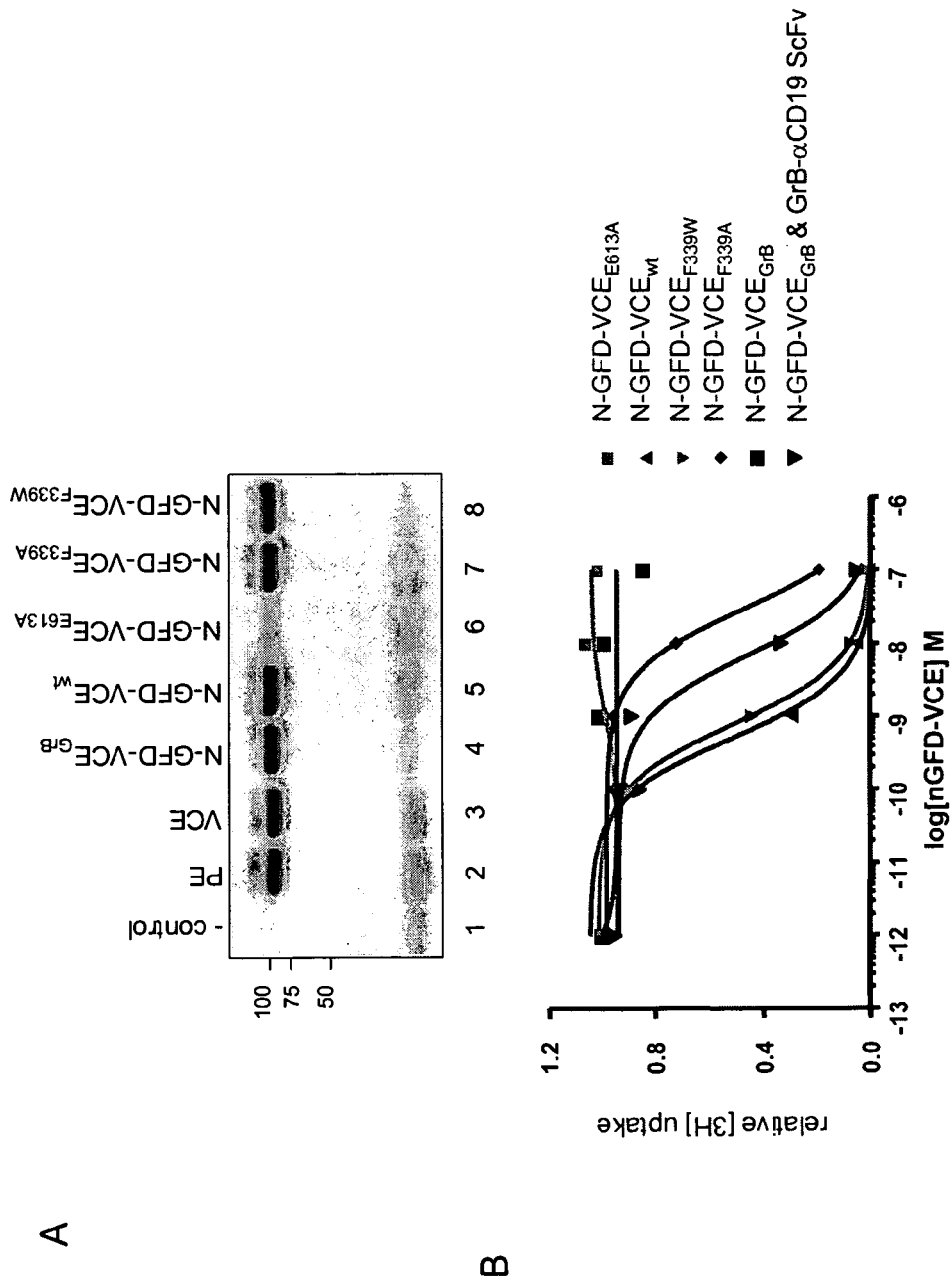

FIG. 4A is an immunoblot showing ADRPT activity of various N-GFD-VCE fusion proteins in comparison to PEA.

FIG. 4B is a graph showing cytotoxicity assay results using CD19+ Jurkat cells.

FIG. 5A is schematic depiction of two VCE-based immunotoxins, CCPE-VCE and CCPE$^2$-VCE. In these immunotoxins, the cell targeting domain of the wild type VCE was replaced with one or two copies of C-terminal domain of *Clostridium perfringens* enterotoxin (CCPE) which has been shown to target cell surface proteins claudin3 and claudin4.

FIGS. 5B and 5C are graphs showing the cytotoxicity assay results of CCPE-VCE on claudin3/4 positive cell lines, including HT29, MCF7, and MB231 and a claudin3/4 negative control cell line Nalm6. Nonlinear regression analysis was performed using the GraphPad Prism 4 program. The EC50 was calculated based on the calculated curves. CCPE$^2$-VCE exhibited 5-10 folds higher toxicity to claudin3/4 positive cells than did CCPE-VCE, while both immunotoxins exhibited similar toxicity to the negative cell line.

FIG. 6A is sequence alignment of the granzyme B cleavage site used in DT-anti-CD5, anti-CD5-PEA and anti-CD5-VCE. The arrow indicates the cleavage site.

FIG. 6B is an electrophoretic gel showing purified DT-anti-CD5, anti-CD5-PEA and anti-CD5-VCE.

FIG. 6C is an electrophoretic gel showing mouse granzyme B cleavage of purified DT-anti-CD5, anti-CD5-PEA and anti-CD5-VCE under different conditions.

Figure 6:
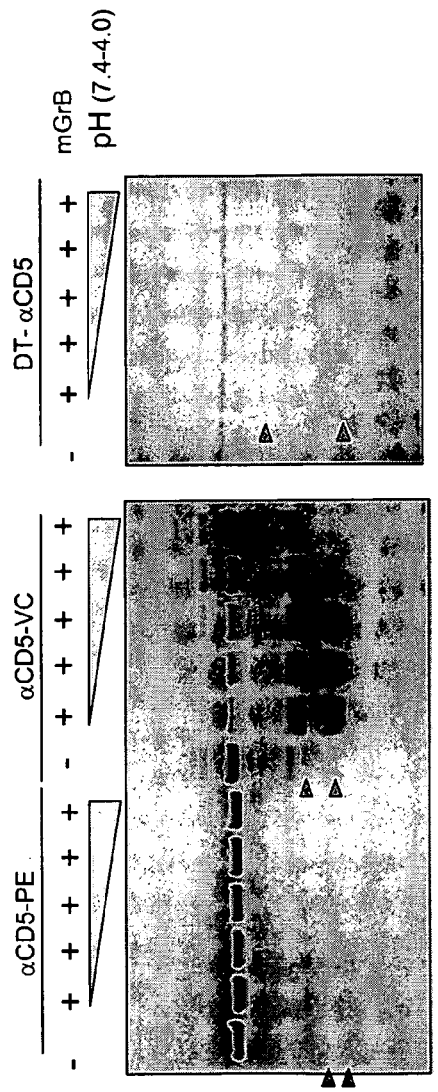
Figure 7:
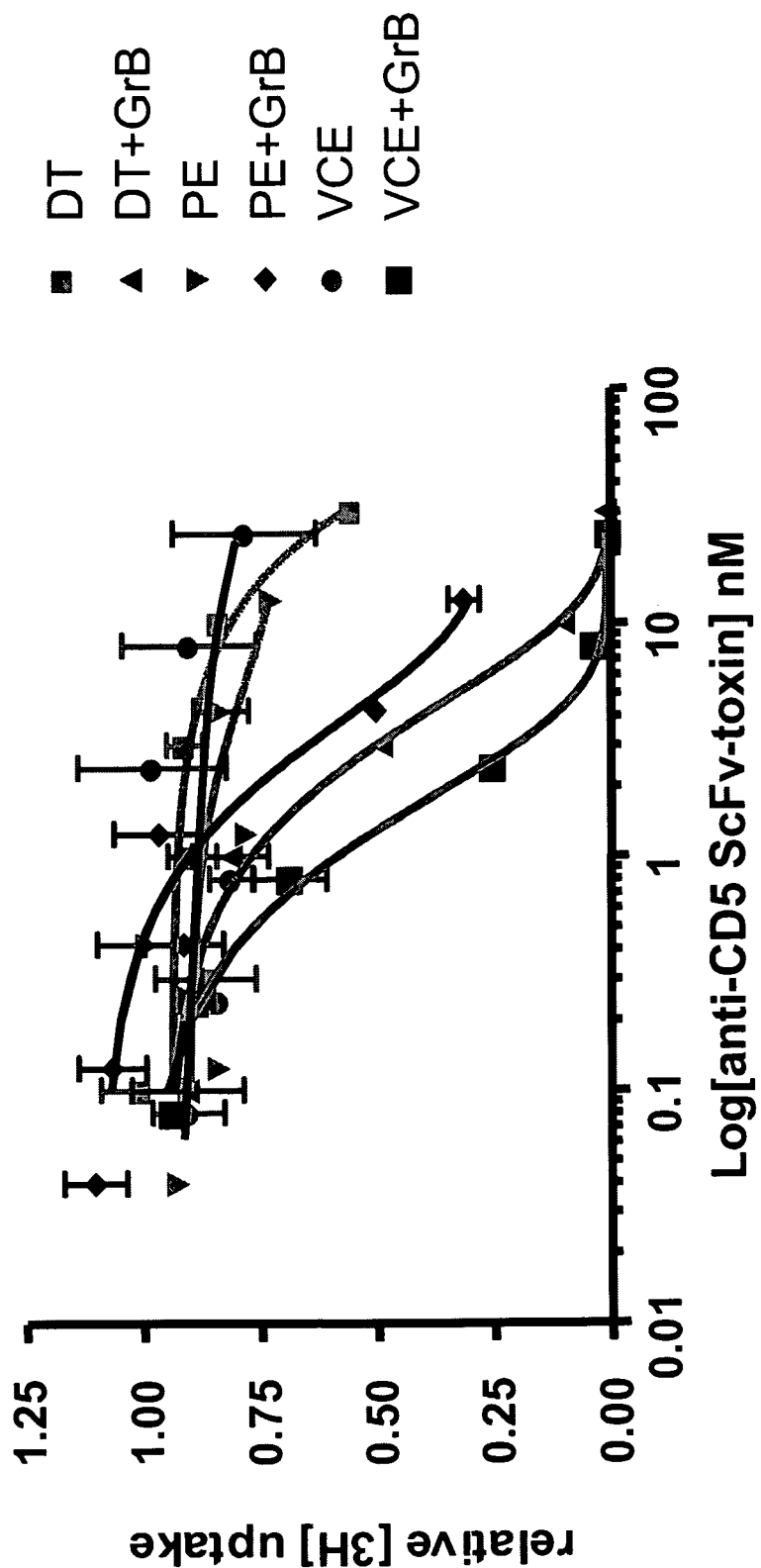

FIG. 7 is a graph showing cytotoxicity assay results of DT-, PEA-, VCE-based combinatorial targeting agents shown in FIG. 6. The cytotoxicity assay was carried out in the absence or presence of 1.0 nM GrB-anti-CD19. Nonlinear regression analysis was performed using the GraphPad Prism 4 program.

Figure 8:
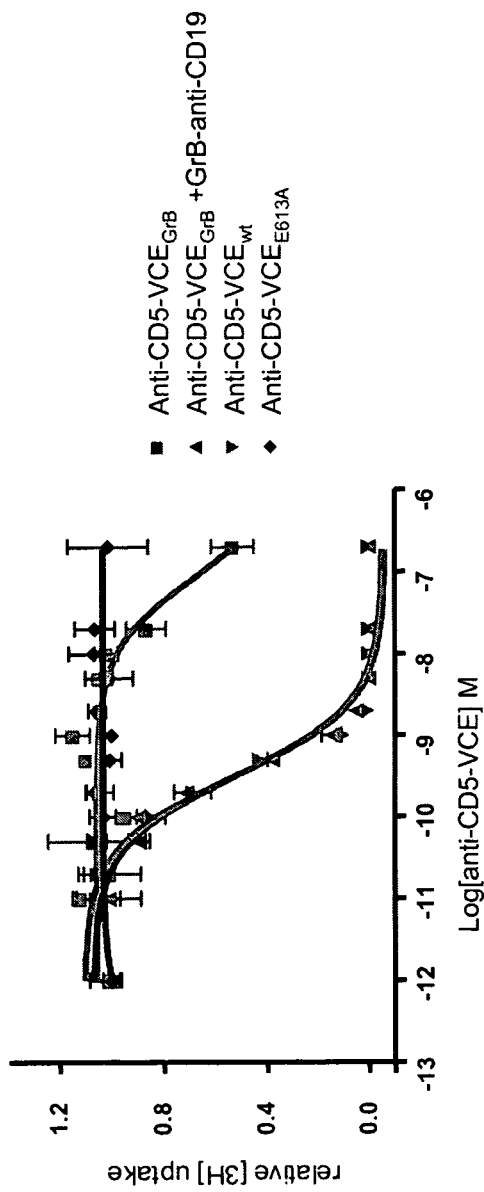

FIG. 8 is a graph showing cytotoxicity assay results of VCE-based combinatorial targeting agents using CD5+Raji cells. The assays were performed with 1.0 nM GrB-anti-CD19 and various concentrations of anti-CD5-VCE. For comparison, we also measured cytotoxicity of anti-CD5-VCE bearing the endogenous furin cleavage sequence (anti-CD5-VCE$_{wt}$) and a mutant anti-CD5-VCE in which one the predicted active site residues glutamic acid 613 was replaced with alanine (anti-CD5-VCE$_{E613A}$). Nonlinear regression analysis was performed as described above.

Figure 9:
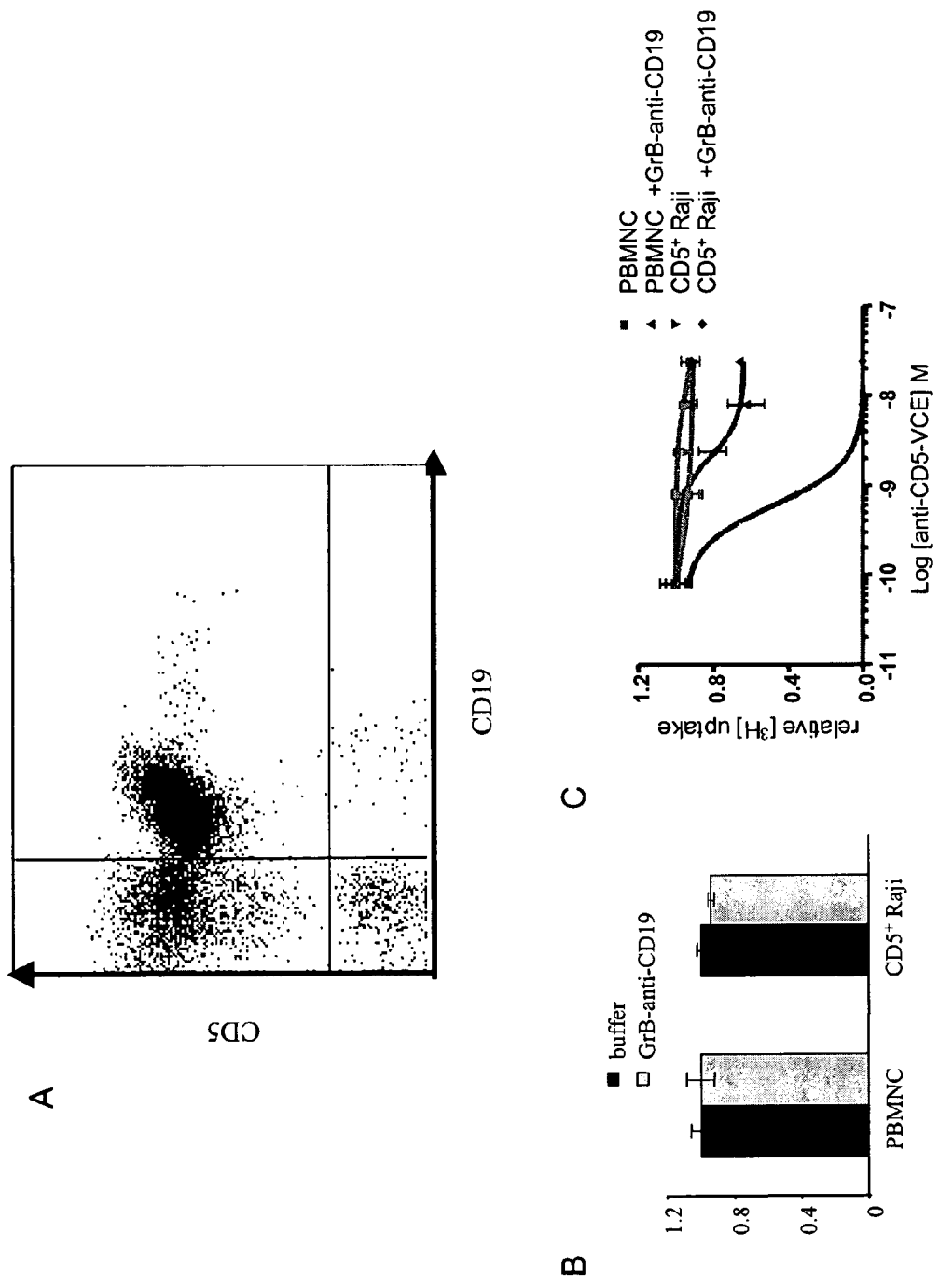

FIG. 9A is a graph showing FACS analysis of purified PBMNC from a B-CLL patient with anti-CD5 and anti-CD19 antibodies.

FIG. 9B is a graph showing 1.0 nM GrB-anti-CD19 alone was not toxic to either PBMNC or CD5+Raji.

FIG. 9C is a graph showing that anti-CD5-VCE selectively kill CD5+Raji cells and a fraction of PBMNC only in the presence of GrB-anti-CD19.

Figure 10:
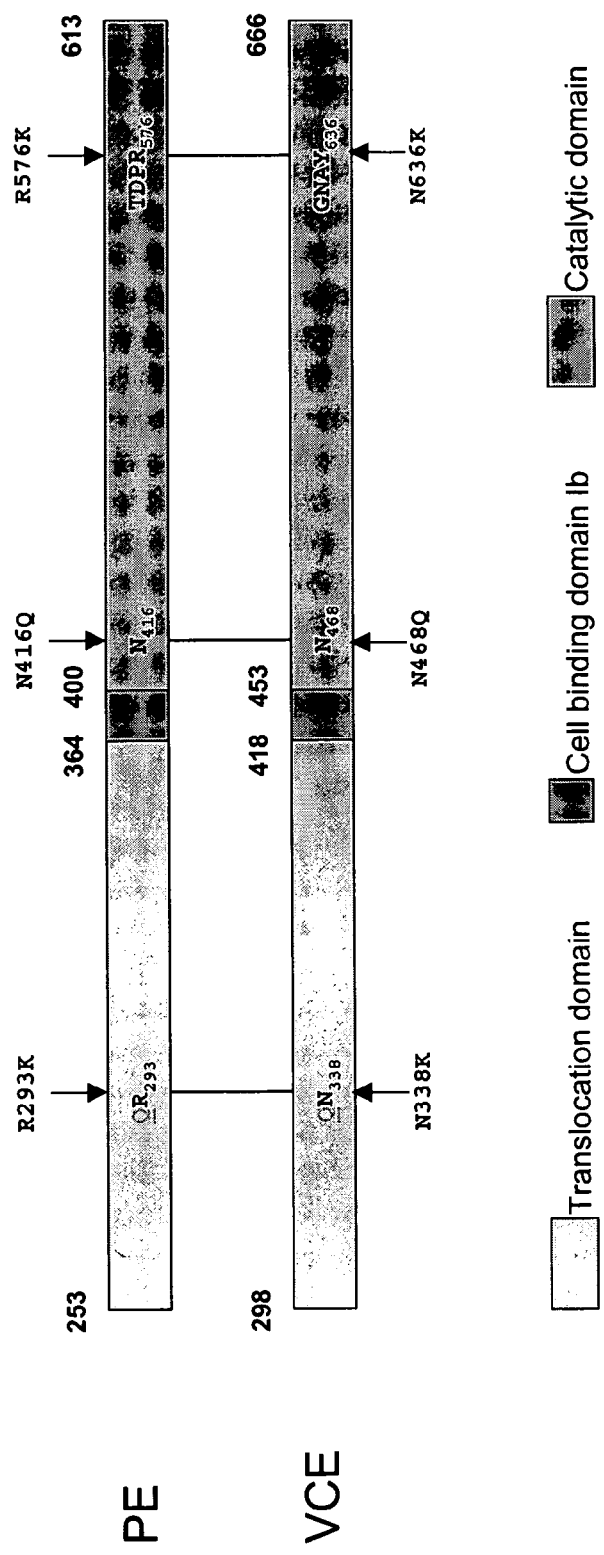

FIG. 10 is a diagram showing mutations that to reduce the likelihood of vascular leak syndrome induced by recombinant VCE-based toxins.

Figure 11:
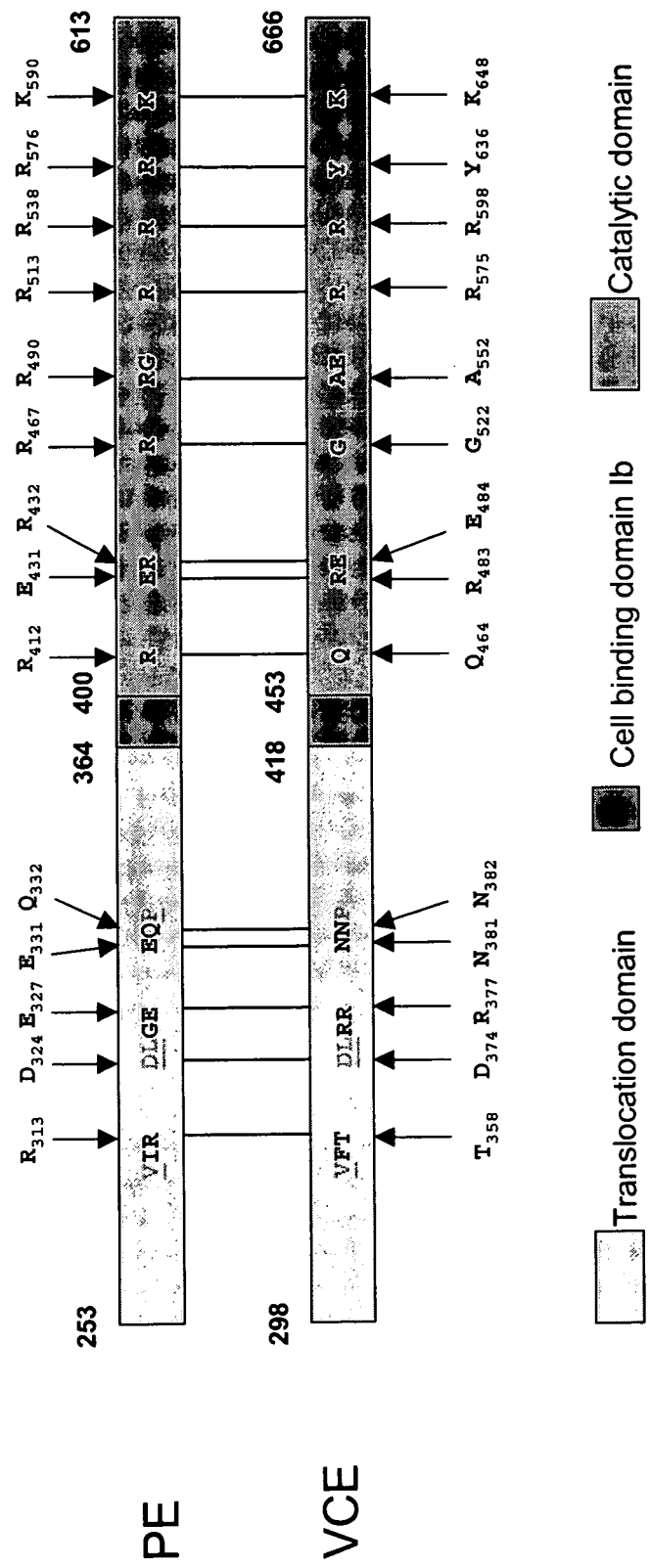

FIG. 11 is a diagram showing mutations to reduce the immunogenicity of recombinant VCE-based toxins.

Figure 12:
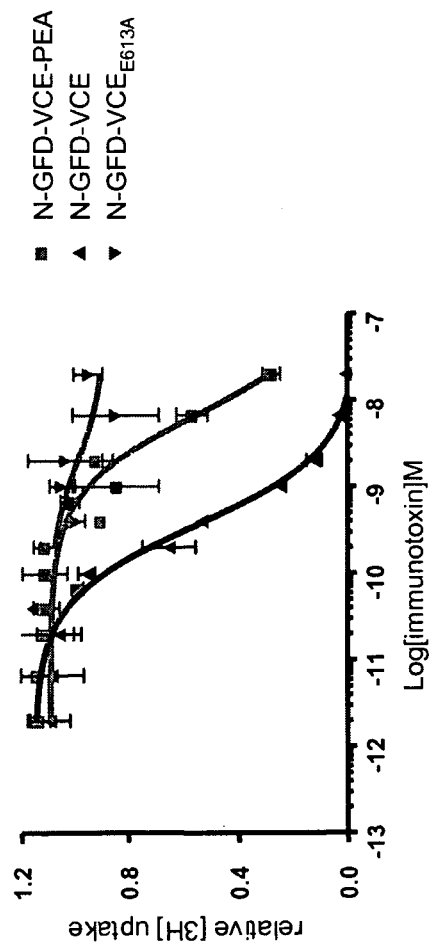

FIG. 12 is a graph showing cytotoxicity assay results of N-GFD-VCE, N-GFD-VCE$_{E613A}$ and N-GFD-VE-PEA fusion proteins using CD19+ Jurkat cells.

Figure 13:
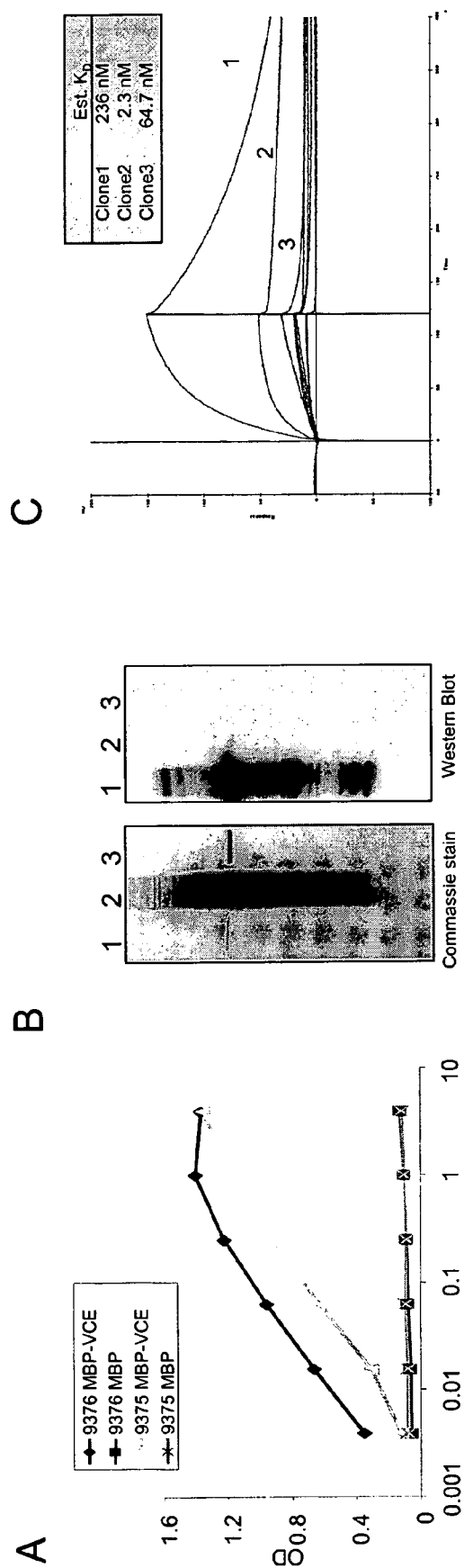

FIG. 13A is a graph showing ELISA results of anti-VCE polyclonal antibodies raised from 2 rabbits (9375 and 9376). Anti-VCE polyclonal antibodies from both animals react specifically to the fusion protein consisting of the ADPRT domain of VCE antigen (MBP-VCE), but not to a control protein (MBP, maltose binding protein).

FIG. 13B is a commassie staining and immunoblot showing showing that anti-VCE polyclonal antibodies can be used for Western blot to detect denatured VCE. The left panel shows a commassie stained SDS-PAGE of the fusion protein containing specific antigen (lane 1, anti-CD19-VCE), cell lysate (lane2, 293T cell lysate) and a negative control protein (anti-CD5-Diphtheria toxin). Left panel shows the western blot results of the same set of proteins probed with anti-VCE polyclonal antibody from rabbit 9375, and visualized with HRP conjugated anti-rabbit Fc antibody.

FIG. 13C is a graph showing the results of affinity measurement of several anti-VCE monoclonal antibodies by surface plasma resonance. Affinity ($K_D$) of three represented clones was shown.

DETAILED DESCRIPTION OF THE INVENTION

Recombinant exotoxins from *Vibrio cholerae* are useful for the therapeutic treatment of a variety of human diseases, particularly diseases characterized by an abundance or excess of undesired cells. *Vibrio* exotoxins have superior biophysical properties, including robust folding and enhanced solubility when expressed at high levels in *E. coli* compared to similar toxins known in the art. *Vibrio* exotoxin fusion proteins comprising exogenous cell-targeting moieties bind to selected surface targets of cells of interest and induce intoxication. In addition, such fusion proteins in which the native activation sequence has been replaced with a modifiable activation moiety can be acted upon by a second proactivator or activator that can be made to be or is naturally specific to the cell that is to be targeted for intoxication. When *Vibrio* exotoxin activation sequences are replaced with those of exogenous proteases, the resulting engineered toxins are more easily activated by site-specific proteolysis than comparable toxins based on *Pseudomonas* exotoxin A or Diphtheria toxin. *Vibrio* exotoxin proteins are more potent as combinatorial toxins than either *Pseudomonas* or Diphtheria toxins.

The present invention provides a recombinant *Vibrio cholerae* Exotoxin (VCE), which has ~32% sequence identity with *Pseudomonas* exotoxin A (PEA), and demonstrates similar domain organization, furin activation, ADP-ribosyltransferase (ADPRT) activity to EF-2, and related cytotoxicity. The present invention also provides mutant VCE fusion proteins that comprise the native ADP-ribosyltransferase activity, a modified cell binding domain that binds to one or more specific cell surface proteins, as well as a modified translocation domain cleavable by selected proteolytic activities.

In particular, the present invention provides modified VCE fusion proteins with an altered proteolytic activation site so that they are activated not by furin, but instead by another protease of choice. One preferred embodiment includes modified VCE fusion proteins activatable by endogenous proteases that are present or upregulated in targeted cells. Another preferred embodiment of the present invention includes modified VCE fusion proteins that are activated by exogenous proteases fusion proteins that are bound to a cell surface marker on a targeted cell.

One aspect of the present invention is that the cell surface targeting moiety of VCE may be replaced with alternative binding principles of different specificities to target specific cell surface target of the targeted cells. Another aspect of the present invention is that the translocation domain of VCE may be modified such that they are activated by enzymatic activities other than furin, including those of different proteases.

An additional aspect of the present invention is the native or modified translocation domain of VCE, which has only 31% sequence identity (35/112) to that of PEA. The translocation domain of VCE may be used to facilitate translocation other cell killing principles into targeted cells in conjunction with an ER retention sequence such as KDEL (SEQ ID NO:10). Such cytotoxic agents include, without limitation, small toxic molecules, oligonucleotides such as RNAi agents, and catalytic domains of protein toxins such as ADP-ribosyltransferase domain of PEA and N-glycosidase domain of ricin A.

The ADPRT domain of VCE is another embodiment of this invention. Only 86 out of 199 residues (43%) of this domain are identical to that of PEA. This catalytic domain may be used in combination with a translocation domain of different origin, such as that of PEA, as well as a different binding principle that binds to a specific cell surface marker of a targeted cell.

Antibodies generated against VCE or modified VCE of mouse, rat, goat, or other origin are also embodiments of this invention. Other biological or chemical probes specific for VCE are additional embodiments of the present invention.

I. Recombinant VCE

VCE is a recombinant product of toxA gene of *V. cholerae* TP strain. VCE was analyzed by X-ray crystallography and the resulting structural data confirmed that it is a member of the diphthamide-specific class of ADP-ribose transferases (Jorgensen et al. J. Biol. Chem. 283 (16):10671-10678 (2008)). VCE possesses an N-terminal cell-targeting moiety (residues Met1-Lys297 and residues Ala419-Asn457), followed by a translocation domain (Gly298 to Ala418) and a C-terminal ADP-ribosyltransferase domain (Arg458 to Lys666) comprising an ER retention signal $^{662}$KDEL$^{665}$ (SEQ ID NO:10). A putative furin cleavage site (RKPR↓DL) (SEQ ID NO:48) is located near the N-terminus of the putative translocation domain.

In comparison, the native cell binding domain of *Pseudomonas* Exotoxin A (PEA) is composed of Domain Ia (residues Ala1 to Glu252) and Domain Ib (residues Ala365-Gly404) (U.S. Pat. No. 4,892,827). Deletion of domain Ia from PEA have been found to reduce non-specific cytotoxicity (U.S. Pat. No. 4,892,827), and replacing it with another cell binding moiety such as a single chain antibody afforded modified PEA fusion proteins that are capable of effectively and selectively killing cells bearing appropriate antigens or receptors (U.S. Pat. No. 5,863,745).

Furin has been identified as the intracellular protease responsible for cleaving modified PEA at $^{276}$RQPR↓GW$^{279}$ (SEQ ID NO:12) and activating translocation, and this furin-mediated cleavage occurs preferentially under acidic conditions (Chiron et al. J. Biol. Chem. 272(50):31701-31711 (1997)). Deletion of residues 1-28 of translocation domain comprising the furin cleavage site, i.e., residues Gly253 to Gly280, from native PEA substantially increased its toxicity (U.S. Pat. No. 5,602,095). It has also been disclosed that changing the furin cleavage site to a sequence recognized by a different protease, i.e., prostate specific antigen (PSA), enabling preferential inhibition of protein synthesis in PSA-expressing LNCap cells as compared to the DU145 cells that do not express PSA (U.S. Pat. No. 6,426,075). A similar approach was applied to diphtheria toxin (DT), where its furin cleavage site was replaced by a urokinase plasminogen activator (uPA) cleavage site, resulting in selective killing of acute myeloid leukemia (AML) cells that overexpress uPA receptors (Abi-Habib et al. Blood 104 (7):2143-2148 (2004)).

Like the catalytic moieties of diphtheria toxin (DT) and *Pseudomonas* exotoxin A (PEA), the VCE catalytic moiety specifically ADP-ribosylates diphthamide on eEF2. ADP-ribosylation of diphthamide impairs the function of eEF2 and leads to inhibition of protein synthesis which results in profound physiological changes and ultimately cell death. In several regards, VCE resembles PEA more closely than it resembles DT. First, the domain organization of VCE appears similar to that of PEA, in which the cell-targeting domain is followed by the translocation domain and then the enzymatic domain. VCE and PEA both possess a masked ER retention signal at the C-terminus, suggesting that VCE and PEA enter the cytosol of target cells via endoplasmic reticulum. Both VCE and PEA have low lysine content, thought to be consistent with the mechanism of introduction of toxin into the cytoplasm through the endoplasmic reticulum associated degradation (ERAD) pathway. The present data support the view that the proteolytic event that activates PEA and VCE occurs in an acidic endosomal compartment, whereas furin cleavage of DT might take place in more neutral environment.

The C-terminus of VCE bears a characteristic endoplasmic reticulum retention signal (KDEL) (SEQ ID NO:10) followed by a lysine residue at the very C-terminus of the VCE which is removed by a ubiquitous carboxyl-peptidase activity such as carboxypeptidase B. VCE enters the cytosol of target cell in a manner similar to PEA and the C-terminal sequence of VCE is essential for full cytotoxicity. Thus, for maximum cytotoxic properties of a preferred VCE molecule, an appropriate carboxyl terminal sequence is preferred to translocate the molecule into the cytosol of target cells. Such preferred amino acid sequences include, without limitation, KDELK, RDELK, KDELR and RDELR (SEQ ID NOs:13-16).

The invention features compositions and methods including recombinant DNA constructs and expression of the modified VCE fusion proteins they encode. For example, modified VCE fusion comprising different cell binding specificity and altered protease recognition site can be produced from nucleic acid constructs encoding amino acid residues 1-666 of VCE, in which the native furin cleavage site (RKPR↓DL) (SEQ ID NO:48) is replaced by a recognition sequence of an exogenous protease such as GrB, GrM, and TEV protease, and the cell binding domain (residues 1-295) is replaced by a polypeptide that can bind to a specific cell surface target. Methods to introduce mutations into the nucleic acid sequence encoding VCE or to synthesize nucleic acid sequences that encode the mutant VCE are well known in the art (e.g., *Current Protocols in Molecular Biology* (Ausubel et al., eds., 2005)). The nucleic acid constructs can be generated using PCR. For example, the construct encoding the VCE fusion protein can be produced by mutagenic PCR, where primers encoding an alternative protease recognition site can be used to substitute the DNA sequence coding the furin cleavage site (residues 321-326: RKPR↓DL) (SEQ ID NO:48). Constructs containing the mutations can also be made through sequence assembly of oligonucleotides. Either approach can be used to introduce nucleic acid sequences encoding the granzyme B cleavage site IEPD↓DL (SEQ ID NO:17)in place of that which encodes (RKPR↓DL) (SEQ ID NO:48). In addition to IEPD (SEQ ID NO:18), GrB has been shown to recognize and cleave other similar peptide sequences with high efficiency, including IAPD and IETD (SEQ ID NOs:19 and 20). These and other sequences specifically cleavable by GrB may be incorporated. Genetically modified proteases of higher than natural specificity or displaying a different specificity than the naturally occurring protease may be of use in avoiding undesirable side effects attributable to the normal action of the protease.

DNA sequences encoding a cell-targeting polypeptide can be similarly cloned using PCR, and the full-length construct encoding the VCE fusion protein can be assembled by restriction digest of PCR products and the VCE construct followed by ligation. The construct may be designed to position a nucleic acid sequence encoding the modified VCE near the translation start site and the DNA sequence encoding the cell-targeting moiety close to the translation termination site. Such a sequence arrangement uses native VCE to confer optimal translocation efficiency of the catalytic domain of VCE to the cytosol.

VCE fusion proteins may be expressed in bacterial, insect, yeast, or mammalian cells, using established methods known to those skilled in the art, many of which are described, for example, in *Current Protocols in Protein Science* (Coligan et al., eds., 2006). DNA constructs intended for expression in each of these hosts may be modified to accommodate preferable codons for each host (Gustafsson et al., Trends Biotechnol. 22:346 (2004)), which may be achieved using established methods, for example, as described in *Current Protocols in Molecular Biology* (Ausubel et al., eds., 2005), e.g., site-directed mutagenesis. To quickly identify an appropriate host system for the production of a particular VCE fusion, the Gateway cloning method (Invitrogen) may also be applied for shuffling a gene to be cloned among different expression vectors by in vitro site-specific recombination.

In addition to codon changes, other sequence modifications to the construct of a VCE fusion protein may include naturally occurring variations of VCE sequences that do not significantly affect its cytotoxicity and variants of the cell-targeting domain that do not abolish its ability to selectively bind to targeted cells.

Further, the sequence of the cell-targeting domain can be modified to select for variants with improved characteristics, e.g., reduced immunogenicity, higher binding affinity and/or specificity, superior pharmacokinetic profile, or improved production of the VCE fusion protein. Libraries of cell-targeting domains and/or VCE fusions can be generated using site-directed mutagenesis, error-prone PCR, or PCR using degenerate oligonucleotide primers. Sequence modifications may be necessary to remove or add consensus glycosylation sites, for maintaining desirable protein function or introducing sites of glycosylation to reduce immunogenicity.

For high yield expression of VCE fusion proteins, the encoding polynucleotide may be subcloned into one of many commercially available expression vectors, which typically contain a selectable marker, a controllable transcriptional promoter, and a transcription/translation terminator. In addition, signal peptides are often used to direct the localization of the expressed proteins, while other peptide sequences such as 6 His tags, FLAG tags, and myc tags may be introduced to facilitate detection, isolation, and purification of fusion proteins. To help successful folding of each domain within the VCE fusion, a flexible linker may be inserted between the modified VCE domain and the cell-targeting moiety in the expression construct.

VCE fusion proteins may be expressed in the bacterial expression system *Escherichia coli*. In this system a ribosome-binding site is used to enhance translation initiation. To increase the likelihood of obtaining soluble protein fusion, its expression construct may include DNA that encodes a carrier protein such as MBP, GST, or thioredoxin, either 5' or 3' to the VCE fusion, to assist protein folding. The carrier protein(s) may be proteolytically removed after expression. Proteolytic cleavage sites are routinely incorporated to remove protein or peptide tags and generate active fusion proteins. Most reports on successful *E. coli* expression of fusion proteins containing a VCE moiety have been in the form of inclusion bodies, which may be refolded to afford soluble proteins.

VCE fusion proteins may be expressed in the methylotrophic yeast expression system *Pichia pastoris*. The expression vectors for this purpose may contain several common features, including a promoter from the *Pichia* alcohol oxidase (AOX1) gene, transcription termination sequences derived from the native *Pichia* AOX1 gene, a selectable marker wild-type gene for histidinol dehydrogenase HIS4, and the 3'AOX1 sequence derived from a region of the native gene that lies 3' to the transcription termination sequences, which is required for integration of vector sequence by gene replacement or gene insertion 3' to the chromosomal AOX1 gene. Although *P. pastoris* has been used successfully to express a wide range of heterologous proteins as either intracellular or secreted proteins, secretion is more commonly used because *Pichia* secretes very low levels of native proteins. A secretion signal peptide MAT factor prepro peptide (MF-α1) is often used to direct the expressed protein to the secretory pathway.

Post-translational modifications such as N-linked glycosylation in *Pichia* occurs by adding approximately 8-14 mannose residues per side chain. Any consensus N-glycosylation sites NXS(T) within an expression construct can be mutated to avoid glycosylation.

VCE is potently toxic to eukaryotic cells if the catalytic domain translocates to or is localized to the cytosol. *Pichia* can support VCE expression because the expression of a toxic DT fusion by the secretory route has been successful (Woo et al., Protein Expr. Purif. 25:270 (2002)). Because the secretion of expressed heterologous protein in *Pichia* involves cleavage of signal peptide MF-α1 by Kex2, a furin-like protease, a DT or VCE fusion protein with its furin cleavage site replaced should be less toxic to *Pichia* than the corresponding wild type fusion proteins. Alternatively, VCE fusion proteins can be expressed in a mutant strain of *Pichia*, whose chromosomal EF-2 locus has been mutated to resist GDP ribosylation by catalytic domain of VCE (Liu et al., Protein Expr. Purif. 30:262 (2003)).

VCE fusion proteins may also be expressed in mammalian cells. Mutant cell lines that confer resistance to ADP-ribosylation have been described (Kohno and Uchida, J. Biol. Chem. 262:12298 (1987); Liu et al., Protein Expr. Purif. 19:304 (2000); Shulga-Morskoy and Rich, Protein Eng. Des. Sel. 18:25 (2005)) and can be used to express soluble VCE fusion proteins. For example, the toxin-resistant cell line CHO-K1 RE1.22c has been selected and used to express a DT-ScFv fusion protein (Liu et al., Protein Expr. Purif. 19:304 (2000)) and a mutant 293T cell line has been selected and used to express a DT-IL7 fusion protein (Shulga-Morskoy and Rich, Protein Eng. Des. Sel. 18:25 (2005)). It has been determined that a G-to-A transition in the first position of codon 717 of the EF-2 gene results in substitution of arginine for glycine and prevents post-translational modification of diphthamide at histidine 715 of EF-2, which is the target amino acid for ADP-ribosylation by DT. EF-2 produced by the mutant gene is fully functional in protein synthesis (Foley et al., Somat. Cell Mol. Genet. 18:227 (1992)). Based on this information and established methods such as described in *Current Protocols in Molecular Biology* (Ausubel et al., eds., 2005), different mammalian cells may be transfected with vectors containing G717A mutant of EF-2 gene and select for cells that are resistant to VCE.

Stable expression in mammalian cells also requires the transfer of the foreign DNA encoding the fusion protein and transcription signals into the chromosomal DNA of the host cell. A variety of vectors are commercially available, which typically contain phenotypic markers for selection in *E. coli* (Ap$^r$) and CHO cells (DHFR), a replication origin for *E. coli*, a polyadenylation sequence from SV40, a eukaryotic origin of replication such as SV40, and promoter and enhancer sequences. Based on methods described in *Current Protocols in Protein Science* (Coligan et al., eds., 2006), and starting with the VCE-resistant cell lines, vectors containing DNA encoding VCE fusion proteins may be used to transfect host cells, which may be screened for high producers of the fusion proteins.

Because VCE is of bacterial origin, potential N-glycosylation sites within its sequence can be mutated in order to retain the cytotoxicity potential of native VCE. Further, glycosylation within cell-targeting domain can be avoided, maintaining its desirable binding characteristics. However, consensus N-glycosylation sites may be introduced to linkers or terminal sequences so that such glycosylation do not hamper the functions of VCE and cell-targeting moiety.

Various modifications have been described in the art that improved toxicity of PEA. These modifications are also useful for improving the toxicity of VCE immunotoxins.

Mere et al. J. Biol. Chem. 280: 21194-21201 (2005) teach that exposure to low endosomal pH during internalization of PEA triggers membrane insertion of its translocation domain, a process that is a prerequisite for PEA translocation to the cytosol where it inactivates protein synthesis. Membrane insertion is promoted by exposure of a key tryptophan residue (Trp 305). At neutral pH, this residue is buried in a hydrophobic pocket closed by the smallest α-helix (helix F) of the translocation domain. Upon acidification, protonation of the Asp that is the N-cap residue of the helix leads to its destabilization, enabling Trp side chain insertion into the endo some membrane. A mutant PEA in which the first two N-terminal amino acids (Asp 358 and Glu 359) of helix F replaced with non-acidic amino acids, showed destabilization of helix F, leading to exposure of tryptophan 305 to the outside of the molecule in the absence of an acidic environment and resulting in 7-fold higher toxicity than wild type PEA. Similarly, the mutant PEA in which entire helix F is removed was shown to exhibit 3-fold higher toxicity than wild type PEA. Although by sequence alignment, we did not find a helix corresponding to the helix F of PEA, we found that, similar to the proteolytic cleavage of PEA, cleavage of VCE by furin is favored in mildly acidic conditions, suggesting that a similar acid triggered conformational change might take place during membrane insertion of VCE. Mutations that facilitate membrane insertion of VCE, and thereby enhance cytotoxicity, might be found through means such as random mutagenesis.

Thus, preferable forms of VCE molecules for the present invention include those that exhibit more efficient membrane insertion, leading to higher toxicity.

One of the important factors determining the toxicity of the PEA-based or VCE-based immunotoxins depends on whether the immunotoxins are internalized by the target cell upon receptor binding. The internalization is considered the rate-limiting step in immunotoxin-mediated cytotoxicity (Li and Ramakrishnan. *J. Biol. Chem.* 269: 2652-2659 (1994)). He et al. fused Arg$_9$-peptide, a well known membrane translocational signal, to an anti-CEA (carcinoembryonic antigen) immunotoxin, PE35/CEA(Fv)/KDEL, at the position between the toxin moiety and the binding moiety. Strong binding and internalization of this fusion protein was observed in all detected cell lines, but little cytotoxicity to the cells that lack the CEA molecules on the cell surface was detected. However, the cytotoxicity beside the binding activity of the fusion protein to specific tumor cells expressing large amount of CEA molecules on the cell surface was improved markedly, indicating that the Arg$_9$-peptide is capable of facilitating the receptor-mediated endocytosis of this immunotoxin, which leads to the increase of the specific cytotoxicity of this immunotoxin (He et al. *International Journal of Biochemistry and Cell Biology*, 37:192-205 (2005)). Accordingly, one preferred embodiment of protoxins that depend on translocation to the endoplasmic reticulum for intoxication includes the operable linkage of Arg9-peptide or related membrane translocation signals, such as, without limitation, those derived from HIV-Tat, Antennapedia, or Herpes simplex VP22, to such protoxins. A further preferred embodiment of the present invention includes modified PEA or VCE protoxins operably linked to Arg9-peptide or related membrane translocation signals, such as, without limitation, those derived from HIV-Tat, Antennapedia, or Herpes simplex VP22.

Toxicities that are independent of ligand binding have been observed with most targeted toxins. These include either hepatocyte injury causing abnormal liver function tests or vascular endothelial damage with resultant vascular leak syndrome (VLS). Both the hepatic lesion and the vascular lesion may relate to nonspecific uptake of targeted toxins by normal human tissues. U.S. Patent Application Publication No. 2006/0159708 A1 and U.S. Pat. No. 6,566,500 describes methods and compositions relating to modified variants of diphtheria toxin and immunotoxins in general that reduce binding to vascular endothelium or vascular endothelial cells, and therefore, reduce the incidence of Vascular Leak Syndrome (VLS). In one example, variant of DT, V7AV29A, in which two of (X)D(Y) motifs are mutated is shown to maintain full cytotoxicity, but to exhibit reduced binding activity to human vascular endothelial cells (HUVECs), wherein the (X)D(Y) sequence is GDL, GDS, GDV, IDL, IDS, IDV, LDL, LDS, and LDV. U.S. Pat. No. 5,705,156 teaches the use of modified PEA molecules in which 4 amino acids (57, 246, 247, 249) in domain I are mutated to glutamine or glycine to reduce non-specific toxicity of PEA to animals. Hence one embodiment of the present invention includes modified VCE protoxins bearing sequence changes that favorably reduce toxicity to normal tissues.

The plasma half-lives of several therapeutic proteins have been improved using a variety of techniques such as those described by Collen et al., Bollod 71:216-219 (1998); Hotchkiss et al., Thromb. Haemostas. 60:255-261 (1988); Browne wt al., J. Biol. Chem. 263:1599-1602 (1988); Abuchowski et al., Cancer Biochem. Biophys. 7:175 (1984)). Antibodies have been chemically conjugated to toxins to generate immunotoxins which have increased half-lives in serum as compared with unconjugated toxins and the increased half-life is attributed to the native antibody. WO94/04689 teaches the use of modified immunotoxins in which the immunotoxin is linked to the IgG constant region domain having the property of increasing the half-life of the protein in mammalian serum. The IgG constant region domain is CH2 or a fragment thereof. Similar strategy can be applied to creating variants of VCE immunotoxin with increased serum half-life. In addition operable linkage to albumin, polyethylene glycol, or related nonimmunogenic polymers may promote the plasma persistence of therapeutic toxins.

Upon repeated treatment of immunotoxins, patients may develop antibodies that neutralize, hence lessen the effectiveness of immunotoxins. To circumvent the problem of high titer antibodies to a given immunotoxin, U.S. Pat. No. 6,099,842 teaches the uses of a combination of immunotoxins bearing the same targeting principle, but differs in their cytotoxic moieties. In one example, anti-Tac(Fv)-PE40 and DT(1-388)-anti-Tac(Fv) immunotoxins are used in combination to reduced the possibility of inducing human anti-toxin antibodies. In principle, a similar strategy can be applied to the present invention wherein VCE fusions can be alternated with one or more other protoxins based on PEA and/or DT.

II. Translocation Domain and Catalytic Domain of VCE

Extensive X-ray crystallographic and biochemical analyses have shown that ADP-ribosylating toxins such as PEA and VCE consist of well-defined domains including a cell binding domain, translocation domain, and ADP-ribosyl transferase domain (Wedekind et al. J. Mol. Biol. 314:823-837 (2001), Jorgensen et al. J. Biol. Chem. 283 (16):10671-10678 (2008), and references cited therein). It has been established that the cell-binding domain of these toxins may be deleted from the native toxin sequences and replaced with other cell targeting moieties such as antibodies, cytokines, and small molecules (Pastan et al. Annu. Rev. Med. 58:221-37 (2007) & Hilgenbrink and Low, J Pharm Sci. 94(10):2135-46 (2005)). The resulting immunotoxins have clinical utility in the treatment of oncologic diseases as first demonstrated by the successful development of diphtheria toxin-interleukin-2 conjugate (Ontak®) for the treatment of cutaneous T cell lymphoma (Foss, Clin. Lymphoma 1(2):110-6 (2000)).

Additionally, it has been disclosed that an ADPRT may be substituted by catalytic domains of other AB toxins. For example, it has been disclosed that a hybrid toxin may be generated by combining the catalytic ADP-ribosyltransferase domain of PEA (Gly405 to Lys613) with a ricin A chain, and appending it with C-terminus ER retention signal KDEL. This hybrid toxin showed similar cytoxicity to PEA. (Pitcher et al. Bioconj. Chem. 6:624-629 (1995)). The present invention provides the ADP-ribosyl transferase sequence of VCE as a catalytic, cytotoxic principle that may be used for applications in targeted cell killing in the context of the translocation domains of other toxins.

U.S. Pat. No. 6,086,900 disclosed the application of PEA lacking its intrinsic ADP-ribosyltransferase activity is useful for facilitating the transportation of a therapeutic agent that is attached to a non-terminal chemical binding site across a membrane into cytoplasm. Detoxification of PEA was achieved by deleting the glutamate residue in the active site of the catalytic domain at position 553. A cysteine residue was inserted into the deactivated catalytic domain to serve as a conjugation site for the molecule to be transported, a peptide nucleic acid (PNA). In another previously discussed example, the translocation domain of PEA (Gly253 to Asn364), along with a C-terminus ER retention signal KDEL(SEQ ID NO:10), enabled the observed cytoxicity of a recombinant hybrid toxin that utilizes ricin A chain as a cytotoxic agent (Pitcher et al. Bioconj. Chem. 6:624-629 (1995)). It has been shown that the translocation domain of PEA can support the introduction of barnase, the extracellular ribonuclease of *Bacillus amyloliquefaciens*, into the cytosol of mammalian cells (Prior et al. Biochemistry 31(14):3555-9 (1992)). Furthermore, the translocation domain of DT has been successfully utilized to transport Bad, a proapoptotic member of the Bcl-2 family, into human glioma cells and induce apoptosis (Ichinose et al. Cancer Res. 62(5):1433-8 (2002)).

The present invention provides the translocation domain sequence of VCE, which in combination with ER retention signal such as KDEL may be used to facilitate the transportation of various biological probes or therapeutic agents into the cytosol.

III. Disease Indications and Targeted Cell Surface Markers

The VCE protoxins disclosed in the present invention are useful for targeting and killing specific subsets of cells while sparing closely related cells, thereby providing a more specific and effective treatment for cancer. The targeting specificity of VCE protoxins can be conferred by progressively more selective cell targeting strategies: (i) replacing the native cell binding domain (residues 1-295) with a cell binding moiety that is operably linked and specifically targets a selected cell surface marker; (ii) replacing the native furin cleavage site (residues 321-326: RKPK↓DL) with a sequence recognized by a different protease that is overexpressed in the targeted cell; and (iii) combinatorial use of the modified VCE protoxin comprising both the selective cell surface binding moiety and an alternative proteolytic cleavage site with a protease fusion protein that is directed to the same cell by an operably linked cell surface binding moiety and that can specifically activate the protoxin.

The utility of the modified VCE protoxins lies in the selective elimination of subsets of cells to achieve a desired therapeutic effect. In particular the selectivity is provided by one or more cell-binding moieties, which can target cell surface targets on the targeted cancer cells, or on targeted noncancer cells that are preferably eliminated to achieve a therapeutic benefit.

A. Cell Surface Targets

Depending on the targeting strategy, modified VCE protoxins may be used alone, or in combination with protease fusion proteins. In any case, one or more of cell-targeting moieties can target a cell surface target typical of a specific type of cells, for example by recognizing lineage-specific markers found on subsets of cells and representing their natural origin, such as markers of the various organs of the body or specific cell types within such organs, or cells of the hematopoietic, nervous, or vascular systems. Alternatively one or more cell-targeting moieties can target cell surface markers aberrantly expressed on a diseased tissue, such as a cancer cell or a cell eliciting or effecting an autoimmune activity (e.g., B cells, T cells, dendritic cells, NK cells, neutrophils, leukocytes, macrophages, platelets, macrophages, myeloid cells, and granulocytes). One or more agents can target a cell surface marker that is aberrantly overexpressed by a cancer cell.

In particular, modified VCE protoxins, used alone or in combination with a protease fusion protein as heterologous activator, is used to destruct neoplastic or undesired cells selectively without severe damage to normal or desired cells, thereby providing treatments for cancers including leukemias and lymphomas, such as chronic B cell leukemia, mantle cell lymphoma, acute myelogenous leukemia, chronic myelogenous leukemia, acute lymphocytic leukemia, chronic lymphocytic leukemia, multiple myeloma, acute lymphoblastic leukemia, adult T-cell leukemia, Hodgkin's lymphoma, and non-Hodgkin's lymphoma; as well as solid tumors, including melanoma, colon cancer, breast cancer, prostate cancer, ovarian cancer, lung cancer, pancreatic cancer, kidney cancer, stomach cancer, liver cancer, bladder cancer, thyroid cancer, brain cancer, bone cancer, testicular cancer, uterus cancer, soft tissue tumors, nervous system tumors, and head and neck cancer.

Modified VCE protoxins can also be used to target non-cancerous cells, including autoreactive B or T cells, providing treatment for chronic inflammatory diseases including multiple sclerosis, rheumatoid arthritis, systemic lupus erythematosus, Sjogren's syndrome, scleroderma, primary biliary cirrhosis, Graves' disease, Hashimoto's thyroiditis, type 1 diabetes, pernicious anemia, myasthenia gravis, Reiter's syndrome, immune thrombocytopenia, celiac disease, inflammatory bowel disease, and asthma and atopic disorders.

In addition the modified VCE protoxins can be used to ablate cells in the nervous system that are responsible for pathological or undesired activity, for example nociceptive neurons in the peripheral nervous system, or to treat sensory phantom sensation, or to control neuropathic pain, such as the pain caused by diabetic neuropathy or viral reactivation.

The modified VCE protoxins can also target cells infected by viral, microbial, or parasitic pathogens that are difficult to eradicate, providing treatment for acquired syndromes such as HIV, HBV, HCV or papilloma virus infections, tuberculosis, malaria, dengue, Chagas' disease, trypanosomiasis, leishmaniasis, or Lyme disease.

Furthermore, they can target specific cell types including, without limitation, parenchymal cells of the major organs of the body, as well as adipocytes, endothelial cells, cells of the nervous system, pneumocytes, B cells or T cells of specific lineage, dendritic cells, NK cells, neutrophils, leukocytes, macrophages, platelets, macrophages, myeloid cells, granulocytes, adipocyte, and any other specific tissue cells.

The recombinant VCE fusion proteins and related protoxins can further target cells which produce disease through benign proliferation, such as prostate cells in benign prostatic hypertrophy, or in various syndromes leading to hyperproliferation of normal tissues or the expansion of undesired cellular compartments as for example of adipocytes in obesity.

It will be well recognized by those skilled in the art that there are many cell surface targets that may be used for targeting the modified VCE protoxins, and where applicable, its companion protease fusion protein to tumor tissues. For example, breast cancer cells may be targeted using overexpressed surface antigens such as claudin-3 (Soini, Hum. Pathol. 35:1531 (2004)), claudin-4 (Soini, Hum. Pathol. 35:1531 (2004)), MUC1 (Taylor-Papadimitriou et al., J. Mammary Gland Biol. Neoplasia 7:209 (2002)), EpCAM (Went et al., Hum. Pathol. 35:122 (2004)), CD24 (Kristiansen et al., J. Mol. Histol. 35:255 (2004)), and EphA2 (Ireton and Chen, Curr. Cancer Drug Targets 5:149 (2005); Zelinski et al., Cancer Res. 61:2301 (2001)), as well as HER2 (Stern, Exp. Cell Res. 284:89 (2003)), EGFR (Stern, Cell Res. 284:89 (2003)), CEA, and uPAR (Han et al., Oncol. Rep. 14:105 (2005)). Colorectal cancer may be targeted using upregulated surface antigens such as A33 (Sakamoto et al., Cancer Chemother. Pharmacol. 46:S27 (2000)), EpCAM (Went et al., Hum. Pathol. 35:122 (2004)), EphA2 (Ireton and Chen, Curr. Cancer Drug Targets 5:149 (2005); Kataoka et al., Cancer Sci. 95:136 (2004)), CEA (Hammarstrom, Semin. Cancer Biol. 9:67 (1999)), CSAp, EGFR (Wong, Clin. Ther. 27:684 (2005)), and EphB2 (Jubb et al., Clin. Cancer Res. 11:5181 (2005)). Non-small cell lung cancer may be targeted using EphA2 (Kinch et al., Clin. Cancer Res. 9:613 (2003)), CD24 (Kristiansen et al., Br. J. Cancer 88:231 (2003)), EpCAM (Went et al., Hum. Pathol. 35:122 (2004)), HER2 (Hirsch et al., Br. J. Cancer 86:1449 (2002)), and EGFR (Dacic et al., Am. J. Clin. Pathol. 125:860 (2006)). Mesothelin has been targeted by a PEA based immunotoxin for the treatment of NSCLC (Ho et al., Clin. Cancer Res. 13(5):1571 (2007)). Ovarian cancer may be targeted using upregulated claudin-3 (Morin, Cancer Res. 65:9603 (2005)), claudin-4 (ibid.), EpCAM (Went et al., Hum. Pathol. 35:122 (2004)), CD24 (Kristiansen et al., J. Mol. Histol. 35:255 (2004)), MUC1 (Feng et al., Jpn. J. Clin. Oncol. 32:525 (2002)), EphA2 (Ireton and Chen, Curr. Cancer Drug Targets 5:149 (2005)), B7-H4 (Simon et al., Cancer Res. 66:1570 (2006)), and mesothelin (Hassan et al., Appl. Immunohistochem Mol. Morphol. 13:243 (2005)), as well as CXCR4 (Jiang et al., Gynecol. Oncol. 20:20 (2006)) and MUC16/CA125. Pancreatic cancer may be targeted using overexpressed mesothelin (Rodriguez et al., World J. Surg. 29:297 (2005)), PSCA (Rodriguez et al., World J. Surg. 29:297 (2005)), CD24 (Kristiansen et al., J. Mol. Histol. 35:255 (2004)), HER2 (Garcea et al., Eur. J. Cancer 41:2213 (2005)), and EGFR (Garcea et al., Eur. J. Cancer 41:2213 (2005)). Prostate cancer may be targeted using PSMA (Kinoshita et al., World J. Surg. 30:628 (2006)), PSCA (Han et al., J. Urol. 171:1117 (2004)), STEAP (Hubert et al., Proc. Natl. Acad. Sci. USA 96:14523 (1999)), and EphA2 (Ireton and Chen, Curr. Cancer Drug Targets 5:149 (2005)). EpCAM is also upregulated in prostate cancer and has been targeted for the antibody-based treatment (Oberneder et al., Eu. J. Cancer 42:2530 (2006)). The expression of activated leukocyte cell adhesion molecule (ALCAM, as known as CD 166) is a prognostic and diagnostic marker for prostate cancer (Kristiansen et al., J. Pathol. 205:359 (2005)), colorectal cancer (Weichert et al., J. Clin. Pathol. 57:1160 (2004)), and melanoma (van Kempen et al. Am. J. Pathol. 156(3):769 (2000)). All cancers that have been treated with chemotherapy and developed multidrug resistance (MDR) can be targeted using the transmembrane transporter proteins involved, including P-glycoprotein (P-gp), the multidrug resistance associated protein (MRP1), the lung resistance protein (LRP), and the breast cancer resistance protein (BCRP) (Tan et al., Curr. Opin. Oncol. 12:450 (2000)).

Significant advances have been made during the past decade in the identification of unique cell surface marker profiles of cancer stem cells from various cancers, distinguishing them from the bulk of corresponding tumor cells. For example, in acute myeloid leukemia (AML) it has been observed that the CD133+/CD38− AML cells, which constitute a small fraction of CD34+/CD38− AML cells, are responsible for initiating human AML in animal models (Yin et al., Blood 12:5002 (1997)). In addition, CD133 has been recently determined as a cancer stem cell surface marker for several solid tumors as well, including brain tumor (Singh et al., Nature 432:395 (2004) and Bao et al., Nature 444:756 (2006)), colon cancer (O'Brien et al., Nature 445:106 (2007) and Ricci-Vitiani et al, Nature 445:111 (2007)), prostate cancer (Rizzo et al., Cell Prolif. 38:363 (2005)), and heptocellular carcinoma (Suetsugu et al., Biochem. Biophys. Res. Commun. 351:820 (2006) and Yin et al., Int. J. Cancer 120:1444 (2007)). In the case of colon cancer, the CD133+ tumorgenic cells were found to bind antibody Ber-EP4 (Ricci-Vitiani et al, Nature 445:111 (2007)), which recognizes the epithelial cell adhesion molecules (EpCAM), also known as ESA and CD326. More recently, it was reported that CD44+ may more accurately define the CSC population of colorectal cancer than CD133+ does, and the CSCs for colorectal cancer have been identified as EpCAM$^{high}$/CD44+/CD166+ (Dalerba et al., Proc. Natl. Acad. Sci. USA 104(24):10158 (2007)). Based on this information, EpCAM/CD133, EpCAM/CD44, EpCAM/CD166, and CD44/CD166 are possible combinations for combinatorial targeting of colon cancer CSCs. In addition to CD133, prostate cancer stem cells have been separately identified to be CD44+ (Gu et al. Cancer Res. 67:4807 (2007)), thus they may be targetable by using the CD44/CD133 pair of surface markers. Furthermore, CXCR4 was detected in the CD44+/CD133+ putative prostate CSCs, suggesting that the combination of CXCR4 with either CD44 or CD133 may provide useful pairs of targets for combinatorial targeting strategy. In other CSCs where the only currently known surface antigen is CD133, additional surface antigens may be identified through comprehensive antibody screening and then used to complement CD133 in a combinatorial targeting scheme. Likewise, tumorigenic cells for breast cancer have been identified as CD44+/CD24− subpopulation of breast cancer cells. Further analysis revealed that the CD44+/CD24−/EpCAM+ fraction has even higher tumorigenicity (Al-Hajj et al., Proc. Natl. Acad. Sci. USA 100:3983 (2003)).

A combinatorial targeting approach using CD44+ and EpCAM+ as targeted surface markers could specifically kill these CSCs while leaving normal CD44+ leukocytes/erythrocytes and normal EpCAM+ epithelial cells unharmed. Another recent study has shown that pancreatic CSCs are CD44+/CD24+/EpCAM+ (Li et al., Cancer Res. 67:1030 (2007)). Consequently, the pancreatic CSCs may be targeted using a combination of CD44/CD24, CD44/EpCAM, or CD24/EpCAM.

B cell chronic lymphocytic leukemia (B-CLL) is characterized by slowly accumulating CD5$^+$ B cells (Guipaud et al., Lancet Oncol. 4:505 (2003)). CD5 is a cell surface protein found on normal T cells and a small fraction of B cells, known as B1 cells. Immunotoxins that target CD5 have shown high efficacy in killing T cells (Better et al., J. Biol. Chem. 270: 14951 (1995)). The combinatorial targeting strategy described in this invention makes it possible to use CD5 in combination with a B cell marker such as CD19, CD20, CD21, or CD22, thereby distinguishing B-CLL cells or other B cells in the B1 subset from T cells. The B1 subset is thought to give rise to low affinity polyreactive antibodies that are frequently found in the setting of autoimmune disorders, hence ablation of this population without significantly impairing the remainder of B cells could favorably impact the course of autoimmune disease without comprising the immune response of an individual to the same extent that ablation of all B cells would induce.

Examples of surface antigens that can be useful targets for the protease fusion and toxin fusion proteins of the invention are set forth in Table 1 of PCT Application Publication No. 2008/011157, which is herein incorporated by reference in its entirety. For combinatorial targeting each antigen may be targeted in combination with one or more other antigens. Examples for combinatorial use of two surface antigens for binary targeting are also shown.

B. Cell Targeting Moieties

The invention provides recombinant VCE fusion proteins and related protoxins containing a cell-targeting moiety. Such cell targeting moieties of the invention include proteins derived from antibodies, antibody mimetics, ligands specific for certain receptors expressed on a target cell surface, carbohydrates, and peptides that specifically bind cell surface molecules.

One embodiment of the cell-targeting moiety is a protein that can specifically recognize a target on the cell surface. The most common form of target recognition by proteins is antibodies. One embodiment employs intact antibodies in all isotypes, such as IgG, IgD, IgM, IgA, and IgE. Alternatively, the cell-targeting moiety can be a fragment or reengineered version of a full length antibody such as Fabs, Fab', Fab2, or scFv fragments (Huston, et al. 1991. Methods Enzymol. 203: 46-88, Huston, et al. 1988. Proc Natl Acad Sci USA. 85:5879-83). In one embodiment the binding antibody is of human, murine, goat, rat, rabbit, or camel antibody origin. In another embodiment the binding antibody is a humanized version of animal antibodies in which the CDR regions have grafted onto a human antibody framework (Queen and Harold. 1996. U.S. Pat. No. 5,530,101). Human antibodies to human epitopes can be isolated from transgenic mice bearing human antibodies as well as from phage display libraries based on human antibodies (Kellermann and Green. 2002. Curr Opin Biotechnol. 13:593-7, Mendez, et al. 1997. Nat. Genet. 15:146-56, Knappik, et al. 2000. J Mol. Biol. 296:57-86). The binding moiety may also be molecules from the immune system that are structurally related to antibodies such as reengineered T-cell receptors, single chain T-cell receptors, CTLA-4, monomeric Vh or Vl domains (nanobodies), and camelized antibodies (Berry and Davies. 1992. J. Chromatogr. 597:239-45, Martin, et al. 1997. Protein Eng. 10:607-14, Tanha, et al. 2001. J Biol. Chem. 276:24774-80, Nuttall, et al. 1999. Proteins. 36:217-27). A further embodiment may contain diabodies which are genetic fusions of two single chain variable fragments that have specificity for two distinct epitopes on the same cell. As an example, a diabody with an anti-CD19 and anti-CD22 scFv can be fused to protoxins in order to increase the affinity to B-cell targets (Kipriyanov. 2003. Methods Mol. Biol. 207:323-33).

In another embodiment the cell-targeting moiety can also be diversified proteins that act as antibody mimetics. Diversified proteins have portions of their native sequence replaced by sequences that can bind to heterologous targets. Diversified proteins may be superior to antibodies in terms of stability, production, and size. One example is fibronectin type III domain, which has been used previously to isolate affinity reagents to various targets (Lipovsek and Pluckthun. 2004. J Immunol Methods. 290:51-67, Lipovsek, et al. 2007. J Mol. Biol. 368:1024-41, Lipovsek, Wagner, and Kuimelis. 2004. U.S. Patent 20050038229). Lipocalins have been used for molecular diversification and selection (Skerra et al. 2005. U.S. Patent 20060058510). Lipocalins are a class of proteins that bind to steroids and metabolites in the serum. Functional binders to CTLA4 and VEGF have been isolated using phage display techniques (Vogt and Skerra. 2004. Chembiochem. 5:191-9). C-type lectin domains, A-domains and ankyrin repeats provide frameworks that can be oligomerized in order to increase the binding surface of the scaffold (Mosavi, et al. 2004. Protein Sci. 13:1435-48). Other diversified proteins include and are not limited to human serum albumin, green fluorescent protein, PDZ domains, Kunitz domains, charybdotoxin, plant homeodomain, and β-lactamase. A comprehensive review of protein scaffolds is described in (Hosse, et al. 2006. Protein Sci. 15:14-27, Lipovsek. 2005.). Those skilled in the art understand that many diverse proteins or protein domains have the potential to be diversified and may be developed and used as affinity reagents, and these may serve as cell-binding moieties in protoxins.

In another embodiment, the cell-targeting moiety can be a naturally occurring ligand, adhesion molecule, or receptor for an epitope expressed on the cell surface. Compositions of the ligand may be a peptide, lectin, hormone, fatty acid, nucleic acid, or steroid. For example, human growth hormone could be used as a cell-targeting moiety for cells expressing human growth hormone receptor. Solubilized receptor ligands may also be used in cases in which the natural ligand is an integral membrane protein. Such solubilized integral membrane proteins are well-known in the art and are easily prepared by the formation of a functional fragment of a membrane protein by removing the transmembrane or membrane anchoring domains to afford a soluble active ligand; for example, soluble CD72 may be used as a ligand to localize engineered protoxins to CD5 containing cells. Another example is the binding of urokinase type plasminogen activator (uPA) to its receptor uPAR. It has been shown that the region of u-PA responsible for high affinity binding ($K_d \approx 0.5$ nM) to uPAR is entirely localized within the first 46 amino acids called N-terminal growth factor like domain (N-GFD) (Appella, et al. 1987. J Biol. Chem. 262:4437-40). Avimers refer to multiple receptor binder domains that have been shuffled in order to increase the avidity and specificity to specific targets (Silverman, et al. 2005. Nat. Biotechnol. 23:1556-61). These receptor binding domains and ligands may be genetically fused and produced as a contiguous polypeptide with protoxins or they can be isolated separately and then chemically or enzymatically attached. They may also be non-covalently associated with protoxins.

In a previously reported example, Denileukin difitox is a fusion protein of DT and human interleukin (IL)-2 (Fenton and Perry. 2005 Drugs 65:2405). Denileukin difitox targets any cells that express IL-2 receptor (IL2R), including the intended target CTCL cells. Acute hypersensitivity-type reactions, vascular leak syndrome, and loss of visual acuity have been reported as side effects. Because human normal non-hematopoietic cells of mesenchymal and neuroectodermal origin may express functional IL2R, some cytotoxic effects observed could be due to a direct interaction between IL-2 and non-hematopoietic tissues. In order to overcome this toxicity, the invention features, for example, addition of a T cell marker as a second targeting element, e.g., CD3.

If the moiety is a carbohydrate such as mannose, mannose 6-phosphate, galactose, N-acetylglucosamine, or sialyl-Lewis X, it can target the mannose receptor, mannose 6-phosphate receptor, asialoglycoprotein receptor, N-acetylglucosamine receptor, or E-selectin, respectively. If the moiety comprises a sialyl-Lewis X glycan operably linked to a tyrosine sulfated peptide or a sulfated carbohydrate it can target the P-selectin or L-selectin, respectively.

As another example, the binding partners may be from known interactions between different organisms, as in a pathogen host interaction. The C-terminal domain of the *Clostridium perfringens* enterotoxin (C-CPE) binds with high affinity and specificity to the mammalian claudin3/4 adhesion molecules. Although claudins are components of most cells tight junctions, they are not typically exposed on the apical surface. The C-CPE can be appended to protoxins in order to localize them to cells overexpressing unengaged claudin3/4, a condition of many types of cancers (Takahashi, et al. 2005. J Control Release. 108:56-62, Ebihara, et al. 2006. J Pharmacol Exp Ther. 316:255-60).

An example of a peptide is the use of angiotensin to localize complexes to cells expressing angiotensin receptor. In another embodiment, the binding peptide could be an unnatural peptide selected from a random sequence library. One group has identified a peptide using phage display, termed YSA, which can specifically recognize EphA2 receptors. EphA2 is overexpressed in many breast cancers (Koolpe, et al. 2005. J Biol. Chem. 280:17301-11, Koolpe, et al. 2002. J Biol. Chem. 277:46974-9). In order to increase binding affinity, peptides could be multimerized through sequential repeated fusions or attaching them to a dendrimer which can then be attached to protoxins.

In another embodiment, the cell-targeting moiety can be a nucleic acid that consists of DNA, RNA, PNA or other analogs thereof. Nucleic acid aptamers have been identified to many protein targets and bind with very high affinity through a process of in vitro evolution (Gold. 1991. U.S. Pat. No. 5,475,096, Wilson and Szostak. 1999. Annu Rev Biochem. 68:611-47). RNA aptamers specific for PSMA were shown to specifically localized conjugated gelonin toxin to cells overexpressing PSMA (Chu, et al. 2006. Cancer Res. 66:5989-92). The nucleic acid can be chemically synthesized or biochemically transcribed and then modified to include an attachment group for conjugation to the reengineered toxin. The nucleic acid may be directly conjugated using common crosslinking reagents or enzymatically coupled by processes known in the art. The nucleic acid can also be non-covalently associated with protoxins.

The cell-targeting moiety may be identified using a number of techniques described in the art. Typically natural hormones and peptide ligands can be identified through reported interactions in the reported literature. Additionally, antibody mimics and nucleic acid aptamers can be identified using selection technologies that can isolate rare binding molecules toward epitopes of interest, such as those expressed on cancer cells or other diseased states. These techniques include SELEX, phage display, bacterial display, yeast display, mRNA display, in vivo complementation, yeast two-hybrid system, and ribosome display (Roberts and Szostak. 1997. Proc Natl Acad Sci USA. 94:12297-302, Boder and Wittrup. 1997. Nat. Biotechnol. 15:553-7, Ellington and Szostak. 1990. Nature. 346:818-22, Tuerk and MacDougal-Waugh. 1993. Gene. 137:33-9, Gyuris, et al. 1993. Cell. 75:791-803, Fields and Song. 1989. Nature. 340:245-6, Mattheakis, et al. 1994. Proc Natl Acad Sci USA. 91:9022-6). Antibodies can be generated using the aforementioned techniques or in a traditional fashion through immunizing animals and isolating the resultant antibodies or creating monoclonal antibodies from plasma cells.

The targets of the cell-targeting moieties can be protein receptors, carbohydrates, and lipids on or around the cell surface. Examples of polypeptide modifications known in the art that may advantageously comprise elements of a cell surface target include glycosylation, sulfation, phosphorylation, ADP-ribosylation, and ubiquitination. Examples of carbohydrate modifications that may be distinctive for a specific lineage of cells include sulfation, acetylation, dehydrogenation and dehydration. Examples of lipid modification include glycan substitution and sulfation.

Examples of lipids that may be distinctive for a specific targeted cell include sphingolipids and their derivatives, such as gangliosides, globosides, ceramides and sulfatides, or lipid anchor moieties, such as the glycosyl phosphatidyl inositol-linked protein anchor.

The cell-targeting moiety may indirectly bind to the target cell through another binding intermediary that directly binds to a cell surface epitope, as long as the cell-targeting moiety acts to localize the reengineered toxin to the cell surface. The targets of these binding modules may be resident proteins, receptors, carbohydrates, lipids, cholesterol, and other modifications to the target cell surface. The cell-targeting moiety can be joined to protoxins either through direct translational fusions if the DNA encoding both species is joined. Alternatively, chemical coupling methods and enzymatic crosslinking can also join the two components. The cell-targeting moiety may contain sequences not involved in the structure or binding of the agent, but involved with other processes such as attachment or interaction with protoxins.

IV. Modification of Activation Sequence

VCE protoxins according to the present invention comprise modifications of the naturally occurring activation sequence of the modified VCE permitting activation of the modified VCE in a variety of different cancer types. The modified activation sequence comprises one or more general cleavage site modifications, or a plurality of specific cleavage site modifications, resulting in a single modified VCE that is capable of being activated to kill numerous types of cancer cells.

A. Endogenous Protease Activity Present in Targeted Cells

Modified VCE protoxins with one or more general cleavage site modifications comprise a modification of the naturally occurring activation sequence to provide one or more cleavage sites for a general activating agent, a general activating agent is an enzyme, the presence of which is associated with a variety of different cancer types. For example, the expression of the enzyme can be up-regulated in a cancer cell compared to a normal cell, or the enzyme can be localized to cancer cells as compared to normal cells, or the enzyme may be produced and/or activated by cancer associated tissue or cells. A general activating agent may be, for example, a protease.

In one embodiment, the modified VCE protoxin comprises an activation sequence modified to include two or more general cleavage sites, each of the general cleavage sites can be cleaved by the same general activating agent. Alternatively, each of the general cleavage sites can be cleaved by a different activating agent. When more than one general cleavage site is present, these cleavage sites may either be adjacent to each other, may overlap or may be separated by intervening sequences of varying lengths as is known in the art. In another embodiment, the modified VCE protoxin comprises an activation sequence modified to include one general cleavage site. In still another embodiment, the modified VCE protoxin comprises an activation sequence modified to include two general cleavage sites. In yet another embodiment, the modified VCE protoxin comprises an activation sequence modified to include less than five general cleavage sites.

The one or more general cleavage site modifications to the naturally occurring activation sequence may be achieved as is known in the art. This modification results in functional deletion of the naturally occurring activation sequence, or of one or more naturally occurring cleavage sites in the activation sequence. Functional deletion is achieved by mutation, which can result in, for example, partial or complete deletion, insertion, or other variation made to the naturally occurring activation sequence that renders it inactive. In one embodiment, the native activation sequence of VCE may be functionally deleted by insertion of one or more general cleavage site. In another embodiment, functional deletion of the naturally occurring activation sequence, or of one or more naturally occurring cleavage sites in the activation sequence is achieved via mutations in one or more amino acid residues of the native activation sequence which result in the creation of one or more general cleavage sites, each of which can be cleaved by a general activating agent. In an alternate embodiment, the native activation sequence of VCE is functionally deleted by replacing the naturally occurring activation sequence, or one or more naturally occurring cleavage sites in the activation sequence with one or more general cleavage sites, each of which can be cleaved by a general activating agent. As described above, the modified VCE protoxin according the present invention comprise one or more general cleavage site modifications that provide one or more cleavage sites, each recognized by a general activating agent that is a protease, the presence of which is associated with a variety of different cancer types. In one embodiment of the invention, the general activating agent is a protease that is associated with cancer invasion and metastasis in general.

Examples of such proteases include the matrix metalloproteinase (MMP) family, the caspases, elastase, and the plasminogen activator family, as well as fibroblast activation protein. Members of the MMP family include collagenases, stromelysin, gelatinases, and 5 membrane-type metalloproteases. In particular, MMP-2 (gelatinase A), MMP-9 (gelatinase B), and membrane-type 1 MMP (MT1-MMP) have been reported to be most related to invasion and metastasis in various human cancers. Examples of proteases of the plasminogen activator family include uPA (urokinase-type plasminogen activator) and tPA (tissue-type plasminogen activator).

In another embodiment, the protease is up-regulated and/or secreted by cancer cells.

Examples of these proteases include matrix metalloproteases, some cathepsins, tPA, some caspases, kallikreins, elastase, plasmin, thrombin, and uPAIn a further embodiment, the protease is activated by enzymes expressed by cancer cells. In still another embodiment, the protease is activated by receptors expressed by cancer cells. A non-limiting example of such a protease is uPA (e.g., with a cleavage site of: SGRSAQ), which is activated by the receptor uPAR (urokinase-type plasminogen activator receptor).

In another embodiment, the general activating agent is a protease that is associated with angiogenesis in general (e.g., matrix metalloproteases and caspases).

Modified VCE protoxin with a plurality of specific cleavage site modifications comprise modification of the naturally occurring activation sequence to include two or more different types of specific cleavage sites, each type capable of being cleaved by a specific activating agent. The two or more different types of cleavage sites may further comprise a cleavage site for a general activating agent. A specific activating agent is an enzyme, the presence of which is associated with a specific type of cancer. For example, expression of the enzyme can be up-regulated in a specific type of cancer cell, or the enzyme can be localized to a specific type of cancer cell, or the enzyme may be produced by a cell that is associated with a specific type of cancer. A specific activating agent may be, for example, a protease.

Modifications comprising a plurality of specific cleavage sites may be achieved as is known in the art, and described above. This modification also results in functional deletion of the naturally occurring activation sequence, or of one or more naturally occurring cleavage sites in the activation sequence. In one embodiment, the native activation sequence of the VCE is functionally deleted by insertion of a plurality of specific cleavage sites. In another embodiment, functional deletion of the naturally occurring activation sequence is achieved via mutations in the amino acid sequence of the naturally occurring activation sequence, resulting in the addition of two or more specific cleavage sites, each of which can be cleaved by a specific activating agent. In an alternate embodiment, the native activation sequence of the VCE may be replaced with two or more specific cleavage sites, each of which is capable of being cleaved by a specific activating agent. As is known in the art, the specific cleavage sites may either be adjacent to each other, may overlap or may be separated by intervening sequences of varying lengths as is known in the art.

In another embodiment of the invention, the plurality of specific cleavage site modifications adds two or more cleavage sites, each of which is recognized by a specific activating agent that is a protease. In another embodiment of the invention, the specific activating agent is a protease that is associated with invasion and metastasis of a specific cancer. In a further embodiment of the invention, the specific activating agent is a protease, the expression of which is up-regulated in a specific cancer. In still another embodiment, the specific activating agent is a protease that is produced by a cell that is associated with a specific cancer.

In another embodiment, the specific activating agent is a protease that is associated with colon cancer.

B. Proteolytic Activity Delivered to the Targeted Cells

A major limitation of previously described approaches to targeting cells is their reliance on endogenous proteases, which may not be present on all tumors, or may be present in inadequate abundance, or may be shed in substantial quantities, leading to nonspecific activation of the toxin. The present invention also provides VCE protoxins that are activatable by protease fusions that are independently brought to the targeted cells through specific binding to the cell surface; these VCE protoxins are useful for targeted destruction of tumor cells or other undesired cells that have no appropriate endogenous protease activity.

An exogenous protease and corresponding cleavage site may be chosen for the present invention based on the following considerations. The protease is preferably capable of cleaving a protoxin activation moiety without significantly inactivating the protoxin or itself. The protease is preferably not naturally found in or on cells that are desired to be spared, with the exception that the protease can be naturally found in such cells if its natural location does not allow it to activate an externally administered protoxin. For example, an intracellular protease such as a caspase may be used if the toxin must be activated at the surface of the cell or in some intracellular vesicular compartment that does not naturally contain the intracellular protease, such as the endosome, golgi, or endoplasmic reticulum. In such cases the cells that are desired to be spared could contain the protease but the protease would not activate the protoxin.

The catalytic activity of the protease is preferably stable to in vivo conditions for the time required to exert its therapeutic effect in vivo. If the therapeutic program requires the repeat administration of the protease, the protease is preferably resistant to interference by the formation of antibodies that impair its function, for example neutralizing antibodies. In some embodiments the protease has low immunogenicity or can be optionally substituted to reduce immunogenicity or can be optionally substituted to reduce the effect of antibodies on its activity. The protease preferably has low toxicity itself or has low toxicity in the form of its operable linkage with one or more cell surface binding moieties. The protease is preferably stable or can be made to be stable to conditions associated with the manufacturing and distribution of therapeutic products. The protease is preferably a natural protease, a modified protease, or an artificial enzyme.

Desirable proteases of the present invention include those known to have highly specific substrate selectivities, either by virtue of an extended catalytic site or by the presence of specific substrate-recognition modules that endow a relatively nonselective protease with appropriate specificity. Proteases of limited selectivity can also be made more selective by genetic mutation or chemical modification of residues close to the substrate-binding pocket.

As is known in the art, many proteases recognize certain cleavage sites, and some specific, non-limiting examples are given below. One of skill in the art would understand that cleavage sites other than those listed are recognized by the listed proteases, and can be used as a general protease cleavage site according to the present invention.

Proteases of human origin are preferred embodiments of the present invention due to reduced risk of immunogenicity. A human protease utilizing any catalytic mechanism, i.e., the nature of the amino acid residue or cofactor at the active site that is involved in the hydrolysis of the peptides and proteins, including aspartic proteases, cysteine proteases, metalloproteases, serine proteases, and threonine proteases, may be useful for the present invention.

Because model studies of a potential therapeutic agent must be conducted in animals to determine such properties as toxicity, efficacy, and pharmacokinetics prior to clinical trials in human, the presence of proteinase inhibitors in the plasma of animals could also limit the development of therapeutics comprising proteolytic activities. The proteinase inhibitors in animal plasma can possess inhibitory properties that are different from their human counterparts. For example human GrB has been found to be inhibited by mouse serpina3n, which is secreted by cultured Sertoli cells and is the major component of serpina3 ($\alpha_1$-antichymotrypsin) present in mouse plasma (Sipione et al., J. Immunol. 177:5051-5058 (2006)). However, the human $\alpha_1$-antichymotrypsin has not been shown to be an inhibitor of human GrB. The difference between mouse and human plasma protease inhibitors may be traced to their genetic differences. Whereas the major human plasma protease inhibitors, $\alpha_1$-antitrypsin and $\alpha_1$-antichymotrypsin, are each encoded by a single gene, in the mouse they are represented by clusters of 5 and 14 genes, respectively. Even though there is a high degree of overall sequence similarity within these clusters of inhibitors, the reactive-center loop (RCL) domain, which determines target protease specificity, is markedly divergent. To overcome inhibition by mouse proteases, the screening and mutagenesis strategies described herein can be applied to identify mutant proteases that are resistant to inhibition by inhibitors present in the animal model of choice.

Human Granzymes

Recombinant human granzyme B (GrB) may be used as an exogenous protease within the protease fusion protein. GrB has high substrate sequence specificity with a consensus recognition sequence of IEPD and is known to cleave only a limited number of natural substrates. GrB is found in cytoplasmic granules of cytotoxic T-lymphocytes and natural killer cells, and thus should be useful for the present invention provided these cells are not the targeted cells. The optimum pH for GrB activity is around pH 8, but it retains its activity between pH 5.5 and pH 9.5 (Fynbo et al., Protein Expr. Purif. 39:209 (2005)). GrB cleaves peptides containing IEPD (SEQ ID NO:18) with high efficiency and specificity (Harris et al., J. Biol. Chem. 273:27364 (1998)). Because GrB is involved in regulating programmed cell death, it is tightly regulated in vivo. In addition, GrB is a single chain and single domain serine protease, which could contribute to a simpler composite structure of the fusion protein. Moreover, GrB has recently been found to be very stable in general, and it performs very well in the cleavage of different fusion proteins (Fynbo et al., Protein Expr. Purif. 39:209 (2005)).

Any member of the granzyme family of serine proteases, e.g., granzyme A and granzyme M, may be used as the recombinant protease component of the protease fusion in this invention. For example, granzyme M (GrM) is specifically found in the granules of natural killer cells and can hydrolyze the peptide sequence KV(Y)PL(M) (SEQ ID NO:21) with high efficiency and specificity (Mahrus et al., J. Biol. Chem. 279:54275 (2004)).

In designing and utilizing protease fusions of the invention, it should be noted that proteinase inhibitors may hamper the proteolytic activities of protease fusion proteins. For example, GrB is specifically inhibited by intracellular proteinase inhibitor 9 (PI-9), a member of the serpin superfamily that primarily exists in cytotoxic lymphocytes (Sun et al., J. Biol. Chem. 271:27802 (1996)) and has been detected in human plasma. GrB can also be inhibited by $\alpha_1$-protease inhibitor ($\alpha_1$PI) that is present in human plasma (Poe et al., J. Biol. Chem. 266:98 (1991)). GrM is inhibited by $\alpha_1$-antichymotrypsin (ACT) and $\alpha_1$PI (Mahrus et al., J. Biol. Chem. 279:54275 (2004)), and GrA is inhibited in vitro by protease inhibitors antithrombin III (ATIII) and $\alpha$2-macroglobulin ($\alpha_2$M) (Spaeny-Dekking et al., Blood 95:1465 (2000)). These proteinase inhibitors are also present in human plasma (Travis and Salvesen, Annu. Rev. Biochem. 52:655 (1983)).

One approach to preserve proteolytic activities of granzymes is to utilize complexation with proteoglycan, since the mature and active form of GrA has been observed in human plasma as a complex with serglycin, a granule-associated proteoglycan (Spaeny-Dekking et al., Blood 95:1465 (2000)). Glycosaminglycan complexes of GrB have also been found proteolytically active (Galvin et al., J. Immunol. 162:

5345 (1999)). Thus, it is possible to keep granzyme fusion proteins active in plasma through formulations using chondroitin sulfates.

Cathepsins and Caspases

Any member of the cathepsins (Chwieralski et al., Apoptosis 11:143 (2006)), e.g., cathepsin A, B, C, D, E, F, G, H, K, L, S, W, and X, may also be used as the recombinant protease for the present invention. Cathepsins are proteases that are localized intralysosomally under physiologic conditions, and therefore have optimum activity in acidic environments. Cathepsins comprise proteases of different enzyme classes; e.g., cathepsins A and G are serine proteases, cathepsins D and E are aspartic proteases. Certain cathepsins are caspases, a unique family of cysteine proteases that play a central role in the initiation and execution phases of apoptosis. Among all known mammalian proteases, only the serine protease granzyme B has substrate specificity similar to the caspases.

A cathepsin or caspase can be used as an exogenous activator or proactivator only if the protoxin to be activated is not exposed to that cathepsin or caspase prior to internalization (in the case of toxins that must be internalized) or during the course of the natural formation of the active toxin. For example, the protoxins of pore-forming toxins are activated at the cell surface, followed by oligomerization and pore formation. Because pore forming toxins do not localize to lysosome, cathepsins and caspases can be applied as exogenous activators. On the other hand, because the A-B toxin DT is known to be translocated directly into the cytosol through the endosome and/or lysosome, where cathepsins naturally reside, cathepsins should not be used as exogenous activators for DT-based protoxins. VCE-based toxins may be compatible with the use of lysosomal proteases as exogenous activators, because they are transported to the trans-Golgi network and the ER before the translocation into cytosol. All caspases, including caspase-1, -2, -3, -4, -5, -6, -7, -8, -9 and more, show high selectivity and cleave proteins adjacent to an aspartate residue (Timmer and Salvesen, Cell Death Diff. 14:66-72 (2007)). The preferred cleavage site for caspase-1, 4, -5, and -14 are (W/Y)EXD↓Φ, where X is any residue and Φ represents a Gly, Ala, Thr, Ser, or Asn (SEQ ID NO:22). The preferred substrate for caspase-8, -9, and -10 contains the sequence of (I/L)EXD↓Φ (SEQ ID NO:23), and that of caspase-3 and -7 contains DEXD↓Φ (SEQ ID NO:24). Caspase-6 preferably cleaves at VEXD↓Φ (SEQ ID NO:25), while caspase-2 selectively targets (V/L)DEXD↓Φ (SEQ ID NO:26). Because the naturally occurring inhibitors of caspases, e.g., IAPB, are usually located intracellularly (LeBlanc, Prog. Neuropsychopharmacol. Biol. Psychiatry 27:215 (2003)), the probability of inhibition in plasma is dramatically reduced. Although caspase-1 and caspase-4 can be inhibited by PI-9 at moderate rates, it does not inhibit caspase-3 (Annand et al., Biochem. J. 342:655 (1999)).

Other Human Proteases

Many human proteases, including those have been identified as certain disease markers secreted by diseased cells, or associated with cancer invasion and metastasis, may be useful for the present invention as the heterologous protease. These proteases are well studied and detailed information on proteolytic activity and sequence selectivity is available. Examples of such proteases include urokinase plasminogen activator (uPA), which recognizes and cleaves GSGR↓SA (SEQ ID NO:27); prostate-specific antigen (PSA), which prefers substrate sequence SS(Y/F)Y↓SG (SEQ ID NO:28); renin, which cleaves at HPFHL↓VIH (SEQ ID NO:29); and MMP-2, which can cleave at HPVG↓LLAR (SEQ ID NO:30). Additional examples include the caspases, elastase, kallikreins, the matrix metalloprotease (MMP) family, the plasminogen activator family, as well as fibroblast activation protein.

In certain cases, the protease involved in one disease may be useful for the treatment of another disease that does not usually involve its overexpression. In other instances, the concentration of the secreted protease at native level may not be sufficient to activate corresponding toxin fusion to the extent that is necessary for targeted cell killing, i.e., is not operably present on the targeted cells. Additional proteolytic activity delivered to the cells through targeted protease fusion would provide desired toxin activation. In one embodiment, the protease fusion could have the same sequence specificity as the protease secreted by the diseased cells. In another embodiment, it may be desirable to use a combination of multiple, different, proteolytic cleavage activities to increase overall cleavage efficiency, with at least one of the proteolytic activity being provided by a targeted protease fusion.

Additional examples of endogenous proteases include those have been identified as certain disease markers, which are upregulated in certain disease. Non-limiting examples of such proteases include urokinase plasminogen activator (uPA), which recognizes and cleaves GSGR↓SA (SEQ ID NO:31); prostate-specific antigen (PSA), which prefers substrate sequence SS(Y/F)Y↓SG (SEQ ID NO:32); renin, which cleaves at HPFHL↓VIH (SEQ ID NO:33); and MMP-2, which can cleave at HPVG↓LLAR (SEQ ID NO:34). Although the use of such designed zymogens may not be optimal for protease such as GrB, which requires a specific N-terminus amino acid Ile to be active, such in vivo activation process may be applicable to other proteases and activating enzymes.

Alternatively, potential candidate proteases may be screened in vitro by interactions with known proteinase inhibitors in plasma or with human plasma directly to avoid potential complications posed by these proteinase inhibitors. Alternatively, proteases for which cognate inhibitors are found in plasma can be engineered to provide mutant forms that resist inhibition. For example, in vitro *E. coli* expression-screening methods have been developed to select mutant proteases that are resistant to known HIV-1 protease inhibitors (Melnick et al., Antimicrob. Agents Chemother. 42:3256 (1998)).

Retroviral proteases may also be used for the present invention. Human retroviral proteases, including that of human immunodeficiency virus type 1 (HIV-1) (Beck et al., 2002), human T cell leukemia viruses (HTLV) (Shuker et al., Chem. Biol. 10:373 (2003)), and have been extensively studied as targets of anti-viral therapy. These proteases often have long recognition sequences and high substrate selectivity.

Picornaviral proteases may also be used for the present invention. Such picornaviral proteases have been studied as targets of anti-viral therapy, for example human Rhinovirus (HRV) (Binford et al., Antimicrob. Agents Chemother. 49:619 (2005)), Recombinant heterologous proteases of any origin may be engineered to possess the aforementioned qualities and be used for the present invention. For example, tobacco etch virus (TEV) protease has very high substrate specificity and catalytic efficiency, and is used widely as a tool to remove peptide tags from recombinant proteins (Nunn et al., J. Mol. Biol. 350:145 (2005)). TEV protease recognizes an extended seven amino acid residue long consensus sequence E-X-X-Y-X-Q↓S/G (where X is any residue) (SEQ ID NO:35) that is present at protein junctions. Those skilled in the art would recognize that it is possible to engineer a particular protease such that its sequence specificity is altered to prefer another substrate sequence (Tozser et al., FEBS J. 272:514 (2005)).

Further modifications can be engineered to increase the activity and/or specificity of proteases. These modifications include PEGylation to increase stability to serum or to lower immunogenicity, and genetic engineering/selection may produce mutant proteases that possess altered properties such as resistance to certain inhibitors, increased thermal stability, and improved solubility.

Retroviral Proteases

Recombinant human retroviral proteases may also be used for the present invention. Human retroviral proteases, including that of human immunodeficiency virus type 1 (HIV-1) (Beck et al., 2002), human T cell leukemia viruses (HTLV) (Shuker et al., Chem. Biol. 10:373 (2003)), and severe acute respiratory syndrome coronavirus (SARS), have been extensively studied as targets of anti-viral therapy. These proteases often have long recognition sequences and high substrate selectivity. For example, SQNY↓PIV (SEQ ID NO:36) was determined as a preferred cleavage sequence of HIV-1 protease (Beck et al. Curr. Drug Targets Infect. Disord. 2(1):37-50 (2002), the preferred cleavage sequence for HTLV protease has been determined to be PVIL↓PIQA (SEQ ID NO:37) (Naka et al. Bioorg. Med. Chem. Lett. 16(14):3761-3764 (2006).

Coronaviral Proteases

Coronaviral or toroviral proteases are encoded by members of the animal virus family Coronaviridae and exhibit high cleavage specificity. Such proteases are another preferred embodiment for the present invention. The SARS 3C-like protease has been found to selectively cleave at AVLQ↓SGF (SEQ ID NO:38) (Fan et al. Biochem. Biophys. Res. Commun. 329(3):934-940 (2005)).

Picornaviral Proteases

Picornaviral proteases may also be used for the present invention. Such picornaviral proteases have been studied as targets of anti-viral therapy, for example human Rhinovirus (HRV) (Binford et al., Antimicrob. Agents Chemother. 49:619 (2005)). HRV 3C protease recognizes and cleaves ALFQ↓GP (SEQ ID NO:39) (Cordingley et al. J. Biol. Chem. 265(16):9062-9065 (1990)).

Potyviral Proteases

Potyviral proteases are encoded by members of the plant virus family Potyviridae and exhibiting high cleavage specificity, and are another preferred embodiment for the present invention. For example, tobacco etch virus (TEV) protease has very high substrate specificity and catalytic efficiency, and is used widely as a tool to remove peptide tags from overexpressed recombinant proteins (Nunn et al., J. Mol. Biol. 350:145 (2005)). TEV protease recognizes an extended seven amino acid residue long consensus sequence E-X-X-Y-X-Q↓S/G (where X is any residue) that is present at protein junctions (SEQ ID NO:40). Those skilled in the art would recognize that it is possible to engineer a particular protease such that its sequence specificity is altered to prefer another substrate sequence (Tozser et al., FEBS J. 272:514 (2005)).

Proteases of other Origins

Since proteases are physiologically necessary for living organisms, they are ubiquitous, being found in a wide range of sources such as plants, animals, and microorganisms (Rao et al. Microbiol. Mol. Biol. Rev. 62(3):597-635 (1998)). All these proteases are potential candidates for the present invention. In a preferred embodiment, PEGylation may be utilized to reduce the immunological potential of fusion proteases for the present invention, particularly for those that are of non-human origins. PEGylation may confer additional benefits to protease fusion proteins, such as improved plasma persistence and reduced non-specific cell binding.

Additional proteases can be found, for example, in PCT Application Publication No. 2008/011157, which is herein incorporated by reference in its entirety.

V. Linkages

According to the present invention, each moiety within a protoxin fusion protein (e.g., one or more cell targeting moieties, one or more selectively modifiable activations domains, one or more natively activatable domain, and one or more toxin domains) or a protoxin activator fusion, (e.g., one or more cell targeting moieties, one or more modification domains, one or more natively activatable domain, and one or more toxin domains) may function independently but each is operably linked. Within each fusion protein the operable linkage between the two functional moieties acts as a molecular bridge, which may be covalent or non-covalent. The moieties of each fusion protein may be operably linked in any orientation with respect to each other, that is, C-terminal of one to N-terminal of the other, or C-terminal of one to C-terminal of the other, or N-terminal of one to N-terminal of the other, or by internal residues to terminal residues or internal residues to internal residues. An optional linker can serve as a glue to physically join the two moieties, as a separator to allow spatial independence, or as a means to provide additional functionality to each other, or a combination thereof. For example, it may be desirable to separate the cell-targeting moiety from the operably linked enzyme moiety to prevent them from interfering with each other's activity. In this case the linker provides freedom from steric conflict between the operably linked moieties. The linker may also provide, for example, lability to the connection between the two moieties, an enzyme cleavage site (e.g., a cleavage site for protease or a hydrolytic site for esterase), a stability sequence, a molecular tag, a detectable label, or various combinations thereof.

Chemical activation of amino acid residues can be carried out through a variety of methods well known in the art that result in the joining of the side chain of amino acid residues on one molecule with side chains of residues on another molecule, or through the joining of side chains to the alpha amino group or by the joining of two or more alpha amino groups. Typically the joining induced by chemical activation is accomplished through a linker which may be a small molecule, an optionally substituted branched or linear polymer of identical or nonidentical subunits adapted with specific moieties at two or more termini to attach to polypeptides or substitutions on polypeptides, or an optionally substituted polypeptide. Examples of common covalent protein operable linkage agents may be found in various vendor offerings, including those offered for sale by Pierce Chemical Corporation. In general it is preferable to be able to induce operable linkage of components in a site-specific manner, to afford a simple reproducibly manufactured substance. Operable linkage by chemical activation can be the result of chemical activation targeted to specific residues that are functionally unique i.e. are present only once in the moiety to be activated or are preferentially activatable because of a unique chemical environment, for example, such as would produce a reduction in pK of an epsilon amino unit of a lysine residue. Potential groups for chemical activation can be made functionally unique by genetic removal of all other residues having the same properties, for example to remove all but a single cysteine residue, or all but a single lysine reside. Amino terminal residues can be favorably targeted by virtue of the low pK of the alpha amino group, or by suitable chemistry exploiting the increased reactivity of the alpha amino group in close proximity to another activatable group. Examples of the latter include native chemical ligation, Staudinger ligation, and oxidation of amino terminal serine to afford an aldehyde substituent. Chemical activation can also be carried out through reactions that activate naturally occurring protein substituents, such as oxidation of glycans, or other naturally occurring protein modifications such as those formed by biotin or lipoic acid, or can be based on chemical reactions that convert the functionality of one side chain into that of another, or that introduce a novel chemical reactive group that can subsequently activated to produce the desired operable linkage. Examples of the latter include the use of iminodithiolane to endow a lysine residue with a sulfhydryl moiety or the reaction of a cysteine moiety with an appropriate maleimide or haloacetamide to change the functionality of the thiol to another desired reactive moiety. Chemical activation can also be carried out on both species to be operably linked to provide reactive species that interact with one another to provide an operable linkage, for example the introduction of a hydrazide, hydrazine or hydroxylamine on one moiety and an aldehyde on the other.

Noncovalent operable linkage can be obtained by providing a complementary surface between one moiety and another to provide a complex which is stable for the intended useful persistence of the operably linked moieties in therapeutic use. Such noncovalent linkages can be created from either two or more polypeptides that may be the same or dissimilar or one or more polypeptide and a small molecule or ligand attached to the second moiety. Attachment of the small molecule or ligand can take place through in vitro or in vivo processes, such as the incorporation of biotin or lipoic acid into their specific acceptor sequences which may be natural or artificial biotin or lipoic acid acceptor domains and which may be achieved either by natural incorporation in vivo or by enzymatic biotinylation or lipoylation in vitro. Alternatively, the protein may be substituted with biotin or other moieties by chemical reaction with biotin derivatives. Common examples of biotin derivatives used to couple with proteins include aldehydes, amines, haloacetamides, hydrazides, maleimides, and activated esters, such as N-hydroxysuccinimide esters. Examples of commonly employed noncovalent linkage include the linkage induced by binding of biotin and its derivatives or biotin-related substituents such as iminobiotin or diaminobiotin or thiobiotin to streptavidin or avidin or variants thereof, the binding of enzymes to their covalent or noncovalent specific inhibitors, such as the binding of methotrexate to mammalian dihydrofolate reductase, the binding of natural or synthetic leucine zippers to one another, the binding of enzymes to specific or nonspecific inhibitors, such as antitrypsin or leupeptin or alpha-2-macroglobulin, the binding of aryl bis-arsenates to alpha helices bearing appropriately positioned cysteine residues, the binding between a nucleic acid aptamer and its target; between a peptide and a nucleic acid such as Tat-TAR interaction.

Enzymatic activation of one polypeptide to afford coupling with another polypeptide can also be employed. Enzymes or enzyme domains that undergo covalent modification by reaction with substrate-like molecules can also be used to create fusions. Examples of such enzymes or enzyme domains include O6-alkylguanine DNA-alkyltransferase (Gronemeyer et al. Protein Eng Des Sel. 2006 19(7):309-16), thymidylate synthase, or proteases that are susceptible to covalent or stable noncovalent modification of the active site, as for example DPPIV (SEQ ID NO:41).

The present invention also features the use of bifunctional or multifunctional linkers, which contain at least two interactive or reactive functionalities that are positioned near or at opposite ends, each can bind to or react with one of the moieties to be linked. The two or more functionalities can be the same (i.e., the linker is homobifunctional) or they can be different (i.e., the linker is heterobifunctional). A variety of bifunctional or multifunctional cross-linking agents are known in the art are suitable for use as linkers. For example, cystamine, m-maleimidobenzoyl-N-hydroxysuccinimide-ester, N-succinimidyl-3-(2-pyridyldithio)-propionate, methylmercaptobutyrimidate, dithiobis(2-nitrobenzoic acid), and many others are commercially available, e.g., from Pierce Chemical Co. Rockford, Ill. Additional chemically orthogonal reactions suitable for such specific operable linkage reactions include, for example, Staudinger ligation, Cu[I] catalyzed [2+3] cycloaddition, and native ligation.

The bifunctional or multifunctional linkers may be interactive but non-reactive. Such linkers include the composite use of any examples of non-covalent interactions discussed above.

The length and composition of the linker can be varied considerably provided that it can fulfill its purpose as a molecular bridge. The length and composition of the linker are generally selected taking into consideration the intended function of the linker, and optionally other factors such as ease of synthesis, stability, resistance to certain chemical and/or temperature parameters, and biocompatibility. For example, the linker should not significantly interfere with the regulatory ability of the cell-targeting moiety relating to targeting of the toxin, or with the activity of the toxin or enzyme relating to activation and/or cytotoxicity.

Linkers suitable for use according to the present invention may be branched, unbranched, saturated, or unsaturated hydrocarbon chains, including peptides as noted above.

Furthermore, if the linker is a peptide, the linker can be attached to the toxin moiety and enzyme moiety and/or the cell-targeting moiety using recombinant DNA technology.

In one embodiment of the present invention, the linker is a branched or unbranched, saturated or unsaturated, hydrocarbon chain having from 1 to 100 carbon atoms, wherein one or more of the carbon atoms is optionally replaced by —O— or —NR— (wherein R is H, or C1 to C6 alkyl), and wherein the chain is optionally substituted on carbon with one or more substituents selected from the group of (C1-C6) alkoxy, (C3-C6) cycloalkyl, (C1-C6) alkanoyl, (C1-C6) alkanoyloxy, (C1-C6) alkoxycarbonyl, (C1-C6) alkylthio, amide, azido, cyano, nitro, halo, hydroxy, oxo (═O), carboxy, aryl, aryloxy, heteroaryl, and heteroaryloxy.

Examples of suitable linkers include, but are not limited to, peptides having a chain length of 1 to 100 atoms, and linkers derived from groups such as ethanolamine, ethylene glycol, polyethylene with a chain length of 6 to 100 carbon atoms, polyethylene glycol with 3 to 30 repeating units, phenoxyethanol, propanolamide, butylene glycol, butyleneglycolamide, propyl phenyl, and ethyl, propyl, hexyl, steryl, cetyl, and palmitoyl alkyl chains.

In one embodiment, the linker is a branched or unbranched, saturated or unsaturated, hydrocarbon chain, having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (═O), carboxy, aryl and aryloxy.

In another embodiment, the linker is an unbranched, saturated hydrocarbon chain having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy; (C1-C6) alkanoyl, (C1-C6) alkanoyloxy, (C1-C6) alkoxycarbonyl, (C1-C6) alkylthio, amide, hydroxy, oxo (=O), carboxy, aryl and aryloxy.

In a specific embodiment of the present invention, the linker is a peptide having a chain length of 1 to 50 atoms. In another embodiment, the linker is a peptide having a chain length of 1 to 40 atoms.

As known in the art, the attachment of a linker to a protoxin moiety (or of a linker element to cell-targeting moiety or a cell-targeting moiety to a protoxin moiety) need not be a particular mode of attachment or reaction. Various non-covalent interactions or reactions providing a product of suitable stability and biological compatibility are acceptable.

One preferred embodiment of the present invention relies on enzymatic reaction to provide an operable linkage between the moieties of a protoxin, protoxin activator, or protoxin proactivator. Among the enzymatic reactions that produce such operable linkage, it is well-known in the art that transglutaminase ligation, sortase ligation, and intein-mediated ligation provide for high specificity.

The preferred peptide substrate sequences listed above are for example and non-limiting. It is known in the art that these families of enzymes can recognize and utilize different sequences as substrates, and those sequences are included here as embodiments for the present invention.

In some aspects, the invention features the use of natively activatable linkers. Such linkers are cleaved by enzymes of the complement system, urokinase, tissue plasminogen activator, trypsin, plasmin, or another enzyme having proteolytic activity may be used in one embodiment of the present invention. According to another embodiment of the present invention, a protoxin is attached via a linker susceptible to cleavage by enzymes having a proteolytic activity such as a urokinase, a tissue plasminogen activator, plasmin, thrombin or trypsin. In addition, protoxins may be attached via disulfide bonds (for example, the disulfide bonds on a cystine molecule) to the cell-targeting moiety. Since many tumors naturally release high levels of glutathione (a reducing agent) this can reduce the disulfide bonds with subsequent release of the protoxin at the site of delivery.

In one embodiment, the cell-targeting moiety is linked to a protoxin by a cleavable linker region. In another embodiment of the invention, the cleavable linker region is a protease-cleavable linker, although other linkers, cleavable for example by small molecules, may be used. Examples of protease cleavage sites are those cleaved by factor Xa, thrombin and collagenase. In one embodiment of the invention, the protease cleavage site is one that is cleaved by a protease that is up-regulated or associated with cancers in general. Examples of such proteases are uPA, the matrix metalloproteinase (MMP) family, the caspases, elastase, and the plasminogen activator family, as well as fibroblast activation protein. In still another embodiment, the cleavage site is cleaved by a protease secreted by cancer-associated cells. Examples of these proteases include matrix metalloproteases, elastase, plasmin, thrombin, and uPA. In another embodiment, the protease cleavage site is one that is up-regulated or associated with a specific cancer. In yet another embodiment, the proteolytic activity may be provided by a protease fusion targeted to the same cell. Various cleavage sites recognized by proteases are known in the art and the skilled person will have no difficulty in selecting a suitable cleavage site. Non-limiting examples of cleavage sites are provided elsewhere in this document. As is known in the art, other protease cleavage sites recognized by these proteases can also be used. In one embodiment, the cleavable linker region is one which is targeted by endocellular proteases.

Chemical linkers may also be designed to be substrates for carboxylesterases, so that they may be selectively cleaved by these carboxyltransferases or corresponding fusion proteins with a cell-targeting moiety. One preferred embodiment comprises the use of a carboxyl transferase activity to activate the cleavage of an ester linker. For example but without limitation, secreted human carboxyltransferase-1, -2, and -3 may be used for this purpose. Additional examples include carboxyl transferase of other origins.

Another embodiment of the cleavable linkers comprises nucleic acid units that are specifically susceptible to endonucleases. Endonucleases are known to be present in human plasma at high levels.

In another embodiment, the modifiable activation moiety is not a peptide, but a cleavable linker that may be acted upon by a cognate enzymatic activity provided by the activator or proactivator. The cleavable linker is preferably situated at the same location as the furin-like cleavage sequence in an activatable protoxin, or at the location of the zymogen inhibitory peptide in an activatable proactivator. The cleavable linker may replace the furin-like cleavage sequence or be attached in parallel to the furin-like cleavage or another modifiable activation moiety, providing a protoxin that requires both a furin-like cleavage or other proteolytic event and a linker cleavage for activation. In one embodiment the cleavable linker joins the ADP ribosyltransferase domain of a VCE-based protoxin to the translocation domain of that or another protoxin. In another embodiment the cleavable linker joins the translocation domain of a PEA or VCE-based protoxin to the ADP ribosyltransferase domain of the same or a different toxin. In yet another embodiment the cleavable linker joins the pore-forming domain of a pore-forming toxin with the C-terminal inhibitory peptide.

Preferable cleavable linkers are those which are stable to in vivo conditions but susceptible to the action of an activator. Many examples of suitable linkers have been provided in the context of attempts to develop antibody-directed enzyme prodrug therapy. For example a large class of enzyme substrates that lead to release of an active moiety, such as a fluorophore, have been devised through the use of what are known as self-immolative linkers. Self-immolative linkers are designed to liberate an active moiety upon release of an upstream conjugation linkage, for example between a sugar and an aryl moiety. Such linkers are often based on glycosides of aryl methyl ethers, for example the phenolic glycosides of 3-nitro, 4-hydroxy benzyl alcohol; see for example Ho et al. Chembiochem, 2007 Mar. 26; 8(5):560-6, or the phenolic amides of 4-amino benzyl alcohol, for example Niculescu-Duvaz et al. J Med. Chem. 1998 Dec. 17; 41(26):5297-309 or Toki et al. J Org. Chem. 2002 Mar. 22; 67(6):1866-72.

To create self-immolative linkers based on glycosides the phenolic hydroxyl is glycated by reaction with a 1-Br-substituted sugar such as alpha-1-Br galactose or alpha-1-Br glucuronic acid to provide the substrate for the activating enzyme, and the benzyl alcohol moiety is then activated with a carbonylation reagent such as phosgene or carbonyl diimidazole and reacted with a primary amine to afford a carbamate linkage. Upon scission of the aryl glycosidic bond or the aryl ester, the aryl moiety eliminates, leaving a carbamoyl moiety that in turn eliminates, affording CO2 and the regenerated amine. The amine may be the alpha amino group of a polypeptide chain or the epsilon amino of a lysine side chain.

To create self-immolative linkers based on amide bonds the phenyl amine of 4-amino benzyl alcohol is reacted with an activated carboxyl group of a suitable peptide or amino acid to create a phenyl amide that can be a substrate for an appropriate peptidase, for example carboxypeptidase G2 Niculescu-Duvaz et al. J Med. Chem. 41(26):5297-309 (1998). The benzyl alcohol moiety is then activated with a carbonylation reagent such as phosgene or carbonyl diimidazole and reacted with a primary amine to afford a carbamate linkage. Upon scission of the aryl amide bond, the aryl moiety eliminates, leaving a carbamoyl moiety that in turn eliminates, affording $CO_2$ and the regenerated amine. Said amine may be the alpha amino group of a polypeptide chain or the epsilon amino of a lysine side chain.

For the creation of an appropriate self-immolating activation moiety according to the present invention the aryl group is substituted with a reactive moiety that provides a linkage to one element of the protoxin or proactivator, such as the toxin moiety or the translocation moiety or the inhibitory peptide moiety.

Similar forms of self-immolative linker are also well-known in the art. For example Papot et al. Bioorg Med Chem. Lett. 8(18):2545-8 (1998) teach the creation of glucuronide prodrugs based on aryl malonaldehydes that undergo elimination of the aryl linker moiety upon cleavage by a glucuronidase. Suitable linkers based on aryl malonaldehydes in the context of the present invention provide a modifiable activation moiety in which the aryl substituent is operably linked to one terminus of the toxin moiety, for example at the location of the furin cleavage site, and the carbamoyl functionality is operably linked to the translocation moiety or inhibitory moiety. In the system devised by Papot et al, cleavage by glucuronidase will result in elimination of the aryl malonaldehyde and activation of the protoxin. Similar elimination events are known to take place following hydrolysis of the lactam moiety of linkers based on 7-aminocephalosporanic acid, and enzymatically activated prodrugs based on beta-lactam antibiotics or related structures are well known in the art. For example Alderson et al. Bioconjug Chem. 17(2): 410-8 (2006) teach the creation of a 7-aminocephalosporanic acid-based linker that undergoes elimination and scission of a carbamate moiety in similar fashion to that of the aryl malonaldehydes disclosed by Papot et al. In addition, Harding et al. Mol Cancer Ther. 4(11):1791-800 (2005) teach a beta-lactamase that has reduced immunogenicity that can be favorably applied as an activator for a prodrug moiety based on a 7-aminocephalosporanic acid nucleus.

In yet another embodiment the modifiable activation moiety is a peptide but is operably linked by a flexible nonpeptide linker at either or both termini in the same location as the natural furin-like protease cleavage site, or in parallel to the natural furin-like cleavage site. In such embodiments the activator is a cognate protease or peptide hydrolase recognizing the peptide of the modifiable activation moiety. In a doubly triggered protoxin, the furin-like cleavage site is replaced by a modifiable activation moiety and a cleavable linker is attached in parallel to the modifiable activation moiety. In such a protoxin the action of two activators is required to activate the protoxin.

VI. Isolation and Purification of Toxin Fusion and Protease Fusion Proteins

A. General Strategies for Recombinant Protein Purification

There are many established strategies to isolate and purify recombinant proteins known to those skilled in the art, such as those described in *Current Protocols in Protein Science* (Coligan et al., eds. 2006). Conventional chromatography such as ion exchange chromatography, hydrophobic-interaction (reversed phase) chromatography, and size-exclusion (gel filtration) chromatography, which exploit differences of physicochemical properties between the desired recombinant protein and contaminants, are widely used. HPLC can also been used.

To facilitate the purification of recombinant proteins, a variety of vector systems have been developed to express the target protein as part of a fusion protein appended by an N-terminal or C-terminal polypeptide (tag) that can be subsequently removed using a specific protease. Using such tags, affinity chromatography can be applied to purify the proteins. Examples of such tags include proteins and peptides for which there is a specific antibody (e.g., FLAG fusion purified using anti-FLAG antibody columns), proteins that can specifically bind to columns containing a specific ligand (e.g., GST fusion purified by glutathione affinity gel), polyhistidine tags with affinity to immobilized metal columns (e.g., 6 His tag immobilized on $Ni^{2+}$ column and eluted by imidazole), and sequences that can be biotinylated by the host during expression or in vitro after isolation and enable purification on an avidin column (e.g., BirA).

B. Isolation and Purification of Fusion Proteins Expressed in Insoluble Form

Many recombinant fusion proteins are expressed as inclusion bodies in *Escherichia coli*, i.e., dense aggregates that consist mainly of a desired recombinant product in a normative state. In fact, most reported DT-ScFv fusion proteins expressed in *E. coli* are obtained in insoluble forms. Usually, the inclusion bodies form because (a) the target protein is insoluble at the concentrations being produced, (b) the target protein is incapable of folding correctly in the bacterial environment, or (c) the target protein is unable to form correct disulfide bonds in the reducing intracellular environment.

Those skilled in the art recognize that different methods that can be used to obtain soluble, active fusion proteins from inclusion bodies. For example, inclusion bodies can be separated by differential centrifugation from other cellular constituents to afford almost pure insoluble product located in the pellet fraction. Inclusion bodies can be partially purified by extracting with a mixture of detergent and denaturant, either urea or guanidine.HCl, followed by gel filtration, ion exchange chromatography, or metal chelate chromatography as an initial purification step in the presence of denaturants. The solubilized and partially purified proteins can be refolded by controlled removal of the denaturant under conditions that minimize aggregation and allow correct formation of disulfide bonds. To minimize nonproductive aggregation, low protein concentrations should be used during refolding. In addition, various additives such as nondenaturing concentrations of urea or guanidine.HCl, arginine, detergents, and PEG can be used to minimize intermolecular associations between hydrophobic surfaces present in folding intermediates.

C. Isolation and Purification of Fusion Proteins Expressed in Soluble Form

Recombinant proteins can also be expressed and purified in soluble form. Recombinant proteins that are not expressed in inclusion bodies either will be soluble inside the cell or, if using an excretion vector, will be extracellular (or, if *E. coli* is the host, possibly periplasmic). Soluble proteins can be purified using conventional methods afore described.

VI. Assays for Measuring Inhibition of Cell Growth

Various assays well known in the art are useful for determining the efficacy of the protein preparations of the invention, including those assays that measure cell proliferation and death. The following are examples of many assays that can be used for analyzing the cytotoxicity of the reagents in the present invention.

A. Protein Synthesis Inhibition Assays

Because many toxins (e.g., VCE) exert their cytotoxicity through inhibition of protein synthesis, an assay that directly quantifies the protein being synthesized by the cell after its exposure to the toxin is especially useful. In this assay, cells are exposed to a toxin and then incubated transiently with radioactive amino acids such as [$^3$H]-Leu, [$^{35}$S]-Met or [$^{35}$S]-Met-Cys. The amount of radioactive amino acid incorporated into protein is subsequently determined, usually by lysing cells and precipitating proteins with 10% trichloroacetic acid (TCA), providing a direct measure of how much protein is synthesized. Using such an assay, it was demonstrated that, although the entry of DT into a cell is not associated with an immediate block in protein synthesis, prolonged action (4-24 hours) of single DT catalytic fragment molecules in the cytosol is sufficient to obtain complete protein synthesis inhibition at low toxin concentrations (Falnes et al., J. Biol. Chem. 275:4363 (2000)).

An extension of this method is a luciferase-based assay (Zhao and Haslam, J. Med. Microbiol. 54:1023 (2005)). Luciferase cDNA was incorporated into a wide variety of dividing or non-dividing mammalian cells using an adenoviral expression system, and the resulting cells allowed to constitutively transcribe the luciferase cDNA, which had been engineered to contain an additional PEST sequence for a short intracellular half-life. The assay measures the level of protein synthesis in cells through the light output from D-luciferin reaction catalyzed by the short-lived luciferase. In cells constitutively expressing the luciferase mRNA, inhibition of protein synthesis results in diminished luciferase translation and proportionately reduced light output.

B. Thymidine Incorporation Assay

The rate of proliferation of cells can be measured by determining the incorporation of [$^3$H]-thymidine into cellular nucleic acids. This assay may be used for analyzing cytotoxicity of toxins (e.g., DT-based immunotoxins). Using this method a DT-IL3 immunotoxin was shown to be active in inhibiting growth of IL3-receptor bearing human myeloid leukemia cell lines (Frankel et al., Leukemia. 14:576 (2000)). The toxin fusion and protease fusion proteins of the present invention may be tested using such an assay, individually or combinatorially.

C. Colony Formation Assay

Colony formation may provide a much more sensitive measure of toxicity than certain other commonly employed methods. The reason for this increased sensitivity may be the fact that colony formation is assessed while the cells are in a state of proliferation, and thus more susceptible to toxic effects. The sensitivity of the colony-formation assay, and the fact that dose and time-dependent effects are detectable, enables acute and chronic exposure periods to be investigated as well as permitting recovery studies. For example, the cytotoxicity of a recombinant DT-IL6 fusion protein towards human myeloma cell lines was investigated using methylcellulose colony formation by U266 myeloma cells. In cultures containing both normal bone marrow and U266 cells DT-IL-6 effectively inhibited the growth of U266 myeloma colonies but had little effect on normal bone marrow erythroid, granulocyte and mixed erythroid/granulocyte colony growth (Chadwick et al., Haemotol. 85:25 (1993)).

D. MTT Cytotoxicity Assay

The cytotoxicity of a particular fusion protein or a combination of fusion proteins can be assessed using an MTT cytotoxicity assay. The specific cytotoxicity of a DT-GMCSF fusion protein against human leukemia cell lines bearing high affinity receptors for human GMCSF was demonstrated using such an MTT assay, colony formation assay, and protein inhibition assay (Bendel et al., Leuk. Lymphoma. 25:257 (1997)). In a typical MTT assay, the yellow tetrazolium salt (MTT) is reduced in metabolically active cells to form insoluble purple formazan crystals, which are solubilized by the addition of a detergent and quantified by UV-VIS spectrometry. After cells are grown to 80-100% confluence, they are washed with serum-free buffer and treated with cytotoxic agent(s). After incubation of the cells with the MTT reagent for approximately 2 to 4 hours, a detergent solution is added to lyse the cells and solubilize the colored crystals. The samples are analyzed at a wavelength of 570 nm and the amount of color produced is directly proportional to the number of viable cells.

VII. Functional Assays for VCE Fusion Proteins

A. In Vitro Protein Synthesis Inhibition Assay

In eukaryotic cells, VCE inhibits protein synthesis because its catalytic domain can inactivate elongation factor 2 (EF-2) by catalyzing its ADP-ribosylation after endocytosis to cytosol. In vitro eukaryotic translation systems, e.g., using rabbit reticulocyte lysate and wheat germ extract, are potentially suited for examining the catalytic function of recombinant VCE fusion proteins. For example, TNT-coupled wheat germ extract, supplemented by NAD$^+$, amino acids, [$^{35}$S]-Met, DNA template, and an RNA polymerase, has been used to test the inhibition of protein synthesis by a recombinantly expressed catalytic fragment of DT (Epinat and Gilmore, Biochim. Biophys. Acta. 1472:34 (1999)). The level of $^{35}$S-labeled translated protein is an indicator of the extent of DT toxicity.

These in vitro assays can be used to screen inhibitory effects of VCE fusions in the absence or presence of certain proteolytic activity, providing a facile assay to analyze the functional integrity of engineered VCE fusion proteins as well as that of protease fusion proteins.

B. In Vitro EF-2 ADP-ribosylation Assay

VCE inhibits protein synthesis by catalyzing the transfer of ADP-ribose moiety of NAD to a post-translationally modified His715 of EF-2 called diphthamide. Thus the function of VCE fusions can also be directly assayed in vitro by correlating its catalytic activity to rate of transfer of radiolabeled ADP-ribose to recombinant EF-2 as was previously shown for DT (Parikh and Schramm, Biochemistry 43:1204 (2004)). This assay has been applied for testing the inhibition of ADP-ribosyltransferase activity, and is often used as one of the assays for DT-based immunotoxins (Frankel et al., Leukemia. 14:576 (2000)). Non-radioactively labeled NAD, such as biotinylated NAD or etheno-NAD, may also be used as a substrate (Zhang. Method Enzymol. 280:255-265 (1997)).

C. In Vitro Proteolytic Activity Assay

The functional activity of recombinant protease fusion proteins may be assayed in vitro either using a peptide or protein substrate containing the recognition sequence of the protease. Various protocols are well known to those skilled in the art.

VIII. Administration of Proteins

The proteins of the invention are typically administered to the subject by means of injection using any route of administration such as by intrathecal, subcutaneous, submucosal, or intracavitary injection as well as by intravenous or intraarterial injection. Thus, the proteins may be injected systemically, for example, by the intravenous injection of the proteins into the patient's bloodstream or alternatively, the proteins can be directly injected at a specific site. The proteins of the invention can be administered alone, or in combination with other proteins or therapies.

The protoxin of the invention can be administered prior to, simultaneously with, or following the administration of the protoxin activator or protoxin proactivator and optionally administered prior to, simultaneously with, for following the administration of the proactivator activator of the invention. In preferred embodiments the components are administered in such a way as to minimize spontaneous activation during administration. When administered separately, the administration of two or more fusion proteins can be separated from one another by, for example, one minute, 15 minutes, 30 minutes, one hour, two hours, six hours, 12 hours, one day, two days, one week, or longer. Furthermore, one or more of the fusion proteins of the invention may be administered to the subject in a single dose or in multiple doses. When multiple doses are administered, the doses may be separated from one another by, for example, one day, two days, one week, two weeks, or one month. For example, the proteins may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the proteins. For example, the dosage of the proteins can be increased if the lower dose does not sufficiently destroy or inhibit the growth of the desired target cells. Conversely, the dosage of the proteins can be decreased if the target cells are effectively destroyed or inhibited.

While the attending physician ultimately will decide the appropriate amount and dosage regimen, a therapeutically effective amount of the proteins may be, for example, in the range of about 0.0035 µg to 20 µg/kg body weight/day or 0.010 µg to 140 µg/kg body weight/week. A therapeutically effective amount may be in the range of about 0.025 µg to 10 µg/kg, for example, about 0.025, 0.035, 0.05, 0.075, 0.1, 0.25, 0.5, 1.0, 1.5, 2.0, 2.5, 3.0, 3.5, 4.0, 5.0, 6.0, 7.0; 8.0, or 9.0 µg/kg body weight administered daily, every other day, or twice a week. In addition, a therapeutically effective amount may be in the range of about 0.05, 0.7, 0.15, 0.2, 1.0, 2.0, 3.0, 4.0, 5.0, 6.0, 7.0, 8.0, 10.0, 12.0, 14.0, 16.0, or 18.0 µg/kg body weight administered weekly, every other week, or once a month. Furthermore, a therapeutically effective amount of the proteins may be, for example in the range of about 100 µg/m² to 100,000 µg/m² administered every other day, once weekly, or every other week. The therapeutically effective amount may be in the range of about 1000 µg/m² to 20,000 µg/m², for example, about 1000, 1500, 4000, or 14,000 µg/m² of the proteins administered daily, every other day, twice weekly, weekly, or every other week.

In some cases it may be desirable to modify the plasma half-life of a component alone or in the combinatorial therapeutic agent of the present invention. The plasma half-lives of therapeutic proteins have been extended using a variety of techniques such as those described by Collen et al., Bollod 71:216-219 (1998); Hotchkiss et al., Thromb. Haemostas. 60:255-261 (1988); Browne wt al., J. Biol. Chem. 263:1599-1602 (1988); Abuchowski et al., Cancer Biochem. Biophys. 7:175 (1984)). Antibodies have been chemically conjugated to toxins to generate immunotoxins which have increased half-lives in serum as compared with unconjugated toxins and the increased half-life is attributed to the native antibody. WO94/04689 teaches the use of modified immunotoxins in which the immunotoxin is linked to IgG constant region domain having the property of increasing the half-life of the protein in mammalian serum. The IgG constant region domain is CH2 or a fragment thereof.

The administration the proteins of the invention may be by any suitable means that results in a concentration of the proteins that, combined with other components, effectively destroys or inhibits the growth of target cells. The proteins may be contained in any appropriate amount in any suitable carrier substance, and is generally present in an amount of 1-95% by weight of the total weight of the composition. The composition may be provided in a dosage form that is suitable for any parenteral (e.g., subcutaneous, intravenous, intramuscular, or intraperitoneal) administration route. The pharmaceutical compositions are formulated according to conventional pharmaceutical practice (see, e.g., Remington: The Science and Practice of Pharmacy (20th ed.), ed. Gennaro, Williams & Wilkins, 2000 and Encyclopedia of Pharmaceutical Technology, eds. Swarbrick and Boylan, 1988-1999, Marcel Dekker, New York).

Experimental Results

A. Construction of Fusion Proteins and Cell Lines
Construction of Anti-CD19 ScFv VCE (Anti-CD19 VCE) Fusion Gene A synthetic gene encoding VCE was prepared by Codon Devices (Cambridge, Mass.) using codons optimized for expression in *E. Coli*. To facilitate the purification of proteins derived from VCE and to expose the ER retention signal of VCE, the sequence encoding the last 5 amino acids of wild type VCE (Lys-Asp-Glu-Leu-Lys) (SEQ ID NO:42) was replaced with a sequence encoding a Hisx6 tag and an ER retention signal (His-His-His-His-His-His-Lys-Asp-Glu-Leu) (SEQ ID NO:43). The genes encoding anti-CD5-VCE and anti-CD19-VCE fusion were prepared by genetic fusion of anti-CD5 ScFv or anti-CD19 ScFv coding regions with sequences encoding domain II and domain III of VCE, joined by a DNA sequence encoding a flexible linker (Gly-Ser-Gly-Ala-Ser) (SEQ ID NO:44). The granzyme B activable protoxin was prepared by replacing the sequence encoding the furin recognition sequence (RKPRDL) (SEQ ID NO:11) of VCE with a consensus granzyme B recognition sequence ( IEPDDL) (SEQ ID NO:17).

Construction of a Human Granzyme B-anti-CD19 ScFv (GrB-anti-CD19) Fusion Gene

The sequence corresponding to the mature human Granzyme B (amino acids 21 to 247) was amplified from a full length Granzyme B cDNA clone obtained from OriGene Inc. and inserted into the pEAK15 vector together with a synthetic anti-CD 19 ScFv DNA fragment by a three-piece ligation (pEAK15 GrB-anti-CD19L). The promoter for the fusion gene in the resulting expression construct is a CMV/chicken β-actin hybrid promoter. The open reading frame encoding the fusion protein directs the formation of a signal peptide derived from the Gaussia princeps luciferase, a synthetic N-linked glycosylation site, a FLAG tag and an enterokinase cleavage sequence followed by the mature human granzyme B sequence, a flexible linker (Gly-Gly-Gly-Ser)$_3$ (SEQ ID NO:45), the anti-CD19 ScFv, and a C-terminal 6 His tag. The desired structure of the resulting fusion protein coding sequence was confirmed by DNA sequencing.

Construction of Diphtheria Toxin Anti-CD5 ScFv (DT-Anti-CD5) Fusion Gene

A DT-anti-CD5 fusion gene was prepared by chemical synthesis by Retrogen Co. (San Diego) using codons jointly optimized for expression in *Pichia Pastoris* and in human cell lines. The sequence encoding the furin recognition site ($_{190}$RVRRSVG$_{196}$) (SEQ ID NO:46) was replaced with a consensus granzyme B recognition sequence ($_{190}$IEPDSG$_{195}$) (SEQ ID NO:47). Two potential N-linked glycosylation sites were mutated as described (Thompson et al. Protein Eng. 14(12):1035-41 (2001)) and a 6 His tag sequence was added to the C-terminus of the fusion gene for detection and purification. The fusion gene was cloned into XhoI and NotI sites of the pPIC9 vector (Invitrogen) while maintaining the α-factor signal peptide and the Kex2 cleavage site.

Generation of $CD5^+$ Raji, and Cells

Raji cells (ATCC) were maintained in RPMI 1640 (Invitrogen) supplemented with 10% iron supplemented calf serum (Hyclone), 2 mM L-Glutamax.

To prepare recombinant retroviral transducing particles, the GFP coding sequence found in the retroviral vector M3P-GFP was replaced with full length cDNA encoding human CD5. To produce vesicular stomatitis virus envelope glycoprotein (VSVG)-pseudotyped viral particles, linearized M3P-CD5 plasmid was cotransfected with pMD-MLV pMD-VSVG to 293 ETN cells, which were seeded at $5\times10^6$ per 10 $cm^2$ plate a day before transfection. M3P-CD5, pMD-MLV-G/P and pMD-VSVG DNAs were mixed and transfected at 10 μg, 7 μg and 3 μg, respectively, per 10 $cm^2$ plate, using 2.5 μl of TransFectin (Bio-Rad) per μg of DNA. Viral particles were collected 48 hours after transfection and filtered through a 0.45 μm filter (Corning).

For transduction, $5\times10^5$ Raji cells were suspended in 1.5 ml of culture medium and mixed with 1.5 ml of filtered virus in a 6-well plate. Three μl of 8 mg/ml polybrene was added to the mixture to the final concentration of 8 μg/ml. The plate was centrifuged at 2000 rpm for 1 hour before initiation of culture in a 37° C. incubator containing 5% $CO_2$. To isolate Raji cells expressing CD5, the infected cells were sorted after staining with FITC conjugated anti-human CD5 antibody (eBioscience). Raji cells expressing high concentrations of CD5 were collected and used for the cytotoxicity assay.

Flow Cytometric Analysis

The presence of CD5 and CD19 on cell surface was analyzed using indirect immunofluorescence staining. Cells were incubated with mouse anti-human CD5 or mouse anti-human CD19 (Pharmingen, San Diego, Calif.) at a concentration of 0.5 μg per one million cells. Goat $F(ab')_2$ anti-mouse IgG1 conjugated with RPEA (Southern Biotechnology) was used as secondary antibody at a concentration of 0.25 μg per million of cells. The stained cells were analyzed by flow cytometry (FAXCaliber).

B. Expression and Purification GrB-anti-CD19 Fusion from 293ETN Cells

293ETN cells were seeded at 5 $10^6$-6 $10^6$ cells per 10 $cm^2$ plate and were transfected with 12 μg of pEAK15 GrB-anti-CD19L and 25 μl of TransFectin (Bio-Rad) according to the manufacturer's protocol. Transfected cells were cultured in Opti-MEM (Invitrogen) for 3 days to allow fusion protein to accumulate. Supernatants were collected and incubated with pre-equilibrated Ni-NTA resin (Qiagen) and the fusion protein was eluted with buffer containing 50 mM HEPES pH7.5, 150 mM NaCl, 250 mM imidazole and 5% glycerol. The purified GrB-anti-CD19 fusion protein was incubated with enterokinase (New England Biolabs) at room temperature overnight to activate the proteolytic activity of Granzyme B. To remove enterokinase and N-terminal peptide released by enterokinase, the reaction mixture was subjected to affinity purification with Ni-NTA resin. In another form of preparation, the enterokinase and N-terminal peptide released by enterokinase, were removed by gel filtration purification (superdex 200, G E Healthcare). The proteolytic activity of the granzyme B-anti-CD19 ScFv was measured by incubating the purified protein with a fluorogenic peptide substrate (Ac-IEPD-AMC, Sigma Aldrich). Accumulation of fluorescent product was monitored every 30 s at excitation and emission wavelengths of 380 and 460 nm respectively for 15 min.

C. Expression and Purification of DT-anti-CD5 Fusion from *P. Pastoris*

*Pichia Pastoris* KM71 cells (Invitrogen) were transformed with the expression plasmid by electroporation. Positive clones were selected according to manufacturer's protocol.

For large scale purification, a single colony was cultured at 28° C. overnight in 10 ml Buffer Minimal Glycerol medium (BMG) pH 6.0. The overnight culture was transferred to 1 L BMG pH 6.0 and cultured at 28° C. until OD600 reached 6.0. To induce protein expression, the culture was spun down and resuspended with 100 ml Buffered (pH 6.6) Methanol-complex Medium containing 1% casamino acids (BMMYC) and cultured at 15° C. for 48 hours. Supernatants were collected and adjusted to pH 7.6 with 5% NaOH. Clarified supernatants were subjected to affinity purification as described above for the purification of the GrB-anti-CD19 fusion protein.

D. Expression and Purification of Anti-CD5-VCE and Anti-CD19 VCE Fusion Proteins from *E. coli*

DNA sequence corresponding to anti-CD5-VCE, anti-CD19-VCE and various variants thereof were cloned between the NcoI and NotI sites of the pET22b vector (Novagen). Transformed bacterial cells (BL21) were cultured in LB medium at 37° C. Protein expression was induced with 0.2 mM IPTG for overnight at 17° C. at $OD_{600}$=0.3-0.5. The bacterial periplasmic fraction was collected as described (Malik et al. Protein Expr Purif. 55(1):100-11 (2007)) and fusion protein was purified with Ni-NTA resin.

E. Expression and Purification of N-GFD-VCE, CCPE-VCE and $CCPE^2$-VCE Fusion Proteins from *E. coli*

The DNA sequences corresponding to N-GFD-VCE, CCPE-VCE and $CCPE^2$-VCE and their variants were cloned between the NcoI and NotI sites of the pET28a vector (Novagen). Transformed bacterial cells (BL21) were cultured in LB medium at 37° C. Protein expression was induced with 0.2 mM IPTG for overnight at 17° C. at $OD_{600}$=0.5-0.8. Soluble protein fraction was extracted with B-PER11 (Pierce Biotechnology) and subjected to Ni-NTA purification.

F. Identification of Putative *Vibrio cholerae* Exotoxins using BLAST Analysis

Figure 2:
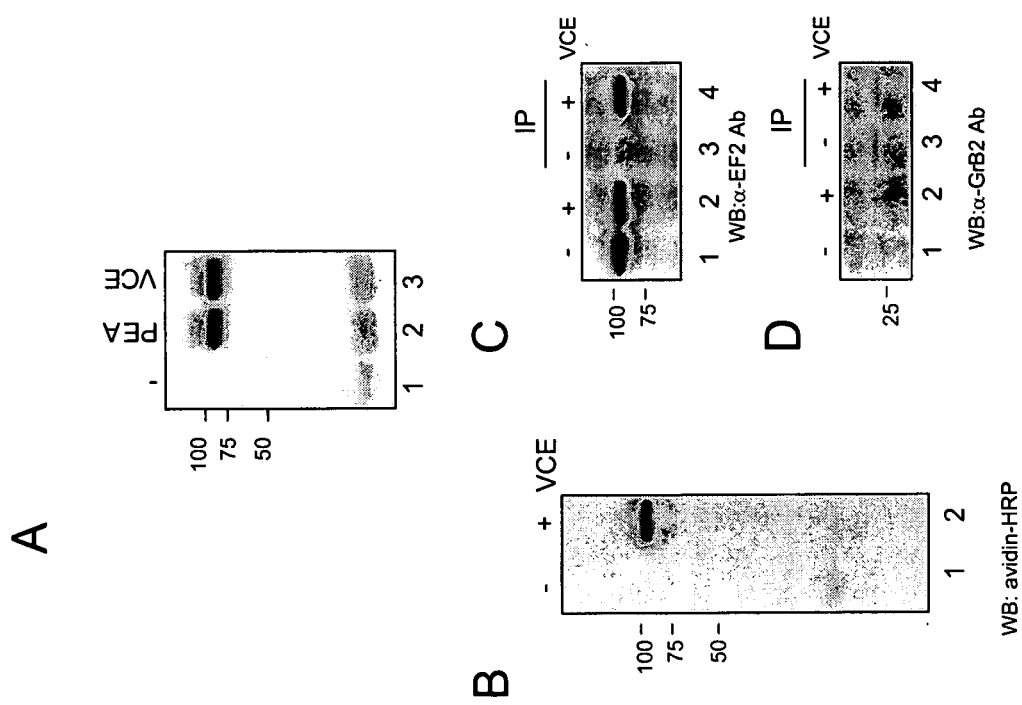
FIG. 2A is an immunoblot showing that the isolated ADPRT domain of VCE can modify a 100 kD protein in 293T cell lysate.

BLAST analysis indicates that the hypothetical toxA gene product from an aquatic strain of *Vibrio cholerae* (GI: 58615288) possesses a conserved diphtheria toxin (DT) like ADP-ribosylation domain, and adopts an overall domain structure very similar to that of *Pseudomonas* exotoxin A (PEA), with moderate amino acid sequence identity (33%). Similar to PEA, the *Vibrio* exotoxin A (VCE) possesses an N-terminal cell binding domain, an ADP-ribosylation catalytic domain near C-terminus, and a translocation domain in the middle. BLAST analysis also identified two additional hypothetical *Vibrio* exotoxins in the NCBI protein database, i.e., hypothetical exotoxin A from *Vibrio cholerae* strain 1587 (GI: 124114053) and hypothetical protein from *Vibrio cholerae* strain V51 (GI:116219709 & 116219710), which have ~97% amino acid sequence identity with the aquatic VCE and low sequence identity to PEA.

Although VCE only shares moderate protein sequence homology to PEA (33% sequence identity, FIG. 1B), residues thought to be critical for the function of PEA are conserved in VCE, including hypothesized active site residues (H440, Y481, E553 in PEA), a furin cleavage site in the domain II, and an ER retention signal at the C-terminus (FIGS. 1A and 1C). Furthermore, the predicted VCE catalytic domain sequence could be threaded onto the structure of the PEA catalytic domain, consistent with the notion that VCE folds into a structure similar to that of PEA and thus might possess similar enzymatic activity (Yates S. P., TIBS 31, 123-133, 2006).

G. Characterization of VCE

Upon cell entry, DT and PEA specifically ribosylate an exposed histidine of eukaryotic elongation factor 2 (eEF2) that has undergone extensive post-translational modification to form a residue known as diphthamide. ADP-ribosylation of diphthamide interferes with the function of eEF2 causing an arrest of protein synthesis which results in profound physiological changes and ultimately cell death. To determine whether VCE intoxicates target cells with the same toxic principle used by PEA and DT, purified ADPRT domain of VCE was incubated with human 293T cell lysate in the presence of biotin-NAD. Biotin-NAD has been shown to be a substrate for ADPRT and, as a result of ADPRT reaction, the target proteins are biotinylated (Zhang, Method Enzymol. 280:255-265 (1997)). We found that in the presence of VCE and biotin-NAD, a protein with apparent molecular weight of 100 kD was biotinylated (FIG. 2A, lane 2). A protein with identical molecular weight was also found to be modified by PEA (FIG. 4A, lane 2), suggesting that VCE and PEA may target the same protein, known in the PEA case to be eEF2. To further investigate the target protein of VCE, the modified target protein was subjected to affinity capture using monomeric avidin beads. The captured proteins were then probed with antibodies recognizing human eEF2 (FIG. 2B) or human GrB2 (FIG. 2C). eEF2, but not GrB2, can be captured by avidin beads upon modification by the ADPRT domain of VCE, supporting the view that eEF2 is the endogenous target of VCE.

Several DT-resistant cell lines have been developed, one of which, Re1.22C, has been derived from a Chinese Hamster Ovary (CHO) cell line (Moehring et al. *Somat. Cell Genet.* 5:453-468 (1979)). The specific mutation that confers DT-resistance upon the cell line Re1.22C is located on eEF2, resulting a mutant eEF2 devoid of diphthamide side-group modification (Foley et al. *J. Biol. Chem.* 270:23218-25, 1995). Although VCE modified eEF2 from wild type CHO cells and 293T cells, VCE failed to modified eEF2 from Re1.22C (FIG. 3B, compare lanes 1 and 2 to 3). These data strongly support the view that VCE, like PEA and DT, specifically modifies eEF2.

H. Replacing the Cell Binding Domain of VCE

To address if VCE can be made to function as conventional immunotoxins, we replaced the DNA sequences encoding domain I of VCE with those encoding the N-terminal growth factor-like domain of urokinase-like plasminogen activator to afford VCE fusion protein N-GFD-VCE. The N-terminal growth factor-like domain of urokinase-like plasminogen activator has been shown to bind urokinase-like plasminogen activator receptor (uPAR/CD87) with very high affinity (~0.1 nM) (Appella et al. J. Biol. Chem. 262:4437-4440 (1987)), and immunotoxins bearing the N-terminal growth factor-like domain of urokinase-like plasminogen activator have been reported to be highly toxic to target cells expressing uPAR/CD87 (Rajagopal and Kreitman. J. Biol. Chem. 275:7566-7573 (2000); Ramage et al. Leuk. Res. 27:79-84 (2003)). The N-GFD-VCE was prepared in *E. coli*, purified, and incubated with Jurkat T cells, which have previously been shown to express a low level of uPAR/CD87 (800+/−50/cell). N-GFD-VCE efficiently killed Jurkat cells with $IC_{50}$=0.4 nM (FIG. 4B triangles). In contrast, N-GFD-VCE has little or no toxicity to Raji cells, which have little or no detectable uPAR/CD87. These results suggest that domain I, but not domain II or III, of VCE is responsible for cell binding and that a fusion protein comprising domain II and III of VCE and a targeting principle replacing domain I can function as a selective cytotoxic agent. In another example domain I of VCE was replaced with a single chain Fv (scFv) domain. scFv-VCE fusion protein targeting CD5 or CD19 efficiently killed cell lines expressing CD5 and CD19, respectively (FIG. 8 triangles and data not shown).

Figure 5:
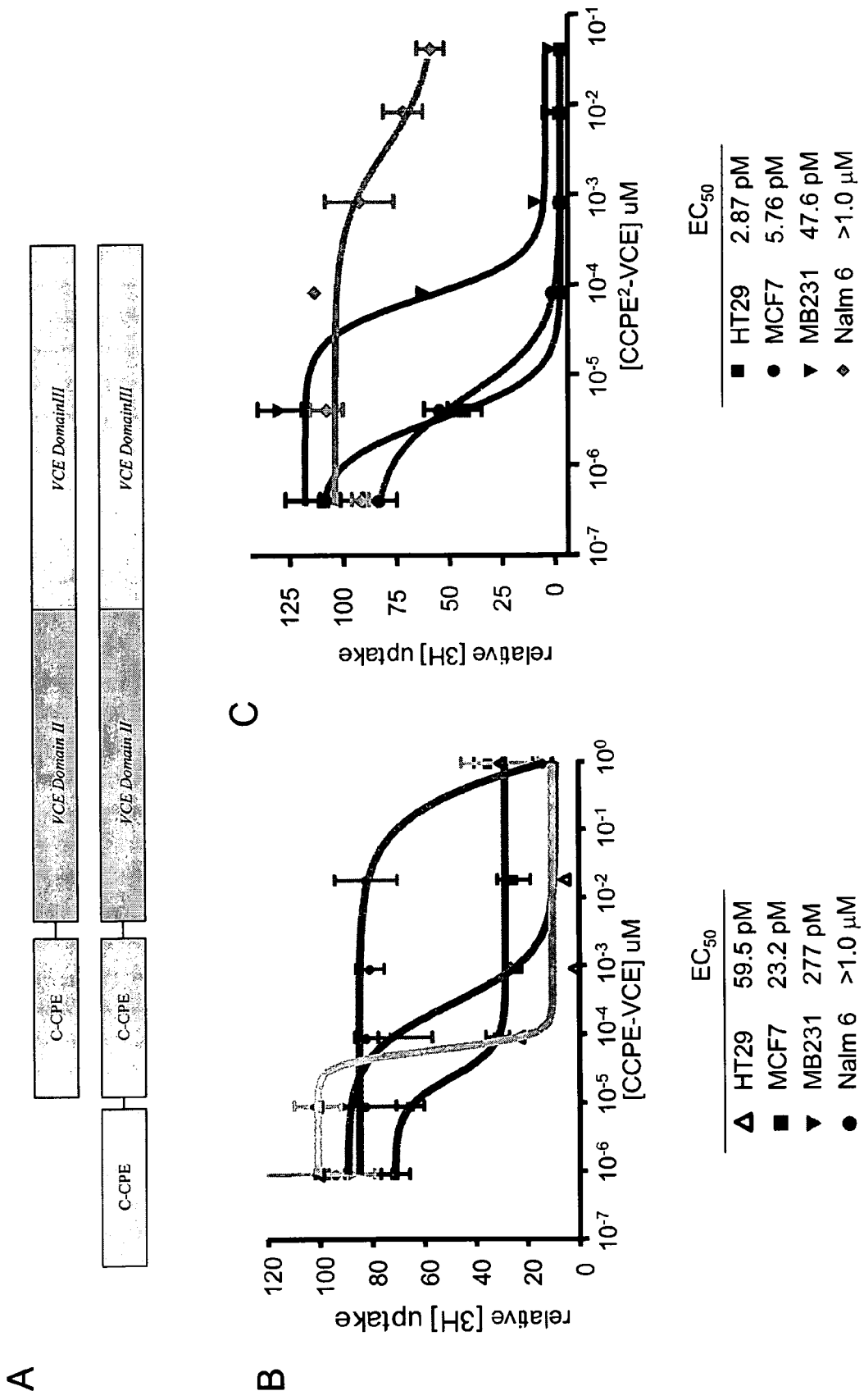

In yet another example domain I of VCE was replaced with a cell targeting domain derived from C-terminal domain of *Clostridium perfringens* enterotoxin (CCPE), known to target the tight junction proteins Claudin3 and 4. CCPE-VCE fusion protein efficiently killed cell lines expressing Claudin3 and/or 4, including HT29, MCF7 and MB231, and was ineffective in killing a negative control cell line Nalm6 (FIG. 5). To increase the affinity of CCPE based immunotoxins to cells expressing Claudin3/4, we replaced domain I of VCE with tandem CCPE domains, resulting in the fusion protein $CCPE^2$-VCE. The EC50 of $CCPE^2$-VCE for the inhibition of protein synthesis by claudin3/4 positive cell lines was about 5-10 times lower than that of CCPE-VCE, whereas toxicity to a negative cell line was relatively unchanged (compare FIGS. 6B to 6C). These results support the notion that VCE can be linked to a number of cell targeting moieties, such as N-GFD of u-PA, ScFv, one of two copies of CCPE and other naturally occurring or artificially created affinity reagents, creating VCE fusion proteins that can selectively target cells of interest.

I. Identification of Residues Critical for Cytotoxicity of VCE

Mutational analyses of DT and PEA have identified several residues critical for various aspects of toxin function. By sequence alignment, we identified corresponding residues in VCE. A putative catalytically inactive mutant was created by replacing glutamic acid 613 (E613A) with alanine. In vitro ADPRT assay with human eEF2 indicated that ADPRT activity of E613A mutant was significantly impaired compared with the wild type counterpart (FIG. 4A, compare lanes 4 and 5), and cell culture experiments showed that N-GFD-$VCE_{E613A}$ was not toxic to Jurkat cells (FIG. 4B). Tryptophan 305 of PEA has been shown to play an important role in initiating membrane insertion of PEA (Mere et al. J. Biol. Chem. 280:21194-21201 (2005)). Mutation of W305 of PEA to phenylalanine or alanine reduced the toxicity of PEA by 3- or 30-fold, respectively. Sequence analysis suggested that the residue functionally corresponding to W305 of PEA might be phenylalanine 343 (F343) in VCE. We mutated F343 of VCE to tryptophan (F343W) and alanine (F343A) and found that although mutations at F343 did not alter the ADPRT activity (FIG. 4A compare lanes 7 and 8 to 5), the cytotoxicity of the mutant N-GFD-VCE forms was reduced by 1.6 fold (F343W) or 60 fold (F343A) (FIG. 4B).

In addition, a mutant N-GFD-VCE fusion protein in which the furin cleavage site was replaced with a granzyme B cleavage site exhibited functional ADPRT activity (FIG. 4A, compare lane 3 and 4), but was not cytotoxic to target cells (FIG. 4B). Together, this series of experiments identified a residue critical for catalytic activity of ADPRT, a residue critical for membrane insertion, and the furin cleavage sequence critical for activation of VCE.

J. Engineering VCE for Specific Cell Surface Targeting and Proteolytic Activation To address whether VCE-based immunotoxins can be adapted as the protoxin component of a combinatorial targeting strategy, the furin cleavage sequence of VCE was replaced with a granzyme B cleavage sequence or with candidate cleavage sequences for a mutant granzyme B. Substitution of the furin cleavage sequence (RKPR↓DL) (SEQ ID NO:48) with a granzyme B cleavage (IEPD↓SG, IEPD↓DL, IAPD↓SG and IAPD↓DL) (SEQ ID NOs:49-52) sequence significantly reduced the toxicity of N-GFD-VCE to Jurkat cells expressing human CD19, although the modified toxin retained full enzymatic activity (FIG. 4A compare lane 3 and 4). In the presence of GrB-anti-CD19, N-GFD-VCE was activated and exhibited cytotoxicity to target cells (FIG. 4B), suggesting that GrB-anti-CD19 was able to proteolytically activate N-GFD-VCE bearing a granzyme B cleavage site in place of the endogenous furin recognition sequence.

Surprisingly, when the ability of granzyme B to cleave three anti-CD-based immunotoxins, anti-CD5-PE, anti-CD5-VCE and DT-anti-CD5, was compared, the engineered granzyme B sites were not equally susceptible to cleavage. Under conditions leading to the cleavage of a majority of VCE fusion protein, only a small fraction of DT and PEA fusion proteins was cleaved (FIGS. 6A-C). These results suggested that VCE might exhibit better specific toxicity in the presence of granzyme B fusion protein. The ability of the three toxin fusion proteins to kill target cells in the presence or absence of GrB-anti-CD 19 was explored. Like DT-anti-CD5 and anti-CD 5-PEA fusion proteins bearing a granzyme B cleavage sequence, anti-CD5-VCE fusion protein bearing a granzyme B cleavage sequence alone was not toxic to target cells and selectively killed target cells only in the presence of GrB-anti-CD 19 fusion protein (FIG. 7). The ability of GrB-anti-CD19 to activate cytotoxicity of modified immunotoxins was found to correlate with the ability of GrB-anti-CD19 to cleave modified immunotoxins in vitro. The relative potency illustrated by observed $EC_{50}$ values were: anti-CD5-VCE (~1.3 nM)<DT-anti-CD5 (~3.0 nM)<anti-CD5-PEA (~4.8 nM).

To further assess the effectiveness of a potential combinatorial targeting strategy, we also compared the anti-CD5-VCE bearing a granzyme B site to an anti-CD5-VCE fusion protein with endogenous furin cleavage site and an anti-CD5-VCE fusion protein in which one of the active sites was mutated (glutamic acid 613 to alanine). As expected, fusion proteins bearing the active site mutation failed to kill target cells at all concentrations tested (FIG. 7, diamonds). Replacing the furin cleavage site with a granzyme B cleavage site substantially reduced the toxicity of anti-CD5-VCE fusion protein (FIG. 8, squares). However, in the presence of 1.0 nM GrB-anti-CD19, the cytotoxicity of anti-CD5-VCE fusion protein was fully restored (FIG. 8, compare triangles with inverted triangles). These results demonstrate that binary targeting agents are highly selective and can be as effective as conventional immunotoxins.

K. Selective Killing of PBMNC from a CLL Patient by the Combination of Anti-CD5-VCE and Anti-CD19-GrB To test whether the binary targeting agents can specifically kill B cell-chronic lymphocytic leukemia cells, we carried out a cytostasis assay with purified peripheral blood mononuclear cells (PBMNC) from a patient with B cell chronic lymphocytic leukemia (B-CLL). FACS analysis indicated that about 30% of the PBMNC from the patient were $CD5^+$ B cells (FIG. 9A). Individual components of the binary targeting agents were not toxic to PBMNC (FIGS. 9B and C). At the concentrations at which the binary targeting agents completely inhibited protein synthesis activity of a reporter cell line ($CD5^+$ Raji), about 30% of total protein synthesis activity from PBMNC was arrested. No further inhibition of protein synthesis was observed as the concentration of DT-anti-CD5 was increased, consistent with the notion that the binary targeting agents only arrest the protein synthetic activity of the target cell population. These data suggested that combinatorial targeting agents can be deployed to eliminate specific cell populations from heterogeneous mixture of cells with minimal toxicity to other cell types.

L. Mutations that Reduce Vascular Leak Syndrome (VLS)

The clinical utility of immunotoxins has been limited by a variety of toxic syndromes, manifest as hepatotoxicity, neurotoxicity, and vascular leak syndrome (VLS). VLS is characterized by hypoalbuminemia, pleural effusion, weight gain, edema, hypotension, increase in hematocrit and organ failure. Dose escalation and hence effectiveness of immunotoxins, including that are PEA-based (Pai, et al., Nat. Med., 2: 350-353, 1996), has been limited by VLS. Using a rat model, the toxin component of a PEA-based immunotoxin was found to be responsible for inducing VLS, and nonsteroidal anti-inflammatory agents were found to block VLS in rats receiving PEA immunotoxin. (Seegall et al., Clin. Cancer Res. 3(3): 339-45 (1997)). The mechanisms underlying VLS are unclear and are likely to involve a cascade of events that are initiated by endothelial cell (EC) damage and involve inflammatory reaction. It has been proposed that a structural motif in VLS-inducing molecules may be responsible for binding to endothelial cells and initiating VLS. The proposed motif is (x)D(y) where x=L, I, G, or V and y=V, L, or S. Previous studies suggested that deletions or mutations within this motif and/or its flanking sequences might prevent VLS (Baluna et al., Proc. Natl. Acad. Sci. USA 96:3957-3962 (1999) and Smallshaw J E et al. Nat. Biotechnol. 21:387-391 (2003)).

A recent study has shown that mutations within the translocation and catalytic domains of PEA that are adjacent to, but not specifically at, the three (x)D(y) motifs, i.e., GDL (323-325), GDV (405-407) and GDV (580-582), may also reduce VLS. In particular, a triple mutant R293K/N416Q/R576K was shown to maintain cytotoxicity to targeted cells while exhibiting much weakened VLS induction (Wang et al. Cancer Immunol Immunother. 56(11):1775-83 (2007)). The residues within PEA are shown in FIG. 10 with corresponding residues in VCE. To illustrate the similarity of the mutated regions between PEA and VCE, the nearest neighboring consensus residues are shown underlined in orange color.

Because VCE folds into a structure similar to that of PEA (Yates S. P., TIBS 31, 123-133, 2006), corresponding mutations on VCE, i.e., N338K/N468Q/N636K, may reduce potential VLS induction by VCE. It is noteworthy that the translocation and catalytic domains of VCE do not contain any (x)D(y) motifs. This may render VCE less toxic. On the other hand, the observed reduction in VLS by R293K/N416Q/R576K PEA mutant may not necessarily be related to these motifs. Corresponding VCE mutations N338K, N468Q, and/or N636K are preferred embodiments for VLS reduction.

M. Mutations that Reduce Antigenicity of VCE

When PEA-based immunotoxins are administered to patients, neutralizing antibodies often develop within 3 weeks. These antibodies, which almost always react with PEA and very infrequently with the cell-targeting domain, limit the number of treatment cycles that can be applied (Roscoe et al. Eur. J. Immunol. 27(6):1459-68 (1997)). The major human B cell epitopes of the translocation and catalytic domains of PEA have been mapped, and the corresponding antibodies characterized (Onda et al., J. Immunol. 177(12): 8822-34 (2006)). The location of each epitope on PEA was determined by preparing 41 mutants of PEA in which bulky surface residues were mutated to either alanine or glycine. All 7 major epitope groups and 9 of 13 epitope subgroups were identified by 14 different mutants and these retained high cytotoxic activity. The 14 mutants reported with diminished binding to antibodies are predicted to be less antigenic forms of PEA in an epitope basis (Onda et al., J. Immunol. 177(12): 8822-34 (2006)). The positions of these mutations within PEA, as well as the corresponding residues within VCE, are shown in FIG. 10 (identified by arrows). To illustrate the similarity of the mutated regions between PEA and VCE, the nearest neighboring consensus residues (including itself if it is a consensus) are shown underlined in orange color. The closest consensus residue to R576 of PEA and Y636 of VCE are four residues away (see also FIG. 10 for illustration of this position).

The reported mutations of PEA include: R313A, D324A, E327A, Q332A, R412A, E431A, R432G, R467A, R490A, R513A, R538A, R576A, K590A. Corresponding residues in VCE are shown in FIG. 11. Potential mutations in VCE include: T358, D374, R377, N381, N382, Q464, R483, E484, G522, A552, R575, R598, Y636, and K648. Mutations may be made to small residues such as Gly and Ala to reduce antigenicity. Some of these, including N381, N382, Q464, G522, and A552, are already small residues and may not need to be mutated.

Additional mutations, including many shown in FIG. 11, have been disclosed in WO27016150A2.

N. Transduction of Heterologous Proteins by the Translocation Domain of VCE

The translocation domain of PEA has been shown to be able to shuttle heterologous proteins or small molecules into the cytosol of target cells (Theuer et al., J. Biol. Chem. 267: 16872-16877 (1992); Prior et al., Cell 64:1017-1023 (1991); U.S. Pat. No. 6,086,900). To address if the translocation domain of VCE also is capable of shuttling heterologous proteins into the cytosol of target cells, we replaced the ADPRT domain of VCE with the ADPRT domain of PEA, which only shares about 39% identity to the ADPRT domain of VCE. We found that the fusion protein bearing the VCE translocation domain and ADPRT domain of PEA (N-GFD-VCE-PEA) is toxic to Jurkat cells, indicating that the ADPRT domain of PEA was shuttled to the cytosol of target cells by the translocation domain of VCE (FIG. 12). These results support the idea that the translocation domain of VCE can be employed to carry proteins, or molecules that are not permeable to lipid bilayer, across cell membranes.

O. Generation of Polyclonal and Monoclonal Antibodies Against VCE

Polyclonal antibodies to VCE were prepared by immunization of rabbits with domain III (the ADPRT domain) of VCE. To reduce any potential toxicity of the antigen to the host animals, a mutant VCE ADPRT domain in which the active site glutamic acid residue was replaced with an alanine (E613A) was used as the antigen. The production of anti-VCE polyclonal antibodies was carried out by the Affinity Bioreagents (Golden, Colo.). Sera from immunized rabbits was affinity purified and titered by ELISA assay. Polyclonal antibodies raised in two rabbits (9375 and 9376) reacted specifically to a fusion protein consisting of the maltose binding protein (VCE antigen) and ADPRT domain of VCE, but not to a maltose binding protein alone (control antigen) (FIG. 13A). The polyclonal antibodies were also used as immunoblot reagents to detect the ADPRT domain of VCE. As shown in FIG. 13B, polyclonal antibodies raised from rabbit 9375 specifically reacted with anti-CD19-VCE fusion protein determinants, but did not recognize anti-CD5-diphtheria toxin fusion protein nor any protein from 293T cell lysate. Similar results were obtained with antibodies from rabbit 9376. These results indicated that the affinity-purified polyclonal antibodies are highly specific to the ADPRT domain of VCE and to fusion proteins containing ADPRT domain of VCE. To create monoclonal antibodies against VCE, the spleen of the animal 9376 was retrieved and sent to Epitomics Inc. (Burlingame, Calif.) for the production of hybridomas. Several high affinity monoclonal antibodies that react with native VCE antigen as well as antibodies that react with both native VCE and blot-transferred VCE. FIG. 13C shows SPR results of several monoclonal antibodies identified from the screening of about 3000 hybridomas.

TABLE 3

Sequences

VCE
(SEQ ID NO: 1)
Wild type sequence
gi|58615288|gb|AAW80252.1|hypothetical exotoxin A
[Vibrio cholerae]
MYLTFYLEKVMKKMLLIAGATVISSMAHPTFAVEDELNIFDECRSPCSLT
PEPGKPIQSKLSIPSDVVLDEGVLYYSMTINDEQNDIKDEDKGESIITIG
EFATVRATRHYVNQDAPFGVIHLDITTENGTKTYSYNRKEGEFAINWLVP
IGEDSPASIKISVDELDQQRNIIEVPKLYSIDLDNQTLEQWKTQGNVSFS
VTRPEHNIAISWPSVSYKAAQKEGSRHKRWAHWHTGLALCWLVPMDAIYN
YITQQNCTLGDNWFGGSYETVAGTPKVITVKQGIEQKPVEQRIHFSKGNA
MSALAAHRVCGVPLETLARSRKPRDLTDDLSCAYQAQNIVSLFVATRILF
SHLDSVFTLNLDEQEPEVAERLSDLRRINENNPGMVTQVLTVARQIYNDY
VTHHPGLTPEQTSAGAQAADILSLFCPDADKSCVASNNDQANINIESRSG
RSYLPENRAVITPQGVTNWTYQELEATHQALTREGYVFVGYHGTNHVAAQ
TIVNRIAPVPRGNNTENEEKWGGLYVATHAEVAHGYARIKEGTGEYGLPT
RAERDARGVMLRVYIPRASLERFYRTNTPLENAEEHITQVIGHSLPLRNE
AFTGPESAGGEDETVIGWDMAIHAVAIPSTIPGNAYEELAIDEEAVAKEQ
SISTKPPYKERKDELK SEQ ID NO: 2
Protein sequence corresponding to ADPRT domain of
VCE
mgpenravitpqgvtnwtyqeleathqaltregyvfvgyhgtnhvaaqti
vnriapvprgnnteneekwgglyvathaevahgyarikegtgeyglptra
erdargvmlrvyipraslerfyrtntplenaeehitqvighslplrneaf
tgpesaggedetvigwdmaihavaipstipgnayeelaideeavakeqsi
stkppykerhhhhhhkdel SEQ ID NO: 3
synthetic gene encoding ADPRT domain of VCE
ATGGGCCCTGAAAATCGCGCGGTTATCACCCCGCAAGGCGTCACGAACTG
GACCTATCAGGAGCTGGAAGCCACTCACCAGGCACTGACACGTGAAGGTT
ACGTGTTTGTAGGGTATCATGGAACGAATCACGTTGCTGCGCAAACCATT
GTGAACCGCATCGCCCCGGTCCCACGTGGCAATAACACTGAGAATGAAGA
GAAATGGGGTGGCCTGTACGTTGCAACACATGCGGAAGTAGCTCACGGTT
ATGCCCGCATTAAAGAAGGGACCGGAGAGTATGGCCTGCCTACGCGTGCA
GAACGCGACGCGCGTGGTGTGATGCTGCGCGTCTACATCCCGCGTGCTTC
GCTGGAGCGCTTCTATCGTACCAACACTCCGCTGGAAAATGCCGAAGAGC
ATATTACACAGGTTATCGGCCACTCTCTGCCACTGCGCAACGAAGCATTT
ACGGGTCCTGAAAGTGCGGGGGAGAGGATGAAACCGTGATTGGCTGGGA
CATGGCTATCCATGCCGTAGCAATTCCGTCAACTATTCCAGGTAATGCGT
ACGAGGAACTGGCCATCGATGAAGAGGCAGTCGCGAAAGAACAATCCATT
TCGACAAAACCGCCTTATAAAGAGCGTCACCATCATCACCATCACAAAGA
TGAACTGTAA SEQ ID NO: 53
N-GFD-VCE
Synthetic gene encoding N-GFD-VCE with endogenous
furin cleavage site
ATGGGCTCCAACGAACTGCATCAGGTGCCGAGCAACTGCGATTGTCTGAA
CGGCGGTACCTGCGTTTCCAACAAATATTTTTCTAACATTCACTGGTGTA
ACTGCCCGAAAAAATTCGGTGGACAACATTGTGAAATCGACGGCGGTGGT
GGTTCGGGCGGTGGCGGTTCGGGTGGCGGTGGCAGCTCTAGCAAGGCAA
TGCCATGAGTGCACTGGCTGCGCACCGCGTATGCGGTGTGCCGCTGGAGA
CACTGGCCCGTTCACGCAAACCACGTGACCTGACCGATGACCTGAGCTGC
GCGTATCAGGCCCAAAATATTGTGTCTCTGTTTGTTGCAACGCGTATCCT
GTTCAGTCATCTGGATTCAGTCTTTACTCTGAACCTGGACGAACAGGAGC
CGGAAGTAGCTGAGCGCCTGTCCGATCTGCGTCGCATTAATGAAAACAAT
CCAGGCATGGTGACACAAGTTCTGACCGTCGCGCGTCAGATCTACAACGA
CTATGTAACGCACCATCCTGGTCTGACTCCGGAACAGACATCGGCCGGGG
CACAAGCTGCGGATATTCTGAGCCTGTTCTGTCCAGATGCCGACAAATCT
TGCGTGGCAAGTAATAACGATCAGGCTAATATCAACATTGAGTCACGCTC
CGGACGTTCGTACCTGCCTGAAAATCGCGCGGTTATCACCCCGCAAGGCG
TCACGAACTGGACCTATCAGGAGCTGGAAGCCACTCACCAGGCACTGACA
CGTGAAGGTTACGTGTTTGTAGGGTATCATGGAACGAATCACGTTGCTGC
GCAAACCATTGTGAACCGCATCGCCCCGGTCCCACGTGGCAATAACACTG
AGAATGAAGAGAAATGGGGTGGCCTGTACGTTGCAACACATGCGGAAGTA
GCTCACGGTTATGCCCGCATTAAAGAAGGGACCGGAGAGTATGGCCTGCC
TACGCGTGCAGAACGCGACGCGCGTGGTGTGATGCTGCGCGTCTACATCC
CGCGTGCTTCGCTGGAGCGCTTCTATCGTACCAACACTCCGCTGGAAAAT
GCCGAAGAGCATATTACACAGGTTATCGGCCACTCTCTGCCACTGCGCAA
CGAAGCATTTACGGGTCCTGAAAGTGCGGGGGAGAGGATGAAACCGTGA
TTGGCTGGGACATGGCTATCCATGCCGTAGCAATTCCGTCAACTATTCCA
GGTAATGCGTACGAGGAACTGGCCATCGATGAAGAGGCAGTCGCGAAAGA
ACAATCCATTTCGACAAAACCGCCTTATAAAGAGCGTCACCATCATCACC
ATCACAAAGATGAACTGTAAGCGGCCGC

TABLE 3-continued

Sequences

SEQ ID NO: 54
Protein sequence corresponding to synthetic N-GFD-VCE with endogenous furin cleavage site
MSNELHQVPSN CDCLNGGTCV SNKYFSNIHW CNCPKKFGGQ HCEID
GGGGSGGGGSGGGGSSSKGNAMSALAAHRVCGVPLETLARSRKPRDLTDD
LSCAYQAQNIVSLFVATRILFSHLDSVFTLNLDEQEPEVAERLSDLRRIN
ENNPGMVTQVLTVARQIYNDYVTHHPGLTPEQTSAGAQAADILSLFCPDA
DKSCVASNNDQANINIESRSGRSYLPENRAVITPQGVTNWTYQELEATHQ
ALTREGYVFVGYHGTNHVAAQTIVNRIAPVPRGNNTENEEKWGGLYVATH
AEVAHGYARIKEGTGEYGLPTRAERDARGVMLRVYIPRASLERFYRTNTP
LENAEEHITQVIGHSLPLRNEAFTGPESAGGEDETVIGWDMAIHAVAIPS
TIPGNAYEELAIDEEAVAKEQSISTKPPYKERHHHHHHKDEL SEQ ID NO: 55
N-GFD-VCE
Synthetic gene encoding N-GFD-VCE with a granzyme B cleavage site
CCATGGGCTCCAACGAACTGCATCAGGTGCCGAGCAACTGCGATTGTCTG
AACGGCGGTACCTGCGTTTCCAACAAATATTTTTCTAACATTCACTGGTG
TAACTGCCCGAAAAAATTCGGTGGACAACATTGTGAAATCGACGGCGGTG
GTGGTTCGGGCGGTGGCGGTTCGGGTGGCGGTGGCAGCTCTAGCAAAGGC
AACGCGATGAGCGCGCTGGCCGCACATCGTGTGTGCGGCGTTCCGCTGGA
AACCCTGGCTCGCTCTATTGAGCCAGATAGTGGTACCGATGACCTGAGC
GCGCGTATCAGGCCCAAAATATTGTGTCTCTGTTTGTTGCAACGCGTATC
CTGTTCAGTCATCTGGATTCAGTCTTTACTCTGAACCTGGACGAACAGGA
GCCGGAAGTAGCTGAGCGCCTGTCCGATCGCGTCGCATTAATGAAAACA
ATCAGGCATGGTGACACAAGTTCTGACCGTCGCGCTCAGATCTACAAC
GACTATGTAACGCACCATCCTGGTCTGACTCCGGAACAGACATCGGCCGG
GGCACAAGCTGCGGATATTCTGAGCCTGTTCGTGTCCAGATGCCGACAAAT
CTTGCGTGGCAAGTAATAACGATCAGGCTAATATCAACATTGAGTCACGC
TCCGGACGTTCGTACCTGCCTGAAAATCGCGCGGTTATCACCCCGCAAGG
CGTCACGAACTGGACCTATCAGGAGCTGGAAGCCACTCACCAGGCACTGA
CACGTGAAGGTTACGTGTTTGTAGGGTATCATGGAACGAATCACGTTGCT
GCGCAAACCATTGTGAACCGCATCGCCCCGGTCCCACGTGGCAATAACAC
TGAGAATGAAGAGAATTGGGGTGGCCTGTACGTTGCAACACATGCGGAAG
TAGCTCACGGTTATGCCCGCATTAAAGAAGGGACCGGAGAGTATGGCCTG
CCTACGCGTGCAGAACGCGACGCGCGTGGTGTGATGCTGCGCGTCTACAT
CCCGCGTGCTTCGCTGGAGCGCTTCTATCGTACCAACACTCCGCTGGAAA
ATGCCGAAGAGCATATTACACAGGTTATCGGCCACTCTCTGCCACTGCGC
AACGAGCATTTACGGGTCCTGAAAGTGCGGGGGGAGGATGAAACCGT
GATTGGCTGGGACATGGCTATCCATGCCGTAGCAATTCCGTCAACTATTC
CAGGTAATGCGTACGAGGAACTGGCCATCGATGAAGAGGCAGTCGCGAAA
GAACAATCCATTTCGACAAAACCGCCTTATAAAGAGCGTCACCATCATCA
CCATCACAAAGATGAACTGTAAGCGGCCGC Sequences replacing bolded underlined region have been made, including sequence encoding IEPDDL SEQ ID NO: 56 (ATTGAGCCAGATGACCTG) SEQ ID NO: 57, IAPDSG SEQ ID NO: 58 (ATTGCTCCAGATAGTGGT) SEQ ID NO: 59, and IAPDDL SEQ ID NO: 60 (ATTGCTCCAGATGACCTG) SEQ ID NO: 61.

SEQ ID NO: 62
Protein sequence corresponding to synthetic N-GFD-VCE with a granzyme B cleavage site
MSNELHQVPSNCDCLNGGTCVSNKYFSNIHWCNCPKKFGGQHCEIDGGGG
SGGGGSGGGGSSSKGNAMSALAAHRVCGVPLETLARSIEPDSGTDDLSCA
YQAQNIVSLFVATRILFSHLDSVFTLNLDEQEPEVAERLSDLRRINENNP
GMVTQVLTVARQIYNDYVTHHPGLTPEQTSAGAQAADILSLFCPDADKSC
VASNNDQANINIESRSGRSYLPENRAVITPQGVTNWTYQELEATHQALTR
EGYVFVGYHGTNHVAAQTIVNRIAPVPRGNNTENEEKWGGLYVATHAEVA
HGYARIKEGTGEYGLPTRAERDARGVMLRVYIPRASLERFYRTNTPLENA
EEHITQVIGHSLPLRNEAFTGPESAGGEDETVIGWDMAIHAVAIPSTIPG
NAYEELAIDEEAVAKEQSISTKPPYKERHHHHHHKDEL Sequences in place of underlined region have been made, including IEPDDL SEQ ID NO: 56, IAPDSG SEQ ID NO: 58 and IAPDDL SEQ ID NO: 60.

N-GFD-VCE
Synthetic gene encoding N-GFD-VCE with a granzyme B cleavage site and a amino acid substitution at Phenylalanine 343 (with alanine F343A, or with tryptophan F343W)

SEQ ID NO: 63
CCATGGGCTCCAACGAACTGCATCAGGTGCCGAGCAACTGCGATTGTCTG
AACGGCGGTACCTGCGTTTCCAACAAATATTTTTCTAACATTCACTGGTG
TAACTGCCCGAAAAAATTCGGTGGACAACATTGTGAAATCGACGGCGGTG
GTGGTTCGGGCGGTGGCGGTTCGGGTGGCGGTGGCAGCTCTAGCAAAGGC
AACGCGATGAGCGCGCTGGCCGCACATCGTGTGTGCGGCGTTCCGCTGGA
AACCCTGGCTCGCTCTATTGAGCCAGATAGTGGTACCGATGACCTGAGCT
GCGCGTATCAGGCCCAAAATATTGTGTCTCTTTTGTTGCAACGCGTATC
CTGTTCAGTCATCTGGATTCAGTCTTTACTCTGAACCTGGACGAACAGGA
GCCGGAAGTAGCTGAGCGCCTGTCCGATCGCGTCGCATTAATGAAAACA
ATCAGGCATGGTGACACAAGTTCTGACCGTCGCGCTCAGATCTACAAC
GACTATGTAACGCACCATCCTGGTCTGACTCCGGAACAGACATCGGCCGG
GGCACAAGCTGCGGATATTCTGAGCCTGTTCGTCCAGATGCCGACAAAT
CTTGCGTGGCAAGTAATAACGATCAGGCTAATATCAACATTGAGTCACGC
TCCGGACGTTCGTACCTGCCTGAAAATCGCGCGGTTATCACCCCGCAAGG
CGTCACGAACTGGACCTATCAGGAGCTGGAAGCCACTCACCAGGCACTGA
CACGTGAAGGTTACGTGTTTGTAGGGTATCATGGAACGAATCACGTTGCT
GCGCAAACCATTGTGAACCGCATCGCCCCGGTCCCACGTGGCAATAACAC
TGAGAATGAAGAGAATTGGGGTGGCCTGTACGTTGCAACACATGCGGAAG
TAGCTCACGGTTATGCCCGCATTAAAGAAGGGACCGGAGAGTATGGCCTG
CCTACGCGTGCAGAACGCGACGCGCGTGGTGTGATGCTGCGCGTCTACAT
CCCGCGTGCTTCGCTGGAGCGCTTCTATCGTACCAACACTCCGCTGGAAA
ATGCCGAAGAGCATATTACACAGGTTATCGGCCACTCTCTGCCACTGCGC
AACGAAGCATTTACGGGTCCTGAAAGTGCCGGGGGGAGAGGATGAAACCGT
GATTGGCTGGGACATGGCTATCCATGCCGTAGCAATTCCGTCAACTATTC
CAGGTAATGCGTACGAGGAACTGGCCATCGATGAAGAGGCAGTCGCGAAA
GAACAATCCATTTCGACAAAACCGCCTTATAAAGAGCGTCACCATCATCA
CCATCACAAAGATGAACTGTAAGCGGCCGC

Underlined TTT was replaced with TGG to yield F343W mutant or with GCG to yield F343A mutant Protein sequence corresponding to synthetic N-GFD-VCE with a granzyme B cleavage site and a amino acid substitution at Phenylalanine 343 (with alanine F3434A, or with tryptophan F343W)

SEQ ID NO: 64
MSNELHQVPSNCDCLNGGTCVSNKYFSNIHWCNCPKKFGGQHCEIDGGGG
SGGGGSGGGGSSSKGNAMSALAAHRVCGVPLETLARSIEPDDLTDDLSCA
YQAQNIVSLFVATRILFSHLDSVFTLNLDEQEPEVAERLSDLRRINENNP
GMVTQVLTVARQTYNDYVTHHPGLTPEQTSAGAQAADILSLFCPDADKSC
VASNNDQANINIESRSGRSYLPENRAVITPQGVTNWTYQELEATHQALTR
EGYVFVGYHGTNHVAAQTIVNRIAPVPRGNNTENEEKWGGLYVATHAEVA
HGYARIKEGTGEYGLPTRAERDARGVMLRVYIPRASLERFYRTNTPLENA
EEHITQVIGHSLPLRNEAFTGPESAGGEDETVIGWDMAIHAVAIPSTIPG
NAYEELAIDEEAVAKEQSISTKPPYKERHHHHHHKDEL

Underlined F was replaced with W to yield F343W mutant or with A to yield F343A mutant N-GFD-VCE
SEQ ID NO: 65
Synthetic gene encoding N-GFD-VCE with endogenous furin cleavage site and substitution of Glu 613 with Ala (E613A)
ATGGGCTCCAACGAACTGCATCAGGTGCCGAGCAACTGCGATTGTCTGAA
CGGCGGTACCTGCGTTTCCAACAAATATTTTTCTAACATTCACTGGTGTA
ACTGCCCGAAAAAATTCGGTGGACAACATTGTGAAATCGACGGCGGTGGT
GGTTCGGGCGGTGGCGGTTCGGGTGGCGGTGGCAGCTCTAGCAAAGGCAA
TGCCATGAGTGCACTGGCTGCGCACCGCGTATGCGGTGTGCCGCTGGAAA
CACTGGCCCGTTCACGCAAACCACGTGACCTGACCGATGACCTGAGCTGC
GCGTATCAGGCCCAAAATATTGTGTCTCTGTTTGTTGCAACGCGTATCCT
GTTCAGTCATCTGGATTCAGTCTTTACTCTGAACCTGGACGAACAGGAGC
CGGAAGTAGCTGAGCGCCTGTCCGATCGCGTCGCATTAATGAAAACAAT
CCAGGCATGGTGACACAAGTTCTGACCGTCGCGCGTCAGATCTACAACGA
CTATGTAACGCACCATCCTGGTCTGACTCCGGAACAGACATCGGCCGGGG
CACAAGCTGCGGATATTCTGAGCCTGTTCTGTCCAGATGCCGACAAATCT
TGCGTGGCAAGTAATAACGATCAGGCTAATATCAACATTGAGTCACGCTC
CGGACGTTCGTACCTGCCTGAAAATCGCGCGGTTATCACCCCGCAAGGCG
TCACGAACTGGACCTATCAGGAGCTGGAAGCCACTCACCAGGCACTGACA
CGTGAAGGTTACGTGTTTGTAGGGTATCATGGAACGAATCACGTTGCTGC
GCAAACCATTGTGAACCGCATCGCCCCGGTCCCACGTGGCAATAACACTG
AGAATGAAGAGAATTGGGGTGGCCTGTACGTTGCAACACATGCGGAAGTA
GCTCACGGTTATGCCCGCATTAAAGAAGGGACCGGAGAGTATGGCCTGCC
TACGCGTGCAGAACGCGACGCGCGTGGTGTGATGCTGCGCGTCTACATCC
CGCGTGCTTCGCTGGAGCGCTTCTATCGTACCAACACTCCGCTGGAAAAT
GCCGAAGAGCATATTACACAGGTTATCGGCCACTCTCTGCCACTGCGCAA
CGAAGCATTTACGGGTCCTGAAAGTGCCGGGGGAGGATGAAACCGTGA
TTGCTGGGACATGGCTATCCATGCCGTAGCAATTCCGTCAACTATTCCA
GGTAATGCGTACGAGGAACTGGCCATCGATGAAGAGGCAGTCGCGAAAGA
ACAATCCATTTCGACAAAACCGCCTTATAAAGAGCGTCACCATCATCACC
ATCACAAAGATGAACTGTAAGCGGCCGC

TABLE 3-continued

Sequences

Underlined TTT was replaced with TGG to yield F343W mutant or with GCG to yield F343A mutant SEQ ID NO: 66
Protein sequence corresponding to synthetic N-GFD-VCE with endogenous furin cleavage site and substitution of Glu 613 with Ala (E613A)
MSNELHQVPSN CDCLNGGTCV SNKYFSNIHW CNCPKKFGGQ HCEID
GGGGSGGGGSGGGGSSSKGNAMSALAAHRVCGVPLETLARSRKPRDLTDD
LSCAYQAQNIVSLFVATRILFSHLDSVFTLNLDEQEPEVAERLSDLRRIN
ENNPGMVTQVLTVARQIYNDYVTHHPGLTPEQTSAGAQAADILSLFCPDA
DKSCVASNNDQANINIESRSGRSYLPENRAVITPQGVTNWTYQELEATHQ
ALTREGYVFVGYHGTNHVAAQTIVNRIAPVPRGNNTENEEKWGGLYVATH
AEVAHGYARIKEGTGEYGLPTRAERDARGVMLRVYIPRASLERFYRTNTP
LENAEEHITQVIGHSLPLRNEAFTGPESAGGADETVIGWDMAIHAVAIPS
TIPGNAYEELAIDEEAVAKEQSISTKPPYKERHHHHHHKDEL Synthetic gene encoding GrB-anti-CD19

SEQ ID NO: 67
ATGGGCGTGAAGGTGCTGTTCGCCCTGATCTGCATCGCCGTGGCCGctcgc
cgacaactcgagctacaaggacgacgacgacaagATCATCGGGGGACATG
AGGCCAAGCCCCACTCCCGCCCTACATGGCTTATCTTATGATCTGGAT
CAGAAGTCTCTGAAGAGGTGCGGTGGCTTCCTGATACAAGACGACTTCGT
GCTGACAGCTGCTCACTGTTGGGGAAGCTCCATAAATGTCACCTTGGGG
CCCACAATATCAAAGAACAGGAGCCGACCCAGCAGTTTATCCCTGTGAAA
AGACCCATCCCCATCCAGCCTATAATCCTAAGAACTTCTCCAACGACAT
CATGCTACTGCAGCTGGAGAGAAAGGCCAAGCGGACCAGAGCTGTGCAGC
CCCTCAGGCTACCTAGCAACAAGGCCAGGTGAAGCCAGGGCAGACATGC
AGTGTGGCCGGCTGGGGGCAGACGGCCCCCTGGGAAAACACTCACACAC
ACTACAAGAGGTGAAGATGACAGTGCAGGAAGATCGAAAGTGCGAATCTG
ACTTACGCCATTATTACGACAGTACCATTGAGTTGTGCGTGGGGGACCCA
GAGATTAAAAGACTTCCTTTAAGGGGGACTCTGGAGGCCCTCTTGTGTG
TAACAAGGTGGCCCAGGGCATTGTCTCCTATGGACGAAACAATGGCATGC
CTCCACGGCCTGCACCAAAGTCTCAAGCTTTGTACACTGGATAAAGAAA
ACCATGAAACGCTACGCCATGGGAGGCGGAGGCTCCGGAGGAGGAGGGTC
CGGGGGCGGCGAAGCATGGCCAGGTGCAGCTGCAGCAGTCCGGCGCTG
AGCTGGTGCGCCCTGGCTCCTCCGTGAAAATCTCCTGCAAGGCTTCCGGC
TACGCTTTCTCCTCCTACTGGATGAACTGGGTGAAGCAGCGCCCTGGCCA
GGGCCTGGAGTGGATCGGCCAAATCTGGCCGGCGACGGCGACACCAACT
ACAACGGCAAGTTCAAGGGCAAGGCTACCCTGACCGCTGACGAGTCCTCC
TCCACCGCTTACATGCAGCTGTCCTCCCTGGCTTCCGAGGACTCCGCTGT
GTACTTCTGCGCTCGCCGCGAGACCACCACCGTGGGCCGCTACTACTACG
CTATGGACTACTGGGGCCAGGGCACCTCGGTGACCGTGTCCTCCGGCGGC
GGCGGCTCCGGCGGCGGCGGCTCCGGCGGCGGAGCTCCGACATCCTGCT
GACCCAGACCCCGGCTTCCCTGGCTGTGTCCCTGGGCCAGCGCGCTACCA
TCTCCTGCAAGGCTTCCCAGTCCGTGGACTACGACGGCGACTCCTACCTG
AACTGGTACCAGCAGATCCCGGGCCAGCCGCCGAAGCTGCTGATCTACGA
CGCTTCCAACCTGGTGTCCGGCATCCCGCCGCGCTTCTCCGGCTCCGGCT
CCGGCACCGACTTCACCCTGAACATCCACCCGGTGGAGAAGGTGGACGCT
GCTACCTACCACTGCCAGCAGTCCACCGAGGACCCGTGGACCTTCGGCGG
CGGCACCAAGCTGGAGATCAAGCGCGGTGGTGACATGCATCACCATCACC
ATCACTGA GrB-anti-CD19 Protein sequence SEQ ID NO: 68
MGVKVLFALICIAVALADNSSYKDDDDKIIGGHEAKPHSRPYMAYLMIWD
QKSLKRCGGFLIQDDFVLTAAHCWGSSINVTLGAHNIKEQEPTQQFIPVK
RPIPHPAYNPKNFSNDIMLLQLERKAKRTRAVQPLRLPSNKAQVKPGQTC
SVAGWGQTAPLGKHSHTLQEVKMTVQEDRKCESDLRHYYDSTIELCVGDP
EIKKTSFKGDSGGPLVCNKVAQGIVSYGRNNGMPPRACTKVSSFVHWIKK
TMKRYAMGGGSGGGGSGGGGSMAQVQLQQSGAELVRPGSSVKISCKASG
YAFSSYWMNWVKQRPGQGLEWIGQIWPGDGDTNYNGKFKGKATLTADESS
STAYMQLSSLASEDSAVYFCARRETTTVGRYYYAMDYWGQGTSVTVSSGG
GGSGGGGSGGGGSSDILLTQTPASLAVSLGQRATISCKASQSVDYDGDSYL
NWYQQIPGQPPKLLIYDASNLVSGIPPRFSGSGSGTDFTLNIHPVEKVDA
ATYHCQQSTEDPWTFGGGTKLEIKRGGDMHHHHHH anti-CD5-VCE
synthetic gene encoding antiCD5-VCE with endo-genous furin cleavage site SEQ ID NO: 69
ATGgccaacatccagctggtgcagtctggtcctgagctgaagaagcctgg
tgagactgtcaaaatcctccaaggcttctgggtatacttcactaact
atggtatgaactgggtgaagcaggctcctggtaagggtctgcgttggatg
ggctggattaacacccacactggtgagcctacttatgctgatgacttcaa
gggacgttttgccttctctctggaaacttctgccagcactgcctatctcc
agatcaacaacctcaaaaatgaggacactgctacttacttctgtacacgt
cgtggttacgactggtacttcgatgtctggggtgctgggaccacggtgac
cgtgttctccggggggaggtggcagcggggggaggtggcagcggcggcggga
gctccgacatcaagatgacccagtctccttcttccatgtatgcttctctg
ggtgagcgtgtcactatcacttgcaaggccagccaggacattaatagcta
tctgagctggttccatcataaacctgggaaatcctccaagaccctgatct
atcgtgctaaccgtctggttgatggggtccctctcgtttcagcggctct
ggttctgggcaagattattctctcaccatcagcagcctggactatgaaga
tatgggtatttattattgtcaacagtatgatgagtctccttggactttcg
gtgggtggcaccaagctggagatgaaaggctctggcGCTAGCAAAGGCAAT
GCCATGAGTGCACTGGCTGCGCACCGCGTATGCGGTGTGCCGCTGGAGAC
ACTGGCCCGTTCACGCAAACCACGTGACCTGACCGATGACCTGAGCTGCG
CGTATCAGGCCCAAAATATTGTGTCTCTGTTTGTTGCAACGCGTATCCTG
TTCAGTCATCTGGATTCAGTCTTTACTCTGAACCTGGACGAACAGGAGCC
GGAAGTAGCTGAGCGCCTGTCCGATCTGCGTCGCATTAATGAAAACAATC
CAGGCATGGTGACACAAGTTCTGACCGTCGCGTCAGATCTACAACGAC
TATGTAACGCACCATCCTGGTCTGACTCCGGAACAGACATCGGCCGGGGC
ACAAGCTGCGGATATTCTGAGCCTGTTCTGTCCAGATGCCGACAAATCTT
GCGTGGCAAGTAATAACGATCAGGCTAATATCAACATTGAGTCACGCTCC
GGACGTTCGTACCTGCCTGAAAATCGCGCGGTTATCACCCCGCAAGGCGT
CACGAACTGGACCTATCAGGAGCTGGAAGCCACTCACCAGGCACTGACAC
GTGAAGGTTACGTGTTTGTAGGGTATCATGGAACGAATCACGTTGCTGCG
CAAACCATTGTGAACCGCATCGCCCCGGTCCCACGTGGCAATAACACTGA
GAATGAAGAGAAATGGGGTGGCCTGTACGTTGCAACACATGCGGAAGTAG
CTCACGGTTATGCCCGCATTAAAGAAGGGACCGGAGAGTATGCCTGCCT
ACGCGTGCAGAACGCGACGCGCTGGTGTGATGCTGCGCGTCTACATCCC
GCGTGCTTCGCTGGAGCGCTTCTATCGTACCAACACTCCGCTGGAAAATG
CCGAAGAGCATATTACACAGGTTATCGGCCACTCTCTGCCCATCGCAAC
GAAGCATTTACGGGTGCTGAAAGTGCGGGGGAGGATGAAACCGTGAT
TGGCTGGGACATGGCTATCCATGCCGTAGCAATTCCGTCAACTATTCCAG
GTAATGCGTACGAGGAACTGGCCATCGATGAAGAGGCAGTCGCGAAAGAA
CAATCCATTTCGACAAAACCGCCTTATAAAGAGCGTCACCATCATCACCA
TCACAAAGATGAACTGTAA Genes with altered underlined sequences encoding various granzyme B cleavage sequences (ATTGAGCCAGATGACCTG-IEPDDL SEQ ID NO: 70; ATTGCTCCAGATAGTGGT-IAPDSG) SEQ ID NO: 71; ATTGAGCCAGATAGTGGT-IEPDSG SEQ ID NO: 72; and ATTGCTCCAGATGACCTG--IAPDDL SEQ ID NO: 73) were also made.

Protein sequence of anti-CD5-VCE with a 15 amino acid linker

SEQ ID NO: 74
MANIQLVQSGPELKKPGETVKISCKASGYTFTNYGMNWVKQAPGKGLRWM
GWINTHTGEPTYADDFKGRFAFSLETSASTAYLQINNLKNEDTATYFCTR
RGYDWYFDVWGAGTTVTVFSGGGGSGGGGSGGGGSSDIKMTQSPSSMYA
SLGERVTITCKASQDINSYLSWFHHKPGKSPKTLIYRANRLVDGVPSRFS
GSGSGQDYSLTISSLDYEDMGIYYCQQYDESPWTFGGGTKLEMKGSGASK
GNAMSALAAHRVCGVPLETLARSRKPRDLTDDLSCAYQAQNIVSLFVATR
ILFSHLDSVFTLNLDEQEPEVAERLSDLRRINENNPGMVTQVLTVARQTY
NDYVTHHPGLTPEQTSAGAQAADILSLFCPDADKSCVASNNDQANINIES
RSGRSYLPENRAVITPQGVTNWTYQELEATHQALTREGYVFVGYHGTNHV
AAQTIVNRIAPVPRGNNTENEEKWGGLYVATHAEVAHGYARIKEGTGEYG
LPTRAERDARGVMLRVYIPRASLERFYRTNTPLENAEEHITQVIGHSLPL
RNEAFTGPESAGGEDETVIGWDMAIHAVAIPSTIPGNAYEELAIDEEAVA
KEQSISTKPPYKERHHHHHHKDEL

Proteins with altered underlined sequence, including IEPDDL SEQ ID NO: 75, IAPDSG SEQ ID NO: 76, IEPDSG SEQ ID NO: 77, and IAPDDL SEQ ID NO: 78 were also made.

Anti-CD19-VCE

SEQ ID NO: 79
ATGGCCCAGGTGCAGCTGCAGCAGTCCGGCGCTGAGCTGGTGCGCCCTGG
CTCCTCCGTGAAAATCTCCTGCAAGGCTTCCGGCTACGCTTTCTCCTCCT
ACTGGATGAACTGGGTGAAGCAGCGCCCTGGCCAGGGCCTGGAGTGGATC
GGCCAAATCTGGCCGGGCGACGGCGACACCAACTACAACGGCAAGTTCAA
GGGCAAGGCTACCCTGACCGCTGACGAGTCCTCCTCCACCGCTTACATGC
AGCTGTCCTCCCTGGCTTCCGAGGACTCCGCTGTGTACTTCTGCGCTCGC
CGCGAGACCACCACCGTGGGCCGCTACTACTACGCTATGGACTACTGGGG
CCAGGGCACCTCGGTGACCGTGTCCTCCGGCGGCGGCGGCTCCGGCGGCG
GCGGCTCCGGCGGCGGTTCCGGAGACATCCTGCTGACCCAGACC
CCGGCTTCCCTGGCTGTGTCCCTGGGCCAGCGCGCTACCATCTCCTGCAA
GGCTTCCCAGTCCGTGGACTACGACGGCGACTCCTACCTGAACTGGTACC
AGCAGATCCCGGGCCAGCCGCCGAAGCTGCTGATCTACGACGCTTCCAAC
CTGGTGTCCGGCATCCCGCCGCGCTTCTCCGGCTCCGGCTCCGGCACCGA

TABLE 3-continued

Sequences

CTTCACCCTGAACATCCACCCGGTGGAGAAGGTGGACGCTGCTACCTACC
ACTGCCAGCAGTCCACCGAGGACCCGTTCGGCCGCGGCACCAAG
CTGGAGATCAAGCGCGGCTCTGGCGCTAGCAAAGGCAATGCCATGAGTGC
ACTGGCTGCGCACCGCGTATGCGGTGTGCCGCTGGAGACACTGGCCCGTT
CACGCAAACCACGTGACCTGACCGATGACCTGAGCTGCGCGTATCAGGCC
CAAAATATTGTGTCTCTGTTTGTTGCAACGCGTATCCTGTTCAGTCATCT
GGATTCAGTCTTTACTCTGAACCTGGACGAACAGGAGCCGGAAGTAGCTG
AGCGCCTGTCCGATCTGCGTCGCATTAATGAAAACAATCCAGGCATGGTG
ACACAAGTTCTGACCGTCGCGCGTCAGATCTACAACGACTATGTAACGCA
CCATCCTGGTCTGACTCCGGAACAGACATCGGCCGGGCACAAGCTGCGG
ATATTCTGAGCCTGTTCTGTCCAGATGCCGACAAATCTTGCGTGGCAAGT
AATAACGATCAGGCTAATATCAACATTGAGTCACGCTCCGGACGTTCGTA
CCTGCCTGAAAATCGCGCGGTTATCACCCCGAAGGCGTCACGAACTGGA
CCTATCAGGAGCTGGAAGCACTCACCAGGCACTGACACGTGAAGGTTAC
GTGTTTGTAGGGTATCATGGAACGAATCACGTTGCTGCGCAAACCATTGT
GAACCGCATCGCCCCGGTCCCACGTGGCAATAACACTGAGAATGAAGAGA
AATGGGGTGGCCTGTACGTTGCAACACATGCGGAAGTAGCTCACGGTTAT
GCCCGCATTAAAGAAGGGACCGGAGAGTATGGCCTGCCTACGCGTGCAGA
ACGCGACGCGCGTGGTGTGACGCTGCGCGTCTACATCCCGCGTGCTTCGC
TGGAGCGCTTCTATCGTACCAACACTCCGCTGGAAAATGCCGAAGAGCAT
ATTACACAGGTTATCGGCCACTCTCTGCCACTGCGCAACGAAGCATTTAC
GGGTCCTGAAAGTGCGGGGGAGAGGATGAAACCGTGATTGGCTGGGACA
TGGCTATCCATGCCGTAGCAATTCCGTCAACTATTCCAGGTAATCGTACT
GAGGAACTGGCCATCGATGAAGAGGCAGTCGCGAAAGAACAATCCATTTC
GACAAAACCGCCTTATAAAGAGCGTCACCATCATCACCATCACAAAGATG
AACTGTAA

Genes with altered underlined sequences encoding various granzyme B cleavage sequences (ATTGAGCCAGATGACCTG-IEPDDL; ATTGCTCCAGATAGTGGT-IAPDSG); ATTGAGCCAGATAGTGGT-IEPDSG; and ATTGCTCCAGATGACCTG--IAPDDL) were also made.

Anti-CD19-VCE protein sequence

SEQ ID NO: 80
MAQVQLQQSGAELVRPGSSVKISCKASGYAFSSYWMNWVKQRPGQGLEWI
GQIWPGDGDTNYNGKFKGKATLTADESSSTAYMQLSSLASEDSAVYFCAR
RETTTVGRYYAMDYWGQGTSVTVSSGGGGSGGGGSGGGGSGSSDILLTQT
PASLAVSLGQRATISCKASQSVDYDGDSYLNWYQQIPGQPPKLLIYDASN
LVSGIPPRFSGSGSGTDFTLNIHPVEKVDAATYHCQQSTEDPWTFGGGTK
LEIKRGSGASKGNAMSALAAHRVCGVPLETLARSRKPRDLTDDLSCAYQA
QNIVSLFVATRILFSHLDSVFTLNLDEQEPEVAERLSDLRRINENNPGMV
TQVLTVARQTYNDYVTHHPGLTPEQTSAGAQAADILSLFCPDADKSCVAS
NNDQANINIESRSGRSYLPENRAVITPQGVTNWTYQELEATHQALTREGY
VFVGYHGTNHVAAQTIVNRIAPVPRGNNTENEEKWGGLYVATHAEVAHGY
ARIKEGTGEYGLPTRAERDARGVMLRVYIPRASLERFYRTNTPLENAEEH
ITQVIGHSLPLRNEAFTGPESAGGEDETVIGWDMAIHAVAIPSTIPGNAY
EELAIDEEAVAKEQSISTKPPYKERHHHHHHKDEL

Proteins with altered underlined sequence, including IEPDDL, IEPDSG, IAPDDL, IAPDSG, were also made.

anti-CD5-PEA
Synthetic gene encoding anti-CD5-PEA

SEQ ID NO: 81
ATGGACTACAAGGACGACGACGACAAGGGCATGgccaacatccagctggt
gcagtctggacctgagctgaagaagcctggtgagactgtcaaaatctcct
gcaaggcttctgggtataccttcactaactatggtatgaactgggtgaag
caggctcctggtaagggtctgcgttggatgggctggattaacacccacac
tggtgagcctacttatgctgacttcaagggacgttttgccttctctc
tggaaacttctgccagcactgcctatctccagatcaacaacctcaaaaat
gaggacactgctacttacttctgtacacgtcgtggttacgactggtactt
cgatgtctggggtgctgggaccacggtgaccgtgttctccggggaggtg
gcagcggggagggtggcagcgggcggggagctccgacataagatgact
cagtctccttcttccatgtatgcttctctgggtgagcgtgtcactatcac
ttgcaaggcagccaggacattaatagctatctgagctggttccatcata
aacctgggaaatctcctaagaccctgatctatcgtgctaaccgtctggtt
gatggggtccctctctgttcagcggctctggttctggcaagattattc
tctcaccatcagcagcctggactatgaagatatgggtatttattattgtc
aacagtatgatgagtcctcttggactttcggtggtgggaccaagctggag
atgaaagaggcggaggctccggaggaggaggcgggtccgctagcctGAT
CGCCCTGACCGCCCACCAGGCCTGCCACCTGCCGCTGGAGACCTTCACCG
CTAGCATCGAGCCGGACGGCTGGGAGCAGCTGGAGCAGTGCGGCTACCCG
GTGCAGCGCCTGGTGGCCCTGTACCTGGCCGCCCGCCTGTCCTGGAACCA
GGTGGACCAGGTGATCCGCAACGCCCTGGCCTCCCCGGGCTCCGGCGGCG
ACCTGGGCGAGGCCATCCGCGAGCAGCCGGAGCAGGCCCGCCTGGCCCTG
ACCCTGGCCGCCGCCGAGTCCGAGCGCTTCGTGCGCCAGGGCACCGGCAA CGACGAGGCCGGCGCCGCCAACGCCGACGTGGTGTCCCTGACCTGCCCGG
TGGCCGCCGGCGAGTGCGCCGGCCCGGCCGACTCCGGCGACGCCCTGCTG
GAGCGCAACTACCCGACCGGCGCCGAGTTCCTGGGCGACGGCGGCGACGT
GTCCTTCTCCACCCGCGGCACCCAGACCTGGACCGTGGAGCGCCTGCTGC
AGGCCCACCGCCAGCTGGAGGAGCGCGGCTACGTGTTCGTGGGCTACCAC
GGCACCTTCCTGGAGGCCGCCCAGTCCATCGTGTTCGGCGGCGTGCGCGC
CCGCTCCCAGGACCTGGACGCCATCTGGCGCGGCTTCTACATCGCCGGCG
ACCCGGCCCTGGCCTACGGCTACGCCCAGGACCAGGAGCCGGACGCCCGC
GGTCGCATCCGCAACGGCGCCCTGCTGCGCGTGTACGTGCCGCGCTCCTC
CCTGCCGGGCTTCTACCGCACCTCCCTGACCGCCGCCCCGGAGGCCG
CCGGCGAGGTGGAGCGCCTGATCGGCCACCCGCTGCCGCTGCGCCTGGAC
GCCATCACCGGCCCGGAGGAGGAGGGCGGTCGCCTGGAGACCATCCTGGG
CTGGCCGCTGGCCGAGCGCACCGTGGTGATCCCGTCCGCCATCCCGACCG
ACCCGCGCAACGTGGGCGGCGACCTGGACCCGTCCTCCATCCCGGACAAG
GAGCAGGCCATCTCCGCCCTGCCGGACTACGCCTCTCAGCCGGGCAAGCC
GCCGCACCACCACCACCACCACAAGGACGAGCTGTAG anti-CD5-PEA protein sequence SEQ ID NO: 82
MDYKDDDDKGMANIQLVQSGPELKKPGETVKISCKASGYTFTNYGMNWVK
QAPGKGLRWMGWINTHTGEPTYADDFKGRFAFSLETSASTAYLQINNLKN
EDTATYFCTRRGYDWYFDVWGAGTTVTVFSGGGGSGGGGSGGGSSDIKMT
QSPSSMYASLGERVTITCKASQDINSYLSWFHHKPGKSPKTLIYRANRLV
DGVPSRFSGSGSGQDYSLTISSLDYEDMGIYYCQQYDESPWTFGGGTKLE
MKGGGGSGGGGSASLIALTAHQACHLPLETFTASIEPDGWEQLEQCGYP
VQRLVALYLAARLSWNQVDQVIRNALASPGSGGDLGEAIREQPEQARLAL
TLAAAESERFVRQGTGNDEAGAANADVVSLTCPVAAGECAGPADSGDALL
ERNYPTGAEFLGDGGDVSFSTRGTQTWTVERLLQAHRQLEERGYVFVGYH
GTFLEAAQSIVFGGVRARSQDLDAIWRGFYIAGDPALAYGYAQDQEPDAR
GRIRNGALLRVYVPRSSLPGFYRTSLTLAAPEAAGEVERLIGHPLPLRLD
AITGPEEEGGRLETILGWPLAERTVVIPSAIPTDPRNVGGDLDPSSIPDK
EQAISALPDYASQPGKPPHHHHHHKDEL

GENE ENCODING
N-GFD-VC-PEA FUSION PROTEIN

SEQ ID NO: 83
ATGGGCTCCAACGAACTGCATCAGGTGCCGAGCAACTGCGATTGTCTGAA
CGGCGGTACCTGCGTTTCCAACAAATATTTTTCTAACATTCACTGGTGTA
ACTGCCCGAAAAAATTCGGTGGACAACATTGTGAAATCGACGGCGGTGGT
GGTTCGGGCGGTGGCGGTTCGGGTGGCGGTGGCAGCTCTAGCAAAGGCAA
TGCCATGAGTGCACTGGCTGCGCACCGCGTATGCGGTGTGCCGCTGGAGA
CACTGGCCCGTTCACGCAAACCACGTGACCTGACCGATGACCTGAGCTGC
GCGTATCAGGCCCAAAATATTGTGTCTCTGTTTGTTGCAACGCGTATCCT
GTTCAGTCATCTGGATTCAGTCTTTACTCTGAACCTGGACGAACAGGAGC
CGGAAGTAGCTGAGCGCCTGTCCGATCTGCGTCGCATTAATGAAAACAAT
CCAGGCATGGTGACACAAGTTCTGACCGTCGCGCGTCAGATCTACAACGA
CTATGTAACGCACCATCCTGGTCTGACTCCGGAACAGACATCGGCCGGGG
CACAAGCTGCCGACGTGGTGTCCCTGACCTGCCCGGTGGCCGCCGGCGAG
TGCGCCGGCCCGGCCGACTCCGGCGACGCCCTGCTGGAGCGCAACTACCC
GACCGGCGCCGAGTTCCTGGGCGACGGCGGCGACGTGTCCTTCTCCACCC
GCGGCACCCAGACCTGGACCGTGGAGCGCCTGCTGCAGGCCCACCGCCAG
CTGGAGGAGCGCGGCTACGTGTTCGTGGGCTACCACGGCACCTTCCTGGA
GGCCGCCCAGTCCATCGTGTTCGGCGGCGTGCGCGCCCGCTCCCAGGACC
TGGACGCCATCTGGCGCGGCTTCTACATCGCCGGCGACCCGGCCCTGGCC
TACGGCTACGCCCAGGACCAGGAGCCGGACGCCCGCGGTCGCATCCGCAA
CGGCGCCCTGCTGCGCGTGTACGTGCCGCGCTCCTCCCTGCCGGGCTTCT
ACCGCACCTCCCTGACCCTGGCCGCCCCGGAGGCCGCCGGCGAGGTGGAG
CGCCTGATCGGCCACCCGCTGCCGCTGCGCCTGGACGCCATCACCGGCCC
GGAGGAGGAGGGCGGTCGCCTGGAGACCATCCTGGGCTGGCCGCTGGCCG
AGCGCACCGTGGTGATCCCGTCCGCCATCCCGACCGACCCGCGCAACGTG
GGCGGCGACCTGGACCCGTCCTCCATCCCGGACAAGGAGCAGGCCATCTC
CGCCCTGCCGGACTACGCCTCTCAGCCGGGCAAGCCGCCGCACCACCACC
ACCACCACAAGGACGAGCTGTAGCGGCCGC

Protein sequence corresponding to synthetic N-GFD-VC-PEA FUSION PROTEIN

SEQ ID NO: 84
MSNELHQVPSNCDCLNGGTCVSNKYFSNIHWCNCPKKFGGQHCEIDGGGG
SGGGGSGGGGSSSKGNAMSALAAHRVCGVPLETLARSRKPRDLTDDLSCA
YQAQNIVSLFVATRILFSHLDSVFTLNLDEQEPEVAERLSDLRRINENNP
GMVTQVLTVARQIYNDYVTHHPGLTPEQTSAGAQAADVVSLTCPVAAGEC
AGPADSGDALLERNYPTGAEFLGDGGDVSFSTRGTQTWNTVERLLQAHRQL
EERGYVFVGYHGTFLEAAQSIVFGGVRARSQDLDAIWRGFYIAGDPALAY
GYAQDQEPDARGRIRNGALLRVYVPRSSLPGFYRTSLTLAAPEAAGEVER
LIGHPLPLRLDAITGPEEEGGRLETILGWPLAERTVVIPSAIPTDPRNVG
GDLDPSSIPDKEQAISALPDYASQPGKPPHHHHHHKDEL

TABLE 3-continued

Sequences

GENE ENCODING
CCPE-VCE FUSION PROTEIN

SEQ ID NO: 85

ATGGGTCATCACCACCATCATCACAAGGGCGAGCTCGAAAGATCCGTTTT
AACAGTTCCATCTACAGATATAGAAAAAGAAATCCTTGATTTAGCTGCTG
CTACAGAAAGATTAAATTTAACTGATGCATTAAACTCAAATCCAGCTGGT
AATTTATATGATTGGCGTTCTTCTAACTCATACCCTTGGACTCAAAAGCT
CAATTTACACTTAACAATTACAGCTACTGGACAAAAATATAGAATCTTAG
CAAGCAAAATTGTTGATTTTAATATTTATTCAAATAATTTTAATAATCTA
GTGAAATTAGAACAGTCCTTAGGTGATGGAGTAAAAGATCATTATGTTGA
TATAAGTTTAGATGCTGGACAATATGTTCTTGTAATGAAAGCTAATTCAT
CATATAGTGGAAATTACCCTTATTCAATATTATTTCAAAAATTTAAGCTT
GAAGGTAAGCCTATCCCTAACCCTCTCCTCGGTCTCGATTCTACGCGTAC
CGGTGGCTCTGGCGCTAGCAAAGGCAATGCCATGAGTGCACTGGCTGCGC
ACCGCGTATGCGGTGTGCCGCTGGAGACACTGGCCCGTTCACGCAAACCA
CGTGACCTGACCGATGACCTGAGCTGCGCGTATCAGGCCCAAAATATTGT
GTCTCTGTTTGTTGCAACGCGTATCCTGTTCAGTCATCTGGATTCAGTCT
TTACTCTGAACCTGGACGAACAGGAGCCGGAAGTAGCTGAGCGCCTGTCC
GATCTGCGTCGCATTAATGAAAACAATCCAGGCATGGTGACACAAGTTCT
GACCGTCGCGCGTCAGATCTACAACGACTATGTAACGCACCATCCTGGTC
TGACTCCGGAACAGACATCGGCCGGGGCACAAGCTGCGGATATTCTGAGC
CTGTTCTGTCCAGATGCCGACAAATCTTGCGTGGCAAGTAATAACGATCA
GGCTAATATCAACATTGAGTCACGCTCCGGACGTTCGTACCTGCCTGAAA
ATCGCGCGGTTATCACCCCGCAAGGCGTCACGAACTGGACCTATCAGGAG
CTGGAAGCCACTCACCAGGCACTGACACGTGAAGGTTACGTGTTTGTAGG
GTATCATGGAACGAATCACGTTGCTGCGCAAACCATTGTGAACCGCATCG
CCCCGGTCCCACGTGGCAATAACACTGAGAATGAAGAGAAATGGGGTGGC
CTGTACGTTGCAACACATGCGGAAGTAGCTCACGGTTATGCCCGCATTAA
AGAAGGGACCGGAGAGTATGGCCTGCCTACGCGTGCAGAACGCGACGCGC
GTGGTGTGATGCTGCGCGTCTACATCCCGCGTGCTTCGCTGGAGCGCTTC
TATCGTACCAACACTCCGCTGGAAAATGCCGAAGAGCATATTACACAGGT
TATCGGCCACTCTCTGCCACTGCGCAACGAAGCATTTACGGGTCCTGAAA
GTGCGGGGGAGAGGATGAAACCGTGATTGGCTGGGACATGGCTATCCAT
GCCGTAGCAATTCCGTCAACTATTCCAGGTAATGCGTACGAGGAACTGGC
CATCGATGAAGAGGCAGTCGCGAAAGAACAATCCATTTCGACAAAACCGC
CTTATAAAGAGCGTCACCATCATCACCATCACAAAGATGAACTGTAA

Protein sequence corresponding to synthetic CCPE-
VCE FUSION PROTEIN

SEQ ID NO: 86

MGHHHHHHKGELERSVLTVPSTDIEKEILDLAAATERLNLTDALNSNPAG
NLYDWRSSNSYPWTQKLNLHLTITATGQKYRILASKIVDFNIYSNNFNNL
VKLEQSLGDGVKDHYVDISLDAGQYVLVMKANSSYSGNYPYSILFQKFKL
EGKPIPNPLLGLDSTRTGGSGASKGNAMSALAAHRVCGVPLETLARSRKP
RDLTDDLSCAYQAQNIVSLFVATRILFSHLDSVFTLNLDEQEPEVAERLS
DLRRINENNPGMVTQVLTVARQIYNDYVTHHPGLTPEQTSAGAQAADILS
LFCPDADKSCVASNNDQANINIESRSGRSYLPENRAVITPQGVTNWTYQE
LEATHQALTREGYVFVGYHGTNHVAAQTIVNRIAPVPRGNNTENEEKWGG
LYVATHAEVAHGYARIKEGTGEYGLPTRAERDARGVMLRVYIPRASLERF
YRTNTPLENAEEHITQVIGHSLPLRNEAFTGPESAGGEDETVIGWDMAIH
AVAIPSTIPGNAYEELAIDEEAVAKEQSISTKPPYKERHHHHHHKDEL

GENE ENCODING CCPE$^2$-VCE FUSION PROTEIN

SEQ ID NO: 87

ATGGGTCTTGATTTAGCTGCTGCTACAGAAAGATTAAATTTAACTGATGC
ATTAAACTCAAATCCAGCTGGTAATTTATATGATTGGCGTTCTTCTAACT
CATACCCTTGGACTCAAAAGCTCAATTTACACTTAACAATTACAGCTACT
GGACAAAAATATAGAATCTTAGCAAGCAAAATTGTTGATTTTAATATTTA
TTCAAATAATTTTAATAATCTAGTGAAATTAGAACAGTCCTTAGGTGATG
GAGTAAAAGATCATTATGTTGATATAAGTTTAGATGCTGGACAATATGTT
CTTGTAATGAAAGCTAATTCATCATATAGTGGAAATTACCCTTATTCAAT
ATTATTTCAAAAATTTGAAGGTGGCGGTTCCGAAGGTGGTGGGTCCGAAG
GTGGTGGCTCCGGCGGTTCCATCCTTGATTTAGCTGCTGCTACAGAAAGA
TTAAATTTAACTGATGCATTAAACTCAAATCCAGCTGGTAATTTATATGA
TTGGCGTTCTTCTAACTCATACCCTTGGACTCAAAAGCTCAATTTACACT
TAACAATTACAGCTACTGGACAAAAATATAGAATCTTAGCAAGCAAAATT
GTTGATTTTAATATTTATTCAAATAATTTTAATAATCTAGTGAAATTAGA
ACAGTCCTTAGGTGATGGAGTAAAAGATCATTATGTTGATATAAGTTTAG
ATGCTGGACAATATGTTCTTGTAATGAAAGCTAATTCATCATATAGTGGA
AATTACCCTTATTCAATATTATTTCAAAAATTTGACGGTTCCGCTAGCAA
AGGCAATGCCATGAGTGCACTGGCTGCGCACCGCGTATGCGGTGTGCCGC
TGGAGACACTGGCCCGTTCACGCAAACCACGTGACCTGACCGATGACCTG
AGCTGCGCGTATCAGGCCCAAAATATTGTGTCTCTGTTTGTTGCAACGCG
TATCCTGTTCAGTCATCTGGATTCAGTCTTTACTCTGAACCTGGACGAAC
AGGAGCCGGAAGTAGCTGAGCGCCTGTCCGATCTGCGTCGCATTAATGAA
AACAATCCAGGCATGGTGACACAAGTTCTGACCGTCGCGCGTCAGATCTA
CAACGACTATGTAACGCACCATCCTGGTCTGACTCCGGAACAGACATCGG
CCGGGGCACAAGCTGCGGATATTCTGAGCCTGTTCTGTCCAGATGCCGAC
AAATCTTGCGTGGCAAGTAATAACGATCAGGCTAATATCAACATTGAGTC
ACGCTCCGGACGTTCGTACCTGCCTGAAAATCGCGCGGTTATCACCCCGC
AAGGCGTCACGAACTGGACCTATCAGGAGCTGGAAGCCACTCACCAGGCA
CTGACACGTGAAGGTTACGTGTTTGTAGGGTATCATGGAACGAATCACGT
TGCTGCGCAAACCATTGTGAACCGCATCGCCCCGGTCCCACGTGGCAATA
ACACTGAGAATGAAGAGAAATGGGGTGGCCTGTACGTTGCAACACATGCG
GAAGTAGCTCACGGTTATGCCCGCATTAAAGAAGGGACCGGAGAGTATGG
CCTGCCTACGCGTGCAGAACGCGACGCGCGTGGTGTGATGCTGCGCGTCT
ACATCCCGCGTGCTTCGCTGGAGCGCTTCTATCGTACCAACACTCCGCTG
GAAAATGCCGAAGAGCATATTACACAGGTTATCGGCCACTCTCTGCCACT
GCGCAACGAAGCATTTACGGGTCCTGAAAGTGCGGGGGGAGAGGATGAAA
CCGTGATTGGCTGGGACATGGCTATCCATGCCGTAGCAATTCCGTCAACT
ATTCCAGGTAATGCGTACGAGGAACTGGCCATCGATGAAGAGGCAGTCGC
GAAAGAACAATCCATTTCGACAAAACCGCCTTATAAAGAGCGTCACCATC
ATCACCATCACAAAGATGAACTGTAA

Protein sequence corresponding to synthetic CCPE$^2$-
VCE FUSION PROTEIN

SEQ ID NO: 88

MGLDLAAATERLNLTDALNSNPAGNLYDWRSSNSYPWTQKLNLHLTITAT
GQKYRILASKIVDFNIYSNNFNNLVKLEQSLGDGVKDHYVDISLDAGQYV
LVMKANSSYSGNYPYSILFQKFEGGGSEGGGSEGGGSGGSILDLAAATER
LNLTDALNSNPAGNLYDWRSSNSYPWTQKLNLHLTITATGQKYRILASKI
VDFNIYSNNFNNLVKLEQSLGDGVKDHYVDISLDAGQYVLVMKANSSYSG
NYPYSILFQKFDGSASKGNAMSALAAHRVCGVPLETLARSRKPRDLTDDL
SCAYQAQNIVSLFVATRILFSHLDSVFTLNLDEQEPEVAERLSDLRRINE
NNPGMVTQVLTVARQIYNDYVTHHPGLTPEQTSAGAQAADILSLFCPDAD
KSCVASNNDQANINIESRSGRSYLPENRAVITPQGVTNWTYQELEATHQA
LTREGYVFVGYHGTNHVAAQTIVNRIAPVPRGNNTENEEKWGGLYVATHA
EVAHGYARIKEGTGEYGLPTRAERDARGVMLRVYIPRASLERFYRTNTPL
ENAEEHITQVIGHSLPLRNEAFTGPESAGGEDETVIGWDMAIHAVAIPST
IPGNAYEELAIDEEAVAKEQSISTKPPYKERHHHHHHKDEL

Other Embodiments

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference. The nucleic acid and amino acid sequences relevant to this application are listed above in Table 3.

What is claimed is:

1. A fusion protein comprising a fragment of VCE (*Vibrio cholerae* exotoxin A), wherein said fragment:
   comprises an amino acid sequence with greater than 90% sequence identity to SEQ ID NO: 2,
   has an inactive native targeting domain or lacks a native targeting domain, and
   optionally comprises the native VCE furin cleavage site;
   and wherein said fusion protein comprises: (1) cell-membrane translocation activity and (2) a non-native cell targeting moiety.

2. The fusion protein of claim 1, wherein said fragment comprises an amino acid sequence with greater than 95% sequence identity to SEQ ID NO:2.

3. The fusion protein of claim 1, wherein the native VCE furin cleavage site of said fragment is replaced with a modifiable activation domain comprising a substrate for an exogenous enzyme.

4. The fusion protein of claim 3, wherein the native VCE furin cleavage site of said fragment is replaced with a cleavage site for granzyme B.

5. The fusion protein of claim 1, wherein said fragment comprises ADP-ribosylating activity.

6. The fusion protein of claim 1, wherein said non-native cell targeting moiety is an antibody, or functional fragment thereof.

7. The fusion protein of claim 1, wherein said non-native cell targeting moiety is an artificially diversified polypeptide binder.

8. A vector comprising a sequence encoding the fusion protein of claim 1.

* * * * *

SEQUENCE LISTING

<160> NUMBER OF SEQ ID NOS: 104

<210> SEQ ID NO 1
<211> LENGTH: 666
<212> TYPE: PRT
<213> ORGANISM: Vibrio cholerae

<400> SEQUENCE: 1

```
Met Tyr Leu Thr Phe Tyr Leu Glu Lys Val Met Lys Met Leu Leu
1               5                   10                  15

Ile Ala Gly Ala Thr Val Ile Ser Ser Met Ala His Pro Thr Phe Ala
                20                  25                  30

Val Glu Asp Glu Leu Asn Ile Phe Asp Glu Cys Arg Ser Pro Cys Ser
            35                  40                  45

Leu Thr Pro Glu Pro Gly Lys Pro Ile Gln Ser Lys Leu Ser Ile Pro
        50                  55                  60

Ser Asp Val Val Leu Asp Glu Gly Val Leu Tyr Tyr Ser Met Thr Ile
65                  70                  75                  80

Asn Asp Glu Gln Asn Asp Ile Lys Asp Glu Asp Lys Gly Glu Ser Ile
                85                  90                  95

Ile Thr Ile Gly Glu Phe Ala Thr Val Arg Ala Thr Arg His Tyr Val
            100                 105                 110

Asn Gln Asp Ala Pro Phe Gly Val Ile His Leu Asp Ile Thr Thr Glu
        115                 120                 125

Asn Gly Thr Lys Thr Tyr Ser Tyr Asn Arg Lys Glu Gly Glu Phe Ala
    130                 135                 140

Ile Asn Trp Leu Val Pro Ile Gly Glu Asp Ser Pro Ala Ser Ile Lys
145                 150                 155                 160

Ile Ser Val Asp Glu Leu Asp Gln Gln Arg Asn Ile Ile Glu Val Pro
                165                 170                 175

Lys Leu Tyr Ser Ile Asp Leu Asp Asn Gln Thr Leu Glu Gln Trp Lys
            180                 185                 190

Thr Gln Gly Asn Val Ser Phe Ser Val Thr Arg Pro Glu His Asn Ile
        195                 200                 205

Ala Ile Ser Trp Pro Ser Val Ser Tyr Lys Ala Ala Gln Lys Glu Gly
    210                 215                 220

Ser Arg His Lys Arg Trp Ala His Trp His Thr Gly Leu Ala Leu Cys
225                 230                 235                 240

Trp Leu Val Pro Met Asp Ala Ile Tyr Asn Tyr Ile Thr Gln Gln Asn
                245                 250                 255

Cys Thr Leu Gly Asp Asn Trp Phe Gly Gly Ser Tyr Glu Thr Val Ala
            260                 265                 270

Gly Thr Pro Lys Val Ile Thr Val Lys Gln Gly Ile Glu Gln Lys Pro
        275                 280                 285

Val Glu Gln Arg Ile His Phe Ser Lys Gly Asn Ala Met Ser Ala Leu
    290                 295                 300

Ala Ala His Arg Val Cys Gly Val Pro Leu Glu Thr Leu Ala Arg Ser
305                 310                 315                 320

Arg Lys Pro Arg Asp Leu Thr Asp Leu Ser Cys Ala Tyr Gln Ala
                325                 330                 335

Gln Asn Ile Val Ser Leu Phe Val Ala Thr Arg Ile Leu Phe Ser His
            340                 345                 350

Leu Asp Ser Val Phe Thr Leu Asn Leu Asp Glu Gln Glu Pro Glu Val
        355                 360                 365
```

```
Ala Glu Arg Leu Ser Asp Leu Arg Arg Ile Asn Glu Asn Asn Pro Gly
    370                 375                 380

Met Val Thr Gln Val Leu Thr Val Ala Arg Gln Ile Tyr Asn Asp Tyr
385                 390                 395                 400

Val Thr His His Pro Gly Leu Thr Pro Glu Gln Thr Ser Ala Gly Ala
                405                 410                 415

Gln Ala Ala Asp Ile Leu Ser Leu Phe Cys Pro Asp Ala Asp Lys Ser
            420                 425                 430

Cys Val Ala Ser Asn Asn Asp Gln Ala Asn Ile Asn Ile Glu Ser Arg
        435                 440                 445

Ser Gly Arg Ser Tyr Leu Pro Glu Asn Arg Ala Val Ile Thr Pro Gln
    450                 455                 460

Gly Val Thr Asn Trp Thr Tyr Gln Glu Leu Glu Ala Thr His Gln Ala
465                 470                 475                 480

Leu Thr Arg Glu Gly Tyr Val Phe Val Gly Tyr His Gly Thr Asn His
                485                 490                 495

Val Ala Ala Gln Thr Ile Val Asn Arg Ile Ala Pro Val Pro Arg Gly
            500                 505                 510

Asn Asn Thr Glu Asn Glu Glu Lys Trp Gly Gly Leu Tyr Val Ala Thr
        515                 520                 525

His Ala Glu Val Ala His Gly Tyr Ala Arg Ile Lys Glu Gly Thr Gly
    530                 535                 540

Glu Tyr Gly Leu Pro Thr Arg Ala Glu Arg Asp Ala Arg Gly Val Met
545                 550                 555                 560

Leu Arg Val Tyr Ile Pro Arg Ala Ser Leu Glu Arg Phe Tyr Arg Thr
                565                 570                 575

Asn Thr Pro Leu Glu Asn Ala Glu Glu His Ile Thr Gln Val Ile Gly
            580                 585                 590

His Ser Leu Pro Leu Arg Asn Glu Ala Phe Thr Gly Pro Glu Ser Ala
        595                 600                 605

Gly Gly Glu Asp Glu Thr Val Ile Gly Trp Asp Met Ala Ile His Ala
    610                 615                 620

Val Ala Ile Pro Ser Thr Ile Pro Gly Asn Ala Tyr Glu Glu Leu Ala
625                 630                 635                 640

Ile Asp Glu Glu Ala Val Ala Lys Glu Gln Ser Ile Ser Thr Lys Pro
                645                 650                 655

Pro Tyr Lys Glu Arg Lys Asp Glu Leu Lys
            660                 665

<210> SEQ ID NO 2
<211> LENGTH: 219
<212> TYPE: PRT
<213> ORGANISM: Artificial Sequence
<220> FEATURE:
<223> OTHER INFORMATION: Synthetic Construct

<400> SEQUENCE: 2

Met Gly Pro Glu Asn Arg Ala Val Ile Thr Pro Gln Gly Val Thr Asn
1               5                   10                  15

Trp Thr Tyr Gln Glu Leu Glu Ala Thr His Gln Ala Leu Thr Arg Glu
            20                  25                  30

Gly Tyr Val Phe Val Gly Tyr His Gly Thr Asn His Val Ala Ala Gln
        35                  40                  45

Thr Ile Val Asn Arg Ile Ala Pro Val Pro Arg Gly Asn Asn Thr Glu
    50                  55                  60
```

```
Asn Glu Glu Lys Trp Gly Gly Leu Tyr Val Ala Thr His Ala Glu Val
 65                  70                  75                  80

Ala His Gly Tyr Ala Arg Ile Lys Glu Gly Thr Gly Glu Tyr Gly Leu
                 85                  90                  95

Pro Thr Arg Ala Glu Arg Asp Ala Arg Gly Val Met Leu Arg Val Tyr
            100                 105                 110

Ile Pro Arg Ala Ser Leu Glu Arg Phe Tyr Arg Thr Asn Thr Pro Leu
        115                 120                 125

Glu Asn Ala Glu Glu His Ile Thr Gln Val Ile Gly His Ser Leu Pro
    130                 135                 140

Leu Arg Asn Glu Ala Phe Thr Gly Pro Glu Ser Ala Gly Gly Glu Asp
145                 150                 155                 160

Glu Thr Val Ile Gly Trp Asp Met Ala Ile His Ala Val Ala Ile Pro
                165                 170                 175

Ser Thr Ile Pro Gly Asn Ala Tyr Glu Glu Leu Ala Ile Asp Glu Glu
            180                 185                 190

Ala Val Ala Lys Glu Gln Ser Ile Ser Thr Lys Pro Pro Tyr Lys Glu
        195                 200                 205

Arg His His His His His Lys Asp Glu Leu
    210                 215

<210> SEQ ID NO 3
<211> LENGTH: 660
<212> TYPE: DNA
<213> ORGANISM: Artificial Sequence
<220> FEATURE:
<223> OTHER INFORMATION: Synthetic Construct

<400> SEQUENCE: 3
atgggccctg aaaatcgcgc ggttatcacc ccgcaaggcg tcacgaactg gacctatcag      60
gagctggaag ccactcacca ggcactgaca cgtgaaggtt acgtgtttgt agggtatcat     120
ggaacgaatc acgttgctgc gcaaaccatt gtgaaccgca tcgccccggt ccacgtggc     180 aataacactg agaatgaaga gaatgggggt ggcctgtacg ttgcaacaca tgcggaagta     240
gctcacggtt atgcccgcat taagaaaggg accggagagt atggcctgcc tacgcgtgca     300
gaacgcgacg cgcgtggtgt gatgctgcgc gtctacatcc cgcgtgcttc gctggagcgc     360
ttctatcgta ccaacactcc gctggaaaat gccgaagagc atattacaca ggttatcggc     420
cactctctgc cactgcgcaa cgaagcattt acgggtcctg aaagtgcggg gggagaggat     480
gaaaccgtga ttggctggga catggctatc catgccgtag caattccgtc aactattcca     540
ggtaatgcgt acgaggaact ggccatcgat gaagaggcag tcgcgaaaga acaatccatt     600
tcgacaaaac cgccttataa agagcgtcac catcatcacc atcacaaaga tgaactgtaa     660

<210> SEQ ID NO 4
<211> LENGTH: 4
<212> TYPE: PRT
<213> ORGANISM: Vibrio cholerae

<400> SEQUENCE: 4

Lys Asp Glu Leu
1

<210> SEQ ID NO 5
<211> LENGTH: 6
<212> TYPE: PRT
<213> ORGANISM: Vibrio cholerae

<400> SEQUENCE: 5
```

```
Arg Lys Pro Lys Asp Leu
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic Construct

<400> SEQUENCE: 6

Leu Leu Gln Gly
1

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Any amino acid

<400> SEQUENCE: 7

Leu Pro Xaa Thr Gly
1               5

<210> SEQ ID NO 8
<211> LENGTH: 612
<212> TYPE: PRT
<213> ORGANISM: Pseudomonas aeruginosa

<400> SEQUENCE: 8

Glu Glu Ala Phe Asp Leu Trp Asn Glu Cys Ala Lys Ala Cys Val Leu
1               5                   10                  15

Asp Leu Lys Asp Gly Val Arg Ser Ser Arg Met Ser Val Asp Pro Ala
                20                  25                  30

Ile Ala Asp Thr Asn Gly Gln Gly Val Leu His Tyr Ser Met Val Leu
            35                  40                  45

Glu Gly Gly Asn Asp Ala Leu Lys Leu Ala Ile Asp Asn Ala Leu Ser
        50                  55                  60

Ile Thr Ser Asp Gly Leu Thr Ile Arg Leu Glu Gly Val Glu Pro
65                  70                  75                  80

Asn Lys Pro Val Arg Tyr Ser Tyr Thr Arg Gln Ala Arg Gly Ser Trp
                85                  90                  95

Ser Leu Asn Trp Leu Val Pro Ile Gly His Glu Lys Pro Ser Asn Ile
            100                 105                 110

Lys Val Phe Ile His Glu Leu Asn Ala Gly Asn Gln Leu Ser His Met
        115                 120                 125

Ser Pro Ile Tyr Thr Ile Glu Met Gly Asp Glu Leu Leu Ala Lys Leu
    130                 135                 140

Ala Arg Asp Ala Thr Phe Phe Val Arg Ala His Glu Ser Asn Glu Met
145                 150                 155                 160

Gln Pro Thr Leu Ala Ile Ser His Ala Gly Val Ser Val Val Met Ala
                165                 170                 175

Gln Thr Gln Pro Arg Arg Glu Lys Arg Trp Ser Glu Trp Ala Ser Gly
            180                 185                 190

Lys Val Leu Cys Leu Leu Asp Pro Leu Asp Gly Val Tyr Asn Tyr Leu
        195                 200                 205
```

```
Ala Gln Gln Arg Cys Asn Leu Asp Asp Thr Trp Glu Gly Lys Ile Tyr
    210                 215                 220

Arg Val Leu Ala Gly Asn Pro Ala Lys His Asp Leu Asp Ile Lys Pro
225                 230                 235                 240

Thr Val Ile Ser His Arg Leu His Phe Pro Glu Gly Gly Ser Leu Ala
                245                 250                 255

Ala Leu Thr Ala His Gln Ala Cys His Leu Pro Leu Glu Thr Phe Thr
            260                 265                 270

Arg His Arg Gln Pro Arg Gly Trp Glu Gln Leu Glu Gln Cys Gly Tyr
        275                 280                 285

Pro Val Gln Arg Leu Val Ala Leu Tyr Leu Ala Ala Arg Leu Ser Trp
    290                 295                 300

Asn Gln Val Asp Gln Val Ile Arg Asn Ala Leu Ala Ser Pro Gly Ser
305                 310                 315                 320

Gly Gly Asp Leu Gly Glu Ala Ile Arg Glu Gln Pro Glu Gln Ala Arg
                325                 330                 335

Leu Ala Leu Thr Leu Ala Ala Ala Glu Ser Glu Arg Phe Val Arg Gln
            340                 345                 350

Gly Thr Gly Asn Asp Glu Ala Gly Ala Ala Asn Ala Asp Val Val Ser
        355                 360                 365

Leu Thr Cys Pro Val Ala Ala Gly Glu Cys Ala Gly Pro Ala Asp Ser
    370                 375                 380

Gly Asp Ala Leu Leu Glu Arg Asn Tyr Pro Thr Gly Ala Glu Phe Leu
385                 390                 395                 400

Gly Asp Gly Gly Asp Val Ser Phe Ser Thr Arg Gly Thr Gln Asn Trp
                405                 410                 415

Thr Val Glu Arg Leu Leu Gln Ala His Arg Gln Leu Glu Glu Arg Gly
            420                 425                 430

Tyr Val Phe Val Gly Tyr His Gly Thr Phe Leu Glu Ala Ala Gln Ser
        435                 440                 445

Ile Val Phe Gly Gly Val Arg Ala Arg Ser Gln Asp Leu Asp Ala Ile
    450                 455                 460

Trp Arg Gly Phe Tyr Ile Ala Gly Asp Pro Ala Leu Ala Tyr Gly Tyr
465                 470                 475                 480

Ala Gln Asp Gln Glu Pro Asp Ala Arg Gly Arg Ile Arg Asn Gly Ala
                485                 490                 495

Leu Leu Arg Val Tyr Val Pro Arg Ser Ser Leu Pro Gly Phe Tyr Arg
            500                 505                 510

Thr Ser Leu Thr Leu Ala Ala Pro Glu Ala Ala Gly Glu Val Glu Arg
        515                 520                 525

Leu Ile Gly His Pro Leu Pro Leu Arg Leu Asp Ala Ile Thr Gly Pro
    530                 535                 540

Glu Glu Glu Gly Gly Arg Leu Glu Thr Ile Leu Gly Trp Pro Leu Ala
545                 550                 555                 560

Glu Arg Thr Val Val Ile Pro Ser Ala Ile Pro Thr Asp Pro Arg Asn
                565                 570                 575

Val Gly Gly Asp Leu Asp Pro Ser Ser Ile Pro Asp Lys Glu Gln Ala
            580                 585                 590

Ile Ser Ala Leu Pro Asp Tyr Ala Ser Gln Pro Gly Lys Pro Pro Arg
        595                 600                 605

Glu Asp Leu Lys
    610
```

```
<210> SEQ ID NO 9
<211> LENGTH: 633
<212> TYPE: PRT
<213> ORGANISM: Vibrio cholerae

<400> SEQUENCE: 9

Glu Asp Glu Leu Asn Ile Phe Asp Glu Cys Arg Ser Pro Cys Ser Leu
1               5                   10                  15

Thr Pro Glu Pro Gly Lys Pro Ile Gln Ser Lys Leu Ser Ile Pro Ser
            20                  25                  30

Asp Val Val Leu Asp Glu Gly Val Leu Tyr Tyr Ser Met Thr Ile Asn
        35                  40                  45

Asp Glu Gln Asn Asp Ile Lys Asp Glu Asp Lys Gly Glu Ser Ile Ile
    50                  55                  60

Thr Ile Gly Glu Phe Ala Thr Val Arg Ala Thr Arg His Tyr Val Asn
65                  70                  75                  80

Gln Asp Ala Pro Phe Gly Val Ile His Leu Asp Ile Thr Thr Glu Asn
                85                  90                  95

Gly Thr Lys Thr Tyr Ser Tyr Asn Arg Lys Glu Gly Glu Phe Ala Ile
            100                 105                 110

Asn Trp Leu Val Pro Ile Gly Glu Asp Ser Pro Ala Ser Ile Lys Ile
        115                 120                 125

Ser Val Asp Glu Leu Asp Gln Gln Arg Asn Ile Ile Glu Val Pro Lys
    130                 135                 140

Leu Tyr Ser Ile Asp Leu Asp Asn Gln Thr Leu Glu Gln Trp Lys Thr
145                 150                 155                 160

Gln Gly Asn Val Ser Phe Ser Val Thr Arg Pro Glu His Asn Ile Ala
                165                 170                 175

Ile Ser Trp Pro Ser Val Ser Tyr Lys Ala Ala Gln Lys Glu Gly Ser
            180                 185                 190

Arg His Lys Arg Trp Ala His Trp His Thr Gly Leu Ala Leu Cys Trp
        195                 200                 205

Leu Val Pro Met Asp Ala Ile Tyr Asn Tyr Ile Thr Gln Gln Asn Cys
    210                 215                 220

Thr Leu Gly Asp Asn Trp Phe Gly Gly Ser Tyr Glu Thr Val Ala Gly
225                 230                 235                 240

Thr Pro Lys Val Ile Thr Val Lys Gln Gly Ile Glu Gln Lys Pro Val
                245                 250                 255

Glu Gln Arg Ile His Phe Ser Lys Gly Asn Ala Met Ser Ala Leu Ala
            260                 265                 270

Ala His Arg Val Cys Gly Val Pro Leu Glu Thr Leu Ala Arg Ser Arg
        275                 280                 285

Lys Pro Arg Asp Leu Thr Asp Asp Leu Ser Cys Ala Tyr Gln Ala Gln
    290                 295                 300

Asn Ile Val Ser Leu Phe Val Ala Thr Arg Ile Leu Phe Ser His Leu
305                 310                 315                 320

Asp Ser Val Phe Thr Leu Asn Leu Asp Glu Gln Glu Pro Glu Val Ala
                325                 330                 335

Glu Arg Leu Ser Asp Leu Arg Arg Ile Asn Glu Asn Asn Pro Gly Met
            340                 345                 350

Val Thr Gln Val Leu Thr Val Ala Arg Gln Ile Tyr Asn Asp Tyr Val
        355                 360                 365

Thr His His Pro Gly Leu Thr Pro Glu Gln Thr Ser Ala Gly Ala Gln
    370                 375                 380

Ala Ala Asp Ile Leu Ser Leu Phe Cys Pro Asp Ala Asp Lys Ser Cys
```

```
                385                 390                 395                 400
        Val Ala Ser Asn Asn Asp Gln Ala Asn Ile Asn Ile Glu Ser Arg Ser
                        405                 410                 415
        Gly Arg Ser Tyr Leu Pro Glu Asn Arg Ala Val Ile Thr Pro Gln Gly
                        420                 425                 430
        Val Thr Asn Trp Thr Tyr Gln Glu Leu Glu Ala Thr His Gln Ala Leu
                        435                 440                 445
        Thr Arg Glu Gly Tyr Val Phe Val Gly Tyr His Gly Thr Asn His Val
                        450                 455                 460
        Ala Ala Gln Thr Ile Val Asn Arg Ile Ala Pro Val Pro Arg Gly Asn
        465                 470                 475                 480
        Asn Thr Glu Asn Glu Glu Lys Trp Gly Gly Leu Tyr Val Ala Thr His
                        485                 490                 495
        Ala Glu Val Ala His Gly Tyr Ala Arg Ile Lys Glu Gly Thr Gly Glu
                        500                 505                 510
        Tyr Gly Leu Pro Thr Arg Ala Glu Arg Asp Ala Arg Gly Val Met Leu
                        515                 520                 525
        Arg Val Tyr Ile Pro Arg Ala Ser Leu Glu Arg Phe Tyr Arg Thr Asn
                        530                 535                 540
        Thr Pro Leu Glu Asn Ala Glu His Ile Thr Gln Val Ile Gly His
        545                 550                 555                 560
        Ser Leu Pro Leu Arg Asn Glu Ala Phe Thr Gly Pro Glu Ser Ala Gly
                        565                 570                 575
        Gly Glu Asp Glu Thr Val Ile Gly Trp Asp Met Ala Ile His Ala Val
                        580                 585                 590
        Ala Ile Pro Ser Thr Ile Pro Gly Asn Ala Tyr Glu Glu Leu Ala Ile
                        595                 600                 605
        Asp Glu Glu Ala Val Ala Lys Glu Gln Ser Ile Ser Thr Lys Pro Pro
                        610                 615                 620
        Tyr Lys Glu Arg Lys Asp Glu Leu Lys
        625                 630

<210> SEQ ID NO 10
<211> LENGTH: 4
<212> TYPE: PRT
<213> ORGANISM: Vibrio cholerae

<400> SEQUENCE: 10

Lys Asp Glu Leu
1

<210> SEQ ID NO 11
<211> LENGTH: 6
<212> TYPE: PRT
<213> ORGANISM: Vibrio cholerae

<400> SEQUENCE: 11

Arg Lys Pro Lys Asp Leu
1               5

<210> SEQ ID NO 12
<211> LENGTH: 6
<212> TYPE: PRT
<213> ORGANISM: Pseudomonas aeruginosa

<400> SEQUENCE: 12

Arg Gln Pro Arg Gly Trp
1               5
```

```
<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Lys Asp Glu Leu Lys
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Arg Asp Glu Leu Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Construct

<400> SEQUENCE: 15

Lys Asp Glu Leu Arg
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Arg Asp Glu Leu Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Ile Glu Pro Asp Asp Leu
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic Construct

<400> SEQUENCE: 18

Ile Glu Pro Asp
1

<210> SEQ ID NO 19
```

```
<211> LENGTH: 4
<212> TYPE: PRT
<213> ORGANISM: Artificial Sequence
<220> FEATURE:
<223> OTHER INFORMATION: Synthetic Construct

<400> SEQUENCE: 19

Ile Ala Pro Asp
1

<210> SEQ ID NO 20
<211> LENGTH: 4
<212> TYPE: PRT
<213> ORGANISM: Artificial Sequence
<220> FEATURE:
<223> OTHER INFORMATION: Synthetic Construct

<400> SEQUENCE: 20

Ile Glu Thr Asp
1

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Lys Val Tyr Pro Leu Met
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Trp or Tyr
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Gly, Ala, Thr, Ser or Asn

<400> SEQUENCE: 22

Xaa Glu Xaa Asp Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Ile or Leu
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
```

<223> OTHER INFORMATION: Gly, Ala, Thr, Ser or Asn

<400> SEQUENCE: 23

Xaa Glu Xaa Asp Xaa
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Gly, Ala, Thr, Ser or Asn

<400> SEQUENCE: 24

Asp Glu Xaa Asp Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Gly, Ala, Thr, Ser or Asn

<400> SEQUENCE: 25

Val Glu Xaa Asp Xaa
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Val or Leu
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Gly, Ala, Thr, Ser or Asn

<400> SEQUENCE: 26

Xaa Asp Glu Xaa Asp Xaa
1               5

<210> SEQ ID NO 27
<211> LENGTH: 6
<212> TYPE: PRT
<213> ORGANISM: Artificial Sequence
<220> FEATURE:

-continued

<223> OTHER INFORMATION: Synthetic Construct

<400> SEQUENCE: 27

Gly Ser Gly Arg Ser Ala
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Tyr or Phe

<400> SEQUENCE: 28

Ser Ser Xaa Tyr Ser Gly
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

His Pro Phe His Leu Val Ile His
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

His Pro Val Gly Leu Leu Ala Arg
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Construct

<400> SEQUENCE: 31

Gly Ser Gly Arg Ser Ala
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Tyr or Phe

<400> SEQUENCE: 32

Ser Ser Xaa Tyr Ser Gly
1               5

```
<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

His Pro Phe His Leu Val Ile His
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

His Pro Val Gly Leu Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Ser or Gly

<400> SEQUENCE: 35

Glu Xaa Xaa Tyr Xaa Gln Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Construct

<400> SEQUENCE: 36

Ser Gln Asn Tyr Pro Ile Val
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Pro Val Ile Leu Pro Ile Gln Ala
1               5

<210> SEQ ID NO 38
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 38

Ala Val Leu Gln Ser Gly Phe
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Construct

<400> SEQUENCE: 39

Ala Leu Phe Gln Gly Pro
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Ser or Gly

<400> SEQUENCE: 40

Glu Xaa Xaa Tyr Xaa Gln Xaa
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Construct

<400> SEQUENCE: 41

Asp Pro Pro Ile Val
1               5

<210> SEQ ID NO 42
<211> LENGTH: 5
<212> TYPE: PRT
<213> ORGANISM: Vibrio cholerae

<400> SEQUENCE: 42

Lys Asp Glu Leu Lys
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 43

His His His His His His Lys Asp Glu Leu
1               5                   10

<210> SEQ ID NO 44
<211> LENGTH: 5
<212> TYPE: PRT
<213> ORGANISM: Artificial Sequence
<220> FEATURE:
<223> OTHER INFORMATION: Synthetic Construct

<400> SEQUENCE: 44

Gly Ser Gly Ala Ser
1               5

<210> SEQ ID NO 45
<211> LENGTH: 12
<212> TYPE: PRT
<213> ORGANISM: Artificial Sequence
<220> FEATURE:
<223> OTHER INFORMATION: Synthetic Construct

<400> SEQUENCE: 45

Gly Gly Gly Ser Gly Gly Gly Ser Gly Gly Gly Ser
1               5                   10

<210> SEQ ID NO 46
<211> LENGTH: 7
<212> TYPE: PRT
<213> ORGANISM: Corynebacterium diphtheriae

<400> SEQUENCE: 46

Arg Val Arg Arg Ser Val Gly
1               5

<210> SEQ ID NO 47
<211> LENGTH: 6
<212> TYPE: PRT
<213> ORGANISM: Vibrio cholerae

<400> SEQUENCE: 47

Ile Glu Pro Asp Ser Gly
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic Construct

<400> SEQUENCE: 48

Arg Lys Pro Arg Asp Leu
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic Construct

<400> SEQUENCE: 49

Ile Glu Pro Asp Ser Gly
1               5
```

<210> SEQ ID NO 50
<211> LENGTH: 6
<212> TYPE: PRT
<213> ORGANISM: Artificial Sequence
<220> FEATURE:
<223> OTHER INFORMATION: Synthetic Construct

<400> SEQUENCE: 50

Ile Glu Pro Asp Asp Leu
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Construct

<400> SEQUENCE: 51

Ile Ala Pro Asp Ser Gly
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Construct

<400> SEQUENCE: 52

Ile Ala Pro Asp Asp Leu
1               5

<210> SEQ ID NO 53
<211> LENGTH: 1328
<212> TYPE: DNA
<213> ORGANISM: Artificial Sequence
<220> FEATURE:
<223> OTHER INFORMATION: Synthetic Construct

<400> SEQUENCE: 53

| | |
|---|---|
| atgggctcca acgaactgca tcaggtgccg agcaactgcg attgtctgaa cggcggtacc | 60 |
| tgcgttttcca acaaatattt ttctaacatt cactggtgta actgcccgaa aaaattcggt | 120 |
| ggacaacatt gtgaaatcga cggcggtggt ggttcgggcg gtggcggttc gggtggcggt | 180 |
| ggcagctcta gcaaaggcaa tgccatgagt gcactggctg cgcaccgcgt atgcggtgtg | 240 |
| ccgctggaga cactggcccg ttcacgcaaa ccacgtgacc tgaccgatga cctgagctgc | 300 |
| gcgtatcagg cccaaaatat tgtgtctctg tttgttgcaa cgcgtatcct gttcagtcat | 360 |
| ctggattcag tctttactct gaacctggac aacaggagc cggaagtagc tgagcgcctg | 420 |
| tccgatctgc gtcgcattaa tgaaaacaat ccaggcatgg tgacacaagt tctgaccgtc | 480 |
| gcgcgtcaga tctacaacga ctatgtaacg caccatcctg gtctgactcc ggaacagaca | 540 |
| tcggccgggg cacaagctgc ggatattctg agcctgttct gtccagatgc cgacaaatct | 600 |
| tgcgtggcaa gtaataacga tcaggctaat atcaacattg agtcacgctc cggacgttcg | 660 |
| tacctgcctg aaaatcgcgc ggttatcacc ccgcaaggcg tcacgaactg gacctatcag | 720 |
| gagctggaag ccactcacca ggcactgaca cgtgaaggtt acgtgtttgt agggtatcat | 780 |
| ggaacgaatc acgttgctgc gcaaaccatt gtgaaccgca tcgccccggt cccacgtggc | 840 |
| aataacactg agaatgaaga gaatgggggt ggcctgtacg ttgcaacaca tgcggaagta | 900 |
| gctcacggtt atgcccgcat taagaaaggg accggagagt atggcctgcc tacgcgtgca | 960 |

```
gaacgcgacg cgcgtggtgt gatgctgcgc gtctacatcc cgcgtgcttc gctggagcgc    1020
ttctatcgta ccaacactcc gctggaaaat gccgaagagc atattacaca ggttatcggc    1080
cactctctgc cactgcgcaa cgaagcattt acgggtcctg aaagtgcggg gggagaggat    1140
gaaaccgtga ttggctggga catggctatc catgccgtag caattccgtc aactattcca    1200
ggtaatgcgt acgaggaact ggccatcgat gaagaggcag tcgcgaaaga acaatccatt    1260
tcgacaaaac cgccttataa agagcgtcac catcatcacc atcacaaaga tgaactgtaa    1320
gcggccgc                                                             1328

<210> SEQ ID NO 54
<211> LENGTH: 438
<212> TYPE: PRT
<213> ORGANISM: Artificial Sequence
<220> FEATURE:
<223> OTHER INFORMATION: Synthetic Construct

<400> SEQUENCE: 54

Met Ser Asn Glu Leu His Gln Val Pro Ser Asn Cys Asp Cys Leu Asn
1               5                   10                  15

Gly Gly Thr Cys Val Ser Asn Lys Tyr Phe Ser Asn Ile His Trp Cys
            20                  25                  30

Asn Cys Pro Lys Lys Phe Gly Gly Gln His Cys Glu Ile Asp Gly Gly
        35                  40                  45

Gly Gly Ser Gly Gly Gly Ser Gly Gly Gly Ser Ser Lys
    50                  55                  60

Gly Asn Ala Met Ser Ala Leu Ala Ala His Arg Val Cys Gly Val Pro
65                  70                  75                  80

Leu Glu Thr Leu Ala Arg Ser Arg Lys Pro Arg Asp Leu Thr Asp Asp
                85                  90                  95

Leu Ser Cys Ala Tyr Gln Ala Gln Asn Ile Val Ser Leu Phe Val Ala
            100                 105                 110

Thr Arg Ile Leu Phe Ser His Leu Asp Ser Val Phe Thr Leu Asn Leu
        115                 120                 125

Asp Glu Gln Glu Pro Glu Val Ala Glu Arg Leu Ser Asp Leu Arg Arg
    130                 135                 140

Ile Asn Glu Asn Asn Pro Gly Met Val Thr Gln Val Leu Thr Val Ala
145                 150                 155                 160

Arg Gln Ile Tyr Asn Asp Tyr Val Thr His His Pro Gly Leu Thr Pro
                165                 170                 175

Glu Gln Thr Ser Ala Gly Ala Gln Ala Ala Asp Ile Leu Ser Leu Phe
            180                 185                 190

Cys Pro Asp Ala Asp Lys Ser Cys Val Ala Ser Asn Asn Asp Gln Ala
        195                 200                 205

Asn Ile Asn Ile Glu Ser Arg Ser Gly Arg Ser Tyr Leu Pro Glu Asn
    210                 215                 220

Arg Ala Val Ile Thr Pro Gln Gly Val Thr Asn Trp Thr Tyr Gln Glu
225                 230                 235                 240

Leu Glu Ala Thr His Gln Ala Leu Thr Arg Glu Gly Tyr Val Phe Val
                245                 250                 255

Gly Tyr His Gly Thr Asn His Val Ala Ala Gln Thr Ile Val Asn Arg
            260                 265                 270

Ile Ala Pro Val Pro Arg Gly Asn Asn Thr Glu Asn Glu Glu Lys Trp
        275                 280                 285

Gly Gly Leu Tyr Val Ala Thr His Ala Glu Val Ala His Gly Tyr Ala
    290                 295                 300
```

Arg Ile Lys Glu Gly Thr Gly Glu Tyr Gly Leu Pro Thr Arg Ala Glu
305                 310                 315                 320

Arg Asp Ala Arg Gly Val Met Leu Arg Val Tyr Ile Pro Arg Ala Ser
            325                 330                 335

Leu Glu Arg Phe Tyr Arg Thr Asn Thr Pro Leu Glu Asn Ala Glu Glu
        340                 345                 350

His Ile Thr Gln Val Ile Gly His Ser Leu Pro Leu Arg Asn Glu Ala
    355                 360                 365

Phe Thr Gly Pro Glu Ser Ala Gly Gly Glu Asp Glu Thr Val Ile Gly
370                 375                 380

Trp Asp Met Ala Ile His Ala Val Ala Ile Pro Ser Thr Ile Pro Gly
385                 390                 395                 400

Asn Ala Tyr Glu Glu Leu Ala Ile Asp Glu Glu Ala Val Ala Lys Glu
                405                 410                 415

Gln Ser Ile Ser Thr Lys Pro Pro Tyr Lys Glu Arg His His His His
            420                 425                 430

His His Lys Asp Glu Leu
        435

<210> SEQ ID NO 55
<211> LENGTH: 1330
<212> TYPE: DNA
<213> ORGANISM: Artificial Sequence
<220> FEATURE:
<223> OTHER INFORMATION: Synthetic Construct

<400> SEQUENCE: 55
ccatgggctc caacgaactg catcaggtgc cgagcaactg cgattgtctg aacggcggta      60
cctgcgtttc caacaaatat ttttctaaca ttcactggtg taactgcccg aaaaaattcg     120
gtggacaaca ttgtgaaatc gacggcggtg gtggttcggg cggtggcggt tcgggtggcg     180
gtggcagctc tagcaaaggc aacgcgatga gcgcgctggc cgcacatcgt gtgtgcggcg     240
ttccgctgga aaccctggct cgctctattg agccagatag tggtaccgat gacctgagct     300
gcgcgtatca ggcccaaaat attgtgtctc tgtttgttgc aacgcgtatc ctgttcagtc     360
atctggattc agtctttact ctgaacctgg acgaacagga gccggaagta gctgagcgcc     420
tgtccgatct cgtcgcatt aatgaaaaca atccaggcat ggtgacacaa gttctgaccg     480
tcgcgcgtca gatctacaac gactatgtaa cgcaccatcc tggtctgact ccggaacaga     540
catcggccgg gcacaagct gcggatattc tgagcctgtt ctgtccagat gccgacaaat     600
cttgcgtggc aagtaataac gatcaggcta atatcaacat tgagtcacgc tccggacgtt     660
cgtacctgcc tgaaaatcgc gcggttatca ccccgcaagg cgtcacgaac tggacctatc     720
aggagctgga agccactcac caggcactga cacgtgaagg ttacgtgttt gtagggtatc     780
atggaacgaa tcacgttgct gcgcaaacca ttgtgaaccg catcgccccg gtcccacgtg     840
gcaataacac tgagaatgaa gagaaatggg gtggcctgta cgttgcaaca catgcggaag     900
tagctcacgg ttatgcccgc attaaagaag gaccggaga gtatggcctg cctacgcgtg     960
cagaacgcga cgcgcgtggt gtgatgctgc gcgtctacat cccgcgtgct cgctggagc    1020
gcttctatcg taccaacact ccgctggaaa tgccgaaga catattaca caggttatcg    1080
gccactctct gccactgcgc aacgaagcat ttacgggtcc tgaaagtgcg gggggagagg    1140
atgaaaccgt gattggctgg acatggcta tccatgccgt agcaattccg tcaactattc    1200
caggtaatgc gtacgaggaa ctggccatcg atgaagaggc agtcgcgaaa gaacaatcca    1260

```
tttcgacaaa accgccttat aaagagcgtc accatcatca ccatcacaaa gatgaactgt    1320
aagcggccgc                                                            1330
```

<210> SEQ ID NO 56
<211> LENGTH: 6
<212> TYPE: PRT
<213> ORGANISM: Artificial Sequence
<220> FEATURE:
<223> OTHER INFORMATION: Synthetic Construct

<400> SEQUENCE: 56

Ile Glu Pro Asp Asp Leu
1               5

<210> SEQ ID NO 57
<211> LENGTH: 18
<212> TYPE: DNA
<213> ORGANISM: Artificial Sequence
<220> FEATURE:
<223> OTHER INFORMATION: Synthetic Construct

<400> SEQUENCE: 57
attgagccag atgacctg                                                      18

<210> SEQ ID NO 58
<211> LENGTH: 6
<212> TYPE: PRT
<213> ORGANISM: Artificial Sequence
<220> FEATURE:
<223> OTHER INFORMATION: Synthetic Construct

<400> SEQUENCE: 58

Ile Ala Pro Asp Ser Gly
1               5

<210> SEQ ID NO 59
<211> LENGTH: 18
<212> TYPE: DNA
<213> ORGANISM: Artificial Sequence
<220> FEATURE:
<223> OTHER INFORMATION: Synthetic Construct

<400> SEQUENCE: 59
attgctccag atagtggt                                                      18

<210> SEQ ID NO 60
<211> LENGTH: 6
<212> TYPE: PRT
<213> ORGANISM: Artificial Sequence
<220> FEATURE:
<223> OTHER INFORMATION: Synthetic Construct

<400> SEQUENCE: 60

Ile Ala Pro Asp Asp Leu
1               5

<210> SEQ ID NO 61
<211> LENGTH: 18
<212> TYPE: DNA
<213> ORGANISM: Artificial Sequence
<220> FEATURE:
<223> OTHER INFORMATION: Synthetic Construct

<400> SEQUENCE: 61
attgctccag atgacctg                                                      18

<210> SEQ ID NO 62
<211> LENGTH: 438
<212> TYPE: PRT
<213> ORGANISM: Artificial Sequence
<220> FEATURE:
<223> OTHER INFORMATION: Synthetic Construct

<400> SEQUENCE: 62

```
Met Ser Asn Glu Leu His Gln Val Pro Ser Asn Cys Asp Cys Leu Asn
1               5                   10                  15

Gly Gly Thr Cys Val Ser Asn Lys Tyr Phe Ser Asn Ile His Trp Cys
            20                  25                  30

Asn Cys Pro Lys Lys Phe Gly Gly Gln His Cys Glu Ile Asp Gly Gly
        35                  40                  45

Gly Gly Ser Gly Gly Gly Ser Gly Gly Gly Ser Ser Ser Lys
    50                  55                  60

Gly Asn Ala Met Ser Ala Leu Ala Ala His Arg Val Cys Gly Val Pro
65                  70                  75                  80

Leu Glu Thr Leu Ala Arg Ser Ile Glu Pro Asp Ser Gly Thr Asp Asp
                85                  90                  95

Leu Ser Cys Ala Tyr Gln Ala Gln Asn Ile Val Ser Leu Phe Val Ala
            100                 105                 110

Thr Arg Ile Leu Phe Ser His Leu Asp Ser Val Phe Thr Leu Asn Leu
        115                 120                 125

Asp Glu Gln Glu Pro Glu Val Ala Glu Arg Leu Ser Asp Leu Arg Arg
    130                 135                 140

Ile Asn Glu Asn Asn Pro Gly Met Val Thr Gln Val Leu Thr Val Ala
145                 150                 155                 160

Arg Gln Ile Tyr Asn Asp Tyr Val Thr His His Pro Gly Leu Thr Pro
                165                 170                 175

Glu Gln Thr Ser Ala Gly Ala Gln Ala Ala Asp Ile Leu Ser Leu Phe
            180                 185                 190

Cys Pro Asp Ala Asp Lys Ser Cys Val Ala Ser Asn Asn Asp Gln Ala
        195                 200                 205

Asn Ile Asn Ile Glu Ser Arg Ser Gly Arg Ser Tyr Leu Pro Glu Asn
    210                 215                 220

Arg Ala Val Ile Thr Pro Gln Gly Val Thr Asn Trp Thr Tyr Gln Glu
225                 230                 235                 240

Leu Glu Ala Thr His Gln Ala Leu Thr Arg Glu Gly Tyr Val Phe Val
                245                 250                 255

Gly Tyr His Gly Thr Asn His Val Ala Ala Gln Thr Ile Val Asn Arg
            260                 265                 270

Ile Ala Pro Val Pro Arg Gly Asn Asn Thr Glu Asn Glu Glu Lys Trp
        275                 280                 285

Gly Gly Leu Tyr Val Ala Thr His Ala Glu Val Ala His Gly Tyr Ala
    290                 295                 300

Arg Ile Lys Glu Gly Thr Gly Glu Tyr Gly Leu Pro Thr Arg Ala Glu
305                 310                 315                 320

Arg Asp Ala Arg Gly Val Met Leu Arg Val Tyr Ile Pro Arg Ala Ser
                325                 330                 335

Leu Glu Arg Phe Tyr Arg Thr Asn Thr Pro Leu Glu Asn Ala Glu Glu
            340                 345                 350

His Ile Thr Gln Val Ile Gly His Ser Leu Pro Leu Arg Asn Glu Ala
        355                 360                 365

Phe Thr Gly Pro Glu Ser Ala Gly Gly Glu Asp Glu Thr Val Ile Gly
    370                 375                 380
```

Trp Asp Met Ala Ile His Ala Val Ala Ile Pro Ser Thr Ile Pro Gly
385                 390                 395                 400

Asn Ala Tyr Glu Glu Leu Ala Ile Asp Glu Glu Ala Val Ala Lys Glu
            405                 410                 415

Gln Ser Ile Ser Thr Lys Pro Pro Tyr Lys Glu Arg His His His
        420                 425                 430

His His Lys Asp Glu Leu
        435

<210> SEQ ID NO 63
<211> LENGTH: 1330
<212> TYPE: DNA
<213> ORGANISM: Artificial Sequence
<220> FEATURE:
<223> OTHER INFORMATION: Synthetic Construct

<400> SEQUENCE: 63
ccatgggctc caacgaactg catcaggtgc cgagcaactg cgattgtctg aacggcggta      60
cctgcgtttc caacaaatat ttttctaaca ttcactggtg taactgcccg aaaaaattcg     120
gtggacaaca ttgtgaaatc gacgcggtg gtggttcggg cggtggcggt tcgggtggcg     180
gtggcagctc tagcaaaggc aacgcgatga gcgcgctggc cgcacatcgt gtgtgcggcg     240
ttccgctgga aaccctggct cgctctattg agccagatag tggtaccgat gacctgagct     300
gcgcgtatca ggcccaaaat attgtgtctc tgtttgttgc aacgcgtatc ctgttcagtc     360
atctggattc agtctttact ctgaacctgg acgaacagga gccggaagta gctgagcgcc     420
tgtccgatct gcgtcgcatt aatgaaaaca atccaggcat ggtgacacaa gttctgaccg     480
tcgcgcgtca gatctacaac gactatgtaa cgcaccatcc tggtctgact ccggaacaga     540
catcggccgg ggcacaagct gcggatattc tgagcctgtt ctgtccagat gccgacaaat     600
cttgcgtggc aagtaataac gatcaggcta atatcaacat tgagtcacgc tccggacgtt     660
cgtacctgcc tgaaaatcgc gcggttatca ccccgcaagg cgtcacgaac tggacctatc     720
aggagctgga agccactcac caggcactga cacgtgaagg ttacgtgttt gtagggtatc     780
atggaacgaa tcacgttgct gcgcaaacca ttgtgaaccg catcgccccg gtcccacgtg     840
gcaataacac tgagaatgaa gagaaatggg gtggcctgta cgttgcaaca catgcggaag     900
tagctcacgg ttatgcccgc attaaagaag ggaccggaga gtatggcctg cctacgcgtg     960
cagaacgcga cgcgcgtggt gtgatgctgc gcgtctacat cccgcgtgct tcgctggagc    1020
gcttctatcg taccaacact ccgctggaaa atgccgaaga gcatattaca caggttatcg    1080
gccactctct gccactgcgc aacgaagcat ttacgggtcc tgaaagtgcg ggggagagg     1140 atgaaaccgt gattggctgg gacatggcta tccatgccgt agcaattccg tcaactattc    1200
caggtaatgc gtacgaggaa ctggccatcg atgaagaggc agtcgcgaaa gaacaatcca    1260
tttcgacaaa accgccttat aaagagcgtc accatcatca ccatcacaaa gatgaactgt    1320
aagcggccgc                                                          1330

<210> SEQ ID NO 64
<211> LENGTH: 438
<212> TYPE: PRT
<213> ORGANISM: Artificial Sequence
<220> FEATURE:
<223> OTHER INFORMATION: Synthetic Construct

<400> SEQUENCE: 64

Met Ser Asn Glu Leu His Gln Val Pro Ser Asn Cys Asp Cys Leu Asn

```
                1               5                    10                   15
Gly Gly Thr Cys Val Ser Asn Lys Tyr Phe Ser Asn Ile His Trp Cys
                20                  25                  30

Asn Cys Pro Lys Lys Phe Gly Gly Gln His Cys Glu Ile Asp Gly Gly
                35                  40                  45

Gly Gly Ser Gly Gly Gly Ser Gly Gly Gly Ser Ser Ser Lys
    50                  55                  60

Gly Asn Ala Met Ser Ala Leu Ala His Arg Val Cys Gly Val Pro
65                  70                  75                  80

Leu Glu Thr Leu Ala Arg Ser Ile Glu Pro Asp Asp Leu Thr Asp Asp
                85                  90                  95

Leu Ser Cys Ala Tyr Gln Ala Gln Asn Ile Val Ser Leu Phe Val Ala
                100                 105                 110

Thr Arg Ile Leu Phe Ser His Leu Asp Ser Val Phe Thr Leu Asn Leu
                115                 120                 125

Asp Glu Gln Glu Pro Glu Val Ala Glu Arg Leu Ser Asp Leu Arg Arg
                130                 135                 140

Ile Asn Glu Asn Asn Pro Gly Met Val Thr Gln Val Leu Thr Val Ala
145                 150                 155                 160

Arg Gln Ile Tyr Asn Asp Tyr Val Thr His His Pro Gly Leu Thr Pro
                165                 170                 175

Glu Gln Thr Ser Ala Gly Ala Gln Ala Ala Asp Ile Leu Ser Leu Phe
                180                 185                 190

Cys Pro Asp Ala Asp Lys Ser Cys Val Ala Ser Asn Asn Asp Gln Ala
                195                 200                 205

Asn Ile Asn Ile Glu Ser Arg Ser Gly Arg Ser Tyr Leu Pro Glu Asn
                210                 215                 220

Arg Ala Val Ile Thr Pro Gln Gly Val Thr Asn Trp Thr Tyr Gln Glu
225                 230                 235                 240

Leu Glu Ala Thr His Gln Ala Leu Thr Arg Glu Gly Tyr Val Phe Val
                245                 250                 255

Gly Tyr His Gly Thr Asn His Val Ala Ala Gln Thr Ile Val Asn Arg
                260                 265                 270

Ile Ala Pro Val Pro Arg Gly Asn Asn Thr Glu Asn Glu Glu Lys Trp
                275                 280                 285

Gly Gly Leu Tyr Val Ala Thr His Ala Glu Val Ala His Gly Tyr Ala
                290                 295                 300

Arg Ile Lys Glu Gly Thr Gly Glu Tyr Gly Leu Pro Thr Arg Ala Glu
305                 310                 315                 320

Arg Asp Ala Arg Gly Val Met Leu Arg Val Tyr Ile Pro Arg Ala Ser
                325                 330                 335

Leu Glu Arg Phe Tyr Arg Thr Asn Thr Pro Leu Glu Asn Ala Glu Glu
                340                 345                 350

His Ile Thr Gln Val Ile Gly His Ser Leu Pro Leu Arg Asn Glu Ala
                355                 360                 365

Phe Thr Gly Pro Glu Ser Ala Gly Gly Glu Asp Glu Thr Val Ile Gly
                370                 375                 380

Trp Asp Met Ala Ile His Ala Val Ala Ile Pro Ser Thr Ile Pro Gly
385                 390                 395                 400

Asn Ala Tyr Glu Glu Leu Ala Ile Asp Glu Ala Val Ala Lys Glu
                405                 410                 415

Gln Ser Ile Ser Thr Lys Pro Pro Tyr Lys Glu Arg His His His His
                420                 425                 430
```

His His Lys Asp Glu Leu
        435

<210> SEQ ID NO 65
<211> LENGTH: 1328
<212> TYPE: DNA
<213> ORGANISM: Artificial Sequence
<220> FEATURE:
<223> OTHER INFORMATION: Synthetic Construct

<400> SEQUENCE: 65

| | | | | | |
|---|---|---|---|---|---|
| atgggctcca | acgaactgca | tcaggtgccg | agcaactgcg | attgtctgaa | cggcggtacc | 60 |
| tgcgttttcca | acaaatattt | ttctaacatt | cactggtgta | actgcccgaa | aaaattcggt | 120 |
| ggacaacatt | gtgaaatcga | cggcggtggt | ggttcgggcg | gtggcggttc | gggtggcggt | 180 |
| ggcagctcta | gcaaaggcaa | tgccatgagt | gcactggctg | cgcaccgcgt | atgcggtgtg | 240 |
| ccgctggaga | cactggcccg | ttcacgcaaa | ccacgtgacc | tgaccgatga | cctgagctgc | 300 |
| gcgtatcagg | cccaaaatat | tgtgtctctg | tttgttgcaa | cgcgtatcct | gttcagtcat | 360 |
| ctggattcag | tctttactct | gaacctggac | gaacaggagc | cggaagtagc | tgagcgcctg | 420 |
| tccgatctgc | gtcgcattaa | tgaaaacaat | ccaggcatgg | tgacacaagt | tctgaccgtc | 480 |
| gcgcgtcaga | tctacaacga | ctatgtaacg | caccatcctg | gtctgactcc | ggaacagaca | 540 |
| tcggccgggg | cacaagctgc | ggatattctg | agcctgttct | gtccagatgc | cgacaaatct | 600 |
| tgcgtggcaa | gtaataacga | tcaggctaat | atcaacattg | agtcacgctc | cggacgttcg | 660 |
| tacctgcctg | aaaatcgcgc | ggttatcacc | ccgcaaggcg | tcacgaactg | gacctatcag | 720 |
| gagctggaag | ccactcacca | ggcactgaca | cgtgaaggtt | acgtgtttgt | agggtatcat | 780 |
| ggaacgaatc | acgttgctgc | gcaaaccatt | gtgaaccgca | tcgccccggt | ccacgtggc | 840 |
| aataacactg | agaatgaaga | gaaatggggt | ggcctgtacg | ttgcaacaca | tgcggaagta | 900 |
| gctcacggtt | atgcccgcat | taagaaggg | accggagagt | atggcctgcc | tacgcgtgca | 960 |
| gaacgcgacg | cgcgtggtgt | gatgctgcgc | gtctacatcc | cgcgtgcttc | gctggagcgc | 1020 |
| ttctatcgta | ccaacactcc | gctggaaaat | gccgaagagc | atattacaca | ggttatcggc | 1080 |
| cactctctgc | cactgcgcaa | cgaagcattt | acgggtcctg | aaagtgcggg | gggagaggat | 1140 |
| gcaaccgtga | ttggctggga | catggctatc | catgccgtag | caattccgtc | aactattcca | 1200 |
| ggtaatgcgt | acgaggaact | ggccatcgat | gaagaggcag | tcgcgaaaga | acaatccatt | 1260 |
| tcgacaaaac | cgccttataa | agagcgtcac | catcatcacc | atcacaaaga | tgaactgtaa | 1320 |
| gcggccgc | | | | | 1328 |

<210> SEQ ID NO 66
<211> LENGTH: 438
<212> TYPE: PRT
<213> ORGANISM: Artificial Sequence
<220> FEATURE:
<223> OTHER INFORMATION: Synthetic Construct

<400> SEQUENCE: 66

Met Ser Asn Glu Leu His Gln Val Pro Ser Asn Cys Asp Cys Leu Asn
1               5                   10                  15

Gly Gly Thr Cys Val Ser Asn Lys Tyr Phe Ser Asn Ile His Trp Cys
            20                  25                  30

Asn Cys Pro Lys Lys Phe Gly Gly Gln His Cys Glu Ile Asp Gly Gly
        35                  40                  45

Gly Gly Ser Gly Gly Gly Gly Ser Gly Gly Gly Gly Ser Ser Ser Lys
    50                  55                  60

Gly Asn Ala Met Ser Ala Leu Ala Ala His Arg Val Cys Gly Val Pro
 65                  70                  75                  80

Leu Glu Thr Leu Ala Arg Ser Arg Lys Pro Arg Asp Leu Thr Asp Asp
                 85                  90                  95

Leu Ser Cys Ala Tyr Gln Ala Gln Asn Ile Val Ser Leu Phe Val Ala
            100                 105                 110

Thr Arg Ile Leu Phe Ser His Leu Asp Ser Val Phe Thr Leu Asn Leu
        115                 120                 125

Asp Glu Gln Glu Pro Glu Val Ala Glu Arg Leu Ser Asp Leu Arg Arg
    130                 135                 140

Ile Asn Glu Asn Asn Pro Gly Met Val Thr Gln Val Leu Thr Val Ala
145                 150                 155                 160

Arg Gln Ile Tyr Asn Asp Tyr Val Thr His His Pro Gly Leu Thr Pro
                165                 170                 175

Glu Gln Thr Ser Ala Gly Ala Gln Ala Ala Asp Ile Leu Ser Leu Phe
            180                 185                 190

Cys Pro Asp Ala Asp Lys Ser Cys Val Ala Ser Asn Asn Asp Gln Ala
        195                 200                 205

Asn Ile Asn Ile Glu Ser Arg Ser Gly Arg Ser Tyr Leu Pro Glu Asn
    210                 215                 220

Arg Ala Val Ile Thr Pro Gln Gly Val Thr Asn Trp Thr Tyr Gln Glu
225                 230                 235                 240

Leu Glu Ala Thr His Gln Ala Leu Thr Arg Glu Gly Tyr Val Phe Val
                245                 250                 255

Gly Tyr His Gly Thr Asn His Val Ala Ala Gln Thr Ile Val Asn Arg
            260                 265                 270

Ile Ala Pro Val Pro Arg Gly Asn Asn Thr Glu Asn Glu Glu Lys Trp
        275                 280                 285

Gly Gly Leu Tyr Val Ala Thr His Ala Glu Val Ala His Gly Tyr Ala
    290                 295                 300

Arg Ile Lys Glu Gly Thr Gly Glu Tyr Gly Leu Pro Thr Arg Ala Glu
305                 310                 315                 320

Arg Asp Ala Arg Gly Val Met Leu Arg Val Tyr Ile Pro Arg Ala Ser
                325                 330                 335

Leu Glu Arg Phe Tyr Arg Thr Asn Thr Pro Leu Glu Asn Ala Glu Glu
            340                 345                 350

His Ile Thr Gln Val Ile Gly His Ser Leu Pro Leu Arg Asn Glu Ala
        355                 360                 365

Phe Thr Gly Pro Glu Ser Ala Gly Gly Ala Asp Glu Thr Val Ile Gly
    370                 375                 380

Trp Asp Met Ala Ile His Ala Val Ala Ile Pro Ser Thr Ile Pro Gly
385                 390                 395                 400

Asn Ala Tyr Glu Glu Leu Ala Ile Asp Glu Glu Ala Val Ala Lys Glu
                405                 410                 415

Gln Ser Ile Ser Thr Lys Pro Pro Tyr Lys Glu Arg His His His His
            420                 425                 430

His His Lys Asp Glu Leu
        435

<210> SEQ ID NO 67
<211> LENGTH: 1608
<212> TYPE: DNA
<213> ORGANISM: Artificial Sequence
<220> FEATURE:
<223> OTHER INFORMATION: Synthetic Construct

<400> SEQUENCE: 67

```
atgggcgtga aggtgctgtt cgccctgatc tgcatcgccg tggcgctcgc cgacaactcg      60
agctacaagg acgacgacga caagatcatc gggggacatg aggccaagcc ccactcccgc     120
ccctacatgg cttatcttat gatctgggat cagaagtctc tgaagaggtg cggtggcttc     180
ctgatacaag acgacttcgt gctgacagct gctcactgtt ggggaagctc cataaatgtc     240
accttggggg cccacaatat caagaacag gagccgaccc agcagtttat ccctgtgaaa      300
agacccatcc cccatccagc ctataatcct aagaacttct ccaacgacat catgctactg     360
cagctggaga gaaaggccaa gcggaccaga gctgtgcagc ccctcaggct acctagcaac     420
aaggcccagg tgaagccagg gcagacatgc agtgtggccg ctgggggca gacggccccc      480
ctgggaaaac actcacacac actacaagag gtgaagatga cagtgcagga agatcgaaag     540
tgcgaatctg acttacgcca ttattacgac agtaccattg agttgtgcgt ggggaccca      600
gagattaaaa agacttcctt taagggggac tctggaggcc ctcttgtgtg taacaaggtg     660
gcccagggca ttgtctccta tggacgaaac aatggcatgc tccacgagcc tgcaccaaa     720
gtctcaagct ttgtacactg gataaagaaa accatgaaac gctacgccat gggaggcgga     780
ggctccggag gaggagggtc cggggcggc ggaagcatgg cccaggtgca gctgcagcag      840
tccggcgctg agctggtgcg ccctggctcc tccgtgaaaa tctcctgcaa ggcttccggc     900
tacgctttct cctcctactg gatgaactgg gtgaagcagc gcctggcca gggcctggag     960
tggatcggcc aaatctggcc gggcgacggc gacaccaact acaacggcaa gttcaagggc    1020
aaggctaccc tgaccgctga cgagtcctcc tccaccgctt acatgcagct gtcctccctg    1080
gcttccgagg actccgctgt gtacttctgc gctcgccgcg agaccaccac cgtgggccgc    1140
tactactacg ctatggacta ctggggccag ggcacctcgg tgaccgtgtc ctccggcggc    1200
ggcggctccg gcggcggcgg ctccggcggc gggagctccg acatcctgct gacccagacc    1260
ccggcttccc tggctgtgtc cctgggccag cgcgctacca tctcctgcaa ggcttcccag    1320
tccgtggact acgacggcga ctcctacctg aactggtacc agcagatccc gggccagccg    1380
ccgaagctgc tgatctacga cgcttccaac ctggtgtccg gcatcccgcc gcgcttctcc    1440
ggctccggct ccggcaccga cttcaccctg aacatccacc cggtggagaa ggtgacgct    1500
gctacctacc actgccagca gtccaccgag gacccgtgga ccttcggcgg cggcaccaag    1560
ctggagatca gcgcggtgg tgacatgcat caccatcacc atcactga                  1608
```

<210> SEQ ID NO 68
<211> LENGTH: 535
<212> TYPE: PRT
<213> ORGANISM: Artificial Sequence
<220> FEATURE:
<223> OTHER INFORMATION: Synthetic Construct

<400> SEQUENCE: 68

```
Met Gly Val Lys Val Leu Phe Ala Leu Ile Cys Ile Ala Val Ala Leu
1               5                   10                  15

Ala Asp Asn Ser Ser Tyr Lys Asp Asp Asp Lys Ile Ile Gly Gly
                20                  25                  30

His Glu Ala Lys Pro His Ser Arg Pro Tyr Met Ala Tyr Leu Met Ile
            35                  40                  45

Trp Asp Gln Lys Ser Leu Lys Arg Cys Gly Gly Phe Leu Ile Gln Asp
        50                  55                  60

Asp Phe Val Leu Thr Ala Ala His Cys Trp Gly Ser Ser Ile Asn Val
```

```
                65                  70                  75                  80
        Thr Leu Gly Ala His Asn Ile Lys Glu Gln Glu Pro Thr Gln Gln Phe
                            85                  90                  95
        Ile Pro Val Lys Arg Pro Ile Pro His Pro Ala Tyr Asn Pro Lys Asn
                        100                 105                 110
        Phe Ser Asn Asp Ile Met Leu Leu Gln Leu Glu Arg Lys Ala Lys Arg
                    115                 120                 125
        Thr Arg Ala Val Gln Pro Leu Arg Leu Pro Ser Asn Lys Ala Gln Val
                130                 135                 140
        Lys Pro Gly Gln Thr Cys Ser Val Ala Gly Trp Gly Gln Thr Ala Pro
        145                 150                 155                 160
        Leu Gly Lys His Ser His Thr Leu Gln Glu Val Lys Met Thr Val Gln
                        165                 170                 175
        Glu Asp Arg Lys Cys Glu Ser Asp Leu Arg His Tyr Tyr Asp Ser Thr
                    180                 185                 190
        Ile Glu Leu Cys Val Gly Asp Pro Glu Ile Lys Lys Thr Ser Phe Lys
                195                 200                 205
        Gly Asp Ser Gly Gly Pro Leu Val Cys Asn Lys Val Ala Gln Gly Ile
            210                 215                 220
        Val Ser Tyr Gly Arg Asn Asn Gly Met Pro Pro Arg Ala Cys Thr Lys
        225                 230                 235                 240
        Val Ser Ser Phe Val His Trp Ile Lys Lys Thr Met Lys Arg Tyr Ala
                        245                 250                 255
        Met Gly Gly Gly Gly Ser Gly Gly Gly Ser Gly Gly Gly Gly Ser
                    260                 265                 270
        Met Ala Gln Val Gln Leu Gln Gln Ser Gly Ala Glu Leu Val Arg Pro
                275                 280                 285
        Gly Ser Ser Val Lys Ile Ser Cys Lys Ala Ser Gly Tyr Ala Phe Ser
            290                 295                 300
        Ser Tyr Trp Met Asn Trp Val Lys Gln Arg Pro Gly Gln Gly Leu Glu
        305                 310                 315                 320
        Trp Ile Gly Gln Ile Trp Pro Gly Asp Gly Asp Thr Asn Tyr Asn Gly
                        325                 330                 335
        Lys Phe Lys Gly Lys Ala Thr Leu Thr Ala Asp Glu Ser Ser Ser Thr
                    340                 345                 350
        Ala Tyr Met Gln Leu Ser Ser Leu Ala Ser Glu Asp Ser Ala Val Tyr
                355                 360                 365
        Phe Cys Ala Arg Arg Glu Thr Thr Thr Val Gly Arg Tyr Tyr Tyr Ala
            370                 375                 380
        Met Asp Tyr Trp Gly Gln Gly Thr Ser Val Thr Val Ser Ser Gly Gly
        385                 390                 395                 400
        Gly Gly Ser Gly Gly Gly Gly Ser Gly Gly Ser Ser Asp Ile Leu
                        405                 410                 415
        Leu Thr Gln Thr Pro Ala Ser Leu Ala Val Ser Leu Gly Gln Arg Ala
                    420                 425                 430
        Thr Ile Ser Cys Lys Ala Ser Gln Ser Val Asp Tyr Asp Gly Asp Ser
                435                 440                 445
        Tyr Leu Asn Trp Tyr Gln Gln Ile Pro Gly Gln Pro Pro Lys Leu Leu
            450                 455                 460
        Ile Tyr Asp Ala Ser Asn Leu Val Ser Gly Ile Pro Pro Arg Phe Ser
        465                 470                 475                 480
        Gly Ser Gly Ser Gly Thr Asp Phe Thr Leu Asn Ile His Pro Val Glu
                        485                 490                 495
```

```
Lys Val Asp Ala Ala Thr Tyr His Cys Gln Gln Ser Thr Glu Asp Pro
            500                 505                 510

Trp Thr Phe Gly Gly Gly Thr Lys Leu Glu Ile Lys Arg Gly Gly Asp
        515                 520                 525

Met His His His His His His
    530                 535

<210> SEQ ID NO 69
<211> LENGTH: 1869
<212> TYPE: DNA
<213> ORGANISM: Artificial Sequence
<220> FEATURE:
<223> OTHER INFORMATION: Synthetic Construct

<400> SEQUENCE: 69
atggccaaca tccagctggt gcagtctggt cctgagctga agaagcctgg tgagactgtc      60
aaaatctcct gcaaggcttc tgggtatacc ttcactaact atggtatgaa ctgggtgaag     120
caggctcctg gtaagggtct tgcgttggatg ggctggatta cacccacac tggtgagcct     180 acttatgctg atgacttcaa gggacgtttt gccttctctc tggaaacttc tgccagcact     240
gcctatctcc agatcaacaa cctcaaaaat gaggacactg ctacttactt ctgtacacgt     300
cgtggttacg actggtactt cgatgtctgg ggtgctggga ccacggtgac cgtgttctcc     360
gggggaggtg gcagcggggg aggtggcagc ggcggcggga gctccgacat caagatgacc     420
cagtctcctt cttccatgta tgcttctctg ggtgagcgtg tcactatcac ttgcaaggcc     480
agccaggaca ttaatagcta tctgagctgg ttccatcata aacctgggaa atctcctaag     540
accctgatct atcgtgctaa ccgtctggtt gatggggtcc cttctcgttt cagcggctct     600
ggttctgggc aagattattc tctcaccatc agcagcctgg actatgaaga tatgggtatt     660
tattattgtc aacagtatga tgagtctcct tggactttcg gtggtggcac caagctggag     720
atgaaaggct ctggcgctag caaaggcaat gccatgagtg cactggctgc gaccgcgta     780 tgcggtgtgc cgctggagac actggcccgt tcacgcaaac cacgtgacct gaccgatgac     840
ctgagctgcg cgtatcaggc ccaaaatatt gtgtctctgt tgttgcaac gcgtatcctg     900 ttcagtcatc tggattcagt ctttactctg aacctggacg aacaggagcc ggaagtagct     960
gagcgcctgt ccgatctgcg tcgcattaat gaaaacaatc caggcatggt gacacaagtt    1020
ctgaccgtcg cgcgtcagat ctacaacgac tatgtaacgc accatcctgg tctgactccg    1080
gaacagacat cggccggggc acaagctgcg gatattctga cctgttctg tccagatgcc    1140 gacaaatctt gcgtggcaag taataacgat caggctaata tcaacattga gtcacgctcc    1200
ggacgttcgt acctgcctga aaatcgcgcg ttatcacccc gcaaggcgt cacgaactgg    1260 acctatcagg agctggaagc cactcaccag gcactgacac gtgaaggtta cgtgtttgta    1320
gggtatcatg aacgaatca cgttgctgcg caaaccattg tgaaccgcat cgccccggtc    1380
ccacgtggca ataacactga gaatgaagag aaatggggtg gcctgtacgt tgcaacacat    1440
gcggaagtag ctcacggtta tgcccgcatt aaagaaggga ccggagagta tggcctgcct    1500
acgcgtgcag aacgcgacgc gcgtggtgtg atgctgcgcg tctacatccc gcgtgcttcg    1560
ctggagcgct tctatcgtac caacactccg ctggaaaatg ccgaagagca tattacacag    1620
gttatcggcc actctctgcc actgcgcaac gaagcattta cgggtcctga agtgcgggg    1680 ggagaggatg aaaccgtgat tggctgggac atggctatcc atgccgtagc aattccgtca    1740
actattccag gtaatgcgta cgaggaactg gccatcgatg aagaggcagt cgcgaaagaa    1800
caatccattt cgacaaaacc gccttataaa gagcgtcacc atcatcacca tcacaaagat    1860
```

-continued gaactgtaa                                                      1869

<210> SEQ ID NO 70
<211> LENGTH: 18
<212> TYPE: DNA
<213> ORGANISM: Artificial Sequence
<220> FEATURE:
<223> OTHER INFORMATION: Synthetic Construct

<400> SEQUENCE: 70
attgagccag atgacctg                                            18

<210> SEQ ID NO 71
<211> LENGTH: 18
<212> TYPE: DNA
<213> ORGANISM: Artificial Sequence
<220> FEATURE:
<223> OTHER INFORMATION: Synthetic Construct

<400> SEQUENCE: 71
attgctccag atagtggt                                            18

<210> SEQ ID NO 72
<211> LENGTH: 18
<212> TYPE: DNA
<213> ORGANISM: Artificial Sequence
<220> FEATURE:
<223> OTHER INFORMATION: Synthetic Construct

<400> SEQUENCE: 72
attgagccag atagtggt                                            18

<210> SEQ ID NO 73
<211> LENGTH: 18
<212> TYPE: DNA
<213> ORGANISM: Artificial Sequence
<220> FEATURE:
<223> OTHER INFORMATION: Synthetic Construct

<400> SEQUENCE: 73
attgctccag atgacctg                                            18

<210> SEQ ID NO 74
<211> LENGTH: 624
<212> TYPE: PRT
<213> ORGANISM: Artificial Sequence
<220> FEATURE:
<223> OTHER INFORMATION: Synthetic Construct

<400> SEQUENCE: 74

Met Ala Asn Ile Gln Leu Val Gln Ser Gly Pro Glu Leu Lys Lys Pro
 1               5                  10                  15

Gly Glu Thr Val Lys Ile Ser Cys Lys Ala Ser Gly Tyr Thr Phe Thr
            20                  25                  30

Asn Tyr Gly Met Asn Trp Val Lys Gln Ala Pro Gly Lys Gly Leu Arg
        35                  40                  45

Trp Met Gly Trp Ile Asn Thr His Thr Gly Glu Pro Thr Tyr Ala Asp
    50                  55                  60

Asp Phe Lys Gly Arg Phe Ala Phe Ser Leu Glu Thr Ser Ala Ser Thr
65                  70                  75                  80

Ala Tyr Leu Gln Ile Asn Asn Leu Lys Asn Glu Asp Thr Ala Thr Tyr
                85                  90                  95

Phe Cys Thr Arg Arg Gly Tyr Asp Trp Tyr Phe Asp Val Trp Gly Ala

-continued

```
                100                 105                 110
Gly Thr Thr Val Thr Val Phe Ser Gly Gly Gly Ser Gly Gly Gly
            115                 120                 125
Gly Ser Gly Gly Gly Gly Ser Ser Asp Ile Lys Met Thr Gln Ser
        130                 135                 140
Pro Ser Ser Met Tyr Ala Ser Leu Gly Glu Arg Val Thr Ile Thr Cys
145                 150                 155                 160
Lys Ala Ser Gln Asp Ile Asn Ser Tyr Leu Ser Trp Phe His His Lys
                165                 170                 175
Pro Gly Lys Ser Pro Lys Thr Leu Ile Tyr Arg Ala Asn Arg Leu Val
            180                 185                 190
Asp Gly Val Pro Ser Arg Phe Ser Gly Ser Gly Ser Gly Gln Asp Tyr
        195                 200                 205
Ser Leu Thr Ile Ser Ser Leu Asp Tyr Glu Asp Met Gly Ile Tyr Tyr
        210                 215                 220
Cys Gln Gln Tyr Asp Glu Ser Pro Trp Thr Phe Gly Gly Gly Thr Lys
225                 230                 235                 240
Leu Glu Met Lys Gly Ser Gly Ala Ser Lys Gly Asn Ala Met Ser Ala
                245                 250                 255
Leu Ala Ala His Arg Val Cys Gly Val Pro Leu Glu Thr Leu Ala Arg
                260                 265                 270
Ser Arg Lys Pro Arg Asp Leu Thr Asp Asp Leu Ser Cys Ala Tyr Gln
            275                 280                 285
Ala Gln Asn Ile Val Ser Leu Phe Val Ala Thr Arg Ile Leu Phe Ser
        290                 295                 300
His Leu Asp Ser Val Phe Thr Leu Asn Leu Asp Glu Gln Glu Pro Glu
305                 310                 315                 320
Val Ala Glu Arg Leu Ser Asp Leu Arg Arg Ile Asn Glu Asn Asn Pro
                325                 330                 335
Gly Met Val Thr Gln Val Leu Thr Val Ala Arg Gln Ile Tyr Asn Asp
            340                 345                 350
Tyr Val Thr His His Pro Gly Leu Thr Pro Glu Gln Thr Ser Ala Gly
        355                 360                 365
Ala Gln Ala Ala Asp Ile Leu Ser Leu Phe Cys Pro Asp Ala Asp Lys
        370                 375                 380
Ser Cys Val Ala Ser Asn Asn Asp Gln Ala Asn Ile Asn Ile Glu Ser
385                 390                 395                 400
Arg Ser Gly Arg Ser Tyr Leu Pro Glu Asn Arg Ala Val Ile Thr Pro
                405                 410                 415
Gln Gly Val Thr Asn Trp Thr Tyr Gln Glu Leu Glu Ala Thr His Gln
            420                 425                 430
Ala Leu Thr Arg Glu Gly Tyr Val Phe Val Gly Tyr His Gly Thr Asn
        435                 440                 445
His Val Ala Ala Gln Thr Ile Val Asn Arg Ile Ala Pro Val Pro Arg
        450                 455                 460
Gly Asn Asn Thr Glu Asn Glu Glu Lys Trp Gly Gly Leu Tyr Val Ala
465                 470                 475                 480
Thr His Ala Glu Val Ala His Gly Tyr Ala Arg Ile Lys Glu Gly Thr
                485                 490                 495
Gly Glu Tyr Gly Leu Pro Thr Arg Ala Glu Arg Asp Ala Arg Gly Val
            500                 505                 510
Met Leu Arg Val Tyr Ile Pro Arg Ala Ser Leu Glu Arg Phe Tyr Arg
            515                 520                 525
```

-continued

```
Thr Asn Thr Pro Leu Glu Asn Ala Glu Glu His Ile Thr Gln Val Ile
    530                 535                 540

Gly His Ser Leu Pro Leu Arg Asn Glu Ala Phe Thr Gly Pro Glu Ser
545                 550                 555                 560

Ala Gly Gly Glu Asp Glu Thr Val Ile Gly Trp Asp Met Ala Ile His
                565                 570                 575

Ala Val Ala Ile Pro Ser Thr Ile Pro Gly Asn Ala Tyr Glu Glu Leu
            580                 585                 590

Ala Ile Asp Glu Glu Ala Val Ala Lys Glu Gln Ser Ile Ser Thr Lys
        595                 600                 605

Pro Pro Tyr Lys Glu Arg His His His His His Lys Asp Glu Leu
    610                 615                 620

<210> SEQ ID NO 75
<211> LENGTH: 6
<212> TYPE: PRT
<213> ORGANISM: Artificial Sequence
<220> FEATURE:
<223> OTHER INFORMATION: Synthetic Construct

<400> SEQUENCE: 75

Ile Glu Pro Asp Asp Leu
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic Construct

<400> SEQUENCE: 76

Ile Ala Pro Asp Ser Gly
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic Construct

<400> SEQUENCE: 77

Ile Glu Pro Asp Ser Gly
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic Construct

<400> SEQUENCE: 78

Ile Ala Pro Asp Asp Leu
1               5

<210> SEQ ID NO 79
<211> LENGTH: 1908
<212> TYPE: DNA
<213> ORGANISM: Artificial Sequence
<220> FEATURE:
<223> OTHER INFORMATION: Synthetic Construct

<400> SEQUENCE: 79
```

```
atggcccagg tgcagctgca gcagtccggc gctgagctgg tgcgccctgg ctcctccgtg    60
aaaatctcct gcaaggcttc cggctacgct ttctcctcct actggatgaa ctgggtgaag   120
cagcgccctg ccagggcct ggagtggatc ggccaaatct ggccgggcga cggcgacacc   180
aactacaacg gcaagttcaa gggcaaggct accctgaccg ctgacgagtc ctcctccacc   240
gcttacatgc agctgtcctc cctggcttcc gaggactccg ctgtgtactt ctgcgctcgc   300
cgcgagacca ccaccgtggg ccgctactac tacgctatgg actactgggg ccagggcacc   360
tcggtgaccg tgtcctccgg cggcggcggc tccggcggcg gcggctccgg cggcgggtcc   420
gggagctccg acatcctgct gacccagacc ccggcttccc tggctgtgtc cctgggccag   480
cgcgctacca tctcctgcaa ggcttcccag tccgtggact acgacggcga ctcctacctg   540
aactggtacc agcagatccc gggccagccg ccgaagctgc tgatctacga cgcttccaac   600
ctggtgtccg gcatcccgcc gcgcttctcc ggctccggct ccggcaccga cttcaccctg   660
aacatccacc cggtggagaa ggtggacgct gctacctacc actgccagca gtccaccgag   720
gacccgtgga ccttcggcgg cggcaccaag ctggagatca gcgcggctc tggcgctagc   780 aaaggcaatg ccatgagtgc actggctgcg caccgcgtat gcggtgtgcc gctggagaca   840
ctggcccgtt cacgcaaacc acgtgacctg accgatgacc tgagctgcgc gtatcaggcc   900 caaatattg tgtctctgtt tgttgcaacg cgtatcctgt tcagtcatct ggattcagtc   960
tttactctga acctggacga acaggagccg gaagtagctg agcgcctgtc cgatctgcgt  1020
cgcattaatg aaaacaatcc aggcatggtg acacaagttc tgaccgtcgc gcgtcagatc  1080
tacaacgact atgtaacgca ccatcctggt ctgactccgg aacagacatc ggccggggca  1140
caagctgcgg atattctgag cctgttctgt ccagatgccg acaaatcttg cgtggcaagt  1200
aataacgatc aggctaatat caacattgag tcacgctccg gacgttcgta cctgcctgaa  1260
aatcgcgcgg ttatcacccc gcaaggcgtc acgaactgga cctatcagga gctggaagcc  1320
actcaccagg cactgacacg tgaaggttac gtgtttgtag ggtatcatgg aacgaatcac  1380
gttgctgcgc aaaccattgt gaaccgcatc gccccggtcc cacgtggcaa taacactgag  1440
aatgaagaga atggggtgg cctgtacgtt gcaacacatg cggaagtagc tcacggttat  1500
gcccgcatta agaagggac cggagagtat ggcctgccta cgcgtgcaga acgcgacgcg  1560
cgtggtgtga tgctgcgcgt ctacatcccg cgtgcttcgc tggagcgctt ctatcgtacc  1620
aacactccgc tggaaaatgc cgaagagcat attacacagg ttatcggcca ctctctgcca  1680
ctgcgcaacg aagcatttac gggtcctgaa agtgcggggg gagaggatga aaccgtgatt  1740
ggctgggaca tggctatcca tgccgtagca attccgtcaa ctattccagg taatgcgtac  1800
gaggaactgg ccatcgatga agaggcagtc gcgaaagaac aatccatttc gacaaaaccg  1860
ccttataaag agcgtcacca tcatcaccat cacaaagatg aactgtaa              1908
```

<210> SEQ ID NO 80
<211> LENGTH: 635
<212> TYPE: PRT
<213> ORGANISM: Artificial Sequence
<220> FEATURE:
<223> OTHER INFORMATION: Synthetic Construct

<400> SEQUENCE: 80

```
Met Ala Gln Val Gln Leu Gln Gln Ser Gly Ala Glu Leu Val Arg Pro
1               5                   10                  15

Gly Ser Ser Val Lys Ile Ser Cys Lys Ala Ser Gly Tyr Ala Phe Ser
            20                  25                  30
```

-continued

```
Ser Tyr Trp Met Asn Trp Val Lys Gln Arg Pro Gly Gln Gly Leu Glu
         35                  40                  45

Trp Ile Gly Gln Ile Trp Pro Gly Asp Gly Asp Thr Asn Tyr Asn Gly
         50                  55                  60

Lys Phe Lys Gly Lys Ala Thr Leu Thr Ala Asp Glu Ser Ser Ser Thr
 65                  70                  75                  80

Ala Tyr Met Gln Leu Ser Ser Leu Ala Ser Glu Asp Ser Ala Val Tyr
                 85                  90                  95

Phe Cys Ala Arg Arg Glu Thr Thr Val Gly Arg Tyr Tyr Tyr Ala
                100                 105                 110

Met Asp Tyr Trp Gly Gln Gly Thr Ser Val Thr Val Ser Ser Gly Gly
            115                 120                 125

Gly Gly Ser Gly Gly Gly Ser Gly Gly Ser Gly Ser Ser Asp
        130                 135                 140

Ile Leu Leu Thr Gln Thr Pro Ala Ser Leu Ala Val Ser Leu Gly Gln
145                 150                 155                 160

Arg Ala Thr Ile Ser Cys Lys Ala Ser Gln Ser Val Asp Tyr Asp Gly
                165                 170                 175

Asp Ser Tyr Leu Asn Trp Tyr Gln Gln Ile Pro Gly Gln Pro Pro Lys
            180                 185                 190

Leu Leu Ile Tyr Asp Ala Ser Asn Leu Val Ser Gly Ile Pro Pro Arg
        195                 200                 205

Phe Ser Gly Ser Gly Ser Gly Thr Asp Phe Thr Leu Asn Ile His Pro
210                 215                 220

Val Glu Lys Val Asp Ala Ala Thr Tyr His Cys Gln Gln Ser Thr Glu
225                 230                 235                 240

Asp Pro Trp Thr Phe Gly Gly Gly Thr Lys Leu Glu Ile Lys Arg Gly
                245                 250                 255

Ser Gly Ala Ser Lys Gly Asn Ala Met Ser Ala Leu Ala Ala His Arg
            260                 265                 270

Val Cys Gly Val Pro Leu Glu Thr Leu Ala Arg Ser Arg Lys Pro Arg
        275                 280                 285

Asp Leu Thr Asp Asp Leu Ser Cys Ala Tyr Gln Ala Gln Asn Ile Val
290                 295                 300

Ser Leu Phe Val Ala Thr Arg Ile Leu Phe Ser His Leu Asp Ser Val
305                 310                 315                 320

Phe Thr Leu Asn Leu Asp Glu Gln Glu Pro Glu Val Ala Glu Arg Leu
                325                 330                 335

Ser Asp Leu Arg Arg Ile Asn Glu Asn Pro Gly Met Val Thr Gln
            340                 345                 350

Val Leu Thr Val Ala Arg Gln Ile Tyr Asn Asp Tyr Val Thr His His
        355                 360                 365

Pro Gly Leu Thr Pro Glu Gln Thr Ser Ala Gly Ala Gln Ala Ala Asp
370                 375                 380

Ile Leu Ser Leu Phe Cys Pro Asp Ala Asp Lys Ser Cys Val Ala Ser
385                 390                 395                 400

Asn Asn Asp Gln Ala Asn Ile Asn Ile Glu Ser Arg Ser Gly Arg Ser
                405                 410                 415

Tyr Leu Pro Glu Asn Arg Ala Val Ile Thr Pro Gln Gly Val Thr Asn
            420                 425                 430

Trp Thr Tyr Gln Glu Leu Glu Ala Thr His Gln Ala Leu Thr Arg Glu
        435                 440                 445

Gly Tyr Val Phe Val Gly Tyr His Gly Thr Asn His Val Ala Ala Gln
450                 455                 460
```

```
Thr Ile Val Asn Arg Ile Ala Pro Val Pro Arg Gly Asn Asn Thr Glu
465                 470                 475                 480

Asn Glu Glu Lys Trp Gly Gly Leu Tyr Val Ala Thr His Ala Glu Val
            485                 490                 495

Ala His Gly Tyr Ala Arg Ile Lys Glu Gly Thr Gly Glu Tyr Gly Leu
            500                 505                 510

Pro Thr Arg Ala Glu Arg Asp Ala Arg Gly Val Met Leu Arg Val Tyr
        515                 520                 525

Ile Pro Arg Ala Ser Leu Glu Arg Phe Tyr Arg Thr Asn Thr Pro Leu
            530                 535                 540

Glu Asn Ala Glu Glu His Ile Thr Gln Val Ile Gly His Ser Leu Pro
545                 550                 555                 560

Leu Arg Asn Glu Ala Phe Thr Gly Pro Glu Ser Ala Gly Gly Glu Asp
                565                 570                 575

Glu Thr Val Ile Gly Trp Asp Met Ala Ile His Ala Val Ala Ile Pro
            580                 585                 590

Ser Thr Ile Pro Gly Asn Ala Tyr Glu Glu Leu Ala Ile Asp Glu Glu
            595                 600                 605

Ala Val Ala Lys Glu Gln Ser Ile Ser Thr Lys Pro Pro Tyr Lys Glu
        610                 615                 620

Arg His His His His His His Lys Asp Glu Leu
625                 630                 635

<210> SEQ ID NO 81
<211> LENGTH: 1887
<212> TYPE: DNA
<213> ORGANISM: Artificial Sequence
<220> FEATURE:
<223> OTHER INFORMATION: Synthetic Construct

<400> SEQUENCE: 81
atggactaca aggacgacga cgacaagggc atggccaaca tccagctggt gcagtctggt     60
cctgagctga agaagcctgg tgagactgtc aaaatctcct gcaaggcttc tgggtatacc    120
ttcactaact atggtatgaa ctgggtgaag caggctcctg gtaagggtct gcgttggatg    180
ggctggatta cacccacac tggtgagcct acttatgctg atgacttcaa gggacgtttt    240
gccttctctc tggaaacttc tgccagcact gcctatctcc agatcaacaa cctcaaaaat    300
gaggacactg ctacttactt ctgtacacgt cgtggttacg actggtactt cgatgtctgg    360
ggtgctggga ccacggtgac cgtgttctcc ggggaggtg gcagcggggg aggtggcagc    420
ggcggcggga gctccgacat caagatgacc cagtctcctt cttccatgta tgcttctctg    480
ggtgagcgtg tcactatcac ttgcaaggcc agccaggaca ttaatagcta tctgagctgg    540
ttccatcata aacctgggaa atctcctaag accctgatct atcgtgctaa ccgtctggtt    600 gatgggtcc cttctcgttt cagcggctct ggttctgggc aagattattc tctcaccatc    660
agcagcctgg actatgaaga tatgggtatt tattattgtc aacagtatga tgagtctcct    720
tggactttcg gtggtggcac caagctggag atgaaaggag gcggaggctc cggaggagga    780
ggcgggtccg ctagcctgat cgccctgacc gccaccagg cctgccacct gccgctggag    840
accttcaccg ctagcatcga gccggacggc tgggagcagc tggagcagtg cggctaccccg    900 gtgcagcgcc tggtggccct gtacctggcc gccgcctgt cctggaacca ggtggaccag    960
gtgatccgca acgccctggc ctccccgggc tccggcggcg acctgggcga ggccatccgc   1020
gagcagccgg agcaggcccg cctggccctg accctggccg ccgccgagtc cgagcgcttc   1080
```

-continued

```
gtgcgccagg gcaccggcaa cgacgaggcc ggcgccgcca acgccgacgt ggtgtccctg    1140
acctgcccgg tggccgccgg cgagtgcgcc ggcccggccg actccggcga cgccctgctg    1200
gagcgcaact acccgaccgg cgccgagttc ctgggcgacg gcggcgacgt gtccttctcc    1260
acccgcggca cccagacctg gaccgtggag cgcctgctgc aggccaccg ccagctggag     1320 gagcgcggct acgtgttcgt gggctaccac ggcaccttcc tggaggccgc ccagtccatc    1380
gtgttcggcg gcgtgcgcgc ccgctcccag gacctggacg ccatctggcg cggcttctac    1440
atcgccggcg acccggccct ggcctacggc tacgcccagg accaggagcc ggacgcccgc    1500
ggtcgcatcc gcaacggcgc cctgctcgcg cgtgtacgtgc cgcgctcctc cctgccgggc    1560
ttctaccgca cctccctgac cctggccgcc ccggaggccg ccggcgaggt ggagcgcctg    1620 atcgccacc cgctgccgct gcgcctggac gccatcaccg gccgaggga ggagggcggt      1680 cgcctggaga ccatcctggg ctggccgctg gccgagcgca ccgtggtgat cccgtccgcc    1740
atcccgaccg acccgcgcaa cgtgggcggc gacctggacc cgtcctccat cccggacaag    1800
gagcaggcca tctccgccct gccggactac gcctctcagc cgggcaagcc gccgcaccac    1860
caccaccacc acaaggacga gctgtag                                       1887
```

<210> SEQ ID NO 82
<211> LENGTH: 628
<212> TYPE: PRT
<213> ORGANISM: Artificial Sequence
<220> FEATURE:
<223> OTHER INFORMATION: Synthetic Construct
<400> SEQUENCE: 82

```
Met Asp Tyr Lys Asp Asp Asp Lys Gly Met Ala Asn Ile Gln Leu
1               5                   10                  15

Val Gln Ser Gly Pro Glu Leu Lys Lys Pro Gly Glu Thr Val Lys Ile
            20                  25                  30

Ser Cys Lys Ala Ser Gly Tyr Thr Phe Thr Asn Tyr Gly Met Asn Trp
        35                  40                  45

Val Lys Gln Ala Pro Gly Lys Gly Leu Arg Trp Met Gly Trp Ile Asn
    50                  55                  60

Thr His Thr Gly Glu Pro Thr Tyr Ala Asp Asp Phe Lys Gly Arg Phe
65                  70                  75                  80

Ala Phe Ser Leu Glu Thr Ser Ala Ser Thr Ala Tyr Leu Gln Ile Asn
                85                  90                  95

Asn Leu Lys Asn Glu Asp Thr Ala Thr Tyr Phe Cys Thr Arg Arg Gly
            100                 105                 110

Tyr Asp Trp Tyr Phe Asp Val Trp Gly Ala Gly Thr Thr Val Thr Val
        115                 120                 125

Phe Ser Gly Gly Gly Ser Gly Gly Gly Ser Gly Gly Gly Ser
    130                 135                 140

Ser Asp Ile Lys Met Thr Gln Ser Pro Ser Ser Met Tyr Ala Ser Leu
145                 150                 155                 160

Gly Glu Arg Val Thr Ile Thr Cys Lys Ala Ser Gln Asp Ile Asn Ser
                165                 170                 175

Tyr Leu Ser Trp Phe His His Lys Pro Gly Lys Ser Pro Lys Thr Leu
            180                 185                 190

Ile Tyr Arg Ala Asn Arg Leu Val Asp Gly Val Pro Ser Arg Phe Ser
        195                 200                 205

Gly Ser Gly Ser Gly Gln Asp Tyr Ser Leu Thr Ile Ser Ser Leu Asp
    210                 215                 220
```

```
Tyr Glu Asp Met Gly Ile Tyr Cys Gln Gln Tyr Asp Glu Ser Pro
225                 230                 235                 240

Trp Thr Phe Gly Gly Gly Thr Lys Leu Glu Met Lys Gly Gly Gly
            245                 250                 255

Ser Gly Gly Gly Gly Gly Ser Ala Ser Leu Ile Ala Leu Thr Ala His
        260                 265                 270

Gln Ala Cys His Leu Pro Leu Glu Thr Phe Thr Ala Ser Ile Glu Pro
    275                 280                 285

Asp Gly Trp Glu Gln Leu Glu Gln Cys Gly Tyr Pro Val Gln Arg Leu
    290                 295                 300

Val Ala Leu Tyr Leu Ala Ala Arg Leu Ser Trp Asn Gln Val Asp Gln
305                 310                 315                 320

Val Ile Arg Asn Ala Leu Ala Ser Pro Gly Ser Gly Asp Leu Gly
                325                 330                 335

Glu Ala Ile Arg Glu Gln Pro Glu Gln Ala Arg Leu Ala Leu Thr Leu
            340                 345                 350

Ala Ala Ala Glu Ser Glu Arg Phe Val Arg Gln Gly Thr Gly Asn Asp
            355                 360                 365

Glu Ala Gly Ala Ala Asn Ala Asp Val Val Ser Leu Thr Cys Pro Val
    370                 375                 380

Ala Ala Gly Glu Cys Ala Gly Pro Ala Asp Ser Gly Asp Ala Leu Leu
385                 390                 395                 400

Glu Arg Asn Tyr Pro Thr Gly Ala Glu Phe Leu Gly Asp Gly Asp
                405                 410                 415

Val Ser Phe Ser Thr Arg Gly Thr Gln Thr Trp Thr Val Glu Arg Leu
            420                 425                 430

Leu Gln Ala His Arg Gln Leu Glu Glu Arg Gly Tyr Val Phe Val Gly
        435                 440                 445

Tyr His Gly Thr Phe Leu Glu Ala Ala Gln Ser Ile Val Phe Gly Gly
    450                 455                 460

Val Arg Ala Arg Ser Gln Asp Leu Asp Ala Ile Trp Arg Gly Phe Tyr
465                 470                 475                 480

Ile Ala Gly Asp Pro Ala Leu Ala Tyr Gly Tyr Ala Gln Asp Gln Glu
                485                 490                 495

Pro Asp Ala Arg Gly Arg Ile Arg Asn Gly Ala Leu Leu Arg Val Tyr
            500                 505                 510

Val Pro Arg Ser Ser Leu Pro Gly Phe Tyr Arg Thr Ser Leu Thr Leu
            515                 520                 525

Ala Ala Pro Glu Ala Ala Gly Glu Val Glu Arg Leu Ile Gly His Pro
    530                 535                 540

Leu Pro Leu Arg Leu Asp Ala Ile Thr Gly Pro Glu Glu Gly Gly
545                 550                 555                 560

Arg Leu Glu Thr Ile Leu Gly Trp Pro Leu Ala Glu Arg Thr Val Val
                565                 570                 575

Ile Pro Ser Ala Ile Pro Thr Asp Pro Arg Asn Val Gly Gly Asp Leu
            580                 585                 590

Asp Pro Ser Ser Ile Pro Asp Lys Glu Gln Ala Ile Ser Ala Leu Pro
        595                 600                 605

Asp Tyr Ala Ser Gln Pro Gly Lys Pro Pro His His His His His His
    610                 615                 620

Lys Asp Glu Leu
625
```

<210> SEQ ID NO 83

<211> LENGTH: 1330
<212> TYPE: DNA
<213> ORGANISM: Artificial Sequence
<220> FEATURE:
<223> OTHER INFORMATION: Synthetic Construct

<400> SEQUENCE: 83

```
atgggctcca acgaactgca tcaggtgccg agcaactgcg attgtctgaa cggcggtacc      60
tgcgtttcca acaaatattt ttctaacatt cactggtgta actgcccgaa aaaattcggt     120
ggacaacatt gtgaaatcga cggcggtggt ggttcgggcg gtggcggttc gggtggcggt     180
ggcagctcta gcaaaggcaa tgccatgagt gcactggctg cgcaccgcgt atgcggtgtg     240
ccgctggaga cactggcccg ttcacgcaaa ccacgtgacc tgaccgatga cctgagctgc     300
gcgtatcagg cccaaaatat tgtgtctctg tttgttgcaa cgcgtatcct gttcagtcat     360
ctggattcag tctttactct gaacctggac gaacaggagc cggaagtagc tgagcgcctg     420
tccgatctgc gtcgcattaa tgaaaacaat ccaggcatgg tgacacaagt tctgaccgtc     480
gcgcgtcaga tctacaacga ctatgtaacg caccatcctg gtctgactcc ggaacagaca     540
tcggccgggg cacaagctgc cgacgtggtg tccctgacct gccggtggc cgccggcgag     600
tgcgccggcc cggccgactc cggcgacgcc ctgctggagc gcaactaccc gaccggcgcc     660
gagttcctgg cgacggcgg cgacgtgtcc ttctccaccc gcggcaccca gacctggacc     720
gtggagcgcc tgctgcaggc ccaccgccag ctggaggagc gggctacgt gttcgtgggc     780
taccacggca ccttcctgga ggccgcccag tccatcgtgt cggcggcgt gcgcccccgc     840
tcccaggacc tggacgccat ctggcgcggc ttctacatcg ccggcgaccc ggccctggcc     900
tacggctacg cccaggacca ggagccgac gcccgcggtc gcatccgcaa cggcgccctg     960
ctgcgcgtgt acgtgccgcg ctcctccctg ccgggcttct accgcacctc cctgaccctg    1020
gccgccccgg aggccgccgg cgaggtggag cgcctgatcg gccacccgct gccgctgcgc    1080
ctggacgcca tcaccggccc ggaggaggag ggcggtcgcc tggagaccat cctgggctgg    1140
ccgctggccg agcgcaccgt ggtgatcccg tccgccatcc cgaccgaccc gcgcaacgtg    1200
ggcggcgacc tggacccgtc ctccatcccg gacaaggagc aggccatctc cgccctgccg    1260
gactacgcct ctcagccggg caagccgccg caccaccacc accaccacaa ggacgagctg    1320
tagcggccgc                                                          1330
```

<210> SEQ ID NO 84
<211> LENGTH: 439
<212> TYPE: PRT
<213> ORGANISM: Artificial Sequence
<220> FEATURE:
<223> OTHER INFORMATION: Synthetic Construct

<400> SEQUENCE: 84

```
Met Ser Asn Glu Leu His Gln Val Pro Ser Asn Cys Asp Cys Leu Asn
1               5                   10                  15

Gly Gly Thr Cys Val Ser Asn Lys Tyr Phe Ser Asn Ile His Trp Cys
            20                  25                  30

Asn Cys Pro Lys Lys Phe Gly Gly Gln His Cys Glu Ile Asp Gly Gly
        35                  40                  45

Gly Gly Ser Gly Gly Gly Gly Ser Gly Gly Gly Gly Ser Ser Ser Lys
    50                  55                  60

Gly Asn Ala Met Ser Ala Leu Ala Ala His Arg Val Cys Gly Val Pro
65                  70                  75                  80

Leu Glu Thr Leu Ala Arg Ser Arg Lys Pro Arg Asp Leu Thr Asp Asp
```

```
                         85                  90                  95
Leu Ser Cys Ala Tyr Gln Ala Gln Asn Ile Val Ser Leu Phe Val Ala
                100                 105                 110

Thr Arg Ile Leu Phe Ser His Leu Asp Ser Val Phe Thr Leu Asn Leu
            115                 120                 125

Asp Glu Gln Glu Pro Glu Val Ala Glu Arg Leu Ser Asp Leu Arg Arg
        130                 135                 140

Ile Asn Glu Asn Asn Pro Gly Met Val Thr Gln Val Leu Thr Val Ala
145                 150                 155                 160

Arg Gln Ile Tyr Asn Asp Tyr Val Thr His His Pro Gly Leu Thr Pro
                165                 170                 175

Glu Gln Thr Ser Ala Gly Ala Gln Ala Ala Asp Val Val Ser Leu Thr
            180                 185                 190

Cys Pro Val Ala Ala Gly Glu Cys Ala Gly Pro Ala Asp Ser Gly Asp
        195                 200                 205

Ala Leu Leu Glu Arg Asn Tyr Pro Thr Gly Ala Glu Phe Leu Gly Asp
    210                 215                 220

Gly Gly Asp Val Ser Phe Ser Thr Arg Gly Thr Gln Asn Trp Thr Val
225                 230                 235                 240

Glu Arg Leu Leu Gln Ala His Arg Gln Leu Glu Arg Gly Tyr Val
                245                 250                 255

Phe Val Gly Tyr His Gly Thr Phe Leu Glu Ala Ala Gln Ser Ile Val
            260                 265                 270

Phe Gly Gly Val Arg Ala Arg Ser Gln Asp Leu Asp Ala Ile Trp Arg
        275                 280                 285

Gly Phe Tyr Ile Ala Gly Asp Pro Ala Leu Ala Tyr Gly Tyr Ala Gln
    290                 295                 300

Asp Gln Glu Pro Asp Ala Arg Gly Arg Ile Arg Asn Gly Ala Leu Leu
305                 310                 315                 320

Arg Val Tyr Val Pro Arg Ser Ser Leu Pro Gly Phe Tyr Arg Thr Ser
                325                 330                 335

Leu Thr Leu Ala Ala Pro Glu Ala Ala Gly Glu Val Glu Arg Leu Ile
            340                 345                 350

Gly His Pro Leu Pro Leu Arg Leu Asp Ala Ile Thr Gly Pro Glu Glu
        355                 360                 365

Glu Gly Gly Arg Leu Glu Thr Ile Leu Gly Trp Pro Leu Ala Glu Arg
    370                 375                 380

Thr Val Val Ile Pro Ser Ala Ile Pro Thr Asp Pro Arg Asn Val Gly
385                 390                 395                 400

Gly Asp Leu Asp Pro Ser Ser Ile Pro Asp Lys Glu Gln Ala Ile Ser
                405                 410                 415

Ala Leu Pro Asp Tyr Ala Ser Gln Pro Gly Lys Pro Pro His His
            420                 425                 430

His His His Lys Asp Glu Leu
        435

<210> SEQ ID NO 85
<211> LENGTH: 1647
<212> TYPE: DNA
<213> ORGANISM: Artificial Sequence
<220> FEATURE:
<223> OTHER INFORMATION: Synthetic Construct

<400> SEQUENCE: 85
atgggtcatc accaccatca tcacaagggc gagctcgaaa gatccgtttt aacagttcca    60
```

```
tctacagata tagaaaaaga aatccttgat ttagctgctg ctacagaaag attaaattta     120
actgatgcat taaactcaaa tccagctggt aatttatatg attggcgttc ttctaactca     180 taccccttgga ctcaaaagct caatttacac ttaacaatta cagctactgg acaaaaatat    240
agaatcttag caagcaaaat tgttgatttt aatatttatt caataatttt taataatcta    300
gtgaaattag aacagtcctt aggtgatgga gtaaagatc attatgttga tataagttta     360
gatgctggac aatatgttct tgtaatgaaa gctaattcat catatagtgg aaattaccct    420
tattcaatat tatttcaaaa atttaagctt gaaggtaagc ctatccctaa ccctctcctc    480
ggtctcgatt ctacgcgtac cggtggctct ggcgctagca aaggcaatgc catgagtgca    540
ctggctgcgc accgcgtatg cggtgtgccg ctggagacac tggcccgttc acgcaaacca    600
cgtgacctga ccgatgacct gagctgcgcg tatcaggccc aaaatattgt gtctctgttt    660
gttgcaacgc gtatcctgtt cagtcatctg gattcagtct ttactctgaa cctggacgaa    720
caggagccgg aagtagctga gcgcctgtcc gatctgcgtc gcattaatga aaacaatcca    780
ggcatggtga cacaagttct gaccgtcgcg cgtcagatct acaacgacta tgtaacgcac    840
catcctggtc tgactccgga acagacatcg gccggggcac aagctgcgga tattctgagc    900
ctgttctgtc cagatgccga caaatcttgc gtggcaagta ataacgatca ggctaatatc    960
aacattgagt cacgctccgg acgttcgtac ctgcctgaaa tcgcgcggt tatcaccccg    1020 caaggcgtca cgaactggac ctatcaggag ctggaagcca ctcaccaggc actgacacgt    1080
gaaggttacg tgtttgtagg gtatcatgga acgaatcacg ttgctgcgca aaccattgtg    1140
aaccgcatcg ccccggtccc acgtggcaat aacactgaga atgaagagaa atggggtggc    1200
ctgtacgttg caacacatgc ggaagtagct cacggttatg cccgcattaa agaagggacc    1260
ggagagtatg gcctgcctac gcgtgcagaa cgcgacgcgc gtggtgtgat gctgcgcgtc    1320
tacatcccgc gtgcttcgct ggagcgcttc tatcgtacca cactccgct ggaaaatgcc    1380 gaagagcata ttacacaggt tatcggccac tctctgccac tgcgcaacga agcatttacg    1440
ggtcctgaaa gtgcgggggg agaggatgaa accgtgattg ctgggacat ggctatccat    1500 gccgtagcaa ttccgtcaac tattccaggt aatgcgtacg aggaactggc catcgatgaa    1560
gaggcagtcg cgaaagaaca atccatttcg acaaaaccgc ttataaaga gcgtcaccat    1620 catcaccatc acaaagatga actgtaa                                        1647
```

<210> SEQ ID NO 86
<211> LENGTH: 548
<212> TYPE: PRT
<213> ORGANISM: Artificial Sequence
<220> FEATURE:
<223> OTHER INFORMATION: Synthetic Construct

<400> SEQUENCE: 86

```
Met Gly His His His His His His Lys Gly Glu Leu Glu Arg Ser Val
1               5                   10                  15

Leu Thr Val Pro Ser Thr Asp Ile Glu Lys Glu Ile Leu Asp Leu Ala
            20                  25                  30

Ala Ala Thr Glu Arg Leu Asn Leu Thr Asp Ala Leu Asn Ser Asn Pro
        35                  40                  45

Ala Gly Asn Leu Tyr Asp Trp Arg Ser Asn Ser Tyr Pro Trp Thr
    50                  55                  60

Gln Lys Leu Asn Leu His Leu Thr Ile Thr Ala Thr Gly Gln Lys Tyr
65                  70                  75                  80

Arg Ile Leu Ala Ser Lys Ile Val Asp Phe Asn Ile Tyr Ser Asn Asn
```

```
                         85                  90                  95
Phe Asn Asn Leu Val Lys Leu Glu Gln Ser Leu Gly Asp Gly Val Lys
                100                 105                 110

Asp His Tyr Val Asp Ile Ser Leu Asp Ala Gly Gln Tyr Val Leu Val
            115                 120                 125

Met Lys Ala Asn Ser Ser Tyr Ser Gly Asn Tyr Pro Tyr Ser Ile Leu
        130                 135                 140

Phe Gln Lys Phe Lys Leu Glu Gly Lys Pro Ile Pro Asn Pro Leu Leu
145                 150                 155                 160

Gly Leu Asp Ser Thr Arg Thr Gly Gly Ser Gly Ala Ser Lys Gly Asn
                165                 170                 175

Ala Met Ser Ala Leu Ala Ala His Arg Val Cys Gly Val Pro Leu Glu
            180                 185                 190

Thr Leu Ala Arg Ser Arg Lys Pro Arg Asp Leu Thr Asp Asp Leu Ser
        195                 200                 205

Cys Ala Tyr Gln Ala Gln Asn Ile Val Ser Leu Phe Val Ala Thr Arg
    210                 215                 220

Ile Leu Phe Ser His Leu Asp Ser Val Phe Thr Leu Asn Leu Asp Glu
225                 230                 235                 240

Gln Glu Pro Glu Val Ala Glu Arg Leu Ser Asp Leu Arg Arg Ile Asn
                245                 250                 255

Glu Asn Asn Pro Gly Met Val Thr Gln Val Leu Thr Val Ala Arg Gln
            260                 265                 270

Ile Tyr Asn Asp Tyr Val Thr His His Pro Gly Leu Thr Pro Glu Gln
        275                 280                 285

Thr Ser Ala Gly Ala Gln Ala Ala Asp Ile Leu Ser Leu Phe Cys Pro
    290                 295                 300

Asp Ala Asp Lys Ser Cys Val Ala Ser Asn Asn Asp Gln Ala Asn Ile
305                 310                 315                 320

Asn Ile Glu Ser Arg Ser Gly Arg Ser Tyr Leu Pro Glu Asn Arg Ala
                325                 330                 335

Val Ile Thr Pro Gln Gly Val Thr Asn Trp Thr Tyr Gln Glu Leu Glu
            340                 345                 350

Ala Thr His Gln Ala Leu Thr Arg Glu Gly Tyr Val Phe Val Gly Tyr
        355                 360                 365

His Gly Thr Asn His Val Ala Ala Gln Thr Ile Val Asn Arg Ile Ala
    370                 375                 380

Pro Val Pro Arg Gly Asn Asn Thr Glu Asn Glu Glu Lys Trp Gly Gly
385                 390                 395                 400

Leu Tyr Val Ala Thr His Ala Glu Val Ala His Gly Tyr Ala Arg Ile
                405                 410                 415

Lys Glu Gly Thr Gly Glu Tyr Gly Leu Pro Thr Arg Ala Glu Arg Asp
            420                 425                 430

Ala Arg Gly Val Met Leu Arg Val Tyr Ile Pro Arg Ala Ser Leu Glu
        435                 440                 445

Arg Phe Tyr Arg Thr Asn Thr Pro Leu Glu Asn Ala Glu Glu His Ile
    450                 455                 460

Thr Gln Val Ile Gly His Ser Leu Pro Leu Arg Asn Glu Ala Phe Thr
465                 470                 475                 480

Gly Pro Glu Ser Ala Gly Gly Glu Asp Glu Thr Val Ile Gly Trp Asp
                485                 490                 495

Met Ala Ile His Ala Val Ala Ile Pro Ser Thr Ile Pro Gly Asn Ala
            500                 505                 510
```

Tyr Glu Glu Leu Ala Ile Asp Glu Glu Ala Val Ala Lys Glu Gln Ser
        515                 520                 525

Ile Ser Thr Lys Pro Pro Tyr Lys Glu Arg His His His His His
        530                 535                 540

Lys Asp Glu Leu
545

<210> SEQ ID NO 87
<211> LENGTH: 1926
<212> TYPE: DNA
<213> ORGANISM: Artificial Sequence
<220> FEATURE:
<223> OTHER INFORMATION: Synthetic Construct

<400> SEQUENCE: 87

| | |
|---|---|
| atgggtcttg atttagctgc tgctacagaa agattaaatt taactgatgc attaaactca | 60 |
| aatccagctg gtaatttata tgattggcgt tcttctaact catacccttg gactcaaaag | 120 |
| ctcaatttac acttaacaat tacagctact ggacaaaaat atagaatctt agcaagcaaa | 180 |
| attgttgatt ttaatatttta ttcaaataat tttaataatc tagtgaaatt agaacagtcc | 240 |
| ttaggtgatg gagtaaaaga tcattatgtt gatataagtt tagatgctgg acaatatgtt | 300 |
| cttgtaatga aagctaattc atcatatagt ggaaattacc cttattcaat attatttcaa | 360 |
| aaatttgaag gtggcggttc cgaaggtggt gggtccgaag gtggtggctc cggcggttcc | 420 |
| atccttgatt tagctgctgc tacagaaaga ttaaatttaa ctgatgcatt aaactcaaat | 480 |
| ccagctggta atttatatga ttggcgttct tctaactcat acccttgcac tcaaaagctc | 540 |
| aatttacact taacaattac agctactgga caaaaatata gaatcttagc aagcaaaatt | 600 |
| gttgatttta atatttattc aaataatttt aataatctag tgaaattaga acagtcctta | 660 |
| ggtgatggag taaaagatca ttatgttgat ataagtttag atgctggaca atatgttctt | 720 |
| gtaatgaaag ctaattcatc atatagtgga aattaccctt attcaatatt atttcaaaaa | 780 |
| tttgacggtt ccgctagcaa aggcaatgcc atgagtgcac tggctgcgca ccgcgtatgc | 840 |
| ggtgtgccgc tggagacact ggcccgttca cgcaaaccac gtgacctgac cgatgacctg | 900 |
| agctgcgcgt atcaggccca aaatattgtg tctctgtttg ttgcaacgcg tatcctgttc | 960 |
| agtcatctgg attcagtctt tactctgaac ctggacgaac aggagccgga agtagctgag | 1020 |
| cgcctgtccg atctgcgtcg cattaatgaa acaatccag gcatggtgac acaagttctg | 1080 |
| accgtcgcgc gtcagatcta caacgactat gtaacgcacc atcctggtct gactccggaa | 1140 |
| cagacatcgg ccggggcaca agctgcggat attctgagcc tgttctgtcc agatgccgac | 1200 |
| aaatcttgcg tggcaagtaa taacgatcag gctaatatca acattgagtc acgctccgga | 1260 |
| cgttcgtacc tgcctgaaaa tcgcgcggtt atcaccccgc aaggcgtcac gaactggacc | 1320 |
| tatcaggagc tggaagccac tcaccaggca ctgacacgtg aaggttacgt gtttgtaggg | 1380 |
| tatcatggaa cgaatcacgt tgctgcgcaa accattgtga accgcatcgc cccggtccca | 1440 |
| cgtggcaata cactgagaa tgaagagaaa tggggtggcc tgtacgttgc aacacatgcg | 1500 |
| gaagtagctc acggttatgc ccgcattaaa gaagggaccg gagagtatgg cctgcctacg | 1560 |
| cgtgcagaac gcgacgcgcg tggtgtgatg ctgcgcgtct acatcccgcg tgcttcgctg | 1620 |
| gagcgcttct atcgtaccaa cactccgctg aaaatgccg aagagcatat tacacaggtt | 1680 |
| atcggccact ctctgccact gcgcaacgaa gcatttacgg gtcctgaaag tgcgggggga | 1740 |
| gaggatgaaa ccgtgattgg ctgggacatg gctatccatg ccgtagcaat tccgtcaact | 1800 |
| attccaggta atgcgtacga ggaactggcc atcgatgaag aggcagtcgc gaaagaacaa | 1860 |

```
tccatttcga caaaaccgcc ttataaagag cgtcaccatc atcaccatca caaagatgaa    1920
ctgtaa                                                                1926
```

<210> SEQ ID NO 88
<211> LENGTH: 641
<212> TYPE: PRT
<213> ORGANISM: Artificial Sequence
<220> FEATURE:
<223> OTHER INFORMATION: Synthetic Construct

<400> SEQUENCE: 88

```
Met Gly Leu Asp Leu Ala Ala Ala Thr Glu Arg Leu Asn Leu Thr Asp
1               5                   10                  15

Ala Leu Asn Ser Asn Pro Ala Gly Asn Leu Tyr Asp Trp Arg Ser Ser
            20                  25                  30

Asn Ser Tyr Pro Trp Thr Gln Lys Leu Asn Leu His Leu Thr Ile Thr
        35                  40                  45

Ala Thr Gly Gln Lys Tyr Arg Ile Leu Ala Ser Lys Ile Val Asp Phe
    50                  55                  60

Asn Ile Tyr Ser Asn Asn Phe Asn Asn Leu Val Lys Leu Glu Gln Ser
65                  70                  75                  80

Leu Gly Asp Gly Val Lys Asp His Tyr Val Asp Ile Ser Leu Asp Ala
                85                  90                  95

Gly Gln Tyr Val Leu Val Met Lys Ala Asn Ser Ser Tyr Ser Gly Asn
            100                 105                 110

Tyr Pro Tyr Ser Ile Leu Phe Gln Lys Phe Glu Gly Gly Gly Ser Glu
        115                 120                 125

Gly Gly Gly Ser Glu Gly Gly Ser Gly Ser Ile Leu Asp Leu
    130                 135                 140

Ala Ala Ala Thr Glu Arg Leu Asn Leu Thr Asp Ala Leu Asn Ser Asn
145                 150                 155                 160

Pro Ala Gly Asn Leu Tyr Asp Trp Arg Ser Ser Asn Ser Tyr Pro Trp
                165                 170                 175

Thr Gln Lys Leu Asn Leu His Leu Thr Ile Thr Ala Thr Gly Gln Lys
            180                 185                 190

Tyr Arg Ile Leu Ala Ser Lys Ile Val Asp Phe Asn Ile Tyr Ser Asn
        195                 200                 205

Asn Phe Asn Asn Leu Val Lys Leu Glu Gln Ser Leu Gly Asp Gly Val
    210                 215                 220

Lys Asp His Tyr Val Asp Ile Ser Leu Asp Ala Gly Gln Tyr Val Leu
225                 230                 235                 240

Val Met Lys Ala Asn Ser Ser Tyr Ser Gly Asn Tyr Pro Tyr Ser Ile
                245                 250                 255

Leu Phe Gln Lys Phe Asp Gly Ser Ala Ser Lys Gly Asn Ala Met Ser
            260                 265                 270

Ala Leu Ala Ala His Arg Val Cys Gly Val Pro Leu Glu Thr Leu Ala
        275                 280                 285

Arg Ser Arg Lys Pro Arg Asp Leu Thr Asp Leu Ser Cys Ala Tyr
    290                 295                 300

Gln Ala Gln Asn Ile Val Ser Leu Phe Val Ala Thr Arg Ile Leu Phe
305                 310                 315                 320

Ser His Leu Asp Ser Val Phe Thr Leu Asn Leu Asp Glu Gln Glu Pro
                325                 330                 335

Glu Val Ala Glu Arg Leu Ser Asp Leu Arg Arg Ile Asn Glu Asn Asn
            340                 345                 350
```

-continued

```
Pro Gly Met Val Thr Gln Val Leu Thr Val Ala Arg Gln Ile Tyr Asn
        355                 360                 365
Asp Tyr Val Thr His His Pro Gly Leu Thr Pro Glu Gln Thr Ser Ala
    370                 375                 380
Gly Ala Gln Ala Ala Asp Ile Leu Ser Leu Phe Cys Pro Asp Ala Asp
385                 390                 395                 400
Lys Ser Cys Val Ala Ser Asn Asn Asp Gln Ala Asn Ile Asn Ile Glu
                405                 410                 415
Ser Arg Ser Gly Arg Ser Tyr Leu Pro Glu Asn Arg Ala Val Ile Thr
            420                 425                 430
Pro Gln Gly Val Thr Asn Trp Thr Tyr Gln Glu Leu Glu Ala Thr His
        435                 440                 445
Gln Ala Leu Thr Arg Glu Gly Tyr Val Phe Val Gly Tyr His Gly Thr
    450                 455                 460
Asn His Val Ala Ala Gln Thr Ile Val Asn Arg Ile Ala Pro Val Pro
465                 470                 475                 480
Arg Gly Asn Asn Thr Glu Asn Glu Glu Lys Trp Gly Gly Leu Tyr Val
                485                 490                 495
Ala Thr His Ala Glu Val Ala His Gly Tyr Ala Arg Ile Lys Glu Gly
            500                 505                 510
Thr Gly Glu Tyr Gly Leu Pro Thr Arg Ala Glu Arg Asp Ala Arg Gly
        515                 520                 525
Val Met Leu Arg Val Tyr Ile Pro Arg Ala Ser Leu Glu Arg Phe Tyr
    530                 535                 540
Arg Thr Asn Thr Pro Leu Glu Asn Ala Glu Glu His Ile Thr Gln Val
545                 550                 555                 560
Ile Gly His Ser Leu Pro Leu Arg Asn Glu Ala Phe Thr Gly Pro Glu
                565                 570                 575
Ser Ala Gly Gly Glu Asp Glu Thr Val Ile Gly Trp Asp Met Ala Ile
            580                 585                 590
His Ala Val Ala Ile Pro Ser Thr Ile Pro Gly Asn Ala Tyr Glu Glu
        595                 600                 605
Leu Ala Ile Asp Glu Glu Ala Val Ala Lys Glu Gln Ser Ile Ser Thr
    610                 615                 620
Lys Pro Pro Tyr Lys Glu Arg His His His His His Lys Asp Glu
625                 630                 635                 640
Leu

<210> SEQ ID NO 89
<211> LENGTH: 5
<212> TYPE: PRT
<213> ORGANISM: Artificial Sequence
<220> FEATURE:
<223> OTHER INFORMATION: Synthetic Construct

<400> SEQUENCE: 89

Asn Pro Gln Thr Asn
1               5

<210> SEQ ID NO 90
<211> LENGTH: 4
<212> TYPE: PRT
<213> ORGANISM: Artificial Sequence
<220> FEATURE:
<223> OTHER INFORMATION: Synthetic Construct

<400> SEQUENCE: 90
```

```
Lys Val Pro Leu
1

<210> SEQ ID NO 91
<211> LENGTH: 6
<212> TYPE: PRT
<213> ORGANISM: Artificial Sequence
<220> FEATURE:
<223> OTHER INFORMATION: Synthetic Construct

<400> SEQUENCE: 91

His His His His His His
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Construct

<400> SEQUENCE: 92

Arg Arg Arg Arg Arg Arg Arg Arg Arg
1               5

<210> SEQ ID NO 93
<211> LENGTH: 6
<212> TYPE: PRT
<213> ORGANISM: Artificial Sequence
<220> FEATURE:
<223> OTHER INFORMATION: Synthetic Construct

<400> SEQUENCE: 93

Ser Gly Arg Ser Ala Gln
1               5

<210> SEQ ID NO 94
<211> LENGTH: 10
<212> TYPE: PRT
<213> ORGANISM: Vibrio cholerae

<400> SEQUENCE: 94

Ala Arg Ser Arg Lys Pro Arg Asp Leu Thr
1               5                   10

<210> SEQ ID NO 95
<211> LENGTH: 10
<212> TYPE: PRT
<213> ORGANISM: Pseudomonas aeruginosa

<400> SEQUENCE: 95

Thr Arg His Arg Gln Pro Arg Gly Trp Glu
1               5                   10

<210> SEQ ID NO 96
<211> LENGTH: 10
<212> TYPE: PRT
<213> ORGANISM: Corynebacterium diphtheriae

<400> SEQUENCE: 96

Ala Gly Asn Arg Val Arg Arg Ser Val Gly
1               5                   10

<210> SEQ ID NO 97
<211> LENGTH: 6
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Any amino acid

<400> SEQUENCE: 97

Ile Glu Pro Asp Xaa Gly
1               5

<210> SEQ ID NO 98
<211> LENGTH: 6
<212> TYPE: PRT
<213> ORGANISM: Corynebacterium diphtheriae

<400> SEQUENCE: 98

Ile Glu Pro Asp Thr Gly
1               5

<210> SEQ ID NO 99
<211> LENGTH: 6
<212> TYPE: PRT
<213> ORGANISM: Pseudomonas aeruginosa

<400> SEQUENCE: 99

Ile Glu Pro Asp Gly Trp
1               5

<210> SEQ ID NO 100
<211> LENGTH: 4
<212> TYPE: PRT
<213> ORGANISM: Pseudomonas aeruginosa

<400> SEQUENCE: 100

Thr Asp Pro Arg
1

<210> SEQ ID NO 101
<211> LENGTH: 4
<212> TYPE: PRT
<213> ORGANISM: Vibrio cholerae

<400> SEQUENCE: 101

Gly Asn Ala Tyr
1

<210> SEQ ID NO 102
<211> LENGTH: 4
<212> TYPE: PRT
<213> ORGANISM: Pseudomonas aeruginosa

<400> SEQUENCE: 102

Asp Leu Gly Glu
1

<210> SEQ ID NO 103
<211> LENGTH: 4
<212> TYPE: PRT
<213> ORGANISM: Vibrio cholerae

<400> SEQUENCE: 103

Asp Leu Arg Arg
1

<210> SEQ ID NO 104
```

```
<211> LENGTH: 6
<212> TYPE: PRT
<213> ORGANISM: Vibrio cholerae

<400> SEQUENCE: 104

Arg Lys Pro Arg Asp Leu
1               5
```